(12) United States Patent
Ouyang et al.

(10) Patent No.: US 12,398,151 B2
(45) Date of Patent: Aug. 26, 2025

(54) SUMO INHIBITOR COMPOUNDS AND USES THEREOF

(71) Applicant: SUVALENT THERAPEUTICS, INC., Thousand Oaks, CA (US)

(72) Inventors: Xiaohu Ouyang, Rosemead, CA (US); Miles Kubota, Monrovia, CA (US); Ted Charles Judd, Granada Hills, CA (US); Andrew S. Tasker, Simi Valley, CA (US)

(73) Assignee: SUVALENT THERAPEUTICS, INC., Thousand Oaks, CA (US)

( * ) Notice: Subject to any disclaimer, the term of this patent is extended or adjusted under 35 U.S.C. 154(b) by 926 days.

(21) Appl. No.: 17/435,855

(22) PCT Filed: Mar. 19, 2020

(86) PCT No.: PCT/US2020/023550
§ 371 (c)(1),
(2) Date: Sep. 2, 2021

(87) PCT Pub. No.: WO2020/191151
PCT Pub. Date: Sep. 24, 2020

(65) Prior Publication Data
US 2022/0177488 A1  Jun. 9, 2022

Related U.S. Application Data

(60) Provisional application No. 62/820,703, filed on Mar. 19, 2019.

(51) Int. Cl.
| | |
|---|---|
| *C07D 495/04* | (2006.01) |
| *C07D 209/08* | (2006.01) |
| *C07D 209/44* | (2006.01) |
| *C07D 217/06* | (2006.01) |
| *C07D 217/14* | (2006.01) |
| *C07D 217/16* | (2006.01) |
| *C07D 223/16* | (2006.01) |
| *C07D 333/54* | (2006.01) |
| *C07D 401/04* | (2006.01) |
| *C07D 401/12* | (2006.01) |
| *C07D 405/06* | (2006.01) |
| *C07D 471/04* | (2006.01) |
| *C07D 491/048* | (2006.01) |
| *G01N 33/573* | (2006.01) |

(52) U.S. Cl.
CPC ......... *C07D 495/04* (2013.01); *C07D 209/08* (2013.01); *C07D 217/06* (2013.01); *C07D 217/14* (2013.01); *C07D 217/16* (2013.01); *C07D 333/54* (2013.01); *C07D 401/04* (2013.01); *C07D 401/12* (2013.01); *C07D 405/06* (2013.01); *C07D 471/04* (2013.01); *C07D 491/048* (2013.01); *G01N 33/573* (2013.01); *G01N 2440/36* (2013.01)

(58) Field of Classification Search
CPC .. C07D 495/04; C07D 209/08; C07D 209/44; C07D 217/06; C07D 217/14; C07D 217/16; C07D 333/54; C07D 401/04; C07D 405/06; C07D 471/04; C07D 491/048; C07D 223/16
See application file for complete search history.

(56) References Cited

U.S. PATENT DOCUMENTS

2016/0272572 A1   9/2016   Dai et al.

FOREIGN PATENT DOCUMENTS

| CN | 104910174 A | 9/2015 |
|---|---|---|
| CN | 107793413 A | 3/2018 |
| EP | 3111960 A1 | 1/2017 |
| WO | 98/40385 A1 | 9/1998 |
| WO | 2007/029106 A1 | 3/2007 |
| WO | 2007/109279 A2 | 9/2007 |
| WO | 2009/033581 A1 | 3/2009 |
| WO | 2013/021051 A1 | 2/2013 |
| WO | 2013/080222 A1 | 6/2013 |
| WO | 2016/002994 A1 | 1/2016 |

OTHER PUBLICATIONS

Chennamanenia et al., Isoquinoline-based analogs of the cancer drug clinical candidate tipifarnib as anti-Trypanosoma cruzi agents, Bioorganic & Medicinal Chemistry Letters, 19(23):6582-6584 (2009).
International Application No. PCT/US20/23550, International Preliminary Report on Patentability, mailed Sep. 30, 2021.
International Application No. PCT/US20/23550, International Search Report and Written Opinion, mailed Jun. 22, 2020.
Rao et al., Leveraging Compound Promiscuity to Identify Targetable Cysteines within the kinome, Cell Chemical Biology, 26:1-11 (2019).

*Primary Examiner* — Sun Jae Yoo
(74) *Attorney, Agent, or Firm* — MARSHALL, GERSTEIN & BORUN LLP

(57) ABSTRACT

The present invention relates to compounds and compositions capable of acting as inhibitors of small ubiquitin-like modifier (SUMO) family of proteins. The compounds and compositions may be used in the treatment of cancer. There are disclosed, inter alia, methods of inhibiting an E1 enzyme, and compounds useful for inhibiting an E1 enzyme.

32 Claims, No Drawings
Specification includes a Sequence Listing.

```
                        SEQUENCE LISTING

<160> NUMBER OF SEQ ID NOS: 6

<210> SEQ ID NO 1
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 1

Leu Val Gly Ala Gly Ala Ile Gly Cys Glu Leu Leu Lys
1               5                   10

<210> SEQ ID NO 2
<211> LENGTH: 13
<212> TYPE: PRT
<213> ORGANISM: Artificial Sequence
<220> FEATURE:
<223> OTHER INFORMATION: Synthetic Polypeptide
```

```
<400> SEQUENCE: 2

Val Val Gly Ala Gly Gly Ile Gly Cys Glu Leu Leu Lys
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 3

Val Ile Gly Ala Gly Gly Leu Gly Cys Glu Leu Leu Lys
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 4

Ile Val Gly Cys Gly Gly Leu Gly Cys Pro Ala Gln
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 5

Leu Val Gly Ala Gly Ala Ile Gly Cys Glu Leu Leu Lys
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 6

Leu Leu Gly Ala Gly Thr Leu Gly Cys Asn Val Ala Arg
1               5                   10
```

SUMO INHIBITOR COMPOUNDS AND USES THEREOF

STATEMENT OF GOVERNMENT SUPPORT

This invention was made with government support under SBIR Grant 2R44CA189499, SBIR Grant 1R43CA217349-01A1 and SBIR Grant 1R43CA239820 awarded by the National Cancer Institute. The government has certain rights in the invention.

INCORPORATION BY REFERENCE OF MATERIALS SUBMITTED ELECTRONICALLY

The application contains, as a separate part of the disclosure, a Sequence Listing in computer readable form [ ], which is incorporated by reference in its entirety.

FIELD OF THE INVENTION

The present invention relates to compounds and compositions capable of acting as inhibitors of small ubiquitin-like modifier (SUMO) family of proteins. The compounds and compositions may be used in the treatment of cancer.

BACKGROUND OF THE INVENTION

Post-translational modifications of cellular proteins by the small ubiquitin-like modifier (SUMO) family of proteins are important epigenetic mechanisms for regulating various cellular functions. Aberrations in post-translational modification of cellular proteins by the small ubiquitin-like modifier (SUMO) family of proteins are associated with the pathogenesis of life-threatening diseases, such as cancer, neurodegenerative disorders, and viral infection. Indeed, the enzymes catalyzing SUMO-modification (e.g., E1 disclosed herein) are present in higher levels in cancer tissues versus normal tissues and in metastasized tumors versus normal cells, and play an important role in cancer proliferation and metastasis. Without wishing to be bound by any theory, it is believed that E1 is a target for the development of therapeutics (e.g., cancer therapeutics). Thus, there are disclosed herein methods of inhibiting an E1 enzyme, and compounds useful for inhibiting an E1 enzyme.

DESCRIPTION OF THE INVENTION

In an aspect is provided a compound of formula I.

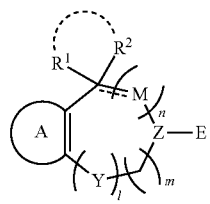

(I)

wherein ⚌ is a single bond or double bond;
wherein 1, m, n are each independently an integer from 0 to 2;
wherein M is selected from $CR^3R^4$, $—NR^5$, $C=O$, O, $S=O$, $O=S=O$, and S;
wherein Y is selected from $CR^6R^7$, $—NR^8$, $C=O$, O, $S=O$, $O=S=O$, and S;
wherein Z is $CR^9$, or N;
wherein ring A is selected from
  a) 5- or 6-membered partially saturated heterocyclyl,
  b) 5- or 6-membered aryl or heteroaryl,
  c) 9-, 10- or 11-membered fused partially saturated heterocyclyl,
  d) 9- or 10-membered fused heteroaryl,
  e) naphthyl, and
  f) 4-, 5- or 6-membered cycloalkenyl;
wherein E is an electrophilic moiety, selected from:

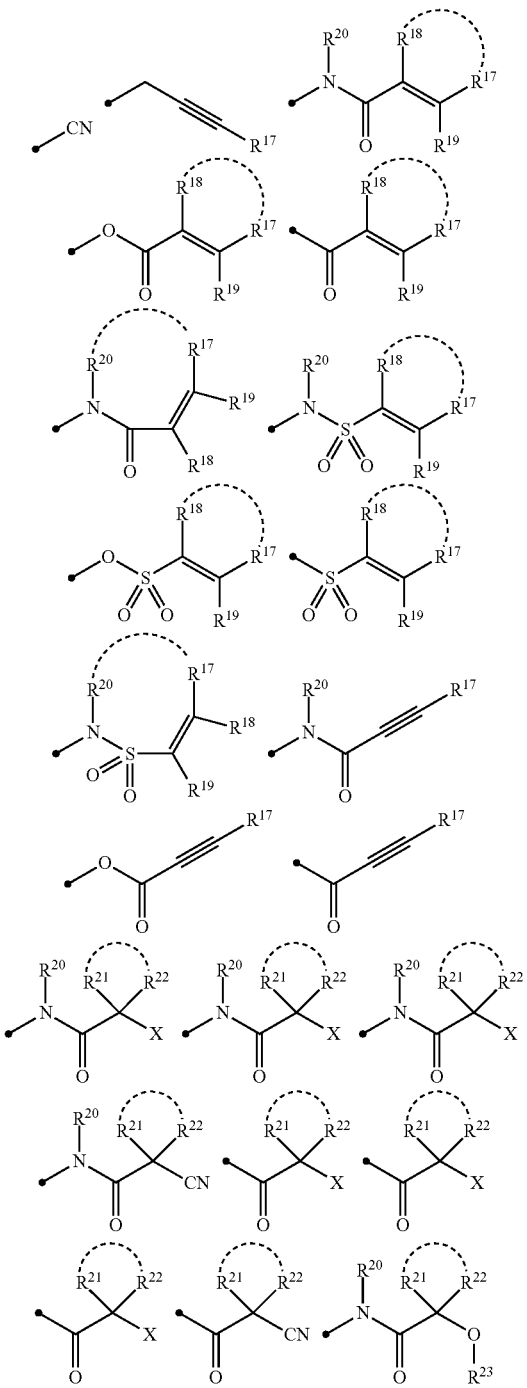

3
-continued

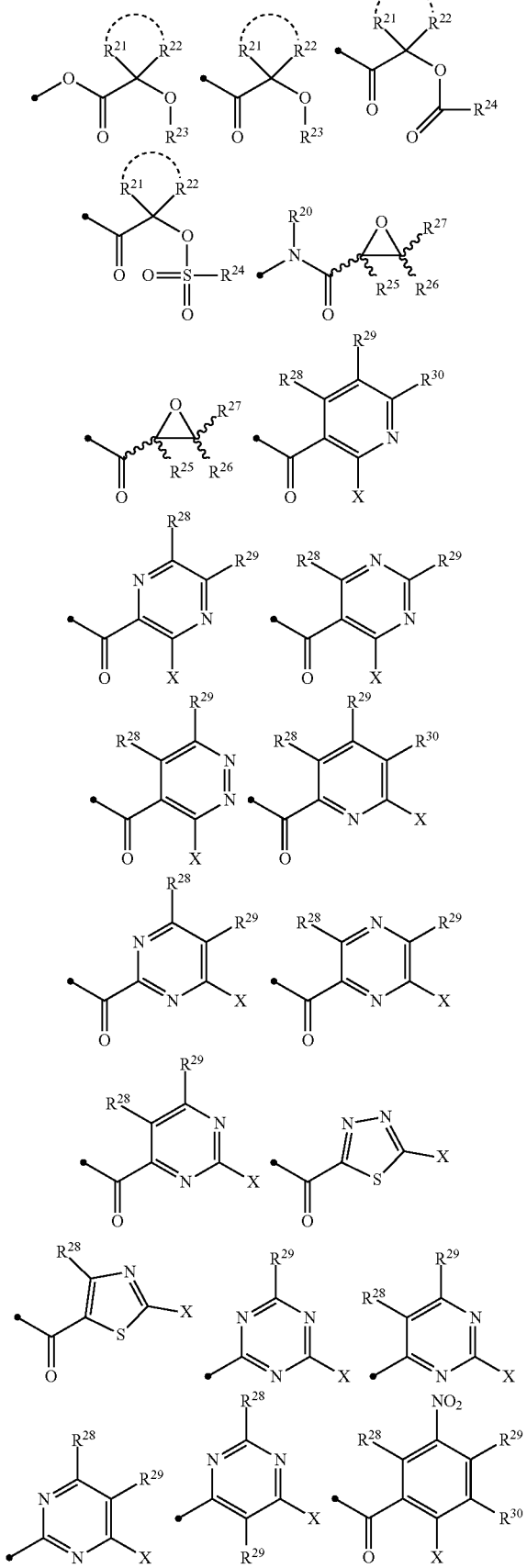

4
-continued

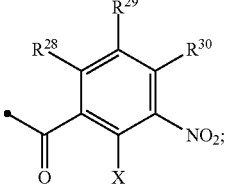

Wherein $R^1$ is selected from hydrogen, halogen, —C($X^1$)$_3$, —CH$X^1_2$, —CH$_2X^1$, —OC$X^1_3$, —OCH$_2X^1$, —OCH$X^1_2$, —CN, —SO$_{n1}R^{1A}$, —SO$_{v1}$N$R^{1A}R^{1B}$, —NHC(O)N$R^{1A}R^{1B}$, —N(O)$_{m1}$, —N$R^{1A}R^{1B}$, —NHN$R^{1A}R^{1B}$, —C(O)$R^{1A}$, —C(O)—O$R^{1A}$, —C(O)N$R^{1A}R^{1B}$, —C(O)NHN$R^{1A}R^{1B}$, —O$R^{1A}$, —N$R^{1A}$SO$_2R^{1B}$, —N$R^{1A}$C(O)$R^{1B}$, —N$R^{1A}$C(O)O$R^{1B}$, —N$R^{1A}$O$R^{1B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

Wherein $R^2$ is selected from hydrogen, halogen, —C$X^2_3$, —CH$X^2_2$, —CH$_2X^2$, —OC$X^2_3$, —OCH$_2X^2$, —OCH$X^2_2$, —CN, —SO$_{n2}R^{2A}$, —SO$_{v2}$N$R^{2A}R^{2B}$, —NHC(O)N$R^{2A}R^{2B}$, —N(O)$_{m2}$, —N$R^{2A}R^{2B}$, —NHN$R^{2A}R^{2B}$, —C(O)$R^{2A}$, —C(O)—O$R^{2A}$, —C(O)N$R^{2A}R^{2B}$, —C(O)NHN$R^{2A}R^{2B}$, —O$R^{2A}$, —N$R^{2A}$SO$_2R^{2B}$, —N$R^{2A}$C(O)$R^{2B}$, —N$R^{2A}$C(O)O$R^{2B}$, —N$R^{2A}$O$R^{2B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; $R^1$ and $R^2$ substituents may optionally be joined to form a substituted or unsubstituted cycloalkyl or heterocycloalkyl;

Wherein $R^3$ is selected from hydrogen, halogen, —C$X^3_3$, —CH$X^3_2$, —CH$_2X^3$, —OC$X^3_3$, —OCH$_2X^3$, —OCH$X^3_2$, —CN, —SO$_{n3}R^{3A}$, —SO$_{v3}$N$R^{3A}R^{3B}$, —NHC(O)N$R^{3A}R^{3B}$, —N(O)$_{m3}$, —N$R^{3A}R^{3B}$, —NHN$R^{3A}R^{3B}$, —C(O)$R^{3A}$, —C(O)—O$R^{3A}$, —C(O)N$R^{3A}R^{3B}$, —O$R^{3A}$, —N$R^{3A}$SO$_2R^{3B}$, —N$R^{3A}$C(O)$R^{3B}$, —N$R^{3A}$C(O)O$R^{3B}$, —N$R^{3A}$O$R^{3B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

Wherein $R^4$ is selected from hydrogen, halogen, —C$X^4_3$, —CH$X^4_2$, —CH$_2X^4$, —OC$X^4_3$, —OCH$_2X^4$, —OCH$X^4_2$, —CN, —SO$_{v4}R^{4A}$, —SO$_4$N$R^{4A}R^{4B}$, —NHC(O)N$R^{4A}R^{4B}$, —N(O)$_{m4}$, —N$R^{4A}R^{4B}$, —NHN$R^{4A}R^{4B}$, —C(O)$R^{4A}$, —C(O)—O$R^{4A}$, —C(O)N$R^{4A}R^{4B}$, —C(O)NHN$R^{4A}R^{4B}$, —O$R^{4A}$, —N$R^{4A}$SO$_2R^{4B}$, —N$R^{4A}$C(O)$R^{4B}$, —N$R^{4A}$C(O)O$R^{4B}$, —N$R^{4A}$O$R^{4B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^3$ and $R^3$ substituents may optionally be joined to form a substituted or unsubstituted cycloalkyl or heterocycloalkyl;

Wherein $R^5$ is selected from hydrogen, halogen, —C$X^5_3$, —CH$X^5_2$, —CH$_2X^5$, —OC$X^5_3$, —OCH$_2X^5$, —OCH$X^5_2$, —CN, —SO$_5R^{5A}$, —SO$_{v5}$N$R^{5A}R^{5B}$, —NHC(O)N$R^{5A}R^{5B}$, —N(O)$_{m5}$, —N$R^{5A}R^{5B}$, —NHN$R^{5A}R^{5B}$, —C(O)$R^{5A}$, —C(O)—O$R^{5A}$, —C(O)

$NR^{5A}R^{5B}$, —C(O)NHNR$^{5A}$R$^{5B}$, —OR$^{5A}$, —NR$^{5A}$SO$_2$R$^{5B}$, —NR$^{5A}$C(O)R$^{5B}$, —NR$^{5A}$C(O)OR$^{5B}$, —NR$^{5A}$OR$^{5B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

Wherein R$^6$ is selected from hydrogen, halogen, —CX$^6_3$, —CHX$^6_2$, —CH$_2$X$^6$, —OCX$^6_3$, —OCH$_2$X$^6$, —OCHX$^6_2$, —CN, —SO$_{v6}$R$^{6A}$, —SO$_6$NR$^{6A}$R$^{6B}$, —NHC(O)NR$^{6A}$R$^{6B}$, —N(O)$_{m6}$, —NR$^{6A}$R$^{6B}$, —NHNR$^{6A}$R$^{6B}$, —C(O)R$^{6A}$, —C(O)—OR$^{6A}$, —C(O)NR$^{6A}$R$^{6B}$, —C(O)NHNR$^{6A}$R$^{6B}$, —OR$^{6A}$, —NR$^{6A}$SO$_2$R$^{6B}$, —NR$^{6A}$C(O)R$^{6B}$, —NR$^{6A}$C(O)OR$^{6B}$, —NR$^{6A}$OR$^{6B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

Wherein R$^7$ is selected from hydrogen, halogen, —CX$^7_3$, —CHX$^7_2$, —CH$_2$X$^7$, —OCX$^7_3$, —OCH$_2$X$^7$, —OCHX$^7_2$, —CN, —SO$_{n7}$R$^{7A}$, —SO$_{v7}$NR$^{7A}$R$^{7B}$, —NHC(O)NR$^{7A}$R$^{7B}$, —N(O)$_{m7}$, —NR$^{7A}$R$^{7B}$, —NHNR$^{7A}$R$^{7B}$, —C(O)R$^{7A}$, —C(O)—OR$^{7A}$, —C(O)NR$^{7A}$R$^{7B}$, —C(O)NHNR$^{7A}$R$^{7B}$, —OR$^{7A}$, —NR$^{7A}$SO$_2$R$^{7B}$, —NR$^{7A}$C(O)R$^{7B}$, —NR$^{7A}$C(O)OR$^{7B}$, —NR$^{7A}$OR$^{7B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

Wherein R$^8$ is selected from hydrogen, halogen, —CX$^8_3$, —CHX$^8_2$, —CH$_2$X$^8$, —OCX$^8_3$, —OCH$_2$X$^8$, —OCHX$^8_2$, —CN, —SO$_{n8}$R$^{8A}$, —SO$_{v8}$NR$^{8A}$R$^{8B}$, —NHC(O)NR$^{8A}$R$^{8B}$, —N(O)$_{m8}$, —NR$^{8A}$7$^{7B}$, —NHNR$^{8A}$R$^{8B}$, —C(O)R$^{8A}$, —C(O)—OR$^{8A}$, —C(O)NR$^{8A}$R$^{8B}$, —C(O)NHNR$^{8A}$R$^{8B}$, —OR$^{8A}$, —NR$^{8A}$SO$_2$R$^{8B}$, —NR$^{8A}$C(O)R$^{8B}$, —NR$^{8A}$C(O)OR$^{8B}$, —NR$^{8A}$OR$^{8B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

Wherein R$^9$ is selected from hydrogen, halogen, —CX$^9_3$, —CHX$^9_2$, —CH$_2$X$^9$, —OCX$^9_3$, —OCH$_2$X$^9$, —OCHX$^9_2$, —CN, —SO$_{v9}$R$^{9A}$, —SO$_{v9}$NR$^{9A}$R$^{9B}$, —NHC(O)NR$^{9A}$R$^{9B}$, —N(O)$_{m9}$, —NR$^{9A}$R$^{9B}$, —NHNR$^{9A}$R$^{9B}$, —C(O)R$^{9A}$, —C(O)—OR$^{9A}$, —C(O)NR$^{9A}$R$^{9B}$, —C(O)NHNR$^{9A}$R$^{9B}$, —OR$^{9A}$, —NR$^{9A}$SO$_2$R$^{9B}$, —NR$^{9A}$C(O)R$^{9B}$, —NR$^{9A}$C(O)OR$^{9B}$, —NR$^{9A}$OR$^{9B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

Wherein R$^{10}$ is selected from hydrogen, halogen, —CX$^{10}_3$, —CHX$^{10}_2$, —CH$_2$X$^{10}$, —OCX$^{10}_3$, —OCH$_2$X$^{10}$, —OCHX$^{10}_2$, —CN, —SO$_{n10}$R$^{10A}$, —SO$_{v10}$NR$^{10A}$R$^{10B}$, —NHC(O)NR$^{10A}$R$^{10B}$, —N(O)$_{m10}$, —NR$^{10A}$R$^{10B}$, —NHNR$^{10A}$R$^{10B}$, —C(O)R$^{10A}$, —C(O)—OR$^{10A}$, —C(O)NR$^{10A}$R$^{10B}$, —C(O)NHNR$^{10A}$R$^{10B}$, —OR$^{10A}$, —NR$^{10A}$SO$_2$R$^{10B}$, —NR$^{10A}$C(O)R$^{10B}$, —NR$^{10A}$C(O)OR$^{10B}$, —NR$^{10A}$OR$^{10B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

Wherein R$^{11}$ is selected from hydrogen, halogen, —CX$^{11}_3$, —CHX$^{11}_2$, —CH$_2$X$^{11}$, —OCX$^{11}_3$, —OCH$_2$X$^{11}$, —OCHX$^{11}_2$, —CN, —SO$_{n11}$R$^{11A}$, —SO$_{v10}$NR$^{11A}$R$^{11B}$, —NHC(O)NR$^{11A}$R$^{11B}$, —N(O)$_{m10}$, —NR$^{11A}$R$^{11B}$, —NHNR$^{11A}$R$^{11B}$, —C(O)R$^{11A}$, —C(O)—OR$^{11A}$, —C(O)NR$^{11A}$R$^{11B}$, —C(O)NHNR$^{11A}$R$^{11B}$, —OR$^{11A}$, —NR$^{11A}$SO$_2$R$^{11B}$, —NR$^{11A}$C(O)R$^{11B}$, —NR$^{11A}$C(O)OR$^{11B}$, —NR$^{11A}$OR$^{11B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

Wherein R$^{12}$ is selected from hydrogen, halogen, —CX$^{12}_3$, —CHX$^{12}_2$, —CH$_2$X$^{12}$, —OCX$^{12}_3$, —OCH$_2$X$^{12}$, —OCHX$^{12}_2$, —CN, —SO$_{n12}$R$^{12A}$, —SO$_{v12}$NR$^{12A}$R$^{12B}$, —NHC(O)NR$^{12A}$R$^{12B}$, —N(O)$_{m12}$, —NR$^{12A}$R$^{12B}$, —NHNR$^{12A}$R$^{12B}$, —C(O)R$^{12A}$, —C(O)—OR$^{12A}$, —C(O)NR$^{12A}$R$^{12B}$, —C(O)NHNR$^{12A}$R$^{12B}$, —OR$^{12A}$, —NR$^{12A}$SO$_2$R$^{12B}$, —NR$^{12A}$C(O)R$^{12B}$, —NR$^{12A}$C(O)OR$^{12B}$, —NR$^{12A}$OR$^{12B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

Wherein R$^{13}$ is selected from hydrogen, halogen, —CX$^{13}_3$, —CHX$^{13}_2$, —CH$_2$X$^{13}$, —OCX$^{13}_3$, —OCH$_2$X$^{13}$, —OCHX$^{13}_2$, —CN, —SO$_{n13}$R$^{13A}$, —SO$_{v13}$NR$^{13A}$R$^{13B}$, —NHC(O)NR$^{13A}$R$^{13B}$, —N(O)$_{m13}$, —NR$^{13A}$R$^{13B}$, —NHNR$^{13A}$R$^{13B}$, —C(O)R$^{13A}$, —C(O)—OR$^{13A}$, —C(O)NR$^{13A}$R$^{13B}$, —C(O)NHNR$^{13A}$R$^{13B}$, —OR$^{13A}$, —NR$^{13A}$SO$_2$R$^{13B}$, —NR$^{13A}$C(O)R$^{13B}$, —NR$^{13A}$C(O)OR$^{13B}$, —NR$^{13A}$OR$^{13B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

Wherein R$^{14}$ is selected from hydrogen, halogen, —CX$^{14}_3$, —CHX$^{14}_2$, —CH$_2$X$^{14}$, —OCX$^{14}_3$, —OCH$_2$X$^{14}$, —OCHX$^{14}_2$, —CN, —SO$_{n14}$R$^{14A}$, —SO$_{v14}$NR$^{14A}$R$^{14B}$, —NHC(O)NR$^{14A}$R$^{14B}$, —N(O)$_{m14}$, —NR$^{14A}$R$^{14B}$, —NHNR$^{14A}$R$^{14B}$, —C(O)R$^{14A}$, —C(O)—OR$^{14A}$, —C(O)NR$^{14A}$R$^{14B}$, —C(O)NHNR$^{14A}$R$^{14B}$, —OR$^{14A}$, —NR$^{14A}$SO$_2$R$^{14B}$, —NR$^{14A}$C(O)R$^{14B}$, —NR$^{14A}$C(O)OR$^{14B}$, —NR$^{14A}$OR$^{14B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

Wherein R$^{15}$ is selected from hydrogen, halogen, —CX$^{15}_3$, —CHX$^{15}_2$, —CH$_2$X$^{15}$, —OCX$^{15}_3$, —OCH$_2$X$^{15}$, —OCHX$^{15}_2$, —CN, —SO$_{n1}$R$^{15A}$, —SO$_{v5}$NR$^{15A}$R$^{15B}$, —NHC(O)NR$^{15A}$R$^{15B}$, —N(O)$_{m15}$, —NR$^{15A}$R$^{15B}$, —NHNR$^{15A}$R$^{15B}$, —C(O)R$^{15A}$, —C(O)—OR$^{15A}$, —C(O)NR$^{15A}$R$^{15B}$, —C(O)NHNR$^{15A}$R$^{15B}$, —OR$^{15A}$, —NR$^{15A}$SO$_2$R$^{15B}$, —NR$^{15A}$C(O)R$^{15B}$, —NR$^{15A}$C(O)OR$^{15B}$, —NR$^{15A}$OR$^{15B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{16}$ is selected from hydrogen, halogen, —$CX^{16}_3$, —$CHX^{16}_2$, —$CH_2X^{16}$, —$OCX^{16}_3$, —$OCH_2X^{16}$, —$OCHX^{16}_2$, —CN, —$SO_{n16}R^{16A}$, —$SO_{v16}NR^{16A}R^{16B}$, —$NHC(O)NR^{16A}R^{16B}$, —$N(O)_{m16}$, —$NR^{16A}R^{16B}$, —$NHNR^{16A}R^{16B}$, —$C(O)R^{16A}$, —$C(O)$—$OR^{16A}$, —$C(O)NR^{16A}R^{16B}$, —$C(O)NHNR^{16A}R^{16B}$, —$OR^{16A}$, —$NR^{16A}SO_2R^{16B}$, —$NR^{16A}C(O)R^{16B}$, —$NR^{16A}C(O)OR^{16B}$, —$NR^{16A}OR^{16B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{17}$ is selected from hydrogen, halogen, —$CX^{17}_3$, —$CHX^{17}_2$, —$CH_2X^{17}$, —$OCX^{17}_3$, —$OCH_2X^{17}$, —$OCHX^{17}_2$, —CN, —$SO_{n17}R^{17A}$, —$SO_{v17}NR^{17A}R^{17B}$, —$NHC(O)NR^{17A}R^{17B}$, —$N(O)_{m17}$, —$NR^{17A}R^{17B}$, —$NHNR^{17A}R^{17B}$, —$C(O)R^{17A}$, —$C(O)$—$OR^{17A}$, —$C(O)NR^{17A}R^{17B}$, —$C(O)NHNR^{17A}R^{17B}$, —$OR^{17A}$, —$NR^{17A}SO_2R^{17B}$, —$NR^{17A}C(O)R^{17B}$, —$NR^{17A}C(O)OR^{17B}$, —$NR^{17A}OR^{17B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{18}$ is selected from hydrogen, halogen, —$CX^{18}_3$, —$CHX^{18}_2$, —$CH_2X^{18}$, —$OCX^{18}_3$, —$OCH_2X^{18}$, —$OCHX^{18}_2$, —CN, —$SO_{n18}R^{18A}$, —$SO_{v18}NR^{18A}R^{18B}$, —$NHC(O)NR^{18A}R^{18B}$, —$N(O)_{m18}$, —$NR^{18A}R^{18B}$, —$NHNR^{18A}R^{18B}$, —$C(O)R^{18A}$, —$C(O)$—$OR^{18A}$, —$C(O)NR^{18A}R^{18B}$, —$C(O)NHNR^{18A}R^{8B}$, —$OR^{18A}$, —$NR^{18A}SO_2R^{18B}$, —$NR^{18A}C(O)R^{18B}$, —$NR^{18A}C(O)OR^{18B}$, —$NR^{18A}OR^{18B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; $R^{17}$ and $R^{18}$ substituents may optionally be joined to form a substituted or unsubstituted cycloalkyl or heterocycloalkyl;

$R^{19}$ is selected from hydrogen, halogen, —$CX^{19}_3$, —$CHX^{19}_2$, —$CH_2X^{19}$, —$OCX^{19}_3$, —$OCH_2X^{19}$, —$OCHX^{19}_2$, —CN, —$SO_{n19}R^{19A}$, —$SO_{v19}NR^{19A}R^{19B}$, —$NHC(O)NR^{19A}R^{19B}$, —$N(O)_{m19}$, —$NR^{19A}R^{19B}$, —$NHNR^{19A}R^{19B}$, —$C(O)R^{19A}$, —$C(O)$—$OR^{19A}$, —$C(O)NR^{19A}R^{19B}$, —$C(O)NHNR^{19A}R^{19B}$, —$OR^{19A}$, —$NR^{19A}SO_2R^{19B}$, —$NR^{19A}C(O)R^{19B}$, —$NR^{19A}C(O)OR^{19B}$, —$NR^{19A}OR^{19B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{20}$ is selected from hydrogen, halogen, —$CX^{20}_3$, —$CHX^{20}_2$, —$CH_2X^{20}$, —$OCX^{20}_3$, —$OCH_2X^{20}$, —$OCHX^{20}_2$, —CN, —$SO_{n20}R^{20A}$, —$SO_{v20}NR^{20A}R^{20B}$, —$NHC(O)NR^{20A}R^{20B}$, —$N(O)_{m20}$, —$NR^{20A}R^{20B}$, —$NHNR^{20A}R^{20B}$, —$C(O)R^{20A}$, —$C(O)$—$OR^{20A}$, —$C(O)NR^{20A}R^{20B}$, —$C(O)NHNR^{20A}R^{20B}$, —$OR^{20A}$, —$NR^{20A}SO_2R^{20B}$, —$NR^{20A}C(O)R^{20B}$, —$NR^{20A}C(O)OR^{20B}$, —$NR^{20A}OR^{20B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; $R^{17}$ and $R^{20}$ substituents may optionally be joined to form a substituted or unsubstituted cycloalkyl or heterocycloalkyl;

$R^{21}$ is selected from hydrogen, halogen, —$CX^{21}_3$, —$CHX^{21}_2$, —$CH_2X^{21}$, —$OCX^{21}_3$, —$OCH_2X^{21}$, —$OCHX^{21}_2$, —CN, —$SO_{n21}R^{21A}$, —$SO_{v21}NR^{21A}R^{21B}$, —$NHC(O)NR^{21A}R^{21B}$, —$N(O)_{m21}$, —$NR^{21A}R^{21B}$, —$NHNR^{21A}R^{21B}$, —$C(O)R^{21A}$, —$C(O)$—$OR^{21A}$, —$C(O)NR^{21A}R^{21B}$, —$C(O)NHNR^{21A}R^{21B}$, —$OR^{21A}$, —$NR^{21A}SO_2R^{21B}$, —$NR^{21A}C(O)R^{21B}$, —$NR^{21A}C(O)OR^{21B}$, —$NR^{21A}OR^{21B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{22}$ is selected from hydrogen, halogen, —$CX^{22}_3$, —$CHX^{22}_2$, —$CH_2X^{22}$, —$OCX^{22}_3$, —$OCH_2X^{22}$, —$OCHX^{22}_2$, —CN, —$SO_{n22}R^{22A}$, —$SO_{v22}NR^{22A}R^{22B}$, —$NHC(O)NR^{22A}R^{22B}$, —$N(O)_{m22}$, —$NR^{22A}R^{22B}$, —$NHNR^{22A}R^{22B}$, —$C(O)R^{22A}$, —$C(O)$—$OR^{22A}$, —$C(O)NR^{22A}R^{22B}$, —$C(O)NHNR^{22A}R^{22B}$, —$OR^{22A}$, —$NR^{22A}SO_2R^{22B}$, —$NR^{22A}C(O)R^{22B}$, —$NR^{22A}C(O)OR^{22B}$, —$NR^{22A}OR^{22B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; $R^{21}$ and $R^{22}$ substituents may optionally be joined to form a substituted or unsubstituted cycloalkyl or heterocycloalkyl;

wherein $R^{23}$ is selected from hydrogen, halogen, —$CX^{23}_3$, —$CHX^{23}_2$, —$CH_2X^{23}$, —$OCX^{23}_3$, —$OCH_2X^{23}$, —$OCHX^{23}_2$, —CN, —$SO_{n23}R^{23A}$, —$SO_{v23}NR^{23A}R^{23B}$, —$NHC(O)NR^{23A}R^{23B}$, —$N(O)_{m23}$, —$NR^{23A}R^{23B}$, —$NHNR^{23A}R^{23B}$, —$C(O)R^{23A}$, —$C(O)$—$OR^{23A}$, —$C(O)NR^{23A}R^{23B}$, —$C(O)NHNR^{23A}R^{23B}$, —$OR^{23A}$, —$NR^{23A}SO_2R^{23B}$, —$NR^{23A}C(O)R^{23B}$, —$NR^{23A}C(O)OR^{23B}$, —$NR^{23A}OR^{23B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

wherein $R^{24}$ is selected from hydrogen, halogen, —$CX^{24}_3$, —$CHX^{24}_2$, —$CH_2X^{24}$, —$OCX^{24}_3$, —$OCH_2X^{24}$, —$OCHX^{24}_2$, —CN, —$SO_{n24}R^{24A}$, —$SO_{v24}NR^{24A}R^{24B}$, —$NHC(O)NR^{24A}R^{24B}$, —$N(O)_{m24}$, —$NR^{24A}R^{24B}$, —$NHNR^{24A}R^{24B}$, —$C(O)R^{24A}$, —$C(O)$—$OR^{24A}$, —$C(O)NR^{24A}R^{24B}$, —$C(O)NHNR^{24A}R^{24B}$, —$OR^{24A}$, —$NR^{24A}SO_2R^{24B}$, —$NR^{24A}C(O)R^{24B}$, —$NR^{24A}C(O)OR^{24B}$, —$NR^{24A}OR^{24B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

wherein $R^{25}$ is selected from hydrogen, halogen, —$CX^{25}_3$, —$CHX^{25}_2$, —$CH_2X^{25}$, —$OCX^{25}_3$, —$OCH_2X^{25}$, —$OCHX^{25}_2$, —CN, —$SO_{n25}R^{25A}$, —$SO_{v25}NR^{25A}R^{25B}$, —$NHC(O)NR^{25A}R^{25B}$, —$N(O)_{m25}$, —$NR^{25A}R^{25B}$, —$NHNR^{25A}R^{25B}$, —$C(O)R^{25A}$, —$C(O)$—$OR^{25A}$, —$C(O)NR^{25A}R^{25B}$, —$C(O)NHNR^{25A}R^{25B}$, —$OR^{25A}$, —$NR^{25A}SO_2R^{25B}$, —$NR^{25A}C(O)R^{25B}$, —$NR^{25A}C(O)OR^{25B}$, —$NR^{25A}OR^{25B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

wherein $R^{26}$ is selected from hydrogen, halogen, —$CX^{26}_3$, —$CHX^{26}_2$, —$CH_2X^{26}$, —$OCX^{26}_3$, —$OCH_2X^{26}$, —$OCHX^{26}_2$, —CN, —$SO_{n26}R^{26A}$, —$SO_{v26}NR^{26A}R^{26B}$, —$NHC(O)NR^{26A}R^{26B}$, —$N(O)_{m26}$, —$NR^{26A}R^{26B}$, —$NHNR^{26A}R^{26B}$, —$C(O)R^{26A}$, —$C(O)$—$OR^{26A}$, —$C(O)NR^{26A}R^{26B}$, —$C(O)NHNR^{26A}R^{26B}$, —$OR^{26A}$, —$NR^{26A}SO_2R^{26B}$, —$NR^{26A}C(O)R^{26B}$, —$NR^{26A}C(O)OR^{26B}$, —$NR^{26A}OR^{26B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

wherein $R^{27}$ is selected from hydrogen, halogen, —$CX^{27}_3$, —$CHX^{27}_2$, —$CH_2X^{27}$, —$OCX^{27}_3$, —$OCH_2X^{27}$, —$OCHX^{27}_2$, —CN, —$SO_{n27}R^{27A}$, —$SO_{v27}NR^{27A}R^{27B}$, —$NHC(O)NR^{27A}R^{27B}$, —$N(O)_{m27}$, —$NR^{27A}R^{27B}$, —$NHNR^{27A}R^{27B}$, —$C(O)R^{27A}$, —$C(O)$—$OR^{27A}$, —$C(O)NR^{27A}R^{27B}$, —$C(O)NHNR^{27A}R^{27B}$, —$OR^{27A}$, —$NR^{27A}SO_2R^{27B}$, —$NR^{27A}C(O)R^{27B}$, —$NR^{27A}C(O)OR^{27B}$, —$NR^{27A}OR^{27B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

Wherein $R^{28}$ is selected from hydrogen, halogen, —$CX^{28}_3$, —$CHX^{28}_2$, —$CH_2X^{28}$, —$OCX^{28}_3$, —$OCH_2X^{28}$, —$OCHX^{28}_2$, —CN, —$SO_{n28}R^{28A}$, —$SO_{v28}NR^{28A}R^{28B}$, —$NHC(O)NR^{28A}R^{28B}$, —$N(O)_{m28}$, —$NR^{28A}R^{28B}$, —$NHNR^{28A}R^{28B}$, —$C(O)R^{28A}$, —$C(O)$—$OR^{28A}$, —$C(O)NR^{28A}R^{28B}$, —$C(O)NHNR^{28A}R^{28B}$, —$OR^{28A}$, —$NR^{28A}SO_2R^{28B}$, —$NR^{28A}C(O)R^{28B}$, —$NR^{28A}C(O)OR^{28B}$, —$NR^{28A}OR^{28B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

Wherein $R^{29}$ is selected from hydrogen, halogen, —$CX^{29}_3$, —$CHX^{29}_2$, —$CH_2X^{29}$, —$OCX^{29}_3$, —$OCH_2X^{29}$, —$OCHX^{29}_2$, —CN, —$SO^{29}R^{9A}$, —$SO_{v29}NR^{29A}R^{29B}$, —$NHC(O)NR^{29A}R^{29B}$, —$N(O)_{m29}$, —$NR^{29A}R^{29B}$, —$NHNR^{29A}R^{29B}$, —$C(O)R^{29A}$, —$C(O)$—$OR^{29A}$, —$C(O)NR^{29A}R^{29B}$, —$C(O)NHNR^{29A}R^{29B}$, —$OR^{29A}$, —$NR^{29A}SO_2R^{29B}$, —$NR^{29A}C(O)R^{29B}$, —$NR^{29A}C(O)OR^{29B}$, —$NR^{29A}OR^{29B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{30}$ is selected from hydrogen, halogen, —$CX^{30}_3$, —$CHX^{30}_2$, —$CH_2X^{30}$, —$OCX^{30}_3$, —$OCH_2X^{30}$, —$OCHX^{30}_2$, —CN, —$SO_{n30}R^{30A}$, —$SO_{v30}NR^{30A}R^{30B}$, —$NHC(O)NR^{30A}R^{30B}$, —$N(O)_{m30}$, —$NR^{30A}R^{30B}$, —$NHNR^{30A}R^{30B}$, —$C(O)R^{30A}$, —$C(O)$—$OR^{30A}$, —$C(O)NR^{30A}R^{30B}$, —$C(O)NHNR^{30A}R^{30B}$, —$OR^{30A}$, —$NR^{30A}SO_2R^{30B}$, —$NR^{30A}C(O)R^{30B}$, —$NR^{30A}C(O)OR^{30B}$, —$NR^{30A}OR^{30B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

Each $R^{1A}$, $R^{1B}$, $R^{2A}$, $R^{2B}$, $R^{3A}$, $R^{3B}$, $R^{4A}$, $R^{4B}$, $R^{5A}$, $R^{5B}$, $R^{6A}$, $R^{6B}$, $R^{7A}$, $R^{7B}$, RA, $R^{8B}$, $R^{9A}$, $R^{9B}$, $R^{10A}$, $R^{10B}$, $R^{11A}$, $R^{11B}$, $R^{12A}$, $R^{12B}$, $R^{13A}$, $R^{13B}$, $R^{14A}$, $R^{14B}$, $R^{15A}$, $R^{15B}$, $R^{16A}$, $R^{16B}$, $R^{17A}$, $R^{17B}$, $R^{18A}$, $R^{18B}$, $R^{19A}$, $R^{19B}$, $R^{20A}$, $R^{20B}$, $R^{21A}$, $R^{21B}$, $R^{22A}$, $R^{22B}$, $R^{23A}$, $R^{23B}$, $R^{24A}$, $R^{24B}$, $R^{25A}$, $R^{25B}$, $R^{26A}$, $R^{26B}$, $R^{27A}$, $R^{27B}$, $R^{28A}$, $R^{28B}$, $R^{29A}$, $R^{29B}$, $R^{30A}$, $R^{30B}$ is independently selected from hydrogen, —$CX_3$, —$CHX_2$, —$CH_2X$, —C(O)OH, —$C(O)NH_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)$NHNH_2$, —NHC═(O)$NH_2$, —$NHSO_2H$, —NHC═(O)H, —NHC(O)OH, —NHOH, —$OCX_3$, —$OCHX_2$, —$OCH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

wherein $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{4A}$ and $R^{4B}$ substituents bonded to the same nitrogen atom may optionally be joined to form a substituted or unsubstituted heterocycloalkyl or substituted or unsubstituted heteroaryl; $R^{5A}$ and $R^{5B}$ substituents bonded to the same nitrogen atom may optionally be joined to form a substituted or unsubstituted heterocycloalkyl or substituted or unsubstituted heteroaryl; $R^{6A}$ and $R^{6B}$ substituents bonded to the same nitrogen atom may optionally be joined to form a substituted or unsubstituted heterocycloalkyl or substituted or unsubstituted heteroaryl; $R^{7A}$ and $R^{7B}$ substituents bonded to the same nitrogen atom may optionally be joined to form a substituted or unsubstituted heterocycloalkyl or substituted or unsubstituted heteroaryl; $R^{8A}$ and $R^{8B}$ substituents bonded to the same nitrogen atom may optionally be joined to form a substituted or unsubstituted heterocycloalkyl or substituted or unsubstituted heteroaryl; $R^{9A}$ and $R^{9B}$ substituents bonded to the same nitrogen atom may optionally be joined to form a substituted or unsubstituted heterocycloalkyl or substituted or unsubstituted heteroaryl; $R^{10A}$ and $R^{10B}$ substituents bonded to the same nitrogen atom may optionally be joined to form a substituted or unsubstituted heterocycloalkyl or substituted or unsubstituted heteroaryl; $R^{11A}$ and $R^{11B}$ substituents bonded to the same nitrogen atom may optionally be joined to form a substituted or unsubstituted heterocycloalkyl or substituted or unsubstituted heteroaryl; $R^{12A}$ and $R^{12B}$ substituents bonded to the same nitrogen atom may optionally be joined to form a substituted or unsubstituted heterocycloalkyl or substituted or unsubstituted heteroaryl; $R^{13A}$ and $R^{13B}$ substituents bonded to the same nitrogen atom may optionally be joined to form a substituted or unsubstituted heterocycloalkyl or substituted or unsubstituted heteroaryl; $R^{14A}$ and $R^{14B}$ substituents bonded to the same nitrogen atom may optionally be joined to form a substituted or unsubstituted heterocycloalkyl or substituted or unsubstituted heteroaryl; $R^{15A}$ and $R^{15B}$ substituents bonded to the same nitrogen atom may optionally be joined to form a substituted or unsubstituted heterocycloalkyl or substituted or unsubstituted heteroaryl; $R^{16A}$ and $R^{16B}$ substituents bonded to the same nitrogen atom may optionally be joined to form a substituted or unsubstituted heterocycloalkyl or substituted or unsubstituted heteroaryl; $R^{17A}$ and $R^{17B}$ substituents bonded to the same nitrogen atom may optionally be joined to form a substituted or unsubstituted heterocycloalkyl or substituted or unsubstituted heteroaryl; $R^{18A}$ and $R^{18B}$ substituents bonded to the same nitrogen atom may optionally be joined to form a substituted or unsubstituted heterocycloalkyl or substituted or unsubstituted heteroaryl; $R^{19A}$ and $R^{19B}$ substituents bonded to the same nitrogen atom may optionally be joined to form a substituted or unsubstituted heterocycloalkyl or substituted or unsubstituted heteroaryl; $R^{20A}$ and $R^{20B}$ substituents bonded to the same nitrogen atom may optionally be joined to form a substituted or unsubstituted heterocycloalkyl or substituted or unsubstituted heteroaryl; $R^{21A}$ and $R^{21B}$ substituents bonded to the same nitrogen atom may optionally be joined to form a substituted or unsubstituted heterocycloalkyl or substituted or unsubstituted heteroaryl; $R^{22A}$ and $R^{22B}$ substituents bonded to the same nitrogen atom may optionally be joined to form a substituted or unsubstituted heterocycloalkyl or substituted or unsubstituted heteroaryl; $R^{23A}$ and $R^{23B}$ substituents bonded to the same nitrogen atom may optionally be joined to form a substituted or unsubstituted heterocycloalkyl or substituted or unsubstituted heteroaryl; $R^{24A}$ and $R^{24B}$ substituents bonded to the same nitrogen atom may optionally be joined to form a substituted or unsubstituted heterocycloalkyl or substituted or unsubstituted heteroaryl; $R^{25A}$ and $R^{25B}$ substituents bonded to the same nitrogen atom may optionally be joined to form a substituted or unsubstituted heterocycloalkyl or substituted or unsubstituted heteroaryl; $R^{26A}$ and $R^{26B}$ substituents bonded to the same nitrogen atom may optionally be joined to form a substituted or unsubstituted heterocycloalkyl or substituted or unsubstituted heteroaryl; $R^{27A}$ and $R^{27B}$ substituents bonded to the same nitrogen atom may optionally be joined to form a substituted or unsubstituted heterocycloalkyl or substituted or unsubstituted heteroaryl; $R^{28A}$ and $R^{28B}$ substituents bonded to the same nitrogen atom may optionally be joined to form a substituted or unsubstituted heterocycloalkyl or substituted or unsubstituted heteroaryl; $R^{29A}$ and $R^{29B}$ substituents bonded to the same nitrogen atom may optionally be joined to form a substituted or unsubstituted heterocycloalkyl or substituted or unsubstituted heteroaryl; $R^{30A}$ and $R^{30B}$ substituents bonded to the same nitrogen atom may optionally be joined to form a substituted or unsubstituted heterocycloalkyl or substituted or unsubstituted heteroaryl;

Wherein each m1, m2, m3, m4, m5, m6, m7, m8, m9, m10, m11, m12, m13, m14, m15, m16, m17, m18, m19, m20, m21, m22, m23, m24, m25, m26, m27, m28, m29, and m30 are independently 1 or 2;

wherein each v1, v2, v3, v4, v5, v6, v7, v8, v9, v10, v11, v12, v13, v14, v15, v16, v17, v18, v19, v20, v21, v22, v23, v24, v25, v26, v27, v28, v29 and v30 are independently 1 or 2;

wherein each n1, n2, n3, n4, n5, n6, n7, n8, n9, n10, n11, n12, n13, n14, n15, n16, n17, n18, n19, n20, n21, n22, n23, n24, n25, n26, n27, n28, n29 and n30 are independently an integer from 0 to 2; and wherein each X, $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, $X^{16}$, $X^{17}$, $X^{18}$, $X^{19}$, $X^{20}$, $X^{21}$, $X^{22}$, $X^{23}$, $X^{24}$, $X^{25}$, $X^{26}$, $X^{27}$, $X^{28}$, $X^{29}$ and $X^{30}$ are independently —Cl, —Br, —I or —F.

In one embodiment, ring A is optionally substituted with one or more substituent groups.

In one embodiment, ring A is selected from dihydropyran, dihydrothienyl, dihydrofuryl, oxo-dihydrofuryl, pyrrolinyl, dihydrothiazolyl, dihydro-oxazolyl, dihydro-isothiazolyl, dihydro-isoxazolyl, imidazolinyl and pyrazolinyl. In one embodiment, the dihydropyran, dihydrothienyl, dihydrofuryl, oxo-dihydrofuryl, pyrrolinyl, dihydrothiazolyl, dihydro-oxazolyl, dihydro-isothiazolyl, dihydro-isoxazolyl, imidazolinyl and pyrazolinyl rings are optionally substituted with one or more substituent groups.

In one embodiment, ring A is selected from thienyl, furanyl, pyrrolyl, thiazolyl, oxazolyl, imidazolyl, pyrazolyl, isoxazolyl, triazolyl and isothiazolyl. In one embodiment, the thienyl, furanyl, pyrrolyl, thiazolyl, oxazolyl, imidazolyl, pyrazolyl, isoxazolyl, triazolyl and isothiazolyl rings are optionally substituted with one or more substituent groups.

In one embodiment, ring A is selected from

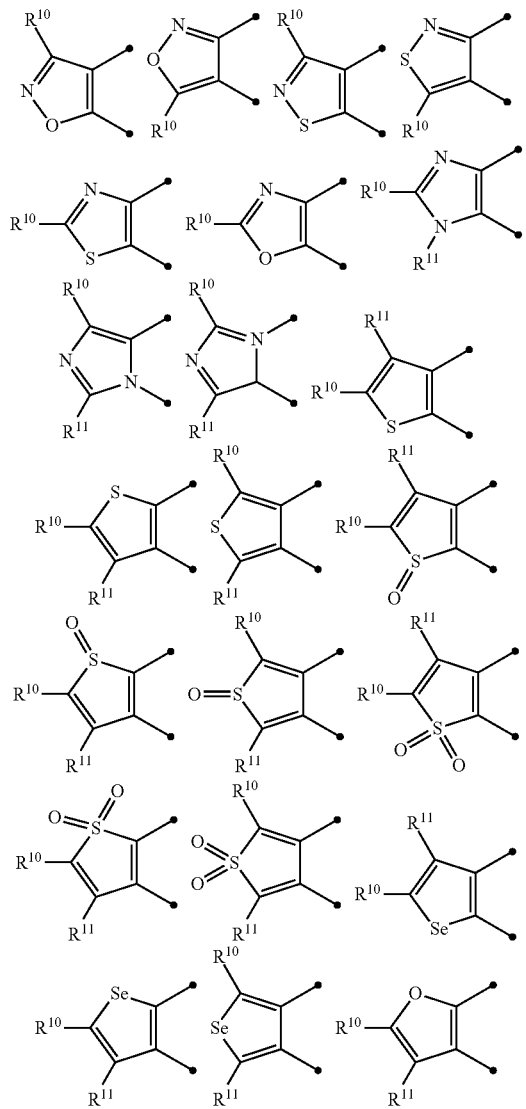

-continued

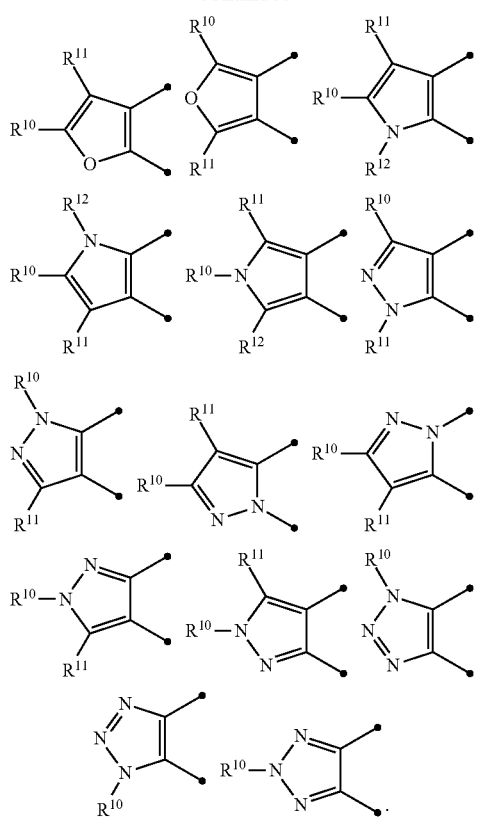

In one embodiment, ring A is

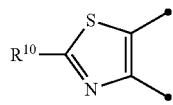

In one embodiment, ring A is selected from phenyl, pyridyl, pyrazinyl, pyrimidinyl, pyridazinyl, and triazinyl. In one embodiment, In one embodiment, the phenyl, pyridyl, pyrazinyl, pyrimidinyl, pyridazinyl, and triazinyl rings are optionally substituted with one or more substituent groups.

In one embodiment, ring A is selected from selected from

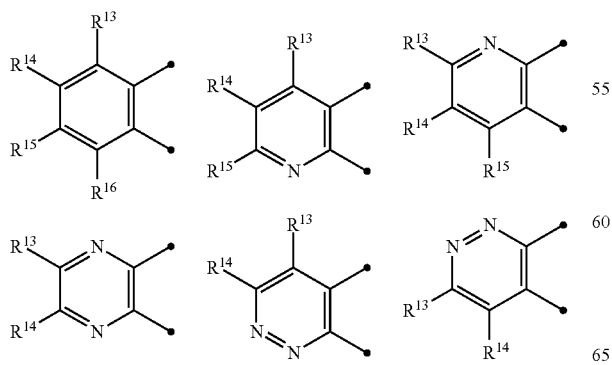

-continued

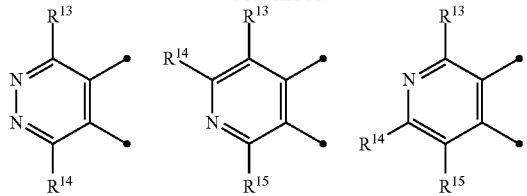

In one embodiment, ring A is selected from benzothienyl, benzothiazolyl, indolyl, benzimidazolyl, benzoxazolyl, benzofuryl, indazolyl and isolindolyl. In one embodiment, the benzothienyl, benzothiazolyl, indolyl, benzimidazolyl, benzoxazolyl, benzofuryl, indazolyl and isolindolyl rings are optionally substituted with one or more substituent groups.

In one embodiment, ring A is selected from quinolyl, isoquinolyl, naphthpyridinyl, quinoxalinyl and quinazolinyl. In one embodiment, the quinolyl, isoquinolyl, naphthpyridinyl, quinoxalinyl and quinazolinyl rings are optionally substituted with one or more substituent groups.

In one embodiment, E is selected from —C(=O)CH=CH$_2$, —C(=O)-ethynyl, —C(=O)CH=CHCF$_3$, —C(=O)CH=CHCHF$_2$, —C(=O)CH=CHCH$_2$F, and —C(=O)CH$_2$Br.

The invention also relates to compounds of Formula II:

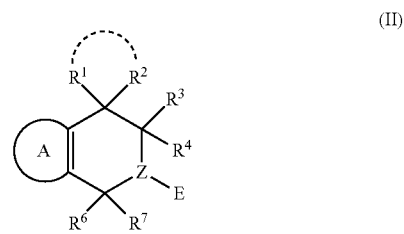

(II)

wherein

Z is selected from CR$^9$, or N.

ring A is selected from selected from
   a) 5- or 6-membered partially saturated heterocyclyl,
   b) 5- or 6-membered aryl or heteroaryl,
   c) 9-, 10- or 11-membered fused partially saturated heterocyclyl,
   d) 9- or 10-membered fused heteroaryl,
   e) naphthyl, and
   f) 4-, 5- or 6-membered cycloalkenyl;

E is an electrophilic moiety, selected from

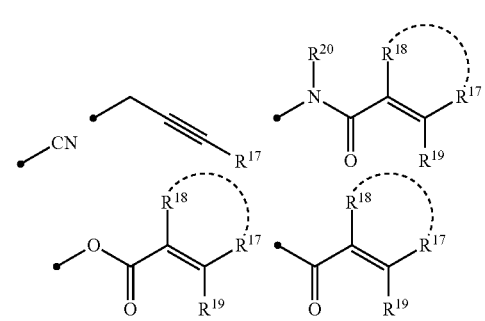

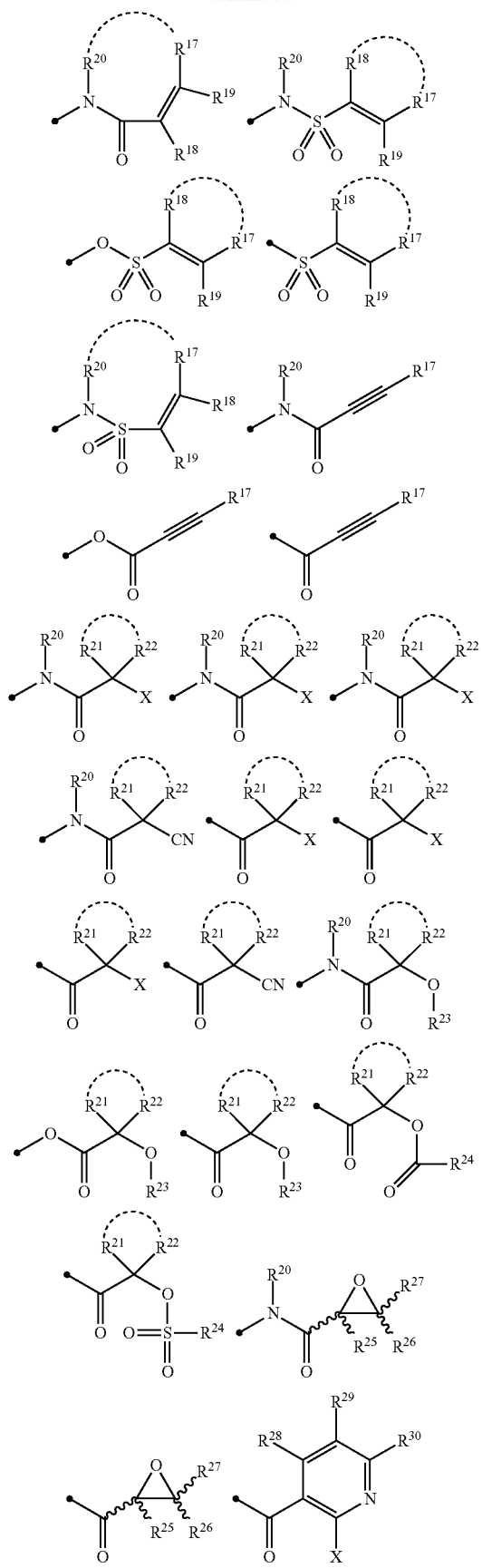
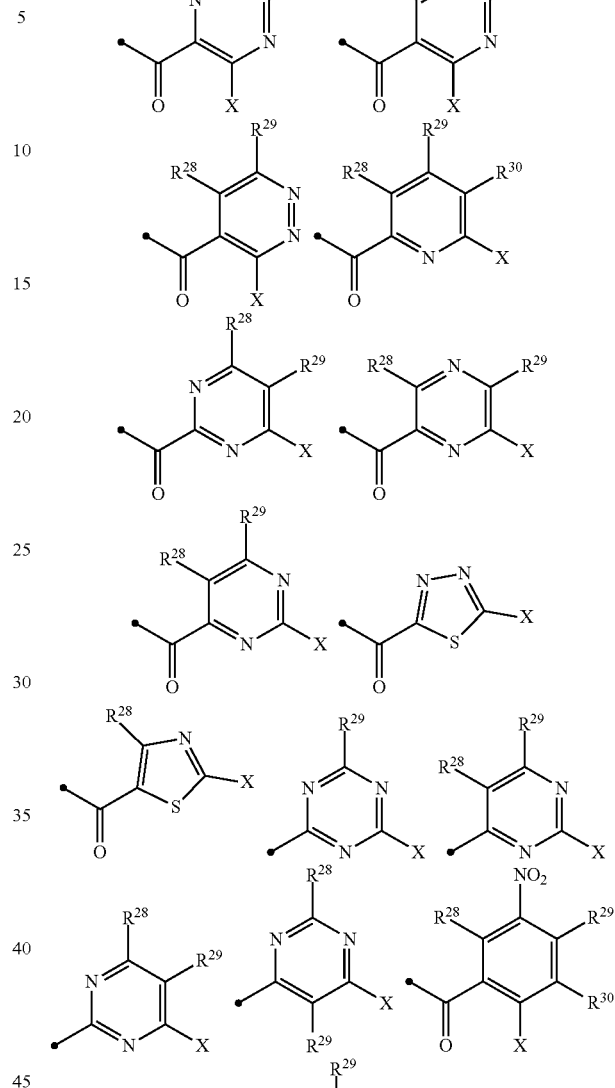

R[1] is selected from hydrogen, halogen, —CX[1]$_3$, —CHX[1]$_2$, —CH$_2$X[1], —OCX[1]$_3$, —OCH$_2$X[1], —OCHX[1]$_2$, —CN, —SO$_{n1}$R[1A], —SO$_{v1}$NR[1A]R[1B], —NHC(O)NR[1A]R[1B], —N(O)$_{m1}$, —NR[1A]R[1B], —NHNR[1A]R[1B], —C(O)R[1A], —C(O)—OR[1A], —C(O)NR[1A]R[1B], —C(O)NHNR[1A]R[1B], —OR[1A], —NR[1A]SO$_2$R[1B], —NR[1A]C(O)R[1B], —NR[1A]C(O)OR[1B], —NR[1A]OR[1B], —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R[2] is selected from hydrogen, halogen, —CX[2]$_3$, —CHX[2]$_2$, —CH$_2$X[2], —OCX[2]$_3$, —OCH$_2$X[2], —OCHX$^2$$_2$, —CN, —SO$_n$$_2$R$^{2A}$, —SO$_{v2}$NR$^{2A}$R$^{2B}$, —NHC(O)NR$^{2A}$R$^{2B}$, —N(O)$_{m2}$, —NR$^{2A}$R$^{2B}$, —NHNR$^{2A}$R$^{2B}$, —C(O)R$^{2A}$, —C(O)—OR$^{2A}$, —C(O)NR$^{2A}$R$^{2B}$, —C(O)NHNR$^{2A}$R$^{2B}$, —OR$^{2A}$, —NR$^{2A}$SO$_2$R$^{2B}$, —NR$^{2A}$C(O)R$^{2B}$, —NR$^{2A}$C(O)OR$^{2B}$, —NR$^{2A}$OR$^{2B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; R$^1$ and R$^2$ substituents may optionally be joined to form a substituted or unsubstituted cycloalkyl or heterocycloalkyl;

R$^3$ is selected from hydrogen, halogen, —CX$^3$$_3$, —CHX$^3$$_2$, —CH$_2$X$^3$, —OCX$^3$$_3$, —OCH$_2$X$^3$, —OCHX$^3$$_2$, —CN, —SO$_3$R$^{3A}$, —SO$_{v3}$NR$^{3A}$R$^{3B}$, —NHC(O)NR$^{3A}$R$^{3B}$, —N(O)$_{m3}$, —NR$^{3A}$R$^{3B}$, —NHNR$^{3A}$R$^{3B}$, —C(O)R$^{3A}$, —C(O)—OR$^{3A}$, —C(O)NR$^{3A}$R$^{3B}$, —OR$^{3A}$, —NR$^{3A}$SO$_2$R$^{3B}$, —NR$^{3A}$C(O)R$^{3B}$, —NR$^{3A}$C(O)OR$^{3B}$, —NR$^{3A}$OR$^{3B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^4$ is selected from hydrogen, halogen, —CX$^4$$_3$, —CHX$^4$$_2$, —CH$_2$X$^4$, —OCX$^4$$_3$, —OCH$_2$X$^4$, —OCHX$^4$$_2$, —CN, —SO$_{v4}$R$^{4A}$, —SO$_4$NR$^{4A}$R$^{4B}$, —NHC(O)NR$^{4A}$R$^{4B}$, —N(O)$_{m4}$, —NR$^{4A}$R$^{4B}$, —NHNR$^{4A}$R$^{4B}$, —C(O)R$^{4A}$, —C(O)—OR$^{4A}$, —C(O)NR$^{4A}$R$^{4B}$, —C(O)NHNR$^{4A}$R$^{4B}$, —OR$^{4A}$, —NR$^{4A}$SO$_2$R$^{4B}$, —NR$^{4A}$C(O)R$^{4B}$, —NR$^{4A}$C(O)OR$^{4B}$, —NR$^{4A}$OR$^{4B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; R$^3$ and R$^3$ substituents may optionally be joined to form a substituted or unsubstituted cycloalkyl or heterocycloalkyl;

R$^6$ is selected from hydrogen, halogen, —CX$^6$$_3$, —CHX$^6$$_2$, —CH$_2$X$^6$, —OCX$^6$$_3$, —OCH$_2$X$^6$, —OCHX$^6$$_2$, —CN, —SO$_{v6}$R$^{6A}$, —SO$_6$NR$^{6A}$R$^{6B}$, —NHC(O)NR$^{6A}$R$^{6B}$, —N(O)$_{m6}$, —NR$^{6A}$R$^{6B}$, —NHNR$^{6A}$R$^{6B}$, —C(O)R$^{6A}$, —C(O)—OR$^{6A}$, —C(O)NR$^{6A}$R$^{6B}$, —C(O)NHNR$^{6A}$R$^{6B}$, —OR$^{6A}$, —NR$^{6A}$SO$_2$R$^{6B}$, —NR$^{6A}$C(O)R$^{6B}$, —NR$^{6A}$C(O)OR$^{6B}$, —NR$^{6A}$OR$^{6B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^7$ is selected from hydrogen, halogen, —CX$^7$$_3$, —CHX$^7$$_2$, —CH$_2$X$^7$, —OCX$^7$$_3$, —OCH$_2$X$^7$, —OCHX$^7$$_2$, —CN, —SO$_7$R$^{7A}$, —SO$_{v7}$NR$^{7A}$R$^{7B}$, —NHC(O)NR$^{7A}$R$^{7B}$, —N(O)$_{m7}$, —NR$^{7A}$R$^{7B}$, —NHNR$^{7A}$R$^{7B}$, —C(O)R$^{7A}$, —C(O)—OR$^{7A}$, —C(O)NR$^{7A}$R$^{7B}$, —C(O)NHNR$^{7A}$R$^{7B}$, —OR$^{7A}$, —NR$^{7A}$SO$_2$R$^{7B}$, —NR$^{7A}$C(O)R$^{7B}$, —NR$^{7A}$C(O)OR$^{7B}$, —NR$^{7A}$OR$^{7B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^9$ is selected from hydrogen, halogen, —CX$^7$$_3$, —CHX$^7$$_2$, —CH$_2$X$^7$, —OCX$^7$$_3$, —OCH$_2$X$^7$, —OCHX$^7$$_2$, —CN, —SO$_{n7}$R$^{7A}$, —SO$_{v7}$NR$^{7A}$R$^{7B}$, —NHC(O)NR$^{7A}$R$^{7B}$, —N(O)$_{m7}$, —NR$^{7A}$R$^{7B}$, —NHNR$^{7A}$R$^{7B}$, —C(O)R$^{7A}$, —C(O)—OR$^{7A}$, —C(O) NR$^{7A}$R$^{7B}$, —C(O)NHNR$^{7A}$R$^{7B}$, —OR$^{7A}$, —NR$^{7A}$SO$_2$R$^{7B}$, —NR$^{7A}$C(O)R$^{7B}$, —NR$^{7A}$C(O)OR$^{7B}$, —NR$^{7A}$OR$^{7B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{10}$ is selected from hydrogen, halogen, —CX$^{10}$$_3$, —CHX$^{10}$$_2$, —CH$_2$X$^{10}$, —OCX$^{10}$$_3$, —OCH$_2$X$^{10}$, —OCHX$^{10}$$_2$, —CN, —SO$_{n10}$R$^{10A}$, —SO$_{v10}$NR$^{10A}$R$^{10B}$, —NHC(O)NR$^{10A}$R$^{10B}$, —N(O)$_{m10}$, —NR$^{10A}$R$^{10B}$, —NHNR$^{10A}$R$^{10B}$, —C(O) R$^{10A}$, —C(O)—OR$^{10A}$, —C(O)NR$^{10A}$R$^{10B}$, —C(O) NHNR$^{10A}$R$^{10B}$, —OR$^{10A}$, —NR$^{10A}$SO$_2$R$^{10B}$, —NR$^{10A}$C(O)R$^{10B}$, —NR$^{10A}$C(O)OR$^{10B}$, —NR$^{10A}$OR$^{10B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{11}$ is selected from hydrogen, halogen, —CX$^{11}$$_3$, —CHX$^{11}$$_2$, —CH$_2$X$^{11}$, —OCX$^{11}$$_3$, —OCH$_2$X$^{11}$, —OCHX$^{11}$$_2$, —CN, —SO$_{n11}$R$^{11A}$, —SO$_{v11}$NR$^{11A}$R$^{11B}$, —NHC(O)NR$^{11A}$R$^{11B}$, —N(O)$_{m1}$, —NR$^{11A}$R$^{1B}$, —NHNR$^{11A}$R$^{11B}$, —C(O) R$^{11A}$, —C(O)—OR$^{11A}$, —C(O)NR$^{11A}$R$^{11B}$, —C(O) NHNR$^{11A}$R$^{11B}$, —OR$^{11A}$, —NR$^{11A}$SO$_2$R$^{11B}$, —NR$^{11A}$C(O)R$^{11B}$, —NR$^{11A}$C(O)OR$^{11B}$, —NR$^{11A}$OR$^{11B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{12}$ is selected from hydrogen, halogen, —CX$^{12}$$_3$, —CHX$^{12}$$_2$, —CH$_2$X$^{12}$, —OCX$^{12}$$_3$, —OCH$_2$X$^{12}$, —OCHX$^{12}$$_2$, —CN, —SO$_{n12}$R$^{12A}$, —SO$_{v12}$NR$^{12A}$R$^{12B}$, —NHC(O)NR$^{12A}$R$^{12B}$, —N(O)$_{m12}$, —NR$^{12A}$R$^{12B}$, —NHNR$^{12A}$R$^{12B}$, —C(O) R$^{12A}$, —C(O)—OR$^{12A}$, —C(O)NR$^{12A}$R$^{12B}$, —C(O) NHNR$^{12A}$R$^{12B}$, —OR$^{12A}$, —NR$^{12A}$SO$_2$R$^{12B}$, —NR$^{12A}$C(O)R$^{12B}$, —NR$^{12A}$C(O)OR$^{12B}$, —NR$^{12A}$OR$^{12B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{13}$ is selected from hydrogen, halogen, —CX$^{13}$$_3$, —CHX$^{13}$$_2$, —CH$_2$X$^{13}$, —OCX$^{13}$$_3$, —OCH$_2$X$^{13}$, —OCHX$^{13}$$_2$, —CN, —SO$_{n13}$R$^{13A}$, —SO$_{v13}$NR$^{13A}$R$^{13B}$, —NHC(O)NR$^{13A}$R$^{13B}$, —N(O)$_{m13}$, —NR$^{13A}$R$^{13B}$, —NHNR$^{13A}$R$^{13B}$, —C(O) R$^{13A}$, —C(O)—OR$^{13A}$, —C(O)NR$^{13A}$R$^{13B}$, —C(O) NHNR$^{13A}$R$^{13B}$, —OR$^{13A}$, —NR$^{13A}$SO$_2$R$^{13B}$, —NR$^{13A}$C(O)R$^{13B}$, —NR$^{13A}$C(O)OR$^{13B}$, —NR$^{13A}$OR$^{13B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{14}$ is selected from hydrogen, halogen, —CX$^{14}$$_3$, —CHX$^{14}$$_2$, —CH$_2$X$^{14}$, —OCX$^{14}$$_3$, —OCH$_2$X$^{14}$, —OCHX$^{14}$$_2$, —CN, —SO$_{n14}$R$^{14A}$, —SO$_{v14}$NR$^{14A}$R$^{14B}$, —NHC(O)NR$^{14A}$R$^{14B}$, —N(O)$_{m14}$, —NR$^{14A}$R$^{14B}$, —NHNR$^{14A}$R$^{14B}$, —C(O) R$^{14A}$, —C(O)—OR$^{14A}$, —C(O)NR$^{14A}$R$^{14B}$, —C(O) NHNR$^{14A}$R$^{14B}$, —OR$^{14A}$, —NR$^{14A}$SO$_2$R$^{14B}$, —NR$^{14A}$C(O)R$^{14B}$, —NR$^{14A}$C(O)OR$^{14B}$, —NR$^{14A}$OR$^{14B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{15}$ is selected from hydrogen, halogen, —CX$^{15}_3$, —CHX$^{15}_2$, —CH$_2$X$^{15}$, —OCX$^{15}_3$, —OCH$_2$X$^1$, —OCHX$^{15}_2$, —CN, —SO$_{n15}$R$^{15A}$, —SO$_{v15}$NR$^{15A}$R$^{15B}$, —NHC(O)NR$^{15A}$R$^{15B}$, —N(O)$_{m15}$, —NR$^{15A}$R$^{15B}$, —NHNR$^{15A}$R$^{15B}$, —C(O)R$^{15A}$, —C(O)—OR$^{15A}$, —C(O)NR$^{15A}$R$^{15B}$, —C(O)NHNR$^{15A}$R$^{15B}$, —OR$^{15A}$, —NR$^{15A}$SO$_2$R$^{15B}$, —NR$^{15A}$C(O)R$^{15B}$, —NR$^{15A}$C(O)OR$^{15B}$, —NR$^{15A}$OR$^{15B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{16}$ is selected from hydrogen, halogen, —CX$^{16}_3$, —CHX$^{16}_2$, —CH$_2$X$^{16}$, —OCX$^{16}_3$, —OCH$_2$X$^{16}$, —OCHX$^{16}_2$, —CN, —SO$_{n16}$R$^{16A}$, —SO$_{v16}$NR$^{16A}$R$^{16B}$, —NHC(O)NR$^{16A}$R$^{16B}$, —N(O)$_{m16}$, —NR$^{16A}$R$^{16B}$, —NHNR$^{16A}$R$^{16B}$, —C(O)R$^{16A}$, —C(O)—OR$^{16A}$, —C(O)NR$^{16A}$R$^{16B}$, —C(O)NHNR$^{16A}$R$^{16B}$, —OR$^{16A}$, —NR$^{16A}$SO$_2$R$^{16B}$, —NR$^{16A}$C(O)R$^{16B}$, —NR$^{16A}$C(O)OR$^{16B}$, —NR$^{16A}$OR$^{16B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{17}$ is selected from hydrogen, halogen, —CX$^{17}_3$, —CHX$^{17}_2$, —CH$_2$X$^{17}$, —OCX$^{17}_3$, —OCH$_2$X$^{17}$, —OCHX$^{17}_2$, —CN, —SO$_{17}$R$^{17A}$, —SO$_{v17}$NR$^{17A}$R$^{17B}$, —NHC(O)NR$^{14}$R$^{17B}$, —N(O)$_{m17}$, —NR$^{17A}$R$^{17B}$, —NHNR$^{17A}$R$^{17B}$, —C(O)R$^{17A}$, —C(O)—OR$^{17A}$, —C(O)NR$^{17A}$R$^{17B}$, —C(O)NHNR$^{17A}$R$^{17B}$, —OR$^{17A}$, —NR$^{17A}$SO$_2$R$^{17B}$, —NR$^{17A}$C(O)R$^{17B}$, —NR$^{17A}$C(O)OR$^{17B}$, —NR$^{17A}$OR$^{17B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{18}$ is selected from hydrogen, halogen, —CX$^{18}_3$, —CHX$^{18}_2$, —CH$_2$X$^{18}$, —OCX$^{18}_3$, —OCH$_2$X$^{11}$, —OCHX$^{18}_2$, —CN, —SO$_{v18}$R$^{18A}$, —SO$_{v18}$NR$^{18A}$R$^{18B}$, —NHC(O)NR$^{18A}$R$^{18B}$, —N(O)$_{m18}$, —NR$^{18A}$R$^{18B}$, —NHNR$^{18A}$R$^{18B}$, —C(O)R$^{18A}$, —C(O)—OR$^{18A}$, —C(O)NR$^{18A}$R$^{18B}$, —C(O)NHNR$^{18A}$R$^{18B}$, —OR$^{18A}$, —NR$^{18A}$SO$_2$R$^{18B}$, —NR$^{18A}$C(O)R$^{18B}$, —NR$^{18A}$C(O)OR$^{18B}$, —NR$^{18A}$OR$^{18B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; R$^{16}$ and R$^{18}$ substituents may optionally be joined to form a substituted or unsubstituted cycloalkyl or heterocycloalkyl;

R$^{19}$ is selected from hydrogen, halogen, —CX$^{19}_3$, —CHX$^{19}_2$, —CH$_2$X$^{19}$, —OCX$^{19}_3$, —OCH$_2$X$^{19}$, —OCHX$^{19}_2$, —CN, —SO$_{n19}$R$^{19A}$, —SO$_{v19}$NR$^{19A}$R$^{19B}$, —NHC(O)NR$^{19A}$R$^{19B}$, —N(O)$_{m19}$, —NR$^{19A}$R$^{19B}$, —NHNR$^{19A}$R$^{19B}$, —C(O)R$^{19A}$, —C(O)—OR$^{19A}$, —C(O)NR$^{19A}$R$^{19B}$, —C(O)NHNR$^{19A}$R$^{19B}$, —OR$^{19A}$, —NR$^{19A}$SO$_2$R$^{19B}$, —NR$^{19A}$C(O)R$^{19B}$, —NR$^{19A}$C(O)OR$^{19B}$, —NR$^{19A}$OR$^{19B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; R$^{16}$ and R$^{19}$ substituents may optionally be joined to form a substituted or unsubstituted cycloalkyl or heterocycloalkyl;

R$^{20}$ is selected from hydrogen, halogen, —CX$^{20}_3$, —CHX$^{20}_2$, —CH$_2$X$^{20}$, —OCX$^{20}_3$, —OCH$_2$X$^{20}$, —OCHX$^{20}_2$, —CN, —SO$_{n20}$R$^{20A}$, —SO$_{v20}$NR$^{20A}$R$^{20B}$, —NHC(O)NR$^{20A}$R$^{20B}$, —N(O)$_{n20}$, —NR$^{20A}$R$^{20B}$, —NHNR$^{20A}$R$^{20B}$, —C(O)R$^{20A}$, —C(O)—OR$^{20A}$, —C(O)NR$^{20A}$R$^{20B}$, —C(O)NHNR$^{20A}$R$^{20B}$, —OR$^{20A}$, —NR$^{20A}$, —SO$_2$R$^{20B}$, —NR$^{20A}$C(O)R$^{20B}$, —NR$^{20A}$C(O)OR$^{20B}$, —NR$^{20A}$OR$^{20B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{21}$ is selected from hydrogen, halogen, —CX$^{21}_3$, —CHX$^{21}_2$, —CH$_2$X$^{21}$, —OCX$^{21}_3$, —OCH$_2$X$^{21}$, —OCHX$^{21}_2$, —CN, —SO$_{n21}$R$^{21A}$, —SO$_{v21}$NR$^{21A}$R$^{21B}$, —NHC(O)NR$^{21A}$R$^{21B}$, —N(O)$_{m21}$, —NR$^{21A}$R$^{21B}$, —NHNR$^{21A}$R$^{21B}$, —C(O)R$^{21A}$, —C(O)—OR$^{21A}$, —C(O)NR$^{21A}$R$^{21B}$, —C(O)NHNR$^{21A}$R$^{21B}$, —OR$^{21A}$, —NR$^{21A}$SO$_2$R$^{21B}$, —NR$^{21A}$C(O)R$^{21B}$, —NR$^{21A}$C(O)OR$^{21B}$, —NR$^{21A}$OR$^{21B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; R$^{20}$ and R$^{21}$ substituents may optionally be joined to form a substituted or unsubstituted cycloalkyl or heterocycloalkyl;

R$^{22}$ is selected from hydrogen, halogen, —CX$^{22}_3$, —CHX$^{22}_2$, —CH$_2$X$^{22}$, —OCX$^{22}_3$, —OCH$_2$X$^{22}$, —OCHX$^{22}_2$, —CN, —SO$_{n22}$R$^{22A}$, —SO$_{v22}$NR$^{22A}$R$^{22B}$, —NHC(O)NR$^{22A}$R$^{22B}$, —N(O)$_{m22}$, —NR$^{22A}$R$^{22B}$, —NHNR$^{22A}$R$^{22B}$, —C(O)R$^{22A}$, —C(O)—OR$^{22A}$, —C(O)NR$^{22A}$R$^{22B}$, —C(O)NHNR$^{22A}$R$^{22B}$, —OR$^{22A}$, —NR$^{22A}$SO$_2$R$^{22B}$, —NR$^{22A}$C(O)R$^{22B}$, —NR$^{22A}$C(O)OR$^{22B}$, —NR$^{22A}$OR$^{22B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{23}$ is selected from hydrogen, halogen, —CX$^{23}_3$, —CHX$^{23}_2$, —CH$_2$X$^{23}$, —OCX$^{23}_3$, —OCH$_2$X$^{23}$, —OCHX$^{23}_2$, —CN, —SO$_{n23}$R$^{23A}$, —SO$_{v23}$NR$^{23A}$R$^{23B}$, —NHC(O)NR$^{23A}$R$^{23B}$, —N(O)$_{m23}$, —NR$^{23A}$R$^{23B}$, —NHNR$^{23A}$R$^{23B}$, —C(O)R$^{23A}$, —C(O)—OR$^{23A}$, —C(O)NR$^{23A}$R$^{23B}$, —C(O)NHNR$^{23A}$R$^{23B}$, —OR$^{23A}$, —NR$^{23A}$SO$_2$R$^{23B}$, —NR$^{23A}$C(O)R$^{23B}$, —NR$^{23A}$C(O)OR$^{23B}$, —NR$^{23A}$OR$^{23B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{24}$ is selected from hydrogen, halogen, —CX$^{24}_3$, —CHX$^{24}_2$, —CH$_2$X$^{24}$, —OCX$^{24}_3$, —OCH$_2$X$^{24}$, —OCHX$^{24}_2$, —CN, —SO$_{n24}$R$^{24A}$, —SO$_{v24}$NR$^{24A}$R$^{24B}$, —NHC(O)NR$^{24A}$R$^{24B}$, —N(O)$_{m24}$, —NR$^{24A}$R$^{24B}$, —NHNR$^{24A}$R$^{24B}$, —C(O)R$^{24A}$, —C(O)—OR$^{24A}$, —C(O)NR$^{24A}$R$^{24B}$, —C(O)NHNR$^{24A}$R$^{24B}$, —OR$^{24A}$, —NR$^{24A}$SO$_2$R$^{24B}$, —NR$^{24A}$C(O)R$^{24B}$, —NR$^{24A}$C(O)OR$^{24B}$, —NR$^{24A}$OR$^{24B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{25}$ is selected from hydrogen, halogen, —CX$^{25}$$_3$, —CHX$^{25}$$_2$, —CH$_2$X$^{25}$, —OCX$^{25}$$_3$, —OCH$_2$X$^{25}$, —OCHX$^{25}$$_2$, —CN, —SO$_{n25}$R$^{25A}$, —SO$_{v25}$NR$^{25A}$R$^{25B}$, —NHC(O)NR$^{25A}$R$^{25B}$, —N(O)$_{m25}$, —NR$^{25A}$R$^{25B}$, —NHNR$^{25A}$R$^{25B}$, —C(O)R$^{25A}$, —C(O)—OR$^{25A}$, —C(O)NR$^{25A}$R$^{25B}$, —C(O)NHNR$^{25A}$R$^{25B}$, —OR$^{25A}$, —NR$^{25A}$SO$_2$R$^{25B}$, —NR$^{25A}$C(O)R$^{25B}$, —NR$^{25A}$C(O)OR$^{25B}$, —NR$^{25A}$OR$^{25B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{26}$ is selected from hydrogen, halogen, —CX$^{26}$$_3$, —CHX$^{26}$$_2$, —CH$_2$X$^{26}$, —OCX$^{26}$$_3$, —OCH$_2$X$^{26}$, —OCHX$^{26}$$_2$, —CN, —SO$_{n26}$R$^{26A}$, —SO$_{v26}$NR$^{26A}$R$^{26B}$, —NHC(O)NR$^{26A}$R$^{26B}$, —N(O)$_{m26}$, —NR$^{26A}$R$^{26B}$, —NHNR$^{26A}$R$^{26B}$, —C(O)R$^{26A}$, —C(O)—OR$^{26A}$, —C(O)NR$^{26A}$R$^{26B}$, —C(O)NHNR$^{26A}$R$^{26B}$, —OR$^{26A}$, —NR$^{26A}$SO$_2$R$^{26B}$, —NR$^{26A}$C(O)R$^{26B}$, —NR$^{26A}$C(O)OR$^{26B}$, —NR$^{26A}$OR$^{26B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{27}$ is selected from hydrogen, halogen, —CX$^{27}$$_3$, —CHX$^{27}$$_2$, —CH$_2$X$^{27}$, —OCX$^{27}$$_3$, —OCH$_2$X$^{27}$, —OCHX$^{27}$$_2$, —CN, —SO$_{n27}$R$^{27A}$, —SO$_{v27}$NR$^{27A}$R$^{27B}$, —NHC(O)NR$^{27A}$R$^{27B}$, —N(O)$_{m27}$, —NR$^{27A}$R$^{27B}$, —NHNR$^{27A}$R$^{27B}$, —C(O)R$^{27A}$, —C(O)—OR$^{27A}$, —C(O)NR$^{27A}$R$^{27B}$, —C(O)NHNR$^{27A}$R$^{27B}$, —OR$^{27A}$, —NR$^{27A}$SO$_2$R$^{27B}$, —NR$^{27A}$C(O)R$^{27B}$, —NR$^{27A}$C(O)OR$^{27B}$, —NR$^{27A}$OR$^{27B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{28}$ is selected from hydrogen, halogen, —CX$^{28}$$_3$, —CHX$^{28}$$_2$, —CH$_2$X$^{28}$, —OCX$^{28}$$_3$, —OCH$_2$X$^{28}$, —OCHX$^{28}$$_2$, —CN, —SO$_{n28}$R$^{28A}$, —SO$_{v28}$NR$^{28A}$R$^{28B}$, —NHC(O)NR$^{28A}$R$^{28B}$, —N(O)$_{m2}$, —NR$^{28A}$R$^{28B}$, —NHNR$^{28A}$R$^{28B}$, —C(O)R$^{28A}$, —C(O)—OR$^{28A}$, —C(O)NR$^{28A}$R$^{28B}$, —C(O)NHNR$^{28A}$R$^{28B}$, —OR$^{28A}$, —NR$^{28A}$SO$_2$R$^{28B}$, —NR$^{28A}$C(O)R$^{28B}$, —NR$^{28A}$C(O)OR$^{28B}$, —NR$^{28A}$OR$^{28B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{29}$ is selected from hydrogen, halogen, —CX$^{29}$$_3$, —CHX$^{29}$$_2$, —CH$_2$X$^{29}$, —OCX$^{29}$$_3$, —OCH$_2$X$^{29}$, —OCHX$^{29}$$_2$, —CN, —SO$_{n29}$R$^{29A}$, —SO$_{v29}$NR$^{29A}$R$^{29B}$, —NHC(O)NR$^{29A}$R$^{29B}$, —N(O)$_{m29}$, —NR$^{29A}$R$^{29B}$, —NHNR$^{29A}$R$^{29B}$, —C(O)R$^{29A}$, —C(O)—OR$^{29A}$, —C(O)NR$^{29A}$R$^{29B}$, —C(O)NHNR$^{29A}$R$^{29B}$, —OR$^{29A}$, —NR$^{29A}$SO$_2$R$^{29B}$, —NR$^{29A}$C(O)R$^{29B}$, —NR$^{29A}$C(O)OR$^{29B}$, —NR$^{29A}$OR$^{29B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{30}$ is selected from hydrogen, halogen, —CX$^{30}$$_3$, —CHX$^{30}$$_2$, —CH$_2$X$^{30}$, —OCX$^{30}$$_3$, —OCH$_2$X$^{30}$, —OCHX$^{30}$$_2$, —CN, —SO$_{n30}$R$^{30A}$, —SO$_{v30}$NR$^{30A}$R$^{30B}$, —NHC(O)NR$^{30A}$R$^{30B}$, —N(O)$_{m30}$, —NR$^{30A}$R$^{30B}$, —NHNR$^{30A}$R$^{30B}$, —C(O)R$^{30A}$, —C(O)—OR$^{30A}$, —C(O)NR$^{30A}$R$^{30B}$, —C(O)NHNR$^{30A}$R$^{30B}$, —OR$^{30A}$, —NR$^{30A}$SO$_2$R$^{30B}$, —NR$^{30A}$C(O)R$^{30B}$, —NR$^{30A}$C(O)OR$^{30B}$, —NR$^{30A}$OR$^{30B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

Each R$^{1A}$, R$^{1B}$, R$^{2A}$, R$^{2B}$, R$^{3A}$, R$^{3B}$, R$^{4A}$, R$^{4B}$, R$^{6A}$, R$^{6B}$, R$^{7A}$, R$^{7B}$, R$^{9A}$, R$^{9B}$, R$^{10A}$, R$^{10B}$, R$^{11A}$, R$^{11B}$, R$^{12A}$, R$^{12B}$, R$^{13A}$, R$^{13B}$, R$^{14A}$, R$^{14B}$, R$^{15A}$, R$^{15B}$, R$^{16A}$, R$^{16B}$, R$^{17A}$, R$^{17B}$, R$^{18A}$, R$^{18B}$, R$^{19A}$, R$^{19B}$, R$^{20A}$, R$^{20B}$, R$^{21A}$, R$^{21B}$, R$^{22A}$, R$^{22B}$, R$^{23A}$, R$^{23B}$, R$^{24A}$, R$^{24B}$, R$^{25A}$, R$^{25B}$, R$^{26A}$, R$^{26B}$, R$^{27A}$, R$^{27B}$, R$^{28A}$, R$^{28B}$, R$^{29A}$, R$^{29B}$, R$^{30A}$, R$^{30B}$, is independently selected from hydrogen, —CX$_3$, —CHX$_2$, —CH$_2$X, —C(O)OH, —C(O)NH$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$_3$, —OCHX$_2$, —OCH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{1A}$ and R$^{1B}$ substituents bonded to the same nitrogen atom may optionally be joined to form a substituted or unsubstituted heterocycloalkyl or substituted or unsubstituted heteroaryl; R$^{2A}$ and R$^{2B}$ substituents bonded to the same nitrogen atom may optionally be joined to form a substituted or unsubstituted heterocycloalkyl or substituted or unsubstituted heteroaryl; R$^{4A}$ and R$^{4B}$ substituents bonded to the same nitrogen atom may optionally be joined to form a substituted or unsubstituted heterocycloalkyl or substituted or unsubstituted heteroaryl; R$^{6A}$ and R$^{6B}$ substituents bonded to the same nitrogen atom may optionally be joined to form a substituted or unsubstituted heterocycloalkyl or substituted or unsubstituted heteroaryl; R$^{7A}$ and R$^{7B}$ substituents bonded to the same nitrogen atom may optionally be joined to form a substituted or unsubstituted heterocycloalkyl or substituted or unsubstituted heteroaryl; R$^{9A}$ and R$^{9B}$ substituents bonded to the same nitrogen atom may optionally be joined to form a substituted or unsubstituted heterocycloalkyl or substituted or unsubstituted heteroaryl; R$^{10A}$ and R$^{10B}$ substituents bonded to the same nitrogen atom may optionally be joined to form a substituted or unsubstituted heterocycloalkyl or substituted or unsubstituted heteroaryl; R$^{11A}$ and R$^{1B}$ substituents bonded to the same nitrogen atom may optionally be joined to form a substituted or unsubstituted heterocycloalkyl or substituted or unsubstituted heteroaryl; R$^{12A}$ and R$^{12B}$ substituents bonded to the same nitrogen atom may optionally be joined to form a substituted or unsubstituted heterocycloalkyl or substituted or unsubstituted heteroaryl; $R^{13A}$ and $R^{13B}$ substituents bonded to the same nitrogen atom may optionally be joined to form a substituted or unsubstituted heterocycloalkyl or substituted or unsubstituted heteroaryl; $R^{14A}$ and $R^{14B}$ substituents bonded to the same nitrogen atom may optionally be joined to form a substituted or unsubstituted heterocycloalkyl or substituted or unsubstituted heteroaryl; $R^{15A}$ and $R^{15B}$ substituents bonded to the same nitrogen atom may optionally be joined to form a substituted or unsubstituted heterocycloalkyl or substituted or unsubstituted heteroaryl; $R^{16A}$ and $R^{16B}$ substituents bonded to the same nitrogen atom may optionally be joined to form a substituted or unsubstituted heterocycloalkyl or substituted or unsubstituted heteroaryl; $R^{17A}$ and $R^{17B}$ substituents bonded to the same nitrogen atom may optionally be joined to form a substituted or unsubstituted heterocycloalkyl or substituted or unsubstituted heteroaryl; $R^{18A}$ and $R^{18B}$ substituents bonded to the same nitrogen atom may optionally be joined to form a substituted or unsubstituted heterocycloalkyl or substituted or unsubstituted heteroaryl; $R^{19A}$ and $R^{19B}$ substituents bonded to the same nitrogen atom may optionally be joined to form a substituted or unsubstituted heterocycloalkyl or substituted or unsubstituted heteroaryl; $R^{20A}$ and $R^{20B}$, substituents bonded to the same nitrogen atom may optionally be joined to form a substituted or unsubstituted heterocycloalkyl or substituted or unsubstituted heteroaryl; $R^{21A}$ and $R^{21B}$ substituents bonded to the same nitrogen atom may optionally be joined to form a substituted or unsubstituted heterocycloalkyl or substituted or unsubstituted heteroaryl; $R^{22A}$ and $R^{22B}$ substituents bonded to the same nitrogen atom may optionally be joined to form a substituted or unsubstituted heterocycloalkyl or substituted or unsubstituted heteroaryl; $R^{23A}$ and $R^{23B}$ substituents bonded to the same nitrogen atom may optionally be joined to form a substituted or unsubstituted heterocycloalkyl or substituted or unsubstituted heteroaryl; $R^{24A}$ and $R^{24B}$ substituents bonded to the same nitrogen atom may optionally be joined to form a substituted or unsubstituted heterocycloalkyl or substituted or unsubstituted heteroaryl; $R^{25A}$ and $R^{25B}$ substituents bonded to the same nitrogen atom may optionally be joined to form a substituted or unsubstituted heterocycloalkyl or substituted or unsubstituted heteroaryl; $R^{26A}$ and $R^{26B}$ substituents bonded to the same nitrogen atom may optionally be joined to form a substituted or unsubstituted heterocycloalkyl or substituted or unsubstituted heteroaryl; $R^{27A}$ and $R^{27B}$ substituents bonded to the same nitrogen atom may optionally be joined to form a substituted or unsubstituted heterocycloalkyl or substituted or unsubstituted heteroaryl; $R^{28A}$ and $R^{28B}$ substituents bonded to the same nitrogen atom may optionally be joined to form a substituted or unsubstituted heterocycloalkyl or substituted or unsubstituted heteroaryl; $R^{29A}$ and $R^{29B}$ substituents bonded to the same nitrogen atom may optionally be joined to form a substituted or unsubstituted heterocycloalkyl or substituted or unsubstituted heteroaryl; $R^{30A}$ and $R^{30B}$ substituents bonded to the same nitrogen atom may optionally be joined to form a substituted or unsubstituted heterocycloalkyl or substituted or unsubstituted heteroaryl;

Each m1, m2, m3, m4, m6, m7, m9, m10, m11, m12, m13, m14, m15, m16, m17, m18, m19, m20, m21, m22, m23, m24, m25, m26, m27, m28, m29 and m30 are independently 1 or 2;

Each v1, v2, v3, v4, v6, v7, v9, v10, v11, v12, v13, v14, v15, v16, v17, v18, v19, v20, v21, v22, v23, v24, v25, v26, v27, v28, v29 and v30 are independently 1 or 2;

Each n1, n2, n3, n4, n6, n7, n9, n10, n11, n12, n13, n14, n15, n16, n17, n18, n19, n20, n21, n22, n23, n24, n25, n26, n27, n28, n29 and n30 are independently an integer from 0 to 2; and Each $X^1$, $X^2$, $X^3$, $X^4$, $X^6$, $X^7$, $X^9$, $X^{10}$, $X^{11}$, $X^{12}$, $X^{13}$, $X^{14}$, $X^{15}$, $X^{16}$, $X^{17}$, $X^{18}$, $X^{19}$, $X^{20}$, $X^{21}$, $X^{22}$, $X^{23}$, $X^{24}$, $X^{25}$, $X^{26}$, $X^{27}$, $X^{28}$, $X^{29}$ and $X^{30}$ are independently —Cl, —Br, —I or —F;

Provided $R^6$ is not 2-thienyl when $R^7$, $R^1$ and $R^2$ are H, ring A is thienyl and E is ethenylcarbonyl; further provided $R^{10}$ and $R^{11}$ together do not form 4-amino-pyrimidinyl when $R^6$, $R^7$, $R^1$ and $R^2$ are H, ring A is thienyl and E is ethenylcarbonyl; further provided $R^{13}$ is not substituted indolylcarbonylamino when $R^6$, $R^7$, $R^1$ and $R^2$ are H, ring A is phenyl and E is ethenylcarbonyl; further provided $R^1$ is not substituted 4-amino-1H-pyrazolo[3,4-d]pyrimidin-1-yl when $R^6$, $R^7$ and $R^2$ are H, ring A is phenyl and E is ethenylcarbonyl; further provided $R^{13}$ is not substituted indolylcarbonylamino when R, $R^7$, $R^1$ and $R^2$ are H, ring A is phenyl and E is ethenylcarbonyl; further provided $R^{14}$ is not halo when $R^6$, $R^7$, $R^1$ and $R^2$ are H, ring A is phenyl and E is ethenylcarbonyl; further provided $R^{14}$ is not methoxy when $R^6$, $R^7$, $R^1$ and $R^2$ are H, ring A is phenyl and E is ethenylcarbonyl; further provided $R^6$ is not H, cyano, 2-aminocarbonyl-3-pridyl, cyclohexyl or substituted phenyl when $R^7$, $R^1$ and $R^2$ are H, ring A is phenyl and E is ethenylcarbonyl; and further provided $R^6$ and $R^7$ do not form 4-substituted spirocyclohexyl when $R^1$ and $R^2$ are H, ring A is phenyl and E is ethenylcarbonyl.

In one embodiment, ring A is optionally substituted with one ore more substituent groups.

In one embodiment, ring A is selected from preferably dihydropyran, dihydrothienyl, dihydrofuryl, oxo-dihydrofuryl, pyrrolinyl, dihydrothiazolyl, dihydro-oxazolyl, dihydro-isothiazolyl, dihydro-isoxazolyl, imidazolinyl and pyrazolinyl. In one embodiment, the dihydropyran, dihydrothienyl, dihydrofuryl, oxo-dihydrofuryl, pyrrolinyl, dihydrothiazolyl, dihydro-oxazolyl, dihydro-isothiazolyl, dihydro-isoxazolyl, imidazolinyl and pyrazolinyl rings are optionally substituted with one or more substituent groups.

In one embodiment, ring A is selected from thienyl, furanyl, pyrrolyl, thiazolyl, oxazolyl, imidazolyl, pyrazolyl, isoxazolyl, triazolyl and isothiazolyl. In one embodiment, the thienyl, furanyl, pyrrolyl, thiazolyl, oxazolyl, imidazolyl, pyrazolyl, isoxazolyl, triazolyl and isothiazolyl rings are optionally substituted with one or more substituent groups.

In one embodiment, ring A is selected from

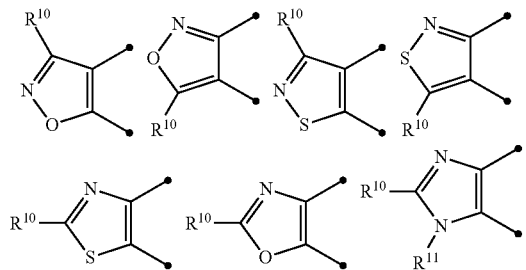

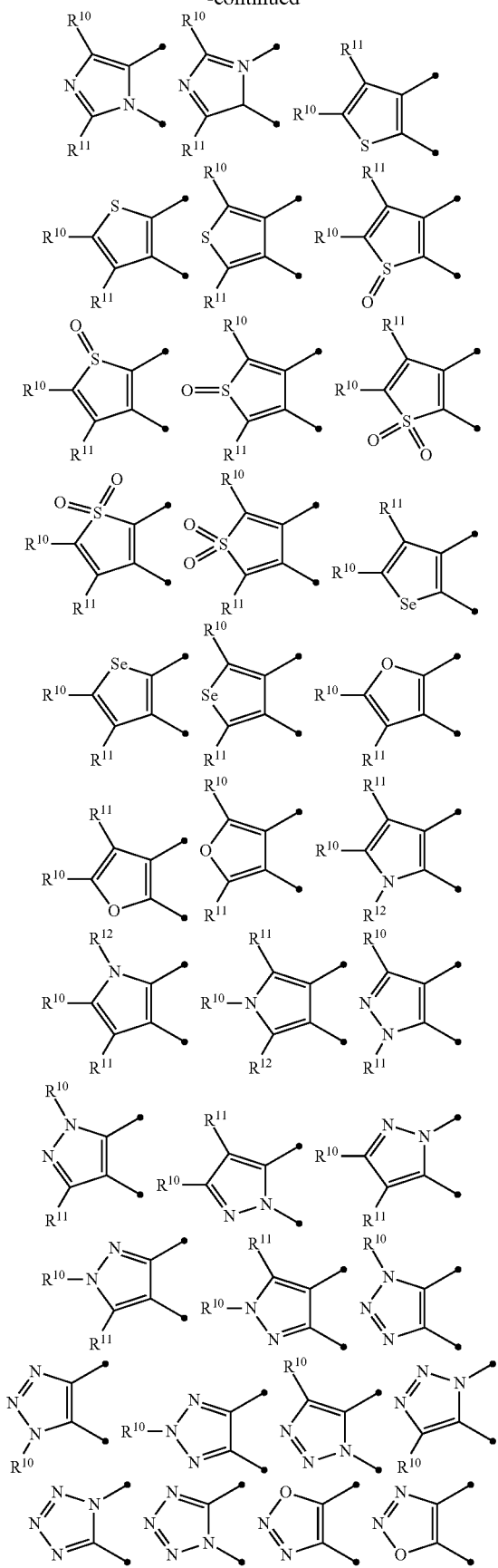

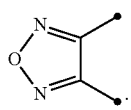

In one embodiment, ring A is

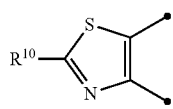

In one embodiment, ring A is selected from phenyl, pyridyl, pyrazinyl, pyrimidinyl, pyridazinyl, and triazinyl. In one embodiment, the phenyl, pyridyl, pyrazinyl, pyrimidinyl, pyridazinyl and triazinyl rings are optionally substituted with one or more substituent groups.

In one embodiment, ring A is selected from selected from

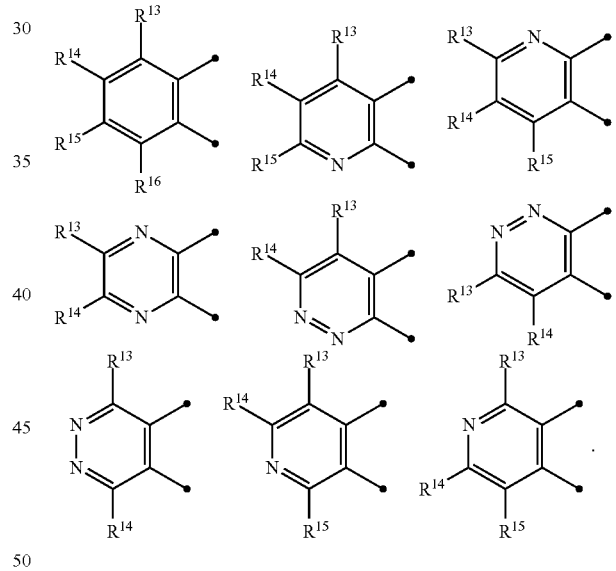

In one embodiment, ring A is selected from benzothienyl, benzothiazolyl, indolyl, benzimidazolyl, benzoxazolyl, benzofuryl, indazolyl and isolindolyl. In one embodiment, the benzothienyl, benzothiazolyl, indolyl, benzimidazolyl, benzoxazolyl, benzofuryl, indazolyl and isolindolyl rings are optionally substituted with one or more substituent groups.

In one embodiment, ring A is selected from quinolyl, isoquinolyl, naphthpyridinyl, quinoxalinyl and quinazolinyl. In one embodiment, the quinolyl, isoquinolyl, naphthpyridinyl, quinoxalinyl and quinazolinyl rings are optionally substituted with one or more substituent groups.

In one embodiment, E is selected from —C(=O)CH=CH$_2$, —C(=O)-ethynyl, —C(=O)CH=CHCF$_3$, —C(=O)CH=CHCHF$_2$, —C(=O)CH=CHCH$_2$F, and —C(=O)CH$_2$Br.

The invention also relates to compounds of Formula III:
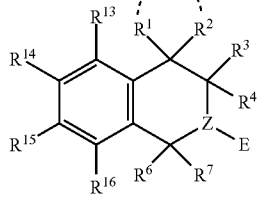
(III)
wherein
Z is $CR^9$, or N;
E is an electrophilic moiety selected from
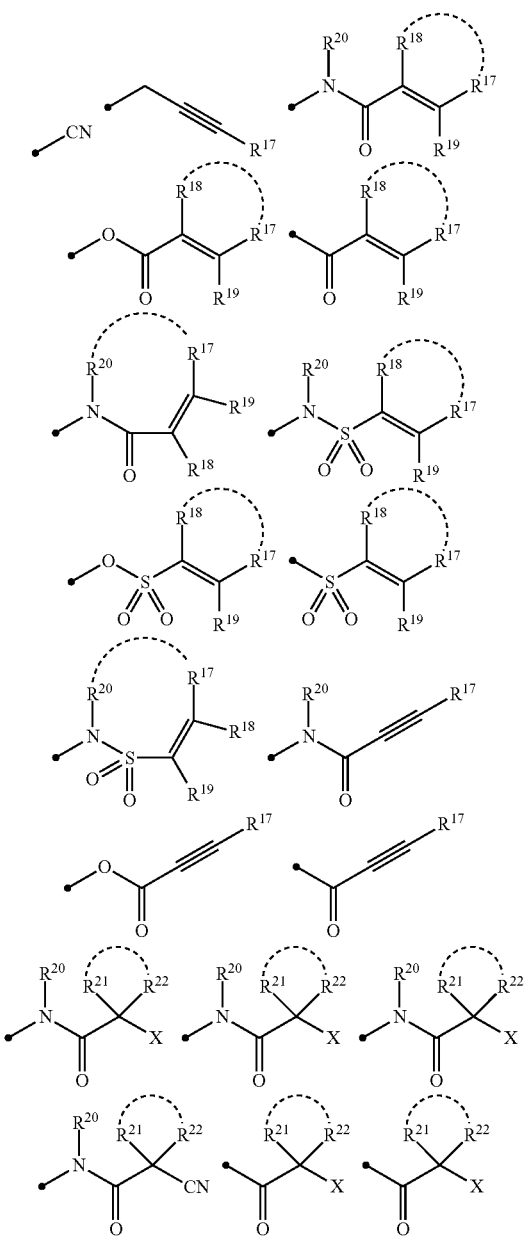
-continued
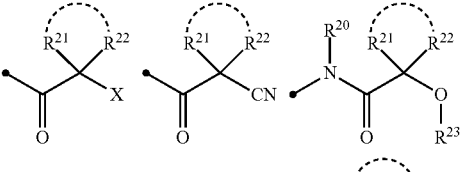
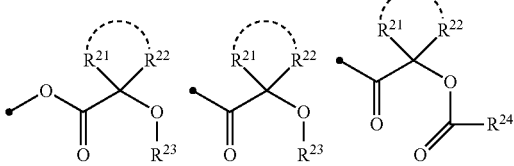
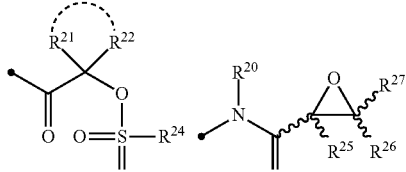
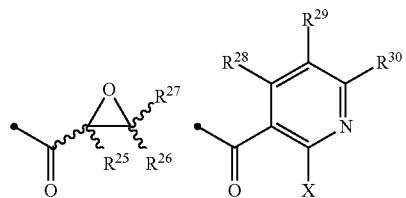
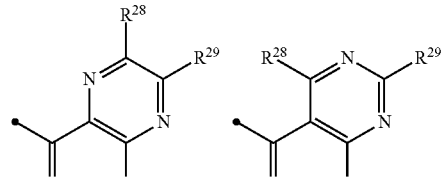
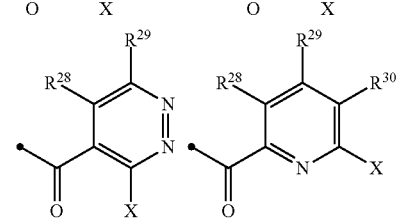
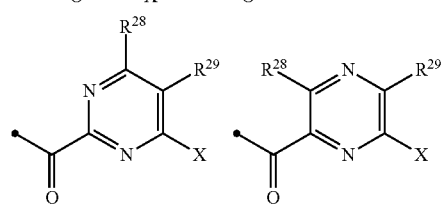
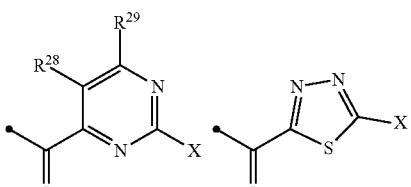
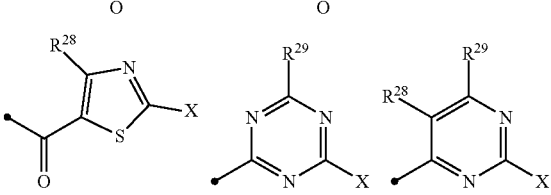

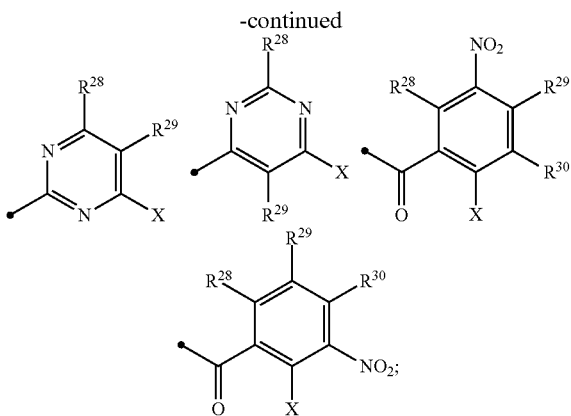

$R^1$ is selected from hydrogen, halogen, $-CX^1_3$, $-CHX^1_2$, $-CH_2X^1$, $-OCX^1_3$, $-OCH_2X^1$, $-OCHX^1_2$, $-CN$, $-SO_{n1}R^{1A}$, $-SO_{v1}NR^{1A}R^{1B}$, $-NHC(O)NR^{1A}R^{1B}$, $-N(O)_{m1}$, $-NR^{1A}R^{1B}$, $-NHNR^{1A}R^{1B}$, $-C(O)R^{1A}$, $-C(O)-OR^{1A}$, $-C(O)NR^{1A}R^{1B}$, $-C(O)NHNR^{1A}R^{1B}$, $-OR^{1A}$, $-NR^{1A}SO_2R^{1B}$, $-NR^{1A}C(O)R^{1B}$, $-NR^{1A}C(O)OR^{1B}$, $-NR^{1A}OR^{1B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^2$ is selected from hydrogen, halogen, $-CX^2_3$, $-CHX^2_2$, $-CH_2X^2$, $-OCX^2_3$, $-OCH_2X^2$, $-OCHX^2_2$, $-CN$, $-SO_{n2}R^{2A}$, $-SO_2NR^{2A}R^{2B}$, $-NHC(O)NR^{2A}R^{2B}$, $-N(O)_{m2}$, $-NR^{2A}R^{2B}$, $-NHNR^{2A}R^{2B}$, $-C(O)R^{2A}$, $-C(O)-OR^{2A}$, $-C(O)NR^{2A}R^{2B}$, $-C(O)NHNR^{2A}R^{2B}$, $-OR^{2A}$, $-NR^{2A}SO_2R^{2B}$, $-NR^{2A}C(O)R^{2B}$, $-NR^{2A}C(O)OR^{2B}$, $-NR^{2A}OR^{2B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; $R^1$ and $R^2$ substituents may optionally be joined to form a substituted or unsubstituted cycloalkyl or heterocycloalkyl;

$R^3$ is selected from hydrogen, halogen, $-CX^3_3$, $-CHX^3_2$, $-CH_2X^3$, $-OCX^3_3$, $-OCH_2X^3$, $-OCHX^3_2$, $-CN$, $-SO_3R^{3A}$, $-SO_{v3}NR^{3A}R^{3B}$, $-NHC(O)NR^{3A}R^{3B}$, $-N(O)_{m3}$, $-NR^{3A}R^{3B}$, $-NHNR^{3A}R^{3B}$, $-C(O)R^{3A}$, $-C(O)-OR^{3A}$, $-C(O)NR^{3A}R^{3B}$, $-OR^{3A}$, $-NR^{3A}SO_2R^{3B}$, $-NR^{3A}C(O)R^{3B}$, $-NR^{3A}C(O)OR^{3B}$, $-NR^{3A}OR^{3B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^4$ is selected from hydrogen, halogen, $-CX^4_3$, $-CHX^4_2$, $-CH_2X^4$, $-OCX^4_3$, $-OCH_2X^4$, $-OCHX^4_2$, $-CN$, $-SO_{v4}R^{4A}$, $-SO_4NR^{4A}R^{4B}$, $-NHC(O)NR^{4A}R^{4B}$, $-N(O)_{m4}$, $-NR^{4A}R^{4B}$, $-NHNR^{4A}R^{4B}$, $-C(O)R^{4A}$, $-C(O)-OR^{4A}$, $-C(O)NR^{4A}R^{4B}$, $-C(O)NHNR^{4A}R^{4B}$, $-OR^{4A}$, $-NR^{4A}SO_2R^{4B}$, $-NR^{4A}C(O)R^{4B}$, $-NR^{4A}C(O)OR^{4B}$, $-NR^{4A}OR^{4B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; $R^3$ and $R^3$ substituents may optionally be joined to form a substituted or unsubstituted cycloalkyl or heterocycloalkyl;

$R^6$ is selected from hydrogen, halogen, $-CX^6_3$, $-CHX^6_2$, $-CH_2X^6$, $-OCX^6_3$, $-OCH_2X^6$, $-OCHX^6_2$, $-CN$, $-SO_{v6}R^{6A}$, $-SO_{v6}NR^{6A}R^{6B}$, $-NHC(O)NR^{6A}R^{6B}$, $-N(O)_{m6}$, $-NR^{6A}R^{6B}$, $-NHNR^{6A}R^{6B}$, $-C(O)R^{6A}$, $-C(O)-OR^{6A}$, $-C(O)NR^{6A}R^{6B}$, $-C(O)NHNR^{6A}R^{6B}$, $-OR^{6A}$, $-NR^{6A}SO_2R^{6B}$, $-NR^{6A}C(O)R^{6B}$, $-NR^{6A}C(O)OR^{6B}$, $-NR^{6A}OR^{6B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^7$ is selected from hydrogen, halogen, $-CX^7_3$, $-CHX^7_2$, $-CH_2X^7$, $-OCX^7_3$, $-OCH_2X^7$, $-OCHX^7_2$, $-CN$, $-SO_{n4}R^{7A}$, $-SO_{v7}NR^{7A}R^{7B}$, $-NHC(O)NR^{7A}R^{7B}$, $-N(O)_{m7}$, $-NR^{7A}R^{7B}$, $-NHNR^{7A}R^{7B}$, $-C(O)R^{7A}$, $-C(O)-OR^{7A}$, $-C(O)NR^{7A}R^{7B}$, $-C(O)NHNR^{7A}R^{7B}$, $-OR^{7A}$, $-NR^{7A}SO_2R^{7B}$, $-NR^{7A}C(O)R^{7B}$, $-NR^{7A}C(O)OR^{7B}$, $-NR^{7A}OR^{7B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^9$ is selected from hydrogen, halogen, $-CX^9_3$, $-CHX^9_2$, $-CH_2X^9$, $-OCX^9_3$, $-OCH_2X^9$, $-OCHX^9_2$, $-CN$, $-SO_{v9}R^{9A}$, $-SO_{v9}NR^{9A}R^{9B}$, $-NHC(O)NR^{9A}R^{9B}$, $-N(O)_{m9}$, $-NR^{9A}R^{9B}$, $-NHNR^{9A}R^{9B}$, $-C(O)R^{9A}$, $-C(O)-OR^{9A}$, $-C(O)NR^{9A}R^{9B}$, $-C(O)NHNR^{9A}R^{9B}$, $-OR^{9A}$, $-NR^{9A}SO_2R^{9B}$, $-NR^{9A}C(O)R^{9B}$, $-NR^{9A}C(O)OR^{9B}$, $-NR^{9A}OR^{9B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{13}$ is selected from hydrogen, halogen, $-CX^{13}_3$, $-CHX^{13}_2$, $-CH_2X^{13}$, $-OCX^{13}_3$, $-OCH_2X^{13}$, $-OCHX^{13}_2$, $-CN$, $-SO_{n13}R^{13A}$, $-SO_{v13}NR^{13A}R^{13B}$, $-NHC(O)NR^{13A}R^{13B}$, $-N(O)_{m13}$, $-NR^{13A}R^{13B}$, $-NHNR^{13A}R^{13B}$, $-C(O)R^{13A}$, $-C(O)-OR^{13A}$, $-C(O)NR^{13A}R^{13B}$, $-C(O)NHNR^{13A}R^{13B}$, $-OR^{13A}$, $-NR^{13A}SO_2R^{13B}$, $-NR^{13A}C(O)R^{13B}$, $-NR^{13A}C(O)OR^{13B}$, $-NR^{13A}OR^{13B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{14}$ is selected from hydrogen, halogen, $-CX^{14}_3$, $-CHX^{14}_2$, $-CH_2X^{14}$, $-OCX^{14}_3$, $-OCH_2X^{14}$, $-OCHX^{14}_2$, $-CN$, $-SO_{n14}R^{14A}$, $-SO_{v14}NR^{14A}R^{14B}$, $-NHC(O)NR^{14A}R^{14B}$, $-N(O)_{m14}$, $-NR^{14A}R^{14B}$, $-NHNR^{14A}R^{14B}$, $-C(O)R^{14A}$, $-C(O)-OR^{14A}$, $-C(O)NR^{14A}R^{14B}$, $-C(O)NHNR^{14A}R^{14B}$, $-OR^{14A}$, $-NR^{14A}SO_2R^{14B}$, $-NR^{14A}C(O)R^{14B}$, $-NR^{14A}C(O)OR^{14B}$, $-NR^{14A}OR^{14B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{15}$ is selected from hydrogen, halogen, $-CX^{15}_3$, $-CHX^5_2$, $-CH_2X^{15}$, $-OCX^{15}_3$, $-OCH_2X^1$, —OCHX$^{15}_2$, —CN, —SO$_{n1}$R$^{15A}$, —SO$_{v15}$NR$^{15A}$R$^{15B}$, —NHC(O)NR$^{15A}$R$^{15B}$, —N(O)$_{m5}$, —NR$^{15A}$R$^{15B}$, —NHNR$^{15A}$R$^{15B}$, —C(O)R$^{15A}$, —C(O)—OR$^{15A}$, —C(O)NR$^{15A}$R$^{15B}$, —C(O)NHNR$^{15A}$R$^{15B}$, —OR$^{15A}$, —NR$^{15A}$SO$_2$R$^{15B}$, —NR$^{15A}$C(O)R$^{15B}$, —NR$^{15A}$C(O)OR$^{15B}$, —NR$^{15A}$OR$^{15B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{16}$ is selected from hydrogen, halogen, —CX$^{16}_3$, —CHX$^{16}_2$, —CH$_2$X$^{16}$, —OCX$^{16}_3$, —OCH$_2$X$^{16}$, —OCHX$^{16}_2$, —CN, —SO$_{n16}$R$^{16A}$, —SO$_{v16}$NR$^{16A}$R$^{16B}$, —NHC(O)NR$^{16A}$R$^{16B}$, —N(O)$_{m16}$, —NR$^{16A}$R$^{16B}$, —NHNR$^{16A}$R$^{16B}$, —C(O)R$^{16A}$, —C(O)—OR$^{16A}$, —C(O)NR$^{16A}$R$^{16B}$, —C(O)NHNR$^{16A}$R$^{16B}$, —OR$^{16A}$, —NR$^{16A}$SO$_2$R$^{16B}$, —NR$^{16A}$C(O)R$^{16B}$, —NR$^{16A}$C(O)OR$^{16B}$, —NR$^{16A}$OR$^{16B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{17}$ is selected from hydrogen, halogen, —CX$^{17}_3$, —CHX$^{17}_2$, —CH$_2$X$^{17}$, —OCX$^{17}_3$, —OCH$_2$X$^{17}$, —OCHX$^{17}_2$, —CN, —SO$_{17}$R$^{17A}$, —SO$_{v17}$NR$^{17A}$R$^{17B}$, —NHC(O)NR$^{1A}$R$^{17B}$, —N(O)$_{m17}$, —NR$^{17A}$R$^{17B}$, —NHNR$^{17A}$R$^{17B}$, —C(O)R$^{17A}$, —C(O)—OR$^{17A}$, —C(O)NR$^{17A}$R$^{17B}$, —C(O)NHNR$^{17A}$R$^{17B}$, —OR$^{17A}$, —NR$^{17A}$SO$_2$R$^{17B}$, —NR$^{17A}$C(O)R$^{17B}$, —NR$^{17A}$C(O)OR$^{17B}$, —NR$^{17A}$OR$^{17B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{18}$ is selected from hydrogen, halogen, —CX$^{18}_3$, —CHX$^{18}_2$, —CH$_2$X$^{18}$, —OCX$^{18}_3$, —OCH$_2$X$^{18}$, —OCHX$^{18}_2$, —CN, —SO$_{n18}$R$^{18A}$, —SO$_{v18}$NR$^{18A}$R$^{18B}$, —NHC(O)NR$^{18A}$R$^{18B}$, —N(O)$_{m18}$, —NR$^{18A}$R$^{18B}$, —NHNR$^{18A}$R$^{18B}$, —C(O)R$^{18A}$, —C(O)—OR$^{18A}$, —C(O)NR$^{18A}$R$^{18B}$, —C(O)NHNR$^{18A}$R$^{18B}$, —OR$^{18A}$, —NR$^{18A}$SO$_2$R$^{18B}$, —NR$^{18A}$C(O)R$^{18B}$, —NR$^{18A}$C(O)OR$^{18B}$, —NR$^{18A}$OR$^{18B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; R$^{16}$ and R$^{18}$ substituents may optionally be joined to form a substituted or unsubstituted cycloalkyl or heterocycloalkyl;

R$^{19}$ is selected from hydrogen, halogen, —CX$^{19}_3$, —CHX$^{19}_2$, —CH$_2$X$^{19}$, —OCX$^{19}_3$, —OCH$_2$X$^{19}$, —OCHX$^{19}_2$, —CN, —SO$_{19}$R$^{19A}$, —SO$_{v19}$NR$^{19A}$R$^{19B}$, —NHC(O)NR$^{19A}$R$^{19B}$, —N(O)$_{m19}$, —NR$^{19A}$R$^{19B}$, —NHNR$^{19A}$R$^{19B}$, —C(O)R$^{19A}$, —C(O)—OR$^{19A}$, —C(O)NR$^{19A}$R$^{19B}$, —C(O)NHNR$^{19A}$R$^{19B}$, —OR$^{19A}$, —NR$^{19A}$SO$_2$R$^{19B}$, —NR$^{19A}$C(O)R$^{19B}$, —NR$^{19A}$C(O)OR$^{19B}$, —NR$^{19A}$OR$^{19B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; R$^{16}$ and R$^{19}$ substituents may optionally be joined to form a substituted or unsubstituted cycloalkyl or heterocycloalkyl;

R$^{20}$ is selected from hydrogen, halogen, —CX$^{20}_3$, —CHX$^{20}_2$, —CH$_2$X$^{20}$, —OCX$^{20}_3$, —OCH$_2$X$^{20}$, —OCHX$^{20}_2$, —CN, —SO$_{n20}$R$^{20A}$, —SO$_{v20}$NR$^{20A}$R$^{20B}$, —NHC(O)NR$^{20A}$R$^{20B}$, —N(O)$_{m20}$, —NR$^{20A}$R$^{20B}$, —NHNR$^{20A}$R$^{20B}$, —C(O)R$^{20A}$, —C(O)—OR$^{20A}$, —C(O)NR$^{20A}$R$^{20B}$, —C(O)NHNR$^{20A}$R$^{20B}$, —OR$^{20A}$, —NR$^{20A}$, —SO$_2$R$^{20B}$, —NR$^{20A}$C(O)R$^{20B}$, —NR$^{20A}$C(O)OR$^{20B}$, —NR$^{20A}$OR$^{20B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{21}$ is selected from hydrogen, halogen, —CX$^{21}_3$, —CHX$^{21}_2$, —CH$_2$X$^{21}$, —OCX$^{21}_3$, —OCH$_2$X$^{21}$, —OCHX$^{21}_2$, —CN, —SO$_{n21}$R$^{21A}$, —SO$_{v21}$NR$^{21A}$R$^{21B}$, —NHC(O)NR$^{21A}$R$^{21B}$, —N(O)$_{m21}$, —NR$^{21A}$R$^{21B}$, —NHNR$^{21A}$R$^{21B}$, —C(O)R$^{21A}$, —C(O)—OR$^{21A}$, —C(O)NR$^{21A}$R$^{21B}$, —C(O)NHNR$^{21A}$R$^{21B}$, —OR$^{21A}$, —NR$^{21A}$SO$_2$R$^{21B}$, —NR$^{21A}$C(O)R$^{21B}$, —NR$^{21A}$C(O)OR$^{21B}$, —NR$^{21A}$OR$^{21B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; R$^{20}$ and R$^{21}$ substituents may optionally be joined to form a substituted or unsubstituted cycloalkyl or heterocycloalkyl;

R$^{22}$ is selected from hydrogen, halogen, —CX$^{22}_3$, —CHX$^{22}_2$, —CH$_2$X$^{22}$, —OCX$^{22}_3$, —OCH$_2$X$^{22}$, —OCHX$^{22}_2$, —CN, —SO$_{n22}$R$^{22A}$, —SO$_{v22}$NR$^{22A}$R$^{22B}$, —NHC(O)NR$^{22A}$R$^{22B}$, —N(O)$_{m22}$, —NR$^{22A}$R$^{22B}$, —NHNR$^{22A}$R$^{22B}$, —C(O)R$^{22A}$, —C(O)—OR$^{22A}$, —C(O)NR$^{22A}$R$^{22B}$, —C(O)NHNR$^{22A}$R$^{22B}$, —OR$^{22A}$, —NR$^{22A}$SO$_2$R$^{22B}$, —NR$^{22A}$C(O)R$^{22B}$, —NR$^{22A}$C(O)OR$^{22B}$, —NR$^{22A}$OR$^{22B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{23}$ is selected from hydrogen, halogen, —CX$^{23}_3$, —CHX$^{23}_2$, —CH$_2$X$^{23}$, —OCX$^{23}_3$, —OCH$_2$X$^{23}$, —OCHX$^{23}_2$, —CN, —SO$_{n23}$R$^{23A}$, —SO$_{v23}$NR$^{23A}$R$^{23B}$, —NHC(O)NR$^{23A}$R$^{23B}$, —N(O)$_{m23}$, —NR$^{23A}$R$^{23B}$, —NHNR$^{23A}$R$^{23B}$, —C(O)R$^{23A}$, —C(O)—OR$^{23A}$, —C(O)NR$^{23A}$R$^{23B}$, —C(O)NHNR$^{23A}$R$^{23B}$, —OR$^{23A}$, —NR$^{23A}$SO$_2$R$^{23B}$, —NR$^{23A}$C(O)R$^{23B}$, —NR$^{23A}$C(O)OR$^{23B}$, —NR$^{23A}$OR$^{23B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{24}$ is selected from hydrogen, halogen, —CX$^{24}_3$, —CHX$^{24}_2$, —CH$_2$X$^{24}$, —OCX$^{24}_3$, —OCH$_2$X$^{24}$, —OCHX$^{24}_2$, —CN, —SO$_{n24}$R$^{24A}$, —SO$_{v24}$NR$^{24A}$R$^{24B}$, —NHC(O)NR$^{24A}$R$^{24B}$, —N(O)$_{m24}$, —NR$^{24A}$R$^{24B}$, —NHNR$^{24A}$R$^{24B}$, —C(O)R$^{24A}$, —C(O)—OR$^{24A}$, —C(O)NR$^{24A}$R$^{24B}$, —C(O)NHNR$^{24A}$R$^{24B}$, —OR$^{24A}$, —NR$^{24A}$SO$_2$R$^{24B}$, —NR$^{24A}$C(O)R$^{24B}$, —NR$^{24A}$C(O)OR$^{24B}$, —NR$^{24A}$OR$^{24B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{25}$ is selected from hydrogen, halogen, $-CX^{25}_3$, $-CHX^{25}_2$, $-CH_2X^{25}$, $-OCX^{25}_3$, $-OCH_2X^{25}$, $-OCHX^{25}_2$, $-CN$, $-SO_{n25}R^{25A}$, $-SO_{v25}NR^{25A}R^{25B}$, $-NHC(O)NR^{25A}R^{25B}$, $-N(O)_{m25}$, $-NR^{25A}R^{25B}$, $-NHNR^{25A}R^{25B}$, $-C(O)R^{25A}$, $-C(O)-OR^{25A}$, $-C(O)NR^{25A}R^{25B}$, $-C(O)NHNR^{25A}R^{25B}$, $-OR^{25A}$, $-NR^{25A}SO_2R^{25B}$, $-NR^{25A}C(O)R^{25B}$, $-NR^{25A}C(O)OR^{25B}$, $-NR^{25A}OR^{25B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{26}$ is selected from hydrogen, halogen, $-CX^{26}_3$, $-CHX^{26}_2$, $-CH_2X^{26}$, $-OCX^{26}_3$, $-OCH_2X^{26}$, $-OCHX^{26}_2$, $-CN$, $-SO_{n26}R^{26A}$, $-SO_{v26}NR^{26A}R^{26B}$, $-NHC(O)NR^{26A}R^{26B}$, $-N(O)_{m26}$, $-NR^{26A}R^{26B}$, $-NHNR^{26A}R^{26B}$, $-C(O)R^{26A}$, $-C(O)-OR^{26A}$, $-C(O)NR^{26A}R^{26B}$, $-C(O)NHNR^{26A}R^{26B}$, $-OR^{26A}$, $-NR^{26A}SO_2R^{26B}$, $-NR^{26A}C(O)R^{26B}$, $-NR^{26A}C(O)OR^{26B}$, $-NR^{26A}OR^{26B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{27}$ is selected from hydrogen, halogen, $-CX^{27}_3$, $-CHX^{27}_2$, $-CH_2X^{27}$, $-OCX^{27}_3$, $-OCH_2X^{27}$, $-OCHX^{27}_2$, $-CN$, $-SO_{n27}R^{27A}$, $-SO_{v27}NR^{27A}R^{27B}$, $-NHC(O)NR^{27A}R^{27B}$, $-N(O)_{m27}$, $-NR^{27A}R^{27B}$, $-NHNR^{27A}R^{27B}$, $-C(O)R^{27A}$, $-C(O)-OR^{27A}$, $-C(O)NR^{27A}R^{27B}$, $-C(O)NHNR^{27A}R^{27B}$, $-OR^{27A}$, $-NR^{27A}SO_2R^{27B}$, $-NR^{27A}C(O)R^{27B}$, $-NR^{27A}C(O)OR^{27B}$, $-NR^{27A}OR^{27B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{28}$ is selected from hydrogen, halogen, $-CX^{28}_3$, $-CHX^{28}_2$, $-CH_2X^{28}$, $-OCX^{28}_3$, $-OCH_2X^{28}$, $-OCHX^{28}_2$, $-CN$, $-SO_{n28}R^{28A}$, $-SO_{v28}NR^{28A}R^{28B}$, $-NHC(O)NR^{28A}R^{28B}$, $-N(O)_{m2}$, $-NR^{28A}R^{28B}$, $-NHNR^{28A}R^{28B}$, $-C(O)R^{28A}$, $-C(O)-OR^{28A}$, $-C(O)NR^{28A}R^{28B}$, $-C(O)NHNR^{28A}R^{28B}$, $-OR^{28A}$, $-NR^{28A}SO_2R^{28B}$, $-NR^{28A}C(O)R^{28B}$, $-NR^{28A}C(O)OR^{28B}$, $-NR^{28A}OR^{28B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{29}$ is selected from hydrogen, halogen, $-CX^{29}_3$, $-CHX^{29}_2$, $-CH_2X^{29}$, $-OCX^{29}_3$, $-OCH_2X^{29}$, $-OCHX^{29}_2$, $-CN$, $-SO_{n29}R^{29A}$, $-SO_{v29}NR^{29A}R^{29B}$, $-NHC(O)NR^{29A}R^{29B}$, $-N(O)_{m29}$, $-NR^{29A}R^{29B}$, $-NHNR^{29A}R^{29B}$, $-C(O)R^{29A}$, $-C(O)-OR^{29A}$, $-C(O)NR^{29A}R^{29B}$, $-C(O)NHNR^{29A}R^{29B}$, $-OR^{29A}$, $-NR^{29A}SO_2R^{29B}$, $-NR^{29A}C(O)R^{29B}$, $-NR^{29A}C(O)OR^{29B}$, $-NR^{29A}OR^{29B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{30}$ is selected from hydrogen, halogen, $-CX^{30}_3$, $-CHX^{30}_2$, $-CH_2X^{30}$, $-OCX^{30}_3$, $-OCH_2X^{30}$, $-OCHX^{30}_2$, $-CN$, $-SO_{n30}R^{30A}$, $-SO_{v30}NR^{30A}R^{30B}$, $-NHC(O)NR^{30A}R^{30B}$, $-N(O)_{m30}$, $-NR^{30A}R^{30B}$, $-NHNR^{30A}R^{30B}$, $-C(O)R^{30A}$, $-C(O)-OR^{30A}$, $-C(O)NR^{30A}R^{30B}$, $-C(O)NHNR^{30A}R^{30B}$, $-OR^{30A}$, $-NR^{30A}SO_2R^{30B}$, $-NR^{30A}C(O)R^{30B}$, $-NR^{30A}C(O)OR^{30B}$, $-NR^{30A}OR^{30B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

Each $R^{1A}$, $R^{1B}$, $R^{2A}$, $R^{2B}$, $R^{3A}$, $R^{3B}$, $R^{4A}$, $R^{4B}$, $R^{6A}$, $R^{6B}$, $R^{7A}$, $R^{7B}$, $R^{9A}$, $R^{9B}$, $R^{13A}$, $R^{13B}$, $R^{14A}$, $R^{14B}$, $R^{15A}$, $R^{15B}$, $R^{16A}$, $R^{16B}$, $R^{17A}$, $R^{17B}$, $R^{18A}$, $R^{18B}$, $R^{19A}$, $R^{19B}$, $R^{20A}$, $R^{20B}$, $R^{21A}$, $R^{21B}$, $R^{22A}$, $R^{22B}$, $R^{23A}$, $R^{23B}$, $R^{24A}$, $R^{24B}$, $R^{25A}$, $R^{25B}$, $R^{26A}$, $R^{26B}$, $R^{27A}$, $R^{27B}$, $R^{28A}$, $R^{28B}$, $R^{29A}$, $R^{29B}$, $R^{30A}$, $R^{30B}$, is independently selected from hydrogen, $-CX_3$, $-CHX_2$, $-CH_2X$, $-C(O)OH$, $-C(O)NH_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)OH$, $-NHOH$, $-OCX_3$, $-OCHX_2$, $-OCH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{4A}$ and $R^{4B}$ substituents bonded to the same nitrogen atom may optionally be joined to form a substituted or unsubstituted heterocycloalkyl or substituted or unsubstituted heteroaryl; $R^{6A}$ and $R^{6B}$ substituents bonded to the same nitrogen atom may optionally be joined to form a substituted or unsubstituted heterocycloalkyl or substituted or unsubstituted heteroaryl; $R^{7A}$ and $R^{7B}$ substituents bonded to the same nitrogen atom may optionally be joined to form a substituted or unsubstituted heterocycloalkyl or substituted or unsubstituted heteroaryl; $R^{9A}$ and $R^{9B}$ substituents bonded to the same nitrogen atom may optionally be joined to form a substituted or unsubstituted heterocycloalkyl or substituted or unsubstituted heteroaryl; $R^{13A}$ and $R^{13B}$ substituents bonded to the same nitrogen atom may optionally be joined to form a substituted or unsubstituted heterocycloalkyl or substituted or unsubstituted heteroaryl; $R^{14A}$ and $R^{14B}$ substituents bonded to the same nitrogen atom may optionally be joined to form a substituted or unsubstituted heterocycloalkyl or substituted or unsubstituted heteroaryl; $R^{15A}$ and $R^{15B}$ substituents bonded to the same nitrogen atom may optionally be joined to form a substituted or unsubstituted heterocycloalkyl or substituted or unsubstituted heteroaryl; $R^{16A}$ and $R^{16B}$ substituents bonded to the same nitrogen atom may optionally be joined to form a substituted or unsubstituted heterocycloalkyl or substituted or unsubstituted heteroaryl; $R^{17A}$ and $R^{17B}$ substituents bonded to the same nitrogen atom may optionally be joined to form a substituted or unsubstituted heterocycloalkyl or substituted or unsubstituted heteroaryl; $R^{18A}$ and $R^{18B}$ substituents bonded to the same nitrogen atom may optionally be joined to form a substituted or unsubstituted heterocycloalkyl or substituted or unsubstituted heteroaryl; $R^{19A}$ and $R^{19B}$ substituents bonded to the same nitrogen atom may optionally be joined to form a substituted or unsubstituted heterocycloalkyl or substituted or unsubstituted heteroaryl; $R^{20A}$ and $R^{20B}$ substituents bonded to the same nitrogen atom may optionally be joined to form a substituted or unsubstituted heterocycloalkyl or substituted or unsubstituted heteroaryl; $R^{21A}$ and $R^{21B}$ substituents bonded to the same nitrogen atom may optionally be joined to form a substituted or unsubstituted heterocycloalkyl or substituted or unsubstituted heteroaryl; $R^{22A}$ and $R^{22B}$ substituents bonded to the same nitrogen atom may optionally be joined to form a substituted or unsubstituted heterocycloalkyl or substituted or unsubstituted heteroaryl; $R^{23A}$ and $R^{23B}$ substituents bonded to the same nitrogen atom may optionally be joined to form a substituted or unsubstituted heterocycloalkyl or substituted or unsubstituted heteroaryl; $R^{24A}$ and $R^{24B}$ substituents bonded to the same nitrogen atom may optionally be joined to form a substituted or unsubstituted heterocycloalkyl or substituted or unsubstituted heteroaryl; $R^{25A}$ and $R^{25B}$ substituents bonded to the same nitrogen atom may optionally be joined to form a substituted or unsubstituted heterocycloalkyl or substituted or unsubstituted heteroaryl; $R^{26A}$ and $R^{26B}$ substituents bonded to the same nitrogen atom may optionally be joined to form a substituted or unsubstituted heterocycloalkyl or substituted or unsubstituted heteroaryl; $R^{27A}$ and $R^{27B}$ substituents bonded to the same nitrogen atom may optionally be joined to form a substituted or unsubstituted heterocycloalkyl or substituted or unsubstituted heteroaryl; $R^{28A}$ and $R^{28B}$ substituents bonded to the same nitrogen atom may optionally be joined to form a substituted or unsubstituted heterocycloalkyl or substituted or unsubstituted heteroaryl; $R^{29A}$ and $R^{29B}$ substituents bonded to the same nitrogen atom may optionally be joined to form a substituted or unsubstituted heterocycloalkyl or substituted or unsubstituted heteroaryl; $R^{30A}$ and $R^{30B}$ substituents bonded to the same nitrogen atom may optionally be joined to form a substituted or unsubstituted heterocycloalkyl or substituted or unsubstituted heteroaryl;

Each m1, m2, m3, m4, m6, m7, m9, m13, m14, m15, m16, m17, m18, m19, m20, m21, m22, m23, m24, m25, m26, m27, m28, m29 and m30 are independently 1 or 2; Each v1, v2, v3, v4, v6, v7, v9, v13, v14, v15, v16, v17, v18, v19, v20, v21, v22, v23, v24, v25, v26, v27, v28, v29 and v30 are independently 1 or 2;

Each n1, n2, n3, n4, n6, n7, n9, n13, n14, n15, n16, n17, n18, n19, n20, n21, n22, n23, n24, n25, n26, n27, n28, n29 and n30 are independently an integer from 0 to 2; and Each $X^1, X^2, X^3, X^4, X^6, X^7, X^9, X^{13}, X^{14}, X^{15}, X^{16}, X^{17}, X^{18}, X^9, X^{20}, X^{21}, X^{22}, X^{23}, X^{24}, X^{25}, X^{26}, X^{27}, X^{28}, X^{29}$ and $X^{30}$ are independently —Cl, —Br, —I or —F; provided $R^1$ is not 4-amino-1H-pyrazolo[3,4-d]pyrimidin-1-yl when $R^2, R^6, R^7, R^{13}, R^{14}, R^5$ and $R^{16}$ are H and E is ethenylcarbonyl.

In one embodiment, E is selected from —C(=O)CH=CH$_2$, —C(=O)-ethynyl, —C(=O)CH=CHCF$_3$, —C(=O)CH=CHCHF$_2$, —C(=O)CH=CHCH$_2$F, and —C(=O)CH$_2$Br.

In one embodiment, U is selected from NR$^{12}$, O, or S.

The invention also relates to compounds of Formula IV:

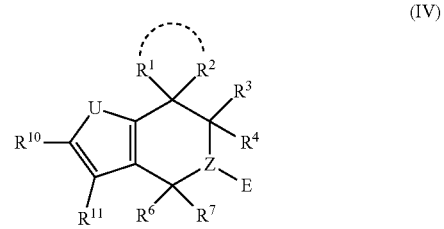

(IV)

wherein

Z is N, or CR$^9$;

U is selected from NR$^{12}$, O, S, S=O, O=S=O, and Se;

E is an electrophilic moiety, selected from

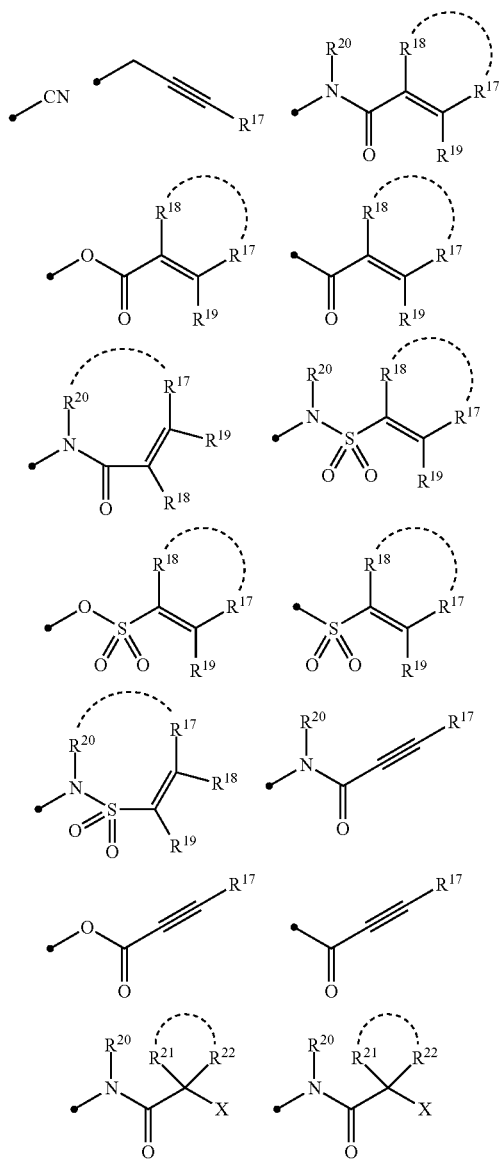

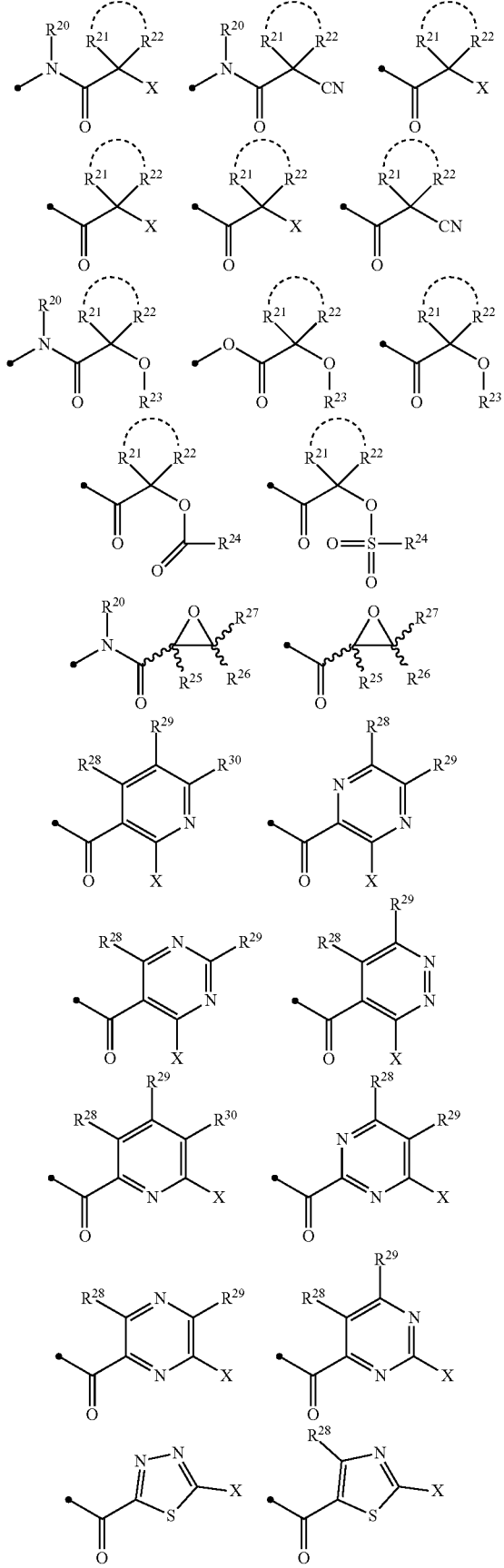

R¹ is selected from hydrogen, halogen, —CX¹₃, —CHX¹₂, —CH₂X¹, —OCX¹₃, —OCH₂X¹, —OCHX¹₂, —CN, —SO$_{n1}$R$^{1A}$, —SO$_{v1}$NR$^{1A}$R$^{1B}$, —NHC(O)NR$^{1A}$R$^{1B}$, —N(O)$_{m1}$, —NR$^{1A}$R$^{1B}$, —NHNR$^{1A}$R$^{1B}$, —C(O)R$^{1A}$, —C(O)—OR$^{1A}$, —C(O)NR$^{1A}$R$^{1B}$, —C(O)NHNR$^{1A}$R$^{1B}$, —OR$^{1A}$, —NR$^{1A}$SO₂R$^{1B}$, —NR$^{1A}$C(O)R$^{1B}$, —NR$^{1A}$C(O)OR$^{1B}$, —NR$^{1A}$OR$^{1B}$, —N₃, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R² is selected from hydrogen, halogen, —CX²₃, —CHX²₂, —CH₂X², —OCX²₃, —OCH₂X², —OCHX²₂, —CN, —SO$_{n2}$R$^{2A}$, —SO₂NR$^{2A}$R$^{2B}$, —NHC(O)NR$^{2A}$R$^{2B}$, —N(O)$_{m2}$, —NR$^{2A}$R$^{2B}$, —NHNR$^{2A}$R$^{2B}$, —C(O)R$^{2A}$, —C(O)—OR$^{2A}$, —C(O)NR$^{2A}$R$^{2B}$, —C(O)NHNR$^{2A}$R$^{2B}$, —OR$^{2A}$, —NR$^{2A}$SO₂R$^{2B}$, —NR$^{2A}$C(O)R$^{2B}$, —NR$^{2A}$C(O)OR$^{2B}$, —NR$^{2A}$OR$^{2B}$, —N₃, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; R¹ and R² substituents may optionally be joined to form a substituted or unsubstituted cycloalkyl or heterocycloalkyl;

R³ is selected from hydrogen, halogen, —CX³₃, —CHX³₂, —CH₂X³, —OCX³₃, —OCH₂X³, —OCHX³₂, —CN, —SO₃R$^{3A}$, —SO$_{v3}$NR$^{3A}$R$^{3B}$, —NHC(O)NR$^{3A}$R$^{3B}$, —N(O)$_{m3}$, —NR$^{3A}$R$^{3B}$, —NHNR$^{3A}$R$^{3B}$, —C(O)R$^{3A}$, —C(O)—OR$^{3A}$, —C(O)NR$^{3A}$R$^{3B}$, —OR$^{3A}$, —NR$^{3A}$SO₂R$^{3B}$, —NR$^{3A}$C(O)R$^{3B}$, —NR$^{3A}$C(O)OR$^{3B}$, —NR$^{3A}$OR$^{3B}$, —N₃, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R⁴ is selected from hydrogen, halogen, —CX⁴₃, —CHX⁴₂, —CH₂X⁴, —OCX⁴₃, —OCH₂X⁴, —OCHX⁴₂, —CN, —SO$_{n4}$R$^{4A}$, —SO₄NR$^{4A}$R$^{4B}$, —NHC(O)NR$^{4A}$R$^{4B}$, —N(O)$_{m4}$, —NR$^{4A}$R$^{4B}$, —NHNR$^{4A}$R$^{4B}$, —C(O)R$^{4A}$, —C(O)—OR$^{4A}$, —C(O)NR$^{4A}$R$^{4B}$, —C(O)NHNR$^{4A}$R$^{4B}$, —OR$^{4A}$, —NR$^{4A}$SO$_2$R$^{4B}$, —NR$^{4A}$C(O)R$^{4B}$, —NR$^{4A}$C(O)OR$^{4B}$, —NR$^{4A}$OR$^{4B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; R$^3$ and R$^3$ substituents may optionally be joined to form a substituted or unsubstituted cycloalkyl or heterocycloalkyl;

R$^6$ is selected from hydrogen, halogen, —CX$^6_3$, —CHX$^6_2$, —CH$_2$X$^6$, —OCX$^6_3$, —OCH$_2$X$^6$, —OCHX$^6_2$, —CN, —SO$_{v6}$R$^{6A}$, —SO$_{v6}$NR$^{6A}$R$^{6B}$, —NHC(O)NR$^{6A}$R$^{6B}$, —N(O)$_{m6}$, —NR$^{6A}$R$^{6B}$, —NHNR$^{6A}$R$^{6B}$, —C(O)R$^{6A}$, —C(O)—OR$^{6A}$, —C(O)NR$^{6A}$R$^{6B}$, —C(O)NHNR$^{6A}$R$^{6B}$, —OR$^{6A}$, —NR$^{6A}$SO$_2$R$^{6B}$, —NR$^{6A}$C(O)R$^{6B}$, —NR$^{6A}$C(O)OR$^{6B}$, —NR$^{6A}$OR$^{6B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^7$ is selected from hydrogen, halogen, —CX$^7_3$, —CHX$^7_2$, —CH$_2$X$^7$, —OCX$^7_3$, —OCH$_2$X$^7$, —OCHX$^7_2$, —CN, —SO$_{n7}$R$^{7A}$, —SO$_{v7}$NR$^{7A}$R$^{7B}$, —NHC(O)NR$^{7A}$R$^{7B}$, —N(O)$_{m7}$, —NR$^{7A}$R$^{7B}$, —NHNR$^{7A}$R$^{7B}$, —C(O)R$^{7A}$, —C(O)—OR$^{7A}$, —C(O)NR$^{7A}$R$^{7B}$, —C(O)NHNR$^{7A}$R$^{7B}$, —OR$^{7A}$, —NR$^{7A}$SO$_2$R$^{7B}$, —NR$^{7A}$C(O)R$^{7B}$, —NR$^{7A}$C(O)OR$^{7B}$, —NR$^{7A}$OR$^{7B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^9$ is selected from hydrogen, halogen, —CX$^9_3$, —CHX$^9_2$, —CH$_2$X$^9$, —OCX$^9_3$, —OCH$_2$X$^9$, —OCHX$^9_2$, —CN, —SO$_{v9}$R$^{9A}$, —SO$_9$NR$^{9A}$R$^{9B}$, —NHC(O)NR$^{9A}$R$^{9B}$, —N(O)$_{m9}$, —NR$^{9A}$R$^{9B}$, —NHNR$^{9A}$R$^{9B}$, —C(O)R$^{9A}$, —C(O)—OR$^{9A}$, —C(O)NR$^{9A}$R$^{9B}$, —C(O)NHNR$^{9A}$R$^{9B}$, —OR$^{9A}$, —NR$^{9A}$SO$_2$R$^{9B}$, —NR$^{9A}$C(O)R$^{9B}$, —NR$^{9A}$C(O)OR$^{9B}$, —NR$^{9A}$OR$^{9B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{10}$ is selected from hydrogen, halogen, —CX$^{13}_3$, —CHX$^{13}_2$, —CH$_2$X$^{13}$, —OCX$^{13}_3$, —OCH$_2$X$^{13}$, —OCHX$^{13}_2$, —CN, —SO$_{n13}$R$^{13A}$, —SO$_{v13}$NR$^{13A}$R$^{13B}$, —NHC(O)NR$^{13A}$R$^{13B}$, —N(O)$_{m13}$, —NR$^{13A}$R$^{13B}$, —NHNR$^{13A}$R$^{13B}$, —C(O)R$^{13A}$, —C(O)—OR$^{13A}$, —C(O)NR$^{13A}$R$^{13B}$, —C(O)NHNR$^{13A}$R$^{13B}$, —OR$^{13A}$, —NR$^{13A}$SO$_2$R$^{13B}$, —NR$^{13A}$C(O)R$^{13B}$, —NR$^{13A}$C(O)OR$^{13B}$, —NR$^{13A}$OR$^{13B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{11}$ is selected from hydrogen, halogen, —CX$^{14}_3$, —CHX$^{14}_2$, —CH$_2$X$^{14}$, —OCX$^{14}_3$, —OCH$_2$X$^{14}$, —OCHX$^{14}_2$, —CN, —SO$_{n14}$R$^{14A}$, —SO$_{v14}$NR$^{14A}$R$^{14B}$, —NHC(O)NR$^{14A}$R$^{14B}$, —N(O)$_{m14}$, —NR$^{14A}$R$^{14B}$, —NHNR$^{14A}$R$^{14B}$, —C(O)R$^{14A}$, —C(O)—OR$^{14A}$, —C(O)NR$^{14A}$R$^{14B}$, —C(O)NHNR$^{14A}$R$^{14B}$, —OR$^{14A}$, —NR$^{14A}$SO$_2$R$^{14B}$, —NR$^{14A}$C(O)R$^{14B}$, —NR$^{14A}$C(O)OR$^{14B}$, —NR$^{14A}$OR$^{14B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{12}$ is selected from hydrogen, halogen, —CX$^{12}_3$, —CHX$^{12}_2$, —CH$_2$X$^{12}$, —OCX$^{12}_3$, —OCH$_2$X$^{12}$, —OCHX$^{12}_2$, —CN, —SO$_{n12}$R$^{12A}$, —SO$_{v12}$NR$^{12A}$R$^{12B}$, —NHC(O)NR$^{12A}$R$^{12B}$, —N(O)$_{m12}$, —NR$^{12A}$R$^{12B}$, —NHNR$^{12A}$R$^{12B}$, —C(O)R$^{12A}$, —C(O)—OR$^{12A}$, —C(O)NR$^{12A}$R$^{12B}$, —C(O)NHNR$^{12A}$R$^{12B}$, —OR$^{12A}$, —NR$^{12A}$SO$_2$R$^{12B}$, —NR$^{12A}$C(O)R$^{12B}$, —NR$^{12A}$C(O)OR$^{12B}$, —NR$^{12A}$OR$^{12B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^7$ is selected from hydrogen, halogen, —CX$^{17}_3$, —CHX$^7_2$, —CH$_2$X$^7$, —OCX$^7_3$, —OCH$_2$X$^{17}$, —OCHX$^{17}_2$, —CN, —SO$_{n17}$R$^{17A}$, —SO$_{v17}$NR$^{17A}$R$^{17B}$, —NHC(O)NR$^{14}$R$^{17B}$, —N(O)$_{m17}$, —NR$^{17A}$R$^{17B}$, —NHNR$^{17A}$R$^{17B}$, —C(O)R$^{14}$, —C(O)—OR$^{17A}$, —C(O)NR$^{17A}$R$^{17B}$, —C(O)NHNR$^{17A}$R$^{17B}$, —OR$^{17A}$, —NR$^{17A}$SO$_2$R$^{17B}$, —NR$^{17A}$C(O)R$^{17B}$, —NR$^{17A}$C(O)OR$^{17B}$, —NR$^{17A}$OR$^{17B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{18}$ is selected from hydrogen, halogen, —CX$^{18}_3$, —CHX$^{18}_2$, —CH$_2$X$^{18}$, —OCX$^{18}_3$, —OCH$_2$X$^{11}$, —OCHX$^{18}_2$, —CN, —SO$_{n18}$R$^{18A}$, —SO$_{v18}$NR$^{18A}$R$^{18B}$, —NHC(O)NR$^{18A}$R$^{18B}$, —N(O)$_{m18}$, —NR$^{18A}$R$^{18B}$, —NHNR$^{18A}$R$^{18B}$, —C(O)R$^{18A}$, —C(O)—OR$^{18A}$, —C(O)NR$^{18A}$R$^{18B}$, —C(O)NHNR$^{18A}$R$^{18B}$, —OR$^{18A}$, —NR$^{18A}$SO$_2$R$^{18B}$, —NR$^{18A}$C(O)R$^{18B}$, —NR$^{18A}$C(O)OR$^{18B}$, —NR$^{18A}$OR$^{18B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; R$^{16}$ and R$^{18}$ substituents may optionally be joined to form a substituted or unsubstituted cycloalkyl or heterocycloalkyl;

R$^{19}$ is selected from hydrogen, halogen, —CX$^{19}_3$, —CHX$^{19}_2$, —CH$_2$X$^{19}$, —OCX$^{19}_3$, —OCH$_2$X$^{19}$, —OCHX$^{19}_2$, —CN, —SO$_{n19}$R$^{19A}$, —SO$_{v19}$NR$^{19A}$R$^{19B}$, —NHC(O)NR$^{19A}$R$^{19B}$, —N(O)$_{m19}$, —NR$^{19A}$R$^{19B}$, —NHNR$^{19A}$R$^{19B}$, —C(O)R$^{19A}$, —C(O)—OR$^{19A}$, —C(O)NR$^{19A}$R$^{19B}$, —C(O)NHNR$^{19A}$R$^{19B}$, —OR$^{19A}$, —NR$^{19A}$SO$_2$R$^{19B}$, —NR$^{19A}$C(O)R$^{19B}$, —NR$^{19A}$C(O)OR$^{19B}$, —NR$^{19A}$OR$^{19B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; R$^{16}$ and R$^{19}$ substituents may optionally be joined to form a substituted or unsubstituted cycloalkyl or heterocycloalkyl;

R$^{20}$ is selected from hydrogen, halogen, —CX$^{20}_3$, —CHX$^{20}_2$, —CH$_2$X$^{20}$, —OCX$^{20}_3$, —OCH$_2$X$^{20}$, —OCHX$^{20}_2$, —CN, —SO$_{n20}$R$^{20A}$, —SO$_{v20}$NR$^{20A}$R$^{20B}$, —NHC(O)NR$^{20A}$R$^{20B}$, —N(O)$_{m20}$, —NR$^{20A}$R$^{20B}$, —NHNR$^{20A}$R$^{20B}$, —C(O)R$^{20A}$, —C(O)—OR$^{20A}$, —C(O)NR$^{20A}$R$^{20B}$, —C(O)

NHNR$^{20A}$R$^{20B}$, —OR$^{20A}$, —NR$^{20A}$, —SO$_2$R$^{20B}$, —NR$^{20A}$C(O)R$^{20B}$, —NR$^{20A}$C(O)OR$^{20B}$, —NR$^{20A}$OR$^{20B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{21}$ is selected from hydrogen, halogen, —CX$^{21}$$_3$, —CHX$^{21}$$_2$, —CH$_2$X$^{21}$, —OCX$^{21}$$_3$, —OCH$_2$X$^{21}$, —OCHX$^{21}$$_2$, —CN, —SO$_{n21}$R$^{21A}$, —SO$_{v21}$NR$^{21A}$R$^{21B}$, —NHC(O)NR$^{21A}$R$^{21B}$, —N(O)$_{m21}$, —NR$^{21A}$R$^{21B}$, —NHNR$^{21A}$R$^{21B}$, —C(O)R$^{21A}$, —C(O)—OR$^{21A}$, —C(O)NR$^{21A}$R$^{21B}$, —C(O)NHNR$^{21A}$R$^{21B}$, —OR$^{21A}$, —NR$^{21A}$SO$_2$R$^{21B}$, —NR$^{21A}$C(O)R$^{21B}$, —NR$^{21A}$C(O)OR$^{21B}$, —NR$^{21A}$OR$^{21B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; R$^{20}$ and R$^{21}$ substituents may optionally be joined to form a substituted or unsubstituted cycloalkyl or heterocycloalkyl;

R$^{22}$ is selected from hydrogen, halogen, —CX$^{22}$$_3$, —CHX$^{22}$$_2$, —CH$_2$X$^{22}$, —OCX$^{22}$$_3$, —OCH$_2$X$^{22}$, —OCHX$^{22}$$_2$, —CN, —SO$_{n22}$R$^{22A}$, —SO$_{v22}$NR$^{22A}$R$^{22B}$, —NHC(O)NR$^{22A}$R$^{22B}$, —N(O)$_{m22}$, —NR$^{22A}$R$^{22B}$, —NHNR$^{22A}$R$^{22B}$, —C(O)R$^{22A}$, —C(O)—OR$^{22A}$, —C(O)NR$^{22A}$R$^{22B}$, —C(O)NHNR$^{22A}$R$^{22B}$, —OR$^{22A}$, —NR$^{22A}$SO$_2$R$^{22B}$, —NR$^{22A}$C(O)R$^{22B}$, —NR$^{22A}$C(O)OR$^{22B}$, —NR$^{22A}$OR$^{22B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{23}$ is selected from hydrogen, halogen, —CX$^{23}$$_3$, —CHX$^{23}$$_2$, —CH$_2$X$^{23}$, —OCX$^{23}$$_3$, —OCH$_2$X$^{23}$, —OCHX$^{23}$$_2$, —CN, —SO$_{n23}$R$^{23A}$, —SO$_{v23}$NR$^{23A}$R$^{23B}$, —NHC(O)NR$^{23A}$R$^{23B}$, —N(O)$_{m23}$, —NR$^{23A}$R$^{23B}$, —NHNR$^{23A}$R$^{23B}$, —C(O)R$^{23A}$, —C(O)—OR$^{23A}$, —C(O)NR$^{23A}$R$^{23B}$, —C(O)NHNR$^{23A}$R$^{23B}$, —OR$^{23A}$, —NR$^{23A}$SO$_2$R$^{23B}$, —NR$^{23A}$C(O)R$^{23B}$, —NR$^{23A}$C(O)OR$^{23B}$, —NR$^{23A}$OR$^{23B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{24}$ is selected from hydrogen, halogen, —CX$^{24}$$_3$, —CHX$^{24}$$_2$, —CH$_2$X$^{24}$, —OCX$^{24}$$_3$, —OCH$_2$X$^{24}$, —OCHX$^{24}$$_2$, —CN, —SO$_{n24}$R$^{24A}$, —SO$_{v24}$NR$^{24A}$R$^{24B}$, —NHC(O)NR$^{24A}$R$^{24B}$, —N(O)$_{m24}$, —NR$^{24A}$R$^{24B}$, —NHNR$^{24A}$R$^{24B}$, —C(O)R$^{24A}$, —C(O)—OR$^{24A}$, —C(O)NR$^{24A}$R$^{24B}$, —C(O)NHNR$^{24A}$R$^{24B}$, —OR$^{24A}$, —NR$^{24A}$SO$_2$R$^{24B}$, —NR$^{24A}$C(O)R$^{24B}$, —NR$^{24A}$C(O)OR$^{24B}$, —NR$^{24A}$OR$^{24B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{25}$ is selected from hydrogen, halogen, —CX$^{25}$$_3$, —CHX$^{25}$$_2$, —CH$_2$X$^{25}$, —OCX$^{25}$$_3$, —OCH$_2$X$^{25}$, —OCHX$^{25}$$_2$, —CN, —SO$_{n25}$R$^{25A}$, —SO$_{v25}$NR$^{25A}$R$^{25B}$, —NHC(O)NR$^{25A}$R$^{25B}$, —N(O)$_{m25}$, —NR$^{25A}$R$^{25B}$, —NHNR$^{25A}$R$^{25B}$, —C(O)R$^{25A}$, —C(O)—OR$^{25A}$, —C(O)NR$^{25A}$R$^{25B}$, —C(O)NHNR$^{25A}$R$^{25B}$, —OR$^{25A}$, —NR$^{25A}$SO$_2$R$^{25B}$, —NR$^{25A}$C(O)R$^{25B}$, —NR$^{25A}$C(O)OR$^{25B}$, —NR$^{25A}$OR$^{25B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{26}$ is selected from hydrogen, halogen, —CX$^{26}$$_3$, —CHX$^{26}$$_2$, —CH$_2$X$^{26}$, —OCX$^{26}$$_3$, —OCH$_2$X$^{26}$, —OCHX$^{26}$$_2$, —CN, —SO$_{n26}$R$^{26A}$, —SO$_{v26}$NR$^{26A}$R$^{26B}$, —NHC(O)NR$^{26A}$R$^{26B}$, —N(O)$_{m26}$, —NR$^{26A}$R$^{26B}$, —NHNR$^{26A}$R$^{26B}$, —C(O)R$^{26A}$, —C(O)—OR$^{26A}$, —C(O)NR$^{26A}$R$^{26B}$, —C(O)NHNR$^{26A}$R$^{26B}$, —OR$^{26A}$, —NR$^{26A}$SO$_2$R$^{26B}$, —NR$^{26A}$C(O)R$^{26B}$, —NR$^{26A}$C(O)OR$^{26B}$, —NR$^{26A}$OR$^{26B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{27}$ is selected from hydrogen, halogen, —CX$^{27}$$_3$, —CHX$^{27}$$_2$, —CH$_2$X$^{27}$, —OCX$^{27}$$_3$, —OCH$_2$X$^{27}$, —OCHX$^{27}$$_2$, —CN, —SO$_{n27}$R$^{27A}$, —SO$_{v27}$NR$^{27A}$R$^{27B}$, —NHC(O)NR$^{27A}$R$^{27B}$, —N(O)$_{m27}$, —NR$^{27A}$R$^{27B}$, —NHNR$^{27A}$R$^{27B}$, —C(O)R$^{27A}$, —C(O)—OR$^{27A}$, —C(O)NR$^{27A}$R$^{27B}$, —C(O)NHNR$^{27A}$R$^{27B}$, —OR$^{27A}$, —NR$^{27A}$SO$_2$R$^{27B}$, —NR$^{27A}$C(O)R$^{27B}$, —NR$^{27A}$C(O)OR$^{27B}$, —NR$^{27A}$OR$^{27B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{28}$ is selected from hydrogen, halogen, —CX$^{28}$$_3$, —CHX$^{28}$$_2$, —CH$_2$X$^{28}$, —OCX$^{28}$$_3$, —OCH$_2$X$^{28}$, —OCHX$^{28}$$_2$, —CN, —SO$_{n28}$R$^{28A}$, —SO$_{v28}$NR$^{28A}$R$^{28B}$, —NHC(O)NR$^{28A}$R$^{28B}$, —N(O)$_{m2}$, —NR$^{28A}$R$^{28B}$, —NHNR$^{28A}$R$^{28B}$, —C(O)R$^{28A}$, —C(O)—OR$^{28A}$, —C(O)NR$^{28A}$R$^{28B}$, —C(O)NHNR$^{28A}$R$^{28B}$, —OR$^{28A}$, —NR$^{28A}$SO$_2$R$^{28B}$, —NR$^{28A}$C(O)R$^{28B}$, —NR$^{28A}$C(O)OR$^{28B}$, —NR$^{28A}$OR$^{28B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{29}$ is selected from hydrogen, halogen, —CX$^{29}$$_3$, —CHX$^{29}$$_2$, —CH$_2$X$^{29}$, —OCX$^{29}$$_3$, —OCH$_2$X$^{29}$, —OCHX$^{29}$$_2$, —CN, —SO$_{n29}$R$^{29A}$, —SO$_{v29}$NR$^{29A}$R$^{29B}$, —NHC(O)NR$^{29A}$R$^{29B}$, —N(O)$_{m29}$, —NR$^{29A}$R$^{29B}$, —NHNR$^{29A}$R$^{29B}$, —C(O)R$^{29A}$, —C(O)—OR$^{29A}$, —C(O)NR$^{29A}$R$^{29B}$, —C(O)NHNR$^{29A}$R$^{29B}$, —OR$^{29A}$, —NR$^{29A}$SO$_2$R$^{29B}$, —NR$^{29A}$C(O)R$^{29B}$, —NR$^{29A}$C(O)OR$^{29B}$, —NR$^{29A}$OR$^{29B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{30}$ is selected from hydrogen, halogen, —CX$^{30}$$_3$, —CHX$^{30}$$_2$, —CH$_2$X$^{30}$, —OCX$^{30}$$_3$, —OCH$_2$X$^{30}$, —OCHX$^{30}$$_2$, —CN, —SO$_{n30}$R$^{30A}$, —SO$_{v30}$NR$^{30A}$R$^{30B}$, —NHC(O)NR$^{30A}$R$^{30B}$, —N(O)$_{m30}$, —NR$^{30A}$R$^{30B}$, —NHNR$^{30A}$R$^{30B}$, —C(O)R$^{30A}$, —C(O)—OR$^{30A}$, —C(O)NR$^{30A}$R$^{30B}$, —C(O)NHNR$^{30A}$R$^{30B}$, —OR$^{30A}$, —NR$^{30A}$SO$_2$R$^{30B}$, —NR$^{30A}$C(O)R$^{30B}$, —NR$^{30A}$C(O)OR$^{30B}$, —NR$^{30A}$OR$^{30B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

Each R$^{1A}$, R$^{1B}$, R$^{2A}$, R$^{2B}$, R$^{3A}$, R$^{3B}$, R$^{4A}$, R$^{4B}$, R$^{6A}$, R$^{6B}$, R$^{7A}$, R$^{7B}$, R$^{9A}$, R$^{9B}$, R$^{10A}$, R$^{10B}$, R$^{11A}$, R$^{11B}$, R$^{17A}$, R$^{17B}$, R$^{18A}$, R$^{18B}$, R$^{19A}$, R$^{19B}$, R$^{20A}$, R$^{20B}$, R$^{21A}$, R$^{21B}$, R$^{22A}$, R$^{22B}$, R$^{23A}$, R$^{23B}$, R$^{24A}$, R$^{24B}$, R$^{25A}$, R$^{25B}$, R$^{26A}$, R$^{26B}$, R$^{27A}$, R$^{27B}$, R$^{28A}$, R$^{28B}$, R$^{29A}$, R$^{29B}$, R$^{29A}$, R$^{29B}$, R$^{30A}$, R$^{30B}$, is independently selected from hydrogen, —CX$_3$, —CHX$_2$, —CH$_2$X, —C(O)OH, —C(O)NH$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)OH, —NHOH, —OCX$_3$, —OCHX$_2$, —OCH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{1A}$ and R$^{1B}$ substituents bonded to the same nitrogen atom may optionally be joined to form a substituted or unsubstituted heterocycloalkyl or substituted or unsubstituted heteroaryl; R$^{2A}$ and R$^{2B}$ substituents bonded to the same nitrogen atom may optionally be joined to form a substituted or unsubstituted heterocycloalkyl or substituted or unsubstituted heteroaryl; R$^{4A}$ and R$^{4B}$ substituents bonded to the same nitrogen atom may optionally be joined to form a substituted or unsubstituted heterocycloalkyl or substituted or unsubstituted heteroaryl; R$^{6A}$ and R$^{6B}$ substituents bonded to the same nitrogen atom may optionally be joined to form a substituted or unsubstituted heterocycloalkyl or substituted or unsubstituted heteroaryl; R$^{7A}$ and R$^{7B}$ substituents bonded to the same nitrogen atom may optionally be joined to form a substituted or unsubstituted heterocycloalkyl or substituted or unsubstituted heteroaryl; R$^{9A}$ and R$^{9B}$ substituents bonded to the same nitrogen atom may optionally be joined to form a substituted or unsubstituted heterocycloalkyl or substituted or unsubstituted heteroaryl; R$^{10A}$ and R$^{10B}$ substituents bonded to the same nitrogen atom may optionally be joined to form a substituted or unsubstituted heterocycloalkyl or substituted or unsubstituted heteroaryl; R$^{11A}$ and R$^{11B}$ substituents bonded to the same nitrogen atom may optionally be joined to form a substituted or unsubstituted heterocycloalkyl or substituted or unsubstituted heteroaryl; R$^{17A}$ and R$^{17B}$ substituents bonded to the same nitrogen atom may optionally be joined to form a substituted or unsubstituted heterocycloalkyl or substituted or unsubstituted heteroaryl; R$^{18A}$ and R$^{18B}$ substituents bonded to the same nitrogen atom may optionally be joined to form a substituted or unsubstituted heterocycloalkyl or substituted or unsubstituted heteroaryl; R$^{19A}$ and R$^{19B}$ substituents bonded to the same nitrogen atom may optionally be joined to form a substituted or unsubstituted heterocycloalkyl or substituted or unsubstituted heteroaryl; R$^{20A}$ and R$^{20B}$, substituents bonded to the same nitrogen atom may optionally be joined to form a substituted or unsubstituted heterocycloalkyl or substituted or unsubstituted heteroaryl; R$^{21A}$ and R$^{21B}$ substituents bonded to the same nitrogen atom may optionally be joined to form a substituted or unsubstituted heterocycloalkyl or substituted or unsubstituted heteroaryl; R$^{22A}$ and R$^{22B}$ substituents bonded to the same nitrogen atom may optionally be joined to form a substituted or unsubstituted heterocycloalkyl or substituted or unsubstituted heteroaryl; R$^{23A}$ and R$^{23B}$ substituents bonded to the same nitrogen atom may optionally be joined to form a substituted or unsubstituted heterocycloalkyl or substituted or unsubstituted heteroaryl; R$^{24A}$ and R$^{24B}$ substituents bonded to the same nitrogen atom may optionally be joined to form a substituted or unsubstituted heterocycloalkyl or substituted or unsubstituted heteroaryl; R$^{25A}$ and R$^{25B}$ substituents bonded to the same nitrogen atom may optionally be joined to form a substituted or unsubstituted heterocycloalkyl or substituted or unsubstituted heteroaryl; R$^{26A}$ and R$^{26B}$ substituents bonded to the same nitrogen atom may optionally be joined to form a substituted or unsubstituted heterocycloalkyl or substituted or unsubstituted heteroaryl; R$^{27A}$ and R$^{27B}$ substituents bonded to the same nitrogen atom may optionally be joined to form a substituted or unsubstituted heterocycloalkyl or substituted or unsubstituted heteroaryl; R$^{28A}$ and R$^{28B}$ substituents bonded to the same nitrogen atom may optionally be joined to form a substituted or unsubstituted heterocycloalkyl or substituted or unsubstituted heteroaryl; R$^{29A}$ and R$^{29B}$ substituents bonded to the same nitrogen atom may optionally be joined to form a substituted or unsubstituted heterocycloalkyl or substituted or unsubstituted heteroaryl; R$^{30A}$ and R$^{30B}$ substituents bonded to the same nitrogen atom may optionally be joined to form a substituted or unsubstituted heterocycloalkyl or substituted or unsubstituted heteroaryl;

Each m1, m2, m3, m4, m6, m7, m9, m10, m11, m17, m18, m19, m20, m21, m22, m23, m24, m25, m26, m27, m28, m29 and m30 are independently 1 or 2;

Each v1, v2, v3, v4, v6, v7, v9, v10, v11, v17, v18, v19, v20, v21, v22, v23, v24, v25, v26, v27, v28, v29 and v30 are independently 1 or 2;

Each n1, n2, n3, n4, n6, n7, n9, n10, n11, n17, n18, n19, n20, n21, n22, n23, n24, n25, n26, n27, n28, n29 and n30 are independently an integer from 0 to 2; and Each X$^1$, X$^2$, X$^3$, X$^4$, X$^6$, X$^7$, X$^9$, X$^{10}$, X$^{11}$, X$^{17}$, X$^{18}$, X$^{19}$, X$^{20}$, X$^{21}$, X$^{22}$, X$^{23}$, X$^{24}$, X$^{25}$, X$^{26}$, X$^{27}$, X$^{28}$, X$^{29}$ and X$^{30}$ are independently —Cl, —Br, —I or —F.

In one embodiment, E is selected from —C(═O)CH═CH$_2$, —C(═O)-ethynyl, —C(═O)CH═CHCF$_3$, —C(═O)CH═CHCHF$_2$, —C(═O)CH═CHCH$_2$F, and —C(═O)CH$_2$Br.

In one embodiment, U is selected from NR$^{12}$, O, or S.

The invention also relates to compounds of Formula V:

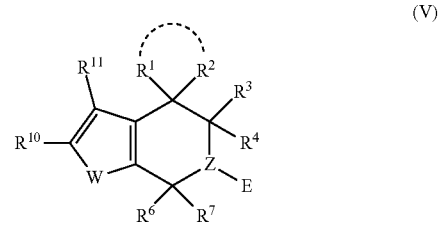

(V)

wherein
Z is selected from N, or $CR^9$;
W is selected from $NR^{12}$, O, S, S=O, O=S=O, and Se;
E is an electrophilic moiety, selected from
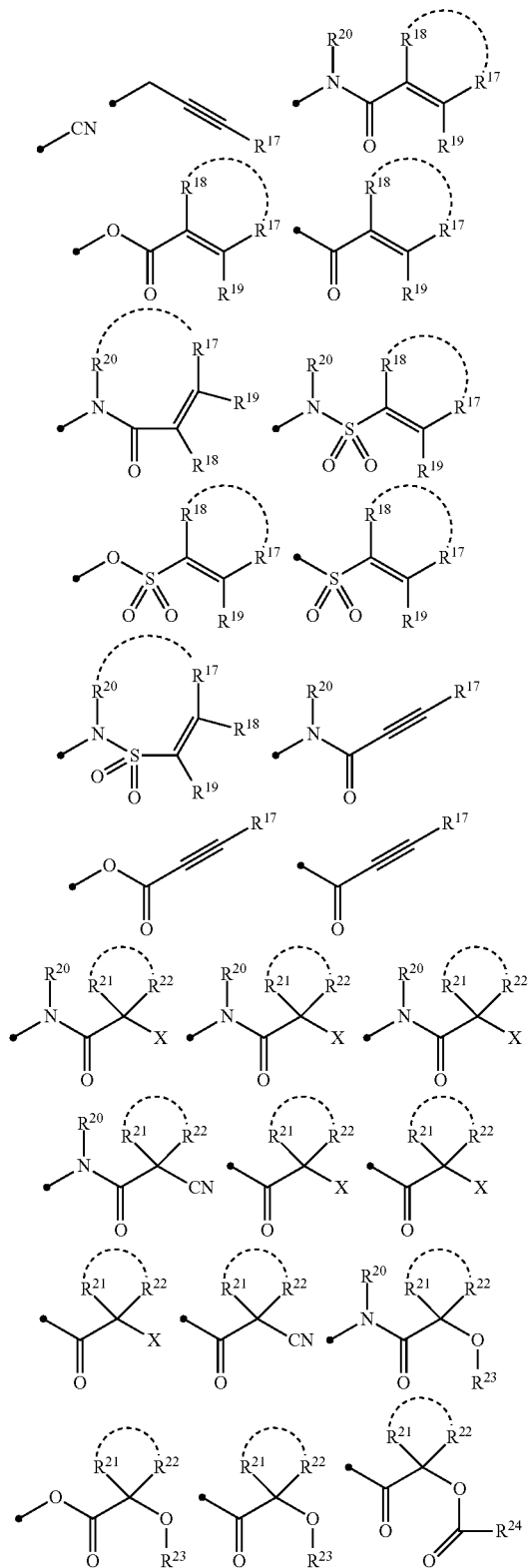
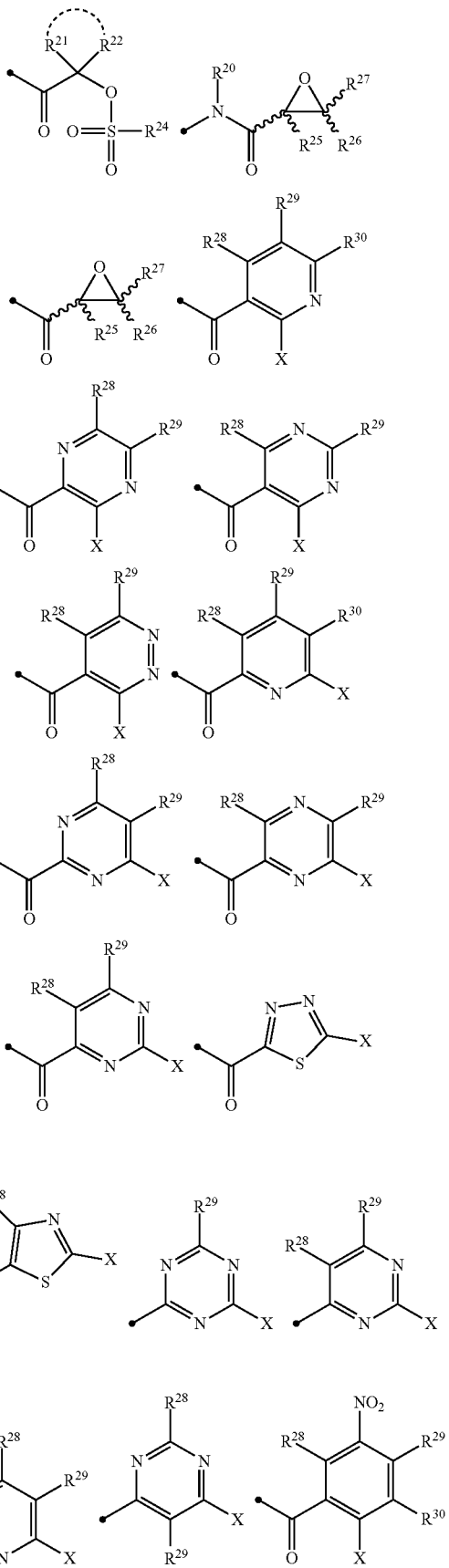

-continued

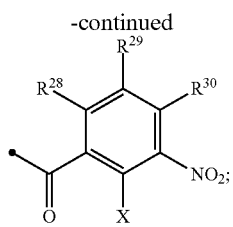

R¹ is selected from hydrogen, halogen, —CX¹₃, —CHX¹₂, —CH₂X¹, —OCX¹₃, —OCH₂X¹, —OCHX¹₂, —CN, —SO$_{n1}$R$^{1A}$, —SO$_{v1}$NR$^{1A}$R$^{1B}$, —NHC(O)NR$^{1A}$R$^{1B}$, —N(O)$_{m1}$, —NR$^{1A}$R$^{1B}$, —NHNR$^{1A}$R$^{1B}$, —C(O)R$^{1A}$, —C(O)—OR$^{1A}$, —C(O)NR$^{1A}$R$^{1B}$, —C(O)NHNR$^{1A}$R$^{1B}$, —OR$^{1A}$, —NR$^{1A}$SO₂R$^{1B}$, —NR$^{1A}$C(O)R$^{1B}$, —NR$^{1A}$C(O)OR$^{1B}$, —NR$^{1A}$OR$^{1B}$, —N₃, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R² is selected from hydrogen, halogen, —CX²₃, —CHX²₂, —CH₂X², —OCX²₃, —OCH₂X², —OCHX²₂, —CN, —SO$_{n2}$R$^{2A}$, —SO₂NR$^{2A}$R$^{2B}$, —NHC(O)NR$^{2A}$R$^{2B}$, —N(O)$_{m2}$, —NR$^{2A}$R$^{2B}$, —NHNR$^{2A}$R$^{2B}$, —C(O)R$^{2A}$, —C(O)—OR$^{2A}$, —C(O)NR$^{2A}$R$^{2B}$, —C(O)NHNR$^{2A}$R$^{2B}$, —OR$^{2A}$, —NR$^{2A}$SO₂R$^{2B}$, —NR$^{2A}$C(O)R$^{2B}$, —NR$^{2A}$C(O)OR$^{2B}$, —NR$^{2A}$OR$^{2B}$, —N₃, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; R¹ and R² substituents may optionally be joined to form a substituted or unsubstituted cycloalkyl or heterocycloalkyl;

R³ is selected from hydrogen, halogen, —CX³₃, —CHX³₂, —CH₂X³, —OCX³₃, —OCH₂X³, —OCHX³₂, —CN, —SO₃R$^{3A}$, —SO$_{v3}$NR$^{3A}$R$^{3B}$, —NHC(O)NR$^{3A}$R$^{3B}$, —N(O)$_{m3}$, —NR$^{3A}$R$^{3B}$, —NHNR$^{3A}$R$^{3B}$, —C(O)R$^{3A}$, —C(O)—OR$^{3A}$, —C(O)NR$^{3A}$R$^{3B}$, —OR$^{3A}$, —NR$^{3A}$SO₂R$^{3B}$, —NR$^{3A}$C(O)R$^{3B}$, —NR$^{3A}$C(O)OR$^{3B}$, —NR$^{3A}$OR$^{3B}$, —N₃, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R⁴ is selected from hydrogen, halogen, —CX⁴₃, —CHX⁴₂, —CH₂X⁴, —OCX⁴₃, —OCH₂X⁴, —OCHX⁴₂, —CN, —SO$_{v4}$R$^{4A}$, —SO₄NR$^{4A}$R$^{4B}$, —NHC(O)NR$^{4A}$R$^{4B}$, —N(O)$_{m4}$, —NR$^{4A}$R$^{4B}$, —NHNR$^{4A}$R$^{4B}$, —C(O)R$^{4A}$, —C(O)—OR$^{4A}$, —C(O)NR$^{4A}$R$^{4B}$, —C(O)NHNR$^{4A}$R$^{4B}$, —OR$^{4A}$, —NR$^{4A}$SO₂R$^{4B}$, —NR$^{4A}$C(O)R$^{4B}$, —NR$^{4A}$C(O)OR$^{4B}$, —NR$^{4A}$OR$^{4B}$, —N₃, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; R³ and R³ substituents may optionally be joined to form a substituted or unsubstituted cycloalkyl or heterocycloalkyl;

R⁶ is selected from hydrogen, halogen, —CX⁶₃, —CHX⁶₂, —CH₂X⁶, —OCX⁶₃, —OCH₂X⁶, —OCHX⁶₂, —CN, —SO$_{v6}$R$^{6A}$, —SO$_{v6}$NR$^{6A}$R$^{6B}$, —NHC(O)NR$^{6A}$R$^{6B}$, —N(O)$_{m6}$, —NR$^{6A}$R$^{6B}$, —NHNR$^{6A}$R$^{6B}$, —C(O)R$^{6A}$, —C(O)—OR$^{6A}$, —C(O) NR$^{6A}$R$^{6B}$, —C(O)NHNR$^{6A}$R$^{6B}$, —OR$^{6A}$, —NR$^{6A}$SO₂R$^{6B}$, —NR$^{6A}$C(O)R$^{6B}$, —NR$^{6A}$C(O)OR$^{6B}$, —NR$^{6A}$OR$^{6B}$, —N₃, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R⁷ is selected from hydrogen, halogen, —CX⁷₃, —CHX⁷₂, —CH₂X⁷, —OCX⁷₃, —OCH₂X⁷, —OCHX⁷₂, —CN, —SO$_{n7}$R$^{7A}$, —SO$_{v7}$NR$^{7A}$R$^{7B}$, —NHC(O)NR$^{7A}$R$^{7B}$, —N(O)$_{m7}$, —NR$^{7A}$R$^{7B}$, —NHNR$^{7A}$R$^{7B}$, —C(O)R$^{7A}$, —C(O)—OR$^{7A}$, —C(O) NR$^{7A}$R$^{7B}$, —C(O)NHNR$^{7A}$R$^{7B}$, —OR$^{7A}$, —NR$^{7A}$SO₂R$^{7B}$, —NR$^{7A}$C(O)R$^{7B}$, —NR$^{7A}$C(O)OR$^{7B}$, —NR$^{7A}$OR$^{7B}$, —N₃, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R⁹ is selected from hydrogen, halogen, —CX⁹₃, —CHX⁹₂, —CH₂X⁹, —OCX⁹₃, —OCH₂X⁹, —OCHX⁹₂, —CN, —SO$_{v9}$R$^{9A}$, —SO$_{v9}$NR$^{9A}$R$^{9B}$, —NHC(O)NR$^{9A}$R$^{9B}$, —N(O)$_{m9}$, —NR$^{9A}$R$^{9B}$, —NHNR$^{9A}$R$^{9B}$, —C(O)R$^{9A}$, —C(O)—OR$^{9A}$, —C(O) NR$^{9A}$R$^{9B}$, —C(O)NHNR$^{9A}$R$^{9B}$, —OR$^{9A}$, —NR$^{9A}$SO₂R$^{9B}$, —NR$^{9A}$C(O)R$^{9B}$, —NR$^{9A}$C(O)OR$^{9B}$, —NR$^{9A}$OR$^{9B}$, —N₃, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R¹⁰ is selected from hydrogen, halogen, —CX¹³₃, —CHX¹³₂, —CH₂X¹³, —OCX¹³₃, —OCH₂X¹³, —OCHX¹³₂, —CN, —SO$_{n13}$R$^{13A}$, —SO$_{v13}$NR$^{13A}$R$^{13B}$, —NHC(O)NR$^{13A}$R$^{13B}$, —N(O)$_{m13}$, —NR$^{13A}$R$^{13B}$, —NHNR$^{13A}$R$^{13B}$, —C(O)R$^{13A}$, —C(O)—OR$^{13A}$, —C(O)NR$^{13A}$R$^{13B}$, —C(O) NHNR$^{13A}$R$^{13B}$, —OR$^{13A}$, —NR$^{13A}$SO₂R$^{13B}$, —NR$^{13A}$C(O)R$^{13B}$, —NR$^{13A}$C(O)OR$^{13B}$, —NR$^{13A}$OR$^{13B}$, —N₃, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R¹¹ is selected from hydrogen, halogen, —CX¹⁴₃, —CHX¹⁴₂, —CH₂X¹⁴, —OCX¹⁴₃, —OCH₂X¹⁴, —OCHX¹⁴₂, —CN, —SO$_{n14}$R$^{14A}$, —SO$_{v14}$NR$^{14A}$R$^{14B}$, —NHC(O)NR$^{14A}$R$^{14B}$, —N(O)$_{m14}$, —NR$^{14A}$R$^{14B}$, —NHNR$^{14A}$R$^{14B}$, —C(O)R$^{14A}$, —C(O)—OR$^{14A}$, —C(O)NR$^{14A}$R$^{14B}$, —C(O) NHNR$^{14A}$R$^{14B}$, —OR$^{14A}$, —NR$^{14A}$SO₂R$^{14B}$, —NR$^{14A}$C(O)R$^{14B}$, —NR$^{14A}$C(O)OR$^{14B}$, —NR$^{14A}$OR$^{14B}$, —N₃, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R¹² is selected from hydrogen, halogen, —CX¹²₃, —CHX¹²₂, —CH₂X¹², —OCX¹²₃, —OCH₂X¹², —OCHX¹²₂, —CN, —SO$_{n12}$R$^{12A}$, —SO$_{v12}$NR$^{12A}$R$^{12B}$, —NHC(O)NR$^{12A}$R$^{12B}$, —N(O)$_{m12}$, —NR$^{12A}$R$^{12B}$, —NHNR$^{12A}$R$^{12B}$, —C(O)R$^{12A}$, —C(O)—OR$^{12A}$, —C(O)NR$^{12A}$R$^{12B}$, —C(O) NHNR$^{12A}$R$^{12B}$, —OR$^{12A}$, —NR$^{12A}$SO₂R$^{12B}$, —NR$^{12A}$C(O)R$^{12B}$, —NR$^{12A}$C(O)OR$^{12B}$, —NR$^{12A}$OR$^{12B}$, —N₃, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{17}$ is selected from hydrogen, halogen, —$CX^{17}_3$, —$CHX^{17}_2$, —$CH_2X^{17}$, —$OCX^{17}_3$, —$OCH_2X^{17}$, —$OCHX^{17}_2$, —CN, —$SO_{n17}R^{17A}$, —$SO_{v17}NR^{17A}R^{17B}$, —$NHC(O)NR^{17A}R^{17B}$, —$N(O)_{m17}$, —$NR^{17A}R^{17B}$, —$NHNR^{17A}R^{17B}$, —$C(O)R^{17A}$, —$C(O)$—$OR^{17A}$, —$C(O)NR^{17A}R^{17B}$, —$C(O)NHNR^{17A}R^{17B}$, —$OR^{17A}$, —$NR^{17A}SO_2R^{17B}$, —$NR^{17A}C(O)R^{17B}$, —$NR^{17A}C(O)OR^{17B}$, —$NR^{17A}OR^{17B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{18}$ is selected from hydrogen, halogen, —$CX^{18}_3$, —$CHX^{18}_2$, —$CH_2X^{18}$, —$OCX^{18}_3$, —$OCH_2X^{18}$, —$OCHX^{18}_2$, —CN, —$SO_{n18}R^{18A}$, —$SO_{v18}NR^{18A}R^{1B}$, —$NHC(O)NR^{18A}R^{1B}$, —$N(O)_{m18}$, —$NR^{18A}R^{18B}$, —$NHNR^{18A}R^{18B}$, —$C(O)R^{18A}$, —$C(O)$—$OR^{18A}$, —$C(O)NR^{18A}R^{18B}$, —$C(O)NHNR^{18A}R^{18B}$, —$OR^{18A}$, —$NR^{18A}SO_2R^{18B}$, —$NR^{18A}C(O)R^{18B}$, —$NR^{18A}C(O)OR^{18B}$, —$NR^{18A}OR^{18B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; $R^{16}$ and $R^{18}$ substituents may optionally be joined to form a substituted or unsubstituted cycloalkyl or heterocycloalkyl;

$R^{19}$ is selected from hydrogen, halogen, —$CX^{19}_3$, —$CHX^{19}_2$, —$CH_2X^{19}$, —$OCX^{19}_3$, —$OCH_2X^{19}$, —$OCHX^{19}_2$, —CN, —$SO_{n19}R^{19A}$, —$SO_{v19}NR^{19A}R^{19B}$, —$NHC(O)NR^{19A}R^{19B}$, —$N(O)_{m19}$, —$NR^{19A}R^{19B}$, —$NHNR^{19A}R^{19B}$, —$C(O)R^{19A}$, —$C(O)$—$OR^{19A}$, —$C(O)NR^{19A}R^{19B}$, —$C(O)NHNR^{19A}R^{19B}$, —$OR^{19A}$, —$NR^{19A}SO_2R^{19B}$, —$NR^{19A}C(O)R^{19B}$, —$NR^{19A}C(O)OR^{19B}$, —$NR^{19A}OR^{19B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; $R^{16}$ and $R^{19}$ substituents may optionally be joined to form a substituted or unsubstituted cycloalkyl or heterocycloalkyl;

$R^{20}$ is selected from hydrogen, halogen, —$CX^{20}_3$, —$CHX^{20}_2$, —$CH_2X^{20}$, —$OCX^{20}_3$, —$OCH_2X^{20}$, —$OCHX^{20}_2$, —CN, —$SO_{n20}R^{20A}$, —$SO_{v20}NR^{20A}R^{20B}$, —$NHC(O)NR^{20A}R^{20B}$, —$N(O)_{m20}$, —$NR^{20A}R^{20B}$, —$NHNR^{20A}R^{20B}$, —$C(O)R^{20A}$, —$C(O)$—$OR^{20A}$, —$C(O)NR^{20A}R^{20B}$, —$C(O)NHNR^{20A}R^{20B}$, —$OR^{20A}$, —$NR^{20A}SO_2R^{20B}$, —$NR^{20A}C(O)R^{20B}$, —$NR^{20A}C(O)OR^{20B}$, —$NR^{20A}OR^{20B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{21}$ is selected from hydrogen, halogen, —$CX^{21}_3$, —$CHX^{21}_2$, —$CH_2X^{21}$, —$OCX^{21}_3$, —$OCH_2X^{21}$, —$OCHX^{21}_2$, —CN, —$SO_{n21}R^{21A}$, —$SO_{v21}NR^{21A}R^{21B}$, —$NHC(O)NR^{21A}R^{21B}$, —$N(O)_{m21}$, —$NR^{21A}R^{21B}$, —$NHNR^{21A}R^{21B}$, —$C(O)R^{21A}$, —$C(O)$—$OR^{21A}$, —$C(O)NR^{21A}R^{21B}$, —$C(O)NHNR^{21A}R^{21B}$, —$OR^{21A}$, —$NR^{21A}SO_2R^{21B}$, —$NR^{21A}C(O)R^{21B}$, —$NR^{21A}C(O)OR^{21B}$, —$NR^{21A}OR^{21B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; $R^{20}$ and $R^{21}$ substituents may optionally be joined to form a substituted or unsubstituted cycloalkyl or heterocycloalkyl;

$R^{22}$ is selected from hydrogen, halogen, —$CX^{22}_3$, —$CHX^{22}_2$, —$CH_2X^{22}$, —$OCX^{22}_3$, —$OCH_2X^{22}$, —$OCHX^{22}_2$, —CN, —$SO_{n22}R^{22A}$, —$SO_{v22}NR^{22A}R^{22B}$, —$NHC(O)NR^{22A}R^{22B}$, —$N(O)_{m22}$, —$NR^{22A}R^{22B}$, —$NHNR^{22A}R^{22B}$, —$C(O)R^{22A}$, —$C(O)$—$OR^{22A}$, —$C(O)NR^{22A}R^{22B}$, —$C(O)NHNR^{22A}R^{22B}$, —$OR^{22A}$, —$NR^{22A}SO_2R^{22B}$, —$NR^{22A}C(O)R^{22B}$, —$NR^{22A}C(O)OR^{22B}$, —$NR^{22A}OR^{22B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{23}$ is selected from hydrogen, halogen, —$CX^{23}_3$, —$CHX^{23}_2$, —$CH_2X^{23}$, —$OCX^{23}_3$, —$OCH_2X^{23}$, —$OCHX^{23}_2$, —CN, —$SO_{n23}R^{23A}$, —$SO_{v23}NR^{23A}R^{23B}$, —$NHC(O)NR^{23A}R^{23B}$, —$N(O)_{m23}$, —$NR^{23A}R^{23B}$, —$NHNR^{23A}R^{23B}$, —$C(O)R^{23A}$, —$C(O)$—$OR^{23A}$, —$C(O)NR^{23A}R^{23B}$, —$C(O)NHNR^{23A}R^{23B}$, —$OR^{23A}$, —$NR^{23A}SO_2R^{23B}$, —$NR^{23A}C(O)R^{23B}$, —$NR^{23A}C(O)OR^{23B}$, —$NR^{23A}OR^{23B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{24}$ is selected from hydrogen, halogen, —$CX^{24}_3$, —$CHX^{24}_2$, —$CH_2X^{24}$, —$OCX^{24}_3$, —$OCH_2X^{24}$, —$OCHX^{24}_2$, —CN, —$SO_{n24}R^{24A}$, —$SO_{v24}NR^{24A}R^{24B}$, —$NHC(O)NR^{24A}R^{24B}$, —$N(O)_{m24}$, —$NR^{24A}R^{24B}$, —$NHNR^{24A}R^{24B}$, —$C(O)R^{24A}$, —$C(O)$—$OR^{24A}$, —$C(O)NR^{24A}R^{24B}$, —$C(O)NHNR^{24A}R^{24B}$, —$OR^{24A}$, —$NR^{24A}SO_2R^{24B}$, —$NR^{24A}C(O)R^{24B}$, —$NR^{24A}C(O)OR^{24B}$, —$NR^{24A}OR^{24B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{25}$ is selected from hydrogen, halogen, —$CX^{25}_3$, —$CHX^{25}_2$, —$CH_2X^{25}$, —$OCX^{25}_3$, —$OCH_2X^{25}$, —$OCHX^{25}_2$, —CN, —$SO_{n25}R^{25A}$, —$SO_{v25}NR^{25A}R^{25B}$, —$NHC(O)NR^{25A}R^{25B}$, —$N(O)_{m25}$, —$NR^{25A}R^{25B}$, —$NHNR^{25A}R^{25B}$, —$C(O)R^{25A}$, —$C(O)$—$OR^{25A}$, —$C(O)NR^{25A}R^{25B}$, —$C(O)NHNR^{25A}R^{25B}$, —$OR^{25A}$, —$NR^{25A}SO_2R^{25B}$, —$NR^{25A}C(O)R^{25B}$, —$NR^{25A}C(O)OR^{25B}$, —$NR^{25A}OR^{25B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{26}$ is selected from hydrogen, halogen, —$CX^{26}_3$, —$CHX^{26}_2$, —$CH_2X^{26}$, —$OCX^{26}_3$, —$OCH_2X^{26}$, —$OCHX^{26}_2$, —CN, —$SO_{n26}R^{26A}$, —$SO_{v26}NR^{26A}R^{26B}$, —$NHC(O)NR^{26A}R^{26B}$, —$N(O)_{m26}$, —$NR^{26A}R^{26B}$, —$NHNR^{26A}R^{26B}$, —$C(O)R^{26A}$, —$C(O)$—$OR^{26A}$, —$C(O)NR^{26A}R^{26B}$, —$C(O)

NHNR$^{26A}$R$^{26B}$, —OR$^{26A}$, —NR$^{26A}$SO$_2$R$^{26B}$, —NR$^{26A}$C(O)R$^{26B}$, —NR$^{26A}$C(O)OR$^{26B}$, —NR$^{26A}$OR$^{26B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{27}$ is selected from hydrogen, halogen, —CX$^{27}_3$, —CHX$^{27}_2$, —CH$_2$X$^{27}$, —OCX$^{27}_3$, —OCH$_2$X$^{27}$, —OCHX$^{27}_2$, —CN, —SO$_{n27}$R$^{27A}$, —SO$_{v27}$NR$^{27A}$R$^{27B}$, —NHC(O)NR$^{27A}$R$^{27B}$, —N(O)$_{m27}$, —NR$^{27A}$R$^{27B}$, —NHNR$^{27A}$R$^{27B}$, —C(O)R$^{27A}$, —C(O)—OR$^{27A}$, —C(O)NR$^{27A}$R$^{27B}$, —C(O)NHNR$^{27A}$R$^{27B}$, —OR$^{27A}$, —NR$^{27A}$SO$_2$R$^{27B}$, —NR$^{27A}$C(O)R$^{27B}$, —NR$^{27A}$C(O)OR$^{27B}$, —NR$^{27A}$OR$^{27B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{28}$ is selected from hydrogen, halogen, —CX$^{28}_3$, —CHX$^{28}_2$, —CH$_2$X$^{28}$, —OCX$^{28}_3$, —OCH$_2$X$^{28}$, —OCHX$^{28}_2$, —CN, —SO$_{n28}$R$^{28A}$, —SO$_{v28}$NR$^{28A}$R$^{28B}$, —NHC(O)NR$^{28A}$R$^{28B}$, —N(O)$_{m2}$, —NR$^{28A}$R$^{28B}$, —NHNR$^{28A}$R$^{28B}$, —C(O)R$^{28A}$, —C(O)—OR$^{28A}$, —C(O)NR$^{28A}$R$^{28B}$, —C(O)NHNR$^{28A}$R$^{28B}$, —OR$^{28A}$, —NR$^{28A}$SO$_2$R$^{28B}$, —NR$^{28A}$C(O)R$^{28B}$, —NR$^{28A}$C(O)OR$^{28B}$, —NR$^{28A}$OR$^{28B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{29}$ is selected from hydrogen, halogen, —CX$^{29}_3$, —CHX$^{29}_2$, —CH$_2$X$^{29}$, —OCX$^{29}_3$, —OCH$_2$X$^{29}$, —OCHX$^{29}_2$, —CN, —SO$_{n29}$R$^{29A}$, —SO$_{v29}$NR$^{29A}$R$^{29B}$, —NHC(O)NR$^{29A}$R$^{29B}$, —N(O)$_{m29}$, —NR$^{29A}$R$^{29B}$, —NHNR$^{29A}$R$^{29B}$, —C(O)R$^{29A}$, —C(O)—OR$^{29A}$, —C(O)NR$^{29A}$R$^{29B}$, —C(O)NHNR$^{29A}$R$^{29B}$, —OR$^{29A}$, —NR$^{29A}$SO$_2$R$^{29B}$, —NR$^{29A}$C(O)R$^{29B}$, —NR$^{29A}$C(O)OR$^{29B}$, —NR$^{29A}$OR$^{29B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{30}$ is selected from hydrogen, halogen, —CX$^{30}_3$, —CHX$^{30}_2$, —CH$_2$X$^{30}$, —OCX$^{30}_3$, —OCH$_2$X$^{30}$, —OCHX$^{30}_2$, —CN, —SO$_{n30}$R$^{30A}$, —SO$_{v30}$NR$^{30A}$R$^{30B}$, —NHC(O)NR$^{30A}$R$^{30B}$, —N(O)$_{m30}$, —NR$^{30A}$R$^{30B}$, —NHNR$^{30A}$R$^{30B}$, —C(O)R$^{30A}$, —C(O)—OR$^{30A}$, —C(O)NR$^{30A}$R$^{30B}$, —C(O)NHNR$^{30A}$R$^{30B}$, —OR$^{30A}$, —NR$^{30A}$SO$_2$R$^{30B}$, —NR$^{30A}$C(O)R$^{30B}$, —NR$^{30A}$C(O)OR$^{30B}$, —NR$^{30A}$OR$^{30B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

Each R$^{1A}$, R$^{1B}$, R$^{2A}$, R$^{2B}$, R$^{3A}$, R$^{3B}$, R$^{4A}$, R$^{4B}$, R$^{6A}$, R$^{6B}$, R$^{7A}$, R$^{7B}$, R$^{9A}$, R$^{9B}$, R$^{10A}$, R$^{10B}$, R$^{11A}$, R$^{11B}$, R$^{17A}$, R$^{17B}$, R$^{18A}$, R$^{18B}$, R$^{19A}$, R$^{19B}$, R$^{20A}$, R$^{20B}$, R$^{21A}$, R$^{21B}$, R$^{22A}$, R$^{22B}$, R$^{23A}$, R$^{23B}$, R$^{24A}$, R$^{24B}$, R$^{25A}$, R$^{25B}$, R$^{26A}$, R$^{26B}$, R$^{27A}$, R$^{27B}$, R$^{28A}$, R$^{28B}$, R$^{29A}$, R$^{29B}$, R$^{29A}$, R$^{29B}$, R$^{30A}$, R$^{30B}$, is independently selected from hydrogen, —CX$_3$, —CHX$_2$, —CH$_2$X, —C(O)OH, —C(O)NH$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)OH, —NHOH, —OCX$_3$, —OCHX$_2$, —OCH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{1A}$ and R$^{1B}$ substituents bonded to the same nitrogen atom may optionally be joined to form a substituted or unsubstituted heterocycloalkyl or substituted or unsubstituted heteroaryl; R$^{2A}$ and R$^{2B}$ substituents bonded to the same nitrogen atom may optionally be joined to form a substituted or unsubstituted heterocycloalkyl or substituted or unsubstituted heteroaryl; R$^{4A}$ and R$^{4B}$ substituents bonded to the same nitrogen atom may optionally be joined to form a substituted or unsubstituted heterocycloalkyl or substituted or unsubstituted heteroaryl; R$^{6A}$ and R$^{6B}$ substituents bonded to the same nitrogen atom may optionally be joined to form a substituted or unsubstituted heterocycloalkyl or substituted or unsubstituted heteroaryl; R$^{7A}$ and R$^{7B}$ substituents bonded to the same nitrogen atom may optionally be joined to form a substituted or unsubstituted heterocycloalkyl or substituted or unsubstituted heteroaryl; R$^{9A}$ and R$^{9B}$ substituents bonded to the same nitrogen atom may optionally be joined to form a substituted or unsubstituted heterocycloalkyl or substituted or unsubstituted heteroaryl; R$^{10A}$ and R$^{10B}$ substituents bonded to the same nitrogen atom may optionally be joined to form a substituted or unsubstituted heterocycloalkyl or substituted or unsubstituted heteroaryl; R$^{11A}$ and R$^{11B}$ substituents bonded to the same nitrogen atom may optionally be joined to form a substituted or unsubstituted heterocycloalkyl or substituted or unsubstituted heteroaryl; R$^{17A}$ and R$^{17B}$ substituents bonded to the same nitrogen atom may optionally be joined to form a substituted or unsubstituted heterocycloalkyl or substituted or unsubstituted heteroaryl; R$^{18A}$ and R$^{18B}$ substituents bonded to the same nitrogen atom may optionally be joined to form a substituted or unsubstituted heterocycloalkyl or substituted or unsubstituted heteroaryl; R$^{19A}$ and R$^{19B}$ substituents bonded to the same nitrogen atom may optionally be joined to form a substituted or unsubstituted heterocycloalkyl or substituted or unsubstituted heteroaryl; R$^{20A}$ and R$^{20B}$ substituents bonded to the same nitrogen atom may optionally be joined to form a substituted or unsubstituted heterocycloalkyl or substituted or unsubstituted heteroaryl; R$^{21A}$ and R$^{21B}$ substituents bonded to the same nitrogen atom may optionally be joined to form a substituted or unsubstituted heterocycloalkyl or substituted or unsubstituted heteroaryl; R$^{22A}$ and R$^{22B}$ substituents bonded to the same nitrogen atom may optionally be joined to form a substituted or unsubstituted heterocycloalkyl or substituted or unsubstituted heteroaryl; R$^{23A}$ and R$^{23B}$ substituents bonded to the same nitrogen atom may optionally be joined to form a substituted or unsubstituted heterocycloalkyl or substituted or unsubstituted heteroaryl; R$^{24A}$ and R$^{24B}$ substituents bonded to the same nitrogen atom may optionally be joined to form a substituted or unsubstituted heterocycloalkyl or substituted or unsubstituted heteroaryl; R$^{25A}$ and R$^{25B}$ substituents bonded to the same nitrogen atom may optionally be joined to form a substituted or unsubstituted heterocycloalkyl or substituted or unsubstituted heteroaryl; $R^{26A}$ and $R^{26B}$ substituents bonded to the same nitrogen atom may optionally be joined to form a substituted or unsubstituted heterocycloalkyl or substituted or unsubstituted heteroaryl; $R^{27A}$ and $R^{27B}$ substituents bonded to the same nitrogen atom may optionally be joined to form a substituted or unsubstituted heterocycloalkyl or substituted or unsubstituted heteroaryl; $R^{28A}$ and $R^{28B}$ substituents bonded to the same nitrogen atom may optionally be joined to form a substituted or unsubstituted heterocycloalkyl or substituted or unsubstituted heteroaryl; $R^{29A}$ and $R^{29B}$ substituents bonded to the same nitrogen atom may optionally be joined to form a substituted or unsubstituted heterocycloalkyl or substituted or unsubstituted heteroaryl; $R^{30A}$ and $R^{30B}$ substituents bonded to the same nitrogen atom may optionally be joined to form a substituted or unsubstituted heterocycloalkyl or substituted or unsubstituted heteroaryl;

Each m1, m2, m3, m4, m6, m7, m9, m10, m11, m17, m18, m19, m20, m21, m22, m23, m24, m25, m26, m27, m28, m29 and m30 are independently 1 or 2;

Each v1, v2, v3, v4, v6, v7, v9, v10, v11, v17, v18, v19, v20, v21, v22, v23, v24, v25, v26, v27, v28, v29 and v30 are independently 1 or 2;

Each n1, n2, n3, n4, n6, n7, n9, n10, n11, n17, n18, n19, n20, n21, n22, n23, n24, n25, n26, n27, n28, n29 and n30 are independently an integer from 0 to 2; and Each $X^1$, $X^2$, $X^3$, $X^4$, $X^6$, $X^7$, $X^9$, $X^{10}$, $X^{11}$, $X^{17}$, $X^{18}$, $X^{19}$, $X^{20}$, $X^{21}$, $X^{22}$, $X^{23}$, $X^{24}$, $X^{25}$, $X^{26}$, $X^{27}$, $X^{28}$, $X^{29}$ and $X^{30}$ are independently —Cl, —Br, —I or —F; provided $R^6$ is not 2-thienyl when $R^7$, $R^1$ and $R^2$ are H, and E is ethenylcarbonyl; further provided $R^{10}$ and $R^{11}$ together do not form 4-amino-pyrimidinyl when $R^6$, R, $R^1$ and $R^2$ are H, and E is ethenylcarbonyl.

In one embodiment, E is selected from —C(=O) CH=CH$_2$, —C(=O)-ethynyl, —C(=O)CH=CHCF$_3$, —C(=O)CH=CHCHF$_2$, —C(=O)CH=CHCH$_2$F, and —C(=O)CH$_2$Br.

In one embodiment, U is selected from NR$^{12}$, O, or S.

The invention also relates to compounds of Formula VI:

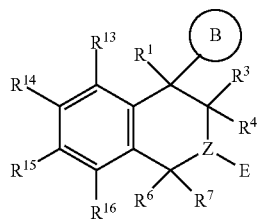

(VI)

wherein

Z is selected from N, CR$^9$;

ring B is selected from selected from
a) 5- or 6-membered cycloalkyl, saturated or partially saturated heterocyclyl,
b) 5- or 6-membered aryl or heteroaryl,
c) 9-, 10- or 11-membered fused partially saturated heterocyclyl,
d) 9- or 10-membered fused heteroaryl,
e) naphthyl, and
f) 4-, 5- or 6-membered cycloalkenyl;

E is selected from an electrophilic moiety, selected from

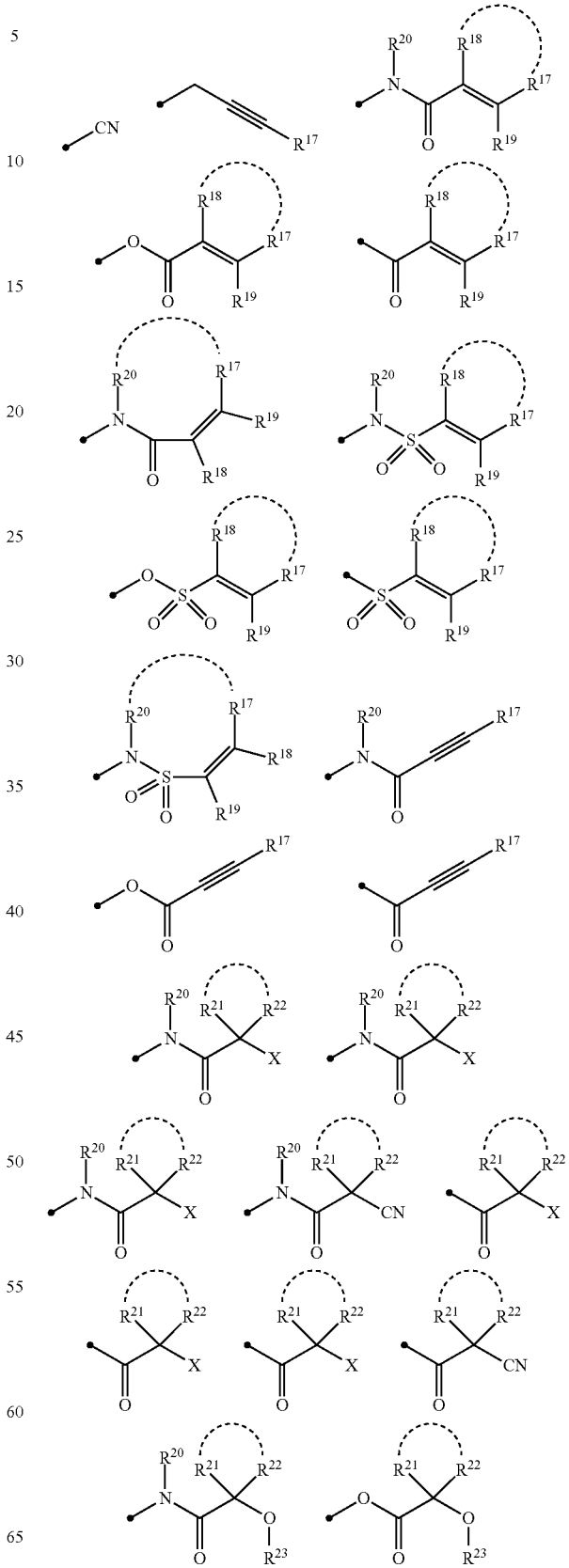

-continued

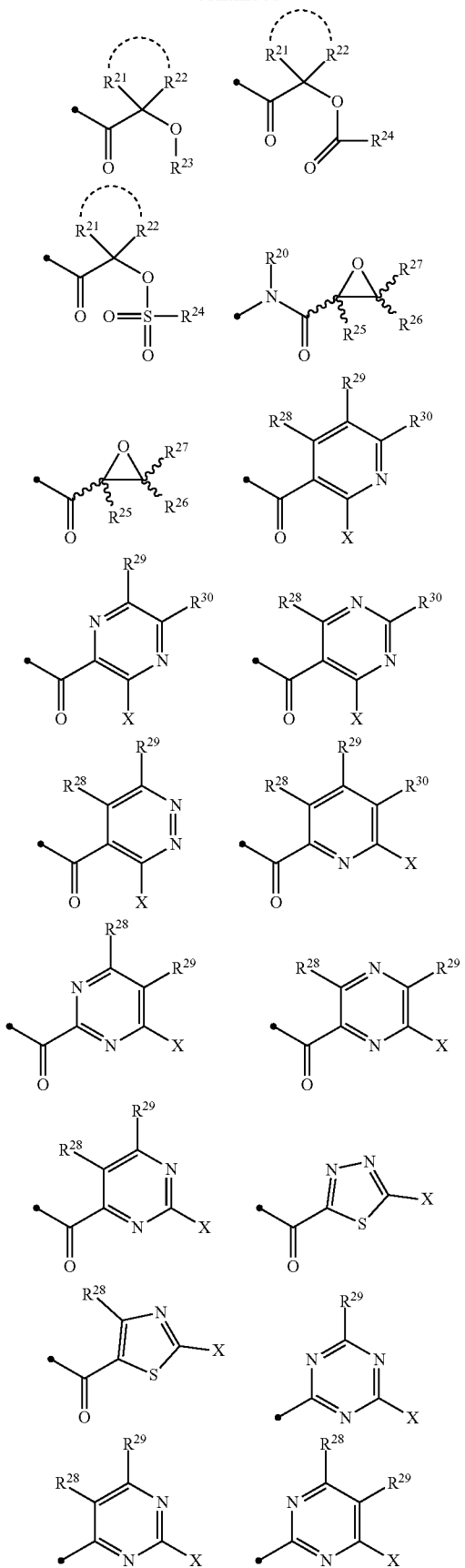

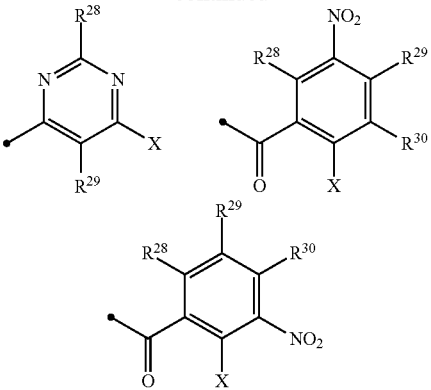

$R^1$ is selected from hydrogen, halogen, $-CX^1_3$, $-CHX^1_2$, $-CH_2X^1$, $-OCX^1_3$, $-OCH_2X^1$, $-OCHX^1_2$, $-CN$, $-SO_{n1}R^{1A}$, $-SO_{v1}NR^{1A}R^{1B}$, $-NHC(O)NR^{1A}R^{1B}$, $-N(O)_{m1}$, $-NR^{1A}R^{1B}$, $-NHNR^{1A}R^{1B}$, $-C(O)R^{1A}$, $-C(O)-OR^{1A}$, $-C(O)NR^{1A}R^{1B}$, $-C(O)NHNR^{1A}R^{1B}$, $-OR^{1A}$, $-NR^{1A}SO_2R^{1B}$, $-NR^{1A}C(O)R^{1B}$, $-NR^{1A}C(O)OR^{1B}$, $-NR^{1A}OR^{1B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^3$ is selected from hydrogen, halogen, $-CX^3_3$, $-CHX^3_2$, $-CH_2X^3$, $-OCX^3_3$, $-OCH_2X^3$, $-OCHX^3_2$, $-CN$, $-SO_{v3}R^{3A}$, $-SO_{v3}NR^{3A}R^{3B}$, $-NHC(O)NR^{3A}R^{3B}$, $-N(O)_{m3}$, $-NR^{3A}R^{3B}$, $-NHNR^{3A}R^{3B}$, $-C(O)R^{3A}$, $-C(O)-OR^{3A}$, $-C(O)NR^{3A}R^{3B}$, $-OR^{3A}$, $-NR^{3A}SO_2R^{3B}$, $-NR^{3A}C(O)R^{3B}$, $-NR^{3A}C(O)OR^{3B}$, $-NR^{3A}OR^{3B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^4$ is selected from hydrogen, halogen, $-CX^4_3$, $-CHX^4_2$, $-CH_2X^4$, $-OCX^4_3$, $-OCH_2X^4$, $-OCHX^4_2$, $-CN$, $-SO_{n4}R^{4A}$, $-SO_{v4}NR^{4A}R^{4B}$, $-NHC(O)NR^{4A}R^{4B}$, $-N(O)_{m4}$, $-NR^{4A}R^{4B}$, $-NHNR^{4A}R^{4B}$, $-C(O)R^{4A}$, $-C(O)-OR^{4A}$, $-C(O)NR^{4A}R^{4B}$, $-C(O)NHNR^{4A}R^{4B}$, $-OR^{4A}$, $-NR^{4A}SO_2R^{4B}$, $-NR^{4A}C(O)R^{4B}$, $-NR^{4A}C(O)OR^{4B}$, $-NR^{4A}OR^{4B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; $R^3$ and $R^3$ substituents may optionally be joined to form a substituted or unsubstituted cycloalkyl or heterocycloalkyl;

$R^6$ is selected from hydrogen, halogen, $-CX^6_3$, $-CHX^6_2$, $-CH_2X^6$, $-OCX^6_3$, $-OCH_2X^6$, $-OCHX^6_2$, $-CN$, $-SO_{v6}R^{6A}$, $-SO_6NR^{6A}R^{6B}$, $-NHC(O)NR^{6A}R^{6B}$, $-N(O)_{m6}$, $-NR^{6A}R^{6B}$, $-NHNR^{6A}R^{6B}$, $-C(O)R^{6A}$, $-C(O)-OR^{6A}$, $-C(O)NR^{6A}R^{6B}$, $-C(O)NHNR^{6A}R^{6B}$, $-OR^{6A}$, $-NR^{6A}SO_2R^{6B}$, $-NR^{6A}C(O)R^{6B}$, $-NR^{6A}C(O)OR^{6B}$, $-NR^{6A}OR^{6B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^7$ is selected from hydrogen, halogen, —$CX^7_3$, —$CHX^7_2$, —$CH_2X^7$, —$OCX^7_3$, —$OCH_2X^7$, —$OCHX^7_2$, —CN, —$SO_{n7}R^{7A}$, —$SO_{v7}NR^{7A}R^{7B}$, —NHC(O)$NR^{7A}R^{7B}$, —N(O)$_{m7}$, —$NR^{7A}R^{7B}$, —$NHNR^{7A}R^{7B}$, —C(O)$R^{7A}$, —C(O)—$OR^{7A}$, —C(O)$NR^{7A}R^{7B}$, —C(O)$NHNR^{7A}R^{7B}$, —$OR^{7A}$, —$NR^{7A}SO_2R^{7B}$, —$NR^{7A}C(O)R^{7B}$, —$NR^{7A}C(O)OR^{7B}$, —$NR^{7A}OR^{7B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^9$ is selected from hydrogen, halogen, —$CX^9_3$, —$CHX^9_2$, —$CH_2X^9$, —$OCX^9_3$, —$OCH_2X^9$, —$OCHX^9_2$, —CN, —$SO_{n9}R^{9A}$, —$SO_{v9}NR^{9A}R^{9B}$, —NHC(O)$NR^{9A}R^{9B}$, —N(O)$_{m9}$, —$NR^{9A}R^{9B}$, —$NHNR^{9A}R^{9B}$, —C(O)$R^{9A}$, —C(O)—$OR^{9A}$, —C(O)$NR^{9A}R^{9B}$, —C(O)$NHNR^{9A}R^{9B}$, —$OR^{9A}$, —$NR^{9A}SO_2R^{9B}$, —$NR^{9A}C(O)R^{9B}$, —$NR^{9A}C(O)OR^{9B}$, —$NR^{9A}OR^{9B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{13}$ is selected from hydrogen, halogen, —$CX^{13}_3$, —$CHX^{13}_2$, —$CH_2X^{13}$, —$OCX^{13}_3$, —$OCH_2X^{13}$, —$OCHX^{13}_2$, —CN, —$SO_{n13}R^{13A}$, —$SO_{v13}NR^{13A}R^{13B}$, —NHC(O)$NR^{13A}R^{13B}$, —N(O)$_{m13}$, —$NR^{13A}R^{13B}$, —$NHNR^{13A}R^{13B}$, —C(O)$R^{13A}$, —C(O)—$OR^{13A}$, —C(O)$NR^{13A}R^{13B}$, —C(O)$NHNR^{13A}R^{13B}$, —$OR^{13A}$, —$NR^{13A}SO_2R^{13B}$, —$NR^{13A}C(O)R^{13B}$, —$NR^{13A}C(O)OR^{13B}$, —$NR^{13A}OR^{13B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{14}$ is selected from hydrogen, halogen, —$CX^{14}_3$, —$CHX^{14}_2$, —$CH_2X^{14}$, —$OCX^{14}_3$, —$OCH_2X^{14}$, —$OCHX^{14}_2$, —CN, —$SO_{n14}R^{14A}$, —$SO_{v11}4NR^{14A}R^{14B}$, —NHC(O)$NR^{14A}R^{14B}$, —N(O)$_{m14}$, —$NR^{14A}R^{14B}$, —$NHNR^{14A}R^{14B}$, —C(O)$R^{14A}$, —C(O)—$OR^{14A}$, —C(O)$NR^{14A}R^{14B}$, —C(O)$NHNR^{14A}R^{14B}$, —$OR^{14A}$, —$NR^{14A}SO_2R^{14B}$, —$NR^{14A}C(O)R^{14B}$, —$NR^{14A}C(O)OR^{14B}$, —$NR^{14A}OR^{14B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{15}$ is selected from hydrogen, halogen, —$CX^{15}_3$, —$CHX^5_2$, —$CH_2X^{15}$, —$OCX^{15}_3$, —$OCH_2X^1$, —$OCHX^{15}_2$, —CN, —$SO_{n1}R^{15A}$, —$SO_{v15}NR^{15A}R^{15B}$, —NHC(O)$NR^{15A}R^{15B}$, —N(O)$_{m5}$, —$NR^{15A}R^{15B}$, —$NHNR^{15A}R^{15B}$, —C(O)$R^{15A}$, —C(O)—$OR^{15A}$, —C(O)$NR^{15A}R^{15B}$, —C(O)$NHNR^{15A}R^{15B}$, —$OR^{15A}$, —$NR^{15A}SO_2R^{15B}$, —$NR^{15A}C(O)R^{15B}$, —$NR^{15A}C(O)OR^{15B}$, —$NR^{15A}OR^{15B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{16}$ is selected from hydrogen, halogen, —$CX^{16}_3$, —$CHX^{16}_2$, —$CH_2X^{16}$, —$OCX^{16}_3$, —$OCH_2X^{16}$, —$OCHX^{16}_2$, —CN, —$SO_{n16}R^{16A}$, —$SO_{v16}NR^{16A}R^{16B}$, —NHC(O)$NR^{16A}R^{16B}$, —N(O)$_{m16}$, —$NR^{16A}R^{16B}$, —$NHNR^{16A}R^{16B}$, —C(O)$R^{16A}$, —C(O)—$OR^{16A}$, —C(O)$NR^{16A}R^{16B}$, —C(O)$NHNR^{16A}R^{16B}$, —$OR^{16A}$, —$NR^{16A}SO_2R^{16B}$, —$NR^{16A}C(O)R^{16B}$, —$NR^{16A}C(O)OR^{16B}$, —$NR^{16A}OR^{16B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^7$ is selected from hydrogen, halogen, —$CX^{17}_3$, —$CHX^7_2$, —$CH_2X^7$, —$OCX^7_3$, —$OCH_2X^{17}$, —$OCHX^{17}_2$, —CN, —$SO_{n17}R^{17A}$, —$SO_{v17}NR^{17A}R^{17B}$, —NHC(O)$NR^{17A}R^{17B}$, —N(O)$_{m17}$, —$NR^{17A}R^{17B}$, —$NHNR^{17A}R^{17B}$, —C(O)$R^{14}$, —C(O)—$OR^{17A}$, —C(O)$NR^{17A}R^{17B}$, —C(O)$NHNR^{17A}R^{17B}$, —$OR^{17A}$, —$NR^{17A}SO_2R^{17B}$, —$NR^{17A}C(O)R^{17B}$, —$NR^{17A}C(O)OR^{17B}$, —$NR^{17A}OR^{17B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{18}$ is selected from hydrogen, halogen, —$CX^{18}_3$, —$CHX^{18}_2$, —$CH_2X^{18}$, —$OCX^{18}_3$, —$OCH_2X^{11}$, —$OCHX^{18}_2$, —CN, —$SO_{n18}R^{18A}$, —$SO_{v18}NR^{18A}R^{18B}$, —NHC(O)$NR^{18A}R^{18B}$, —N(O)$_{m18}$, —$NR^{18A}R^{18B}$, —$NHNR^{18A}R^{18B}$, —C(O)$R^{18A}$, —C(O)—$OR^{18A}$, —C(O)$NR^{18A}R^{18B}$, —C(O)$NHNR^{18A}R^{18B}$, —$OR^{18A}$, —$NR^{18A}SO_2R^{18B}$, —$NR^{18A}C(O)R^{18B}$, —$NR^{18A}C(O)OR^{18B}$, —$NR^{18A}OR^{18B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; $R^{16}$ and $R^{18}$ substituents may optionally be joined to form a substituted or unsubstituted cycloalkyl or heterocycloalkyl;

$R^{19}$ is selected from hydrogen, halogen, —$CX^{19}_3$, —$CHX^{19}_2$, —$CH_2X^{19}$, —$OCX^{19}_3$, —$OCH_2X^{19}$, —$OCHX^{19}_2$, —CN, —$SO_{n19}R^{19A}$, —$SO_{v19}NR^{19A}R^{19B}$, —NHC(O)$NR^{19A}R^{19B}$, —N(O)$_{m19}$, —$NR^{19A}R^{19B}$, —$NHNR^{19A}R^{19B}$, —C(O)$R^{19A}$, —C(O)—$OR^{19A}$, —C(O)$NR^{19A}R^{19B}$, —C(O)$NHNR^{19A}R^{19B}$, —$OR^{19A}$, —$NR^{19A}SO_2R^{19B}$, —$NR^{19A}C(O)R^{19B}$, —$NR^{19A}C(O)OR^{19B}$, —$NR^{19A}OR^{19B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; $R^{16}$ and $R^{19}$ substituents may optionally be joined to form a substituted or unsubstituted cycloalkyl or heterocycloalkyl;

$R^{20}$ is selected from hydrogen, halogen, —$CX^{20}_3$, —$CHX^{20}_2$, —$CH_2X^{20}$, —$OCX^{20}_3$, —$OCH_2X^{20}$, —$OCHX^{20}_2$, —CN, —$SO_{n20}R^{20A}$, —$SO_{v20}NR^{20A}R^{20B}$, —NHC(O)$NR^{20A}R^{20B}$, —N(O)$_{m20}$, —$NR^{20A}R^{20B}$, —$NHNR^{20A}R^{20B}$, —C(O)$R^{20A}$, —C(O)—$OR^{20A}$, —C(O)$NR^{20A}R^{20B}$, —C(O)$NHNR^{20A}R^{20B}$, —$OR^{20A}$, —$NR^{20A}$, —$SO_2R^{20B}$, —$NR^{20A}C(O)R^{20B}$, —$NR^{20A}C(O)OR^{20B}$, —$NR^{20A}OR^{20B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{21}$ is selected from hydrogen, halogen, $-CX^{21}_3$, $-CHX^{21}_2$, $-CH_2X^{21}$, $-OCX^{21}_3$, $-OCH_2X^{21}$, $-OCHX^{21}_2$, $-CN$, $-SO_{n21}R^{21A}$, $-SO_{v21}NR^{21A}R^{21B}$, $-NHC(O)NR^{21A}R^{21B}$, $-N(O)_{m21}$, $-NR^{21A}R^{21B}$, $-NHNR^{21A}R^{21B}$, $-C(O)R^{21A}$, $-C(O)-OR^{21A}$, $-C(O)NR^{21A}R^{21B}$, $-C(O)NHNR^{21A}R^{21B}$, $-OR^{21A}$, $-NR^{21A}SO_2R^{21B}$, $-NR^{21A}C(O)R^{21B}$, $-NR^{21A}C(O)OR^{21B}$, $-NR^{21A}OR^{21B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; $R^{20}$ and $R^{21}$ substituents may optionally be joined to form a substituted or unsubstituted cycloalkyl or heterocycloalkyl;

$R^{22}$ is selected from hydrogen, halogen, $-CX^{22}_3$, $-CHX^{22}_2$, $-CH_2X^{22}$, $-OCX^{22}_3$, $-OCH_2X^{22}$, $-OCHX^{22}_2$, $-CN$, $-SO_{n22}R^{22A}$, $-SO_{v22}NR^{22A}R^{22B}$, $-NHC(O)NR^{22A}R^{22B}$, $-N(O)_{m22}$, $-NR^{22A}R^{22B}$, $-NHNR^{22A}R^{22B}$, $-C(O)R^{22A}$, $-C(O)-OR^{22A}$, $-C(O)NR^{22A}R^{22B}$, $-C(O)NHNR^{22A}R^{22B}$, $-OR^{22A}$, $-NR^{22A}SO_2R^{22B}$, $-NR^{22A}C(O)R^{22B}$, $-NR^{22A}C(O)OR^{22B}$, $-NR^{22A}OR^{22B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{23}$ is selected from hydrogen, halogen, $-CX^{23}_3$, $-CHX^{23}_2$, $-CH_2X^{23}$, $-OCX^{23}_3$, $-OCH_2X^{23}$, $-OCHX^{23}_2$, $-CN$, $-SO_{n23}R^{23A}$, $-SO_{v23}NR^{23A}R^{23B}$, $-NHC(O)NR^{23A}R^{23B}$, $-N(O)_{m23}$, $-NR^{23A}R^{23B}$, $-NHNR^{23A}R^{23B}$, $-C(O)R^{23A}$, $-C(O)-OR^{23A}$, $-C(O)NR^{23A}R^{23B}$, $-C(O)NHNR^{23A}R^{23B}$, $-OR^{23A}$, $-NR^{23A}SO_2R^{23B}$, $-NR^{23A}C(O)R^{23B}$, $-NR^{23A}C(O)OR^{23B}$, $-NR^{23A}OR^{23B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{24}$ is selected from hydrogen, halogen, $-CX^{24}_3$, $-CHX^{24}_2$, $-CH_2X^{24}$, $-OCX^{24}_3$, $-OCH_2X^{24}$, $-OCHX^{24}_2$, $-CN$, $-SO_{n24}R^{24A}$, $-SO_{v24}NR^{24A}R^{24B}$, $-NHC(O)NR^{24A}R^{24B}$, $-N(O)_{m24}$, $-NR^{24A}R^{24B}$, $-NHNR^{24A}R^{24B}$, $-C(O)R^{24A}$, $-C(O)-OR^{24A}$, $-C(O)NR^{24A}R^{24B}$, $-C(O)NHNR^{24A}R^{24B}$, $-OR^{24A}$, $-NR^{24A}SO_2R^{24B}$, $-NR^{24A}C(O)R^{24B}$, $-NR^{24A}C(O)OR^{24B}$, $-NR^{24A}OR^{24B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{25}$ is selected from hydrogen, halogen, $-CX^{25}_3$, $-CHX^{25}_2$, $-CH_2X^{25}$, $-OCX^{25}_3$, $-OCH_2X^{25}$, $-OCHX^{25}_2$, $-CN$, $-SO_{n25}R^{25A}$, $-SO_{v25}NR^{25A}R^{25B}$, $-NHC(O)NR^{25A}R^{25B}$, $-N(O)_{m25}$, $-NR^{25A}R^{25B}$, $-NHNR^{25A}R^{25B}$, $-C(O)R^{25A}$, $-C(O)-OR^{25A}$, $-C(O)NR^{25A}R^{25B}$, $-C(O)NHNR^{25A}R^{25B}$, $-OR^{25A}$, $-NR^{25A}SO_2R^{25B}$, $-NR^{25A}C(O)R^{25B}$, $-NR^{25A}C(O)OR^{25B}$, $-NR^{25A}OR^{25B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{26}$ is selected from hydrogen, halogen, $-CX^{26}_3$, $-CHX^{26}_2$, $-CH_2X^{26}$, $-OCX^{26}_3$, $-OCH_2X^{26}$, $-OCHX^{26}_2$, $-CN$, $-SO_{n26}R^{26A}$, $-SO_{v26}NR^{26A}R^{26B}$, $-NHC(O)NR^{26A}R^{26B}$, $-N(O)_{m26}$, $-NR^{26A}R^{26B}$, $-NHNR^{26A}R^{26B}$, $-C(O)R^{26A}$, $-C(O)-OR^{26A}$, $-C(O)NR^{26A}R^{26B}$, $-C(O)NHNR^{26A}R^{26B}$, $-OR^{26A}$, $-NR^{26A}SO_2R^{26B}$, $-NR^{26A}C(O)R^{26B}$, $-NR^{26A}C(O)OR^{26B}$, $-NR^{26A}OR^{26B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{27}$ is selected from hydrogen, halogen, $-CX^{27}_3$, $-CHX^{27}_2$, $-CH_2X^{27}$, $-OCX^{27}_3$, $-OCH_2X^{27}$, $-OCHX^{27}_2$, $-CN$, $-SO_{n27}R^{27A}$, $-SO_{v27}NR^{27A}R^{27B}$, $-NHC(O)NR^{27A}R^{27B}$, $-N(O)_{m27}$, $-NR^{27A}R^{27B}$, $-NHNR^{27A}R^{27B}$, $-C(O)R^{27A}$, $-C(O)-OR^{27A}$, $-C(O)NR^{27A}R^{27B}$, $-C(O)NHNR^{27A}R^{27B}$, $-OR^{27A}$, $-NR^{27A}SO_2R^{27B}$, $-NR^{27A}C(O)R^{27B}$, $-NR^{27A}C(O)OR^{27B}$, $-NR^{27A}OR^{27B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{28}$ is selected from hydrogen, halogen, $-CX^{28}_3$, $-CHX^{28}_2$, $-CH_2X^{28}$, $-OCX^{28}_3$, $-OCH_2X^{28}$, $-OCHX^{28}_2$, $-CN$, $-SO_{n28}R^{28A}$, $-SO_{v28}NR^{28A}R^{28B}$, $-NHC(O)NR^{28A}R^{28B}$, $-N(O)_{m2}$, $-NR^{28A}R^{28B}$, $-NHNR^{28A}R^{28B}$, $-C(O)R^{28A}$, $-C(O)-OR^{28A}$, $-C(O)NR^{28A}R^{28B}$, $-C(O)NHNR^{28A}R^{28B}$, $-OR^{28A}$, $-NR^{28A}SO_2R^{28B}$, $-NR^{28A}C(O)R^{28B}$, $-NR^{28A}C(O)OR^{28B}$, $-NR^{28A}OR^{28B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{29}$ is selected from hydrogen, halogen, $-CX^{29}_3$, $-CHX^{29}_2$, $-CH_2X^{29}$, $-OCX^{29}_3$, $-OCH_2X^{29}$, $-OCHX^{29}_2$, $-CN$, $-SO_{n29}R^{9A}$, $-SO_{v29}NR^{29A}R^{29B}$, $-NHC(O)NR^{29A}R^{29B}$, $-N(O)_{m29}$, $-NR^{29A}R^{29B}$, $-NHNR^{29A}R^{29B}$, $-C(O)R^{29A}$, $-C(O)-OR^{29A}$, $-C(O)NR^{29A}R^{29B}$, $-C(O)NHNR^{29A}R^{29B}$, $-OR^{29A}$, $-NR^{29A}SO_2R^{29B}$, $-NR^{29A}C(O)R^{29B}$, $-NR^{29A}C(O)OR^{29B}$, $-NR^{29A}OR^{29B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{30}$ is selected from hydrogen, halogen, $-CX^{30}_3$, $-CHX^{30}_2$, $-CH_2X^{30}$, $-OCX^{30}_3$, $-OCH_2X^{30}$, $-OCHX^{30}_2$, $-CN$, $-SO_{n30}R^{30A}$, $-SO_{v30}NR^{30A}R^{30B}$, $-NHC(O)NR^{30A}R^{30B}$, $-N(O)_{m30}$, $-NR^{30A}R^{30B}$, $-NHNR^{30A}R^{30B}$, $-C(O)R^{30A}$, $-C(O)-OR^{30A}$, $-C(O)NR^{30A}R^{30B}$, $-C(O)NHNR^{30A}R^{30B}$, $-OR^{30A}$, $-NR^{30A}SO_2R^{30B}$, $-NR^{30A}C(O)R^{30B}$, $-NR^{30A}C(O)OR^{30B}$, $-NR^{30A}OR^{30B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{31}$ is selected from hydrogen, halogen, —$CX^{31}_3$, —$CHX^{31}_2$, —$CH_2X^{31}$, —$OCX^{31}_3$, —$OCH_2X^{31}$, —$OCHX^{31}_2$, —CN, —$SO_{n31}R^{31A}$, —$SO_{v31}NR^{31A}R^{31B}$, —$NHC(O)NR^{31A}R^{31B}$, —$N(O)_{m31}$, —$NR^{31A}R^{31B}$, —$NHNR^{31A}R^{31B}$, —$C(O)R^{31A}$, —$C(O)$—$OR^{31A}$, —$C(O)NR^{31A}R^{31B}$, —$C(O)NHNR^{31A}R^{31B}$, —$OR^{31A}$, —$NR^{31A}SO_2R^{31B}$, —$NR^{31A}C(O)R^{31B}$, —$NR^{31A}C(O)OR^{31B}$, —$NR^{31A}OR^{31B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{32}$ is selected from hydrogen, halogen, —$CX^{33}_3$, —$CHX^{32}_2$, —$CH_2X^{32}$, —$OCX^{33}_3$, —$OCH_2X^{32}$, —$OCHX^{32}_2$, —CN, —$SO_{n32}R^{32A}$, —$SO_{v32}NR^{32A}R^{32B}$, —$NHC(O)NR^{32A}R^{32B}$, —$N(O)_{m32}$, —$NR^{32A}R^{32B}$, —$NHNR^{32A}R^{32B}$, —$C(O)R^{32A}$, —$C(O)$—$OR^{32A}$, —$C(O)NR^{32A}R^{32B}$, —$C(O)NHNR^{32A}R^{32B}$, —$OR^{32A}$, —$NR^{32A}SO_2R^{32B}$, —$NR^{32A}C(O)R^{32B}$, —$NR^{32A}C(O)OR^{32B}$, —$NR^{32A}OR^{32B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{33}$ is selected from hydrogen, halogen, —$CX^{33}_3$, —$CHX^{33}_2$, —$CH_2X^{33}$, —$OCX^{33}_3$, —$OCH_2X^{33}$, —$OCHX^{33}_2$, —CN, —$SO_{n33}R^{33A}$, —$SO_{v33}NR^{33A}R^{33B}$, —$NHC(O)NR^{33A}R^{33B}$, —$N(O)_{m33}$, —$NR^{33A}R^{33B}$, —$NHNR^{33A}R^{33B}$, —$C(O)R^{33A}$, —$C(O)$—$OR^{33A}$, —$C(O)NR^{33A}R^{33B}$, —$C(O)NHNR^{33A}R^{33B}$, —$OR^{33A}$, —$NR^{33A}SO_2R^{33B}$, —$NR^{33A}C(O)R^{33B}$, —$NR^{33A}C(O)OR^{33B}$, —$NR^{33A}OR^{33B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{34}$ is selected from hydrogen, halogen, —$CX^{34}_3$, —$CHX^{34}_2$, —$CH_2X^{34}$, —$OCX^{34}_3$, —$OCH_2X^{34}$, —$OCHX^{34}_2$, —CN, —$SO_{n34}R^{34A}$, —$SO_{v34}NR^{34A}R^{34B}$, —$NHC(O)NR^{34A}R^{34B}$, —$N(O)_{m34}$, —$NR^{34A}R^{34B}$, —$NHNR^{34A}R^{34B}$, —$C(O)R^{34A}$, —$C(O)$—$OR^{34A}$, —$C(O)NR^{34A}R^{34B}$, —$C(O)NHNR^{34A}R^{34B}$, —$OR^{34A}$, —$NR^{34A}SO_2R^{34B}$, —$NR^{34A}C(O)R^{34B}$, —$NR^{34A}C(O)OR^{34B}$, —$NR^{34A}OR^{34B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{35}$ is selected from hydrogen, halogen, —$CX^{35}_3$, —$CHX^{35}_2$, —$CH_2X^{35}$, —$OCX^{35}_3$, —$OCH_2X^{35}$, —$OCHX^{35}_2$, —CN, —$SO_{n35}R^{35A}$, —$SO_{v35}NR^{35A}R^{35B}$, —$NHC(O)NR^{35A}R^{35B}$, —$N(O)_{m35}$, —$NR^{35A}R^{35B}$, —$NHNR^{35A}R^{35B}$, —$C(O)R^{35A}$, —$C(O)$—$OR^{35A}$, —$C(O)NR^{35A}R^{35B}$, —$C(O)NHNR^{35A}R^{35B}$, —$OR^{35A}$, —$NR^{35A}SO_2R^{35B}$, —$NR^{35A}C(O)R^{35B}$, —$NR^{35A}C(O)OR^{35B}$, —$NR^{35A}OR^{35B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

Each $R^{1A}$, $R^{1B}$, $R^{3A}$, $R^{3B}$, $R^{4A}$, $R^{4B}$, $R^{6A}$, $R^{6B}$, $R^{7A}$, $R^{7B}$, $R^{9A}$, $R^{9B}$, $R^{13A}$, $R^{13B}$, $R^{14A}$, $R^{14B}$, $R^{15A}$, $R^{15B}$, $R^{16A}$, $R^{16B}$, $R^{17A}$, $R^{17B}$, $R^{18A}$, $R^{18B}$, $R^{19A}$, $R^{19B}$, $R^{20A}$, $R^{20B}$, $R^{21A}$, $R^{21B}$, $R^{22A}$, $R^{22B}$, $R^{23A}$, $R^{23B}$, $R^{24A}$, $R^{24B}$, $R^{25A}$, $R^{25B}$, $R^{26A}$, $R^{26B}$, $R^{27A}$, $R^{27B}$, $R^{28A}$, $R^{28B}$, $R^{29A}$, $R^{29B}$, $R^{30A}$, $R^{30B}$, $R^{31A}$, $R^{31B}$, $R^{32A}$, $R^{32B}$, $R^{33A}$, $R^{33B}$, $R^{34A}$, $R^{34B}$, $R^{35A}$, $R^{35B}$ is independently selected from hydrogen, —$CX_3$, —$CHX_2$, —$CH_2X$, —$C(O)OH$, —$C(O)NH_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —$NHC=(O)NHNH_2$, —$NHC=(O)NH_2$, —$NHSO_2H$, —$NHC=(O)H$, —NHC(O)OH, —NHOH, —$OCX_3$, —$OCHX_2$, —$OCH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{4A}$ and $R^{4B}$ substituents bonded to the same nitrogen atom may optionally be joined to form a substituted or unsubstituted heterocycloalkyl or substituted or unsubstituted heteroaryl; $R^{6A}$ and $R^{6B}$ substituents bonded to the same nitrogen atom may optionally be joined to form a substituted or unsubstituted heterocycloalkyl or substituted or unsubstituted heteroaryl; $R^{7A}$ and $R^{7B}$ substituents bonded to the same nitrogen atom may optionally be joined to form a substituted or unsubstituted heterocycloalkyl or substituted or unsubstituted heteroaryl; $R^{9A}$ and $R^{9B}$ substituents bonded to the same nitrogen atom may optionally be joined to form a substituted or unsubstituted heterocycloalkyl or substituted or unsubstituted heteroaryl; $R^{13A}$ and $R^{13B}$ substituents bonded to the same nitrogen atom may optionally be joined to form a substituted or unsubstituted heterocycloalkyl or substituted or unsubstituted heteroaryl; $R^{14A}$ and $R^{14B}$ substituents bonded to the same nitrogen atom may optionally be joined to form a substituted or unsubstituted heterocycloalkyl or substituted or unsubstituted heteroaryl; $R^{15A}$ and $R^{15B}$ substituents bonded to the same nitrogen atom may optionally be joined to form a substituted or unsubstituted heterocycloalkyl or substituted or unsubstituted heteroaryl; $R^{16A}$ and $R^{16B}$ substituents bonded to the same nitrogen atom may optionally be joined to form a substituted or unsubstituted heterocycloalkyl or substituted or unsubstituted heteroaryl; $R^{17A}$ and $R^{17B}$ substituents bonded to the same nitrogen atom may optionally be joined to form a substituted or unsubstituted heterocycloalkyl or substituted or unsubstituted heteroaryl; $R^{18A}$ and $R^{18B}$ substituents bonded to the same nitrogen atom may optionally be joined to form a substituted or unsubstituted heterocycloalkyl or substituted or unsubstituted heteroaryl; $R^{19A}$ and $R^{19B}$ substituents bonded to the same nitrogen atom may optionally be joined to form a substituted or unsubstituted heterocycloalkyl or substituted or unsubstituted heteroaryl; $R^{20A}$ and $R^{20B}$, substituents bonded to the same nitrogen atom may optionally be joined to form a substituted or unsubstituted heterocycloalkyl or substituted or unsubstituted heteroaryl; $R^{21A}$ and $R^{21B}$ substituents bonded to the same nitrogen atom may optionally be joined to form a substituted or unsubstituted heterocycloalkyl or substituted or unsubstituted heteroaryl; $R^{22A}$ and $R^{22B}$ substituents bonded to the same nitrogen atom may optionally be joined to form a substituted or unsubstituted heterocycloalkyl or substituted or unsubstituted heteroaryl; $R^{23A}$ and $R^{23B}$ substituents bonded to the same nitrogen atom may optionally be joined to form a substituted or unsubstituted heterocycloalkyl or substituted or unsubstituted heteroaryl; $R^{24A}$ and $R^{24B}$ substituents bonded to the same nitrogen atom may optionally be joined to form a substituted or unsubstituted heterocycloalkyl or substituted or unsubstituted heteroaryl; $R^{25A}$ and $R^{25B}$ substituents bonded to the same nitrogen atom may optionally be joined to form a substituted or unsubstituted heterocycloalkyl or substituted or unsubstituted heteroaryl; $R^{26A}$ and $R^{26B}$ substituents bonded to the same nitrogen atom may optionally be joined to form a substituted or unsubstituted heterocycloalkyl or substituted or unsubstituted heteroaryl; $R^{27A}$ and $R^{27B}$ substituents bonded to the same nitrogen atom may optionally be joined to form a substituted or unsubstituted heterocycloalkyl or substituted or unsubstituted heteroaryl; $R^{28A}$ and $R^{28B}$ substituents bonded to the same nitrogen atom may optionally be joined to form a substituted or unsubstituted heterocycloalkyl or substituted or unsubstituted heteroaryl; $R^{29A}$ and $R^{29B}$ substituents bonded to the same nitrogen atom may optionally be joined to form a substituted or unsubstituted heterocycloalkyl or substituted or unsubstituted heteroaryl; $R^{30A}$ and $R^{30B}$ substituents bonded to the same nitrogen atom may optionally be joined to form a substituted or unsubstituted heterocycloalkyl or substituted or unsubstituted heteroaryl.

Each m1, m3, m4, m6, m7, m9, m13, m14, m15, m16, m17, m18, m19, m20, m21, m22, m23, m24, m25, m26, m27, m28, m29, m30, m31, m32, m33, m34 and m35 is independently 1 or 2.

Each v1, v3, v4, v6, v7, v9, v13, v14, v15, v16, v17, v18, v19, v20, v21, v22, v23, v24, v25, v26, v27, v28, v29, v30, v31, v32, v33, v34 and v35 is independently 1 or 2.

Each n1, n3, n4, n6, n7, n9, n13, n14, n15, n16, n17, n18, n19, n20, n21, n22, n23, n24, n25, n26, n27, n28, n29, n30, n31, n32, n33, n34 and n35 is an integer from 0 to 2; and Each $X^1$, $X^3$, $X^4$, $X^6$, $X^7$, $X^9$, $X^{13}$, $X^{14}$, $X^{15}$, $X^{16}$, $X^{17}$, $X^{18}$, $X^{19}$, $X^{20}$, $X^{21}$, $X^{22}$, $X^{23}$, $X^{24}$, $X^{25}$, $X^{26}$, $X^{27}$, $X^{28}$, $X^{29}$, $X^{30}$, $X^{31}$, $X^{32}$, $X^{33}$, $X^{34}$, and $X^{35}$ is independently —Cl, —Br, —I or —F.

In one embodiment, ring B is optionally substituted with one or more substituent groups.

In one embodiment of compounds of Formula VI, ring B is selected from thienyl, furanyl, pyrrolyl, thiazolyl, oxazolyl, imidazolyl, pyrazolyl, isoxazolyl, triazolyl and isothiazolyl. In one embodiment, the thienyl, furanyl, pyrrolyl, thiazolyl, oxazolyl, imidazolyl, pyrazolyl, isoxazolyl, triazolyl and isothiazolyl rings are optionally substituted with one or more substituent groups.

In one embodiment of compounds of Formula VI, ring B is selected from phenyl, pyridyl, pyrazinyl, pyrimidinyl, pyridazinyl, and triazinyl. In one embodiment, the phenyl, pyridyl, pyrazinyl, pyrimidinyl, pyridazinyl, and triazinyl rings are optionally substituted with one or more substituent groups.

In one embodiment of compounds of Formula VI, ring B is selected from selected from

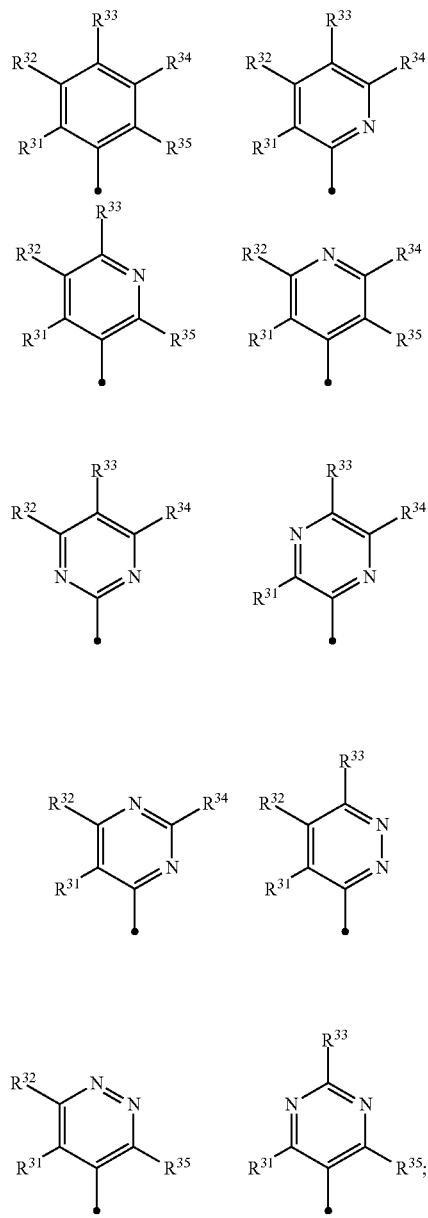

In one embodiment of compounds of Formula VI, ring B is selected from benzothienyl, benzothiazolyl, indolyl, benzimidazolyl, benzoxazolyl, benzofuryl, indazolyl and isolindolyl. In one embodiment, the benzothienyl, benzothiazolyl, indolyl, benzimidazolyl, benzoxazolyl, benzofuryl, indazolyl and isolindolyl rings are optionally substituted with one or more substituent groups.

In one embodiment of compounds of Formula VI, ring B is selected from quinolyl, isoquinolyl, naphthpyridinyl, quinoxalinyl and quinazolinyl. In one embodiment, the quinolyl, isoquinolyl, naphthpyridinyl, quinoxalinyl and quinazolinyl rings are optionally substituted with one or more substituent groups.

In one embodiment of compounds of Formula VI, E is selected from —C(=O)CH=$CH_2$, —C(=O)-ethynyl, —C(=O)CH=$CHCF_3$, —C(=O)CH=$CHCHF_2$, —C(=O)CH=$CHCH_2F$, and —C(=O)$CH_2$Br.

The invention also relates to compounds of Formula VII:

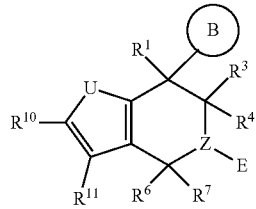

(VII)

wherein
Z is N, or $CR^9$;
U is selected from $NR^{12}$, O, S, S=O, O=S=O, and Se;
ring B is selected from selected from
  a) 5- or 6-membered cycloalkyl, saturated or partially saturated heterocyclyl,
  b) 5- or 6-membered aryl or heteroaryl,
  c) 9-, 10- or 11-membered fused partially saturated heterocyclyl,
  d) 9- or 10-membered fused heteroaryl,
  e) naphthyl, and
  f) 4-, 5- or 6-membered cycloalkenyl;
E is an electrophilic moiety, selected from

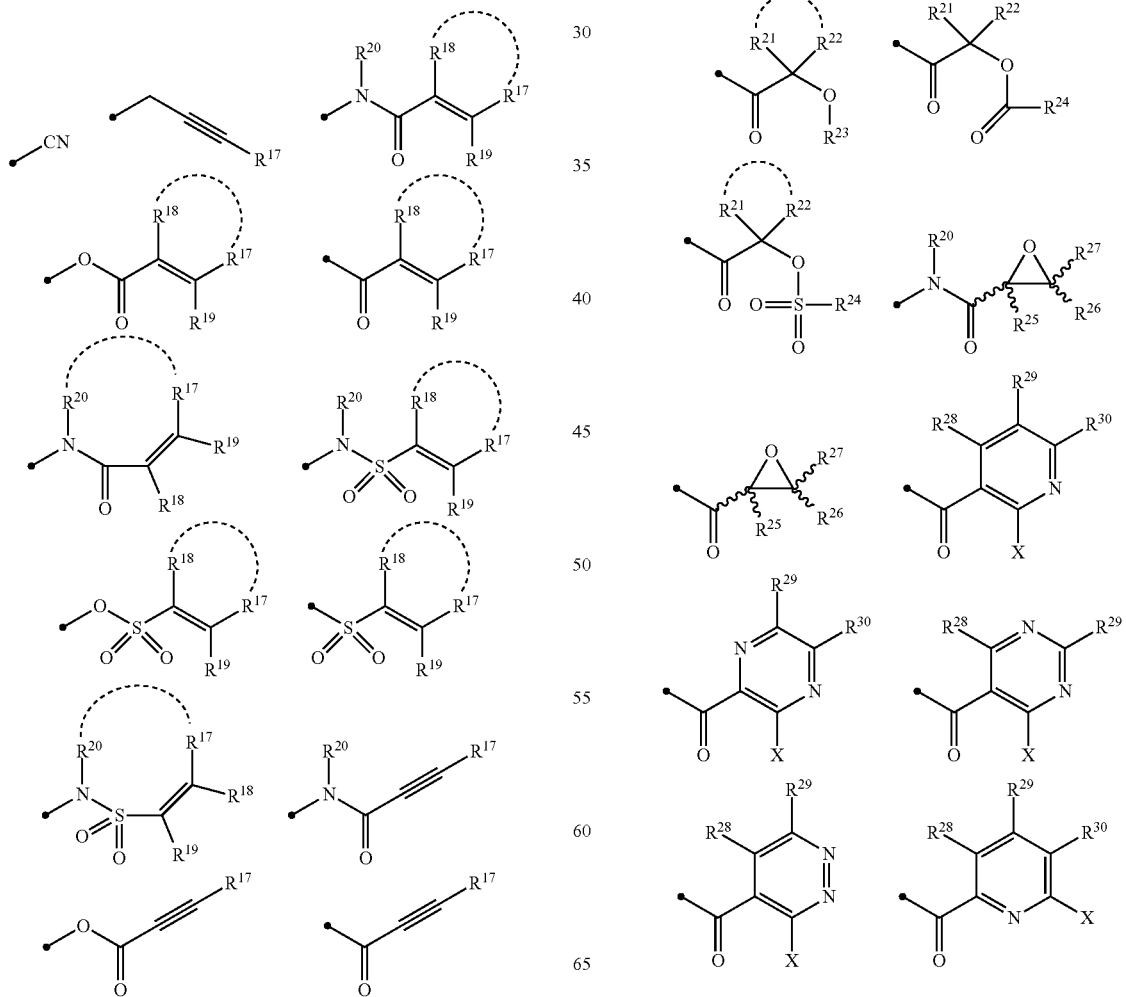

-continued

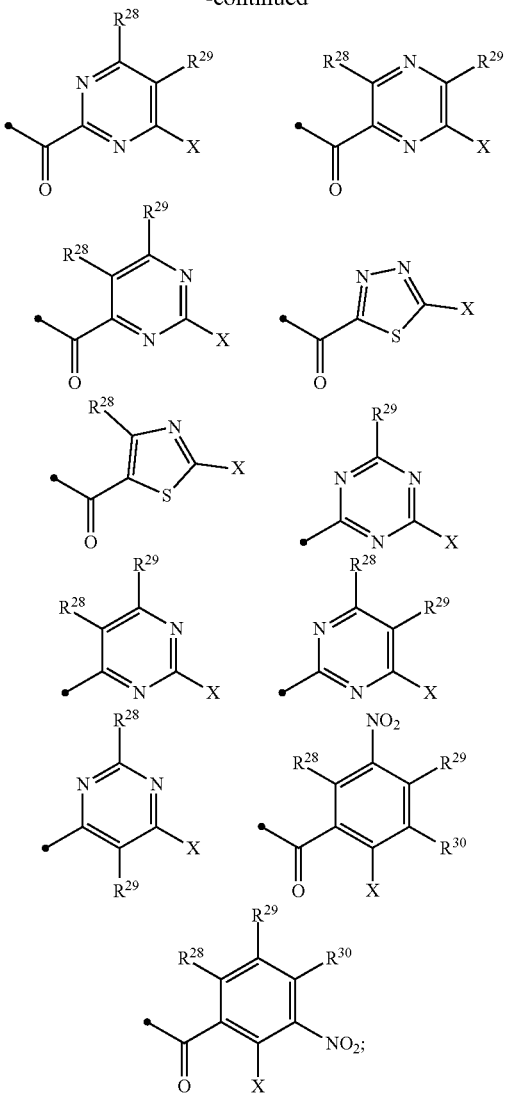

R[1] is selected from hydrogen, halogen, —CX$^1_3$, —CHX$^1_2$, —CH$_2$X$^1$, —OCX$^1_3$, —OCH$_2$X$^1$, —OCHX$^1_2$, —CN, —SO$_{n1}$R$^{1A}$, —SO$_{v1}$NR$^{1A}$R$_{1B}$, —NHC(O)NR$^{1A}$R$^{1B}$, —N(O)$_{m1}$, —NR$^{1A}$R$^{1}$, —NHNR$^{1A}$R$^{1B}$, —C(O)R$^{1A}$, —C(O)—OR$^{1A}$, —C(O)NR$^{1A}$R$^{1B}$, —C(O)NHNR$^{1A}$R$^{1B}$, —OR$^{1A}$, —NR$^{1A}$SO$_2$R$^{1B}$, —NR$^{1A}$C(O)R$^{1B}$, —NR$^{1A}$C(O)OR$^{1B}$, —NR$^{1A}$OR$^{1B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R[3] is selected from hydrogen, halogen, —CX$^3_3$, —CHX$^3_2$, —CH$_2$X$^3$, —OCX$^3_3$, —OCH$_2$X$^3$, —OCHX$^3_2$, —CN, —SO$_3$R$^{3A}$, —SO$_{v3}$NR$^{3A}$R$^{3B}$, —NHC(O)NR$^{3A}$R$^{3B}$, —N(O)$_{m3}$, —NR$^{3A}$R$^{3B}$, —NHNR$^{3A}$R$^{3B}$, —C(O)R$^{3A}$, —C(O)—OR$^{3A}$, —C(O) NR$^{3A}$R$^{3B}$, —OR$^{3A}$, —NR$^{3A}$SO$_2$R$^{3B}$, —NR$^{3A}$C(O)R$^{3B}$, —NR$^{3A}$C(O)OR$^{3B}$, —NR$^{3A}$OR$^{3B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R[4] is selected from hydrogen, halogen, —CX$^4_3$, —CHX$^4_2$, —CH$_2$X$^4$, —OCX$^4_3$, —OCH$_2$X$^4$, —OCHX$^4_2$, —CN, —SO$_{n4}$R$^{4A}$, —SO$_4$NR$^{4A}$R$^{4B}$, —NHC(O)NR$^{4A}$R$^{4B}$, —N(O)$_{m4}$, —NR$^{4A}$R$^{4B}$, —NHNR$^{4A}$R$^{4B}$, —C(O)R$^{4A}$, —C(O)—OR$^{4A}$, —C(O) NR$^{4A}$R$^{4B}$, —C(O)NHNR$^{4A}$R$^{4B}$, —OR$^{4A}$, —NR$^{4A}$SO$_2$R$^{4B}$, —NR$^{4A}$C(O)R$^{4B}$, —NR$^{4A}$C(O)OR$^{4B}$, —NR$^{4A}$OR$^{4B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; R[3] and R[3] substituents may optionally be joined to form a substituted or unsubstituted cycloalkyl or heterocycloalkyl;

R[6] is selected from hydrogen, halogen, —CX$^6_3$, —CHX$^6_2$, —CH$_2$X$^6$, —OCX$^6_3$, —OCH$_2$X$^6$, —OCHX$^6_2$, —CN, —SO$_{v6}$R$^{6A}$, —SO$_{v6}$NR$^{6A}$R$^{6B}$, —NHC(O)NR$^{6A}$R$^{6B}$, —N(O)$_{m6}$, —NR$^{6A}$R$^{6B}$, —NHNR$^{6A}$R$^{6B}$, —C(O)R$^{6A}$, —C(O)—OR$^{6A}$, —C(O) NR$^{6A}$R$^{6B}$, —C(O)NHNR$^{6A}$R$^{6B}$, —OR$^{6A}$, —NR$^{6A}$SO$_2$R$^{6B}$, —NR$^{6A}$C(O)R$^{6B}$, —NR$^{6A}$C(O)OR$^{6B}$, —NR$^{6A}$OR$^{6B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R[7] is selected from hydrogen, halogen, —CX$^7_3$, —CHX$^7_2$, —CH$_2$X$^7$, —OCX$^7_3$, —OCH$_2$X$^7$, —OCHX$^7_2$, —CN, —SO$_7$R$^{7A}$, —SO$_{v7}$NR$^{7A}$R$^{7B}$, —NHC(O)NR$^{7A}$R$^{7B}$, —N(O)$_{m7}$, —NR$^{7A}$R$^{7B}$, —NHNR$^{7A}$R$^{7B}$, —C(O)R$^{7A}$, —C(O)—OR$^{7A}$, —C(O) NR$^{7A}$R$^{7B}$, —C(O)NHNR$^{7A}$R$^{7B}$, —OR$^{7A}$, —NR$^{7A}$SO$_2$R$^{7B}$, —NR$^{7A}$C(O)R$^{7B}$, —NR$^{7A}$C(O)OR$^{7B}$, —NR$^{7A}$OR$^{7B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R[9] is selected from hydrogen, halogen, —CX$^9_3$, —CHX$^9_2$, —CH$_2$X$^9$, —OCX$^9_3$, —OCH$_2$X$^9$, —OCHX$^9_2$, —CN, —SO$_{v9}$R$^{9A}$, —SO$_{v9}$NR$^{9A}$R$^{9B}$, —NHC(O)NR$^{9A}$R$^{9B}$, —N(O)$_{m9}$, —NR$^{9A}$R$^{9B}$, —NHNR$^{9A}$R$^{9B}$, —C(O)R$^{9A}$, —C(O)—OR$^{9A}$, —C(O) NR$^{9A}$R$^{9B}$, —C(O)NHNR$^{9A}$R$^{9B}$, —OR$^{9A}$, —NR$^{9A}$SO$_2$R$^{9B}$, —NR$^{9A}$C(O)R$^{9B}$, —NR$^{9A}$C(O)OR$^{9B}$, —NR$^{9A}$OR$^{9B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R[10] is selected from hydrogen, halogen, —CX$^{10}_3$, —CHX$^{10}_2$, —CH$_2$X$^{10}$, —OCX$^{10}_3$, —OCH$_2$X$^{10}$, —OCHX$^{10}_2$, —CN, —SO$_{n10}$R$^{10A}$, —SO$_{v10}$NR$^{10A}$R$^{10B}$, —NHC(O)NR$^{10A}$R$^{10B}$, —N(O)$_{m10}$, —NR$^{10A}$R$^{10B}$, —NHNR$^{10A}$R$^{10B}$, —C(O) R$^{10A}$, —C(O)—OR$^{10A}$, —C(O)NR$^{10A}$R$^{10B}$, —C(O) NHNR$^{10A}$R$^{10B}$, —OR$^{10A}$, —NR$^{10A}$SO$_2$R$^{10B}$, —NR$^{10A}$C(O)R$^{10B}$, —NR$^{10A}$C(O)OR$^{10B}$, —NR$^{10A}$OR$^{10B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R[11] is selected from hydrogen, halogen, —CX$^{11}_3$, —CHX$^{11}_2$, —CH$_2$X$^{11}$, —OCX$^{11}_3$, —OCH$_2$X$^{11}$, —OCHX$^{11}_2$, —CN, —SO$_{n1}$R$^{11A}$, —SO$_{v11}$NR$^{11A}$R$^{11B}$, —NHC(O)NR$^{11A}$R$^{11B}$, —N(O)$_{m1}$, —NR$^{11A}$R$^{1B}$, —NHNR$^{11A}$R$^{11B}$, —C(O)R$^{11A}$, —C(O)—OR$^{11A}$, —C(O)NR$^{11A}$R$^{11B}$, —C(O)NHNR$^{11A}$R$^{11B}$, —OR$^{11A}$, —NR$^{11A}$SO$_2$R$^{11B}$, —NR$^{11A}$C(O)R$^{11B}$, —NR$^{11A}$C(O)OR$^{11B}$, —NR$^{11A}$OR$^{11B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{12}$ is selected from hydrogen, halogen, —CX$^{12}_3$, —CHX$^{12}_2$, —CH$_2$X$^{12}$, —OCX$^{12}_3$, —OCH$_2$X$^{12}$, —OCHX$^{12}_2$, —CN, —SO$_{n12}$R$^{12A}$, —SO$_{v12}$NR$^{12A}$R$^{12B}$, —NHC(O)NR$^{12A}$R$^{12B}$, —N(O)$_{m12}$, —NR$^{12A}$R$^{12B}$, —NHNR$^{12A}$R$^{12B}$, —C(O)R$^{12A}$, —C(O)—OR$^{12A}$, —C(O)NR$^{12A}$R$^{12B}$, —C(O)NHNR$^{12A}$R$^{12B}$, —OR$^{12A}$, —NR$^{12A}$SO$_2$R$^{12B}$, —NR$^{12A}$C(O)R$^{12B}$, —NR$^{12A}$C(O)OR$^{12B}$, —NR$^{12A}$OR$^{12B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{17}$ is selected from hydrogen, halogen, —CX$^{17}_3$, —CHX$^{17}_2$, —CH$_2$X$^{17}$, —OCX$^{17}_3$, —OCH$_2$X$^{17}$, —OCHX$^{17}_2$, —CN, —SO$_{n17}$R$^{17A}$, —SO$_{v17}$NR$^{17A}$R$^{17B}$, —NHC(O)NR$^{1A}$R$^{17B}$, —N(O)$_{m17}$, —NR$^{17A}$R$^{17B}$, —NHNR$^{17A}$R$^{17B}$, —C(O)R$^{17A}$, —C(O)—OR$^{17A}$, —C(O)NR$^{17A}$R$^{17B}$, —C(O)NHNR$^{17A}$R$^{17B}$, —OR$^{17A}$, —NR$^{17A}$SO$_2$R$^{17B}$, —NR$^{17A}$C(O)R$^{17B}$, —NR$^{17A}$C(O)OR$^{17B}$, —NR$^{17A}$OR$^{17B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{18}$ is selected from hydrogen, halogen, —CX$^{18}_3$, —CHX$^{18}_2$, —CH$_2$X$^{18}$, —OCX$^{18}_3$, —OCH$_2$X$^{18}$, —OCHX$^{18}_2$, —CN, —SO$_{n18}$R$^{18A}$, —SO$_{v18}$NR$^{18A}$R$^{18B}$, —NHC(O)NR$^{18A}$R$^{18B}$, —N(O)$_{m18}$, —NR$^{18A}$R$^{18B}$, —NHNR$^{18A}$R$^{18B}$, —C(O)R$^{18A}$, —C(O)—OR$^{18A}$, —C(O)NR$^{18A}$R$^{18B}$, —C(O)NHNR$^{18A}$R$^{18B}$, —OR$^{18A}$, —NR$^{18A}$SO$_2$R$^{18B}$, —NR$^{18A}$C(O)R$^{18B}$, —NR$^{18A}$C(O)OR$^{18B}$, —NR$^{18A}$OR$^{18B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; R$^{16}$ and R$^{18}$ substituents may optionally be joined to form a substituted or unsubstituted cycloalkyl or heterocycloalkyl;

R$^{19}$ is selected from hydrogen, halogen, —CX$^{19}_3$, —CHX$^{19}_2$, —CH$_2$X$^{19}$, —OCX$^{19}_3$, —OCH$_2$X$^{19}$, —OCHX$^{19}_2$, —CN, —SO$_{n19}$R$^{19A}$, —SO$_{v19}$NR$^{19A}$R$^{19B}$, —NHC(O)NR$^{19A}$R$^{19B}$, —N(O)$_{m19}$, —NR$^{19A}$R$^{19B}$, —NHNR$^{19A}$R$^{19B}$, —C(O)R$^{19A}$, —C(O)—OR$^{19A}$, —C(O)NR$^{19A}$R$^{19B}$, —C(O)NHNR$^{19A}$R$^{19B}$, —OR$^{19A}$, —NR$^{19A}$SO$_2$R$^{19B}$, —NR$^{19A}$C(O)R$^{19B}$, —NR$^{19A}$C(O)OR$^{19B}$, —NR$^{19A}$OR$^{19B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; R$^{16}$ and R$^{19}$ substituents may optionally be joined to form a substituted or unsubstituted cycloalkyl or heterocycloalkyl;

R$^{20}$ is selected from hydrogen, halogen, —CX$^{20}_3$, —CHX$^{20}_2$, —CH$_2$X$^{20}$, —OCX$^{20}_3$, —OCH$_2$X$^{20}$, —OCHX$^{20}_2$, —CN, —SO$_{n20}$R$^{20A}$, —SO$_{v20}$NR$^{20A}$R$^{20B}$, —NHC(O)NR$^{20A}$R$^{20B}$, —N(O)$_{m20}$, —NR$^{20A}$R$^{20B}$, —NHNR$^{20A}$R$^{20B}$, —C(O)R$^{20A}$, —C(O)—OR$^{20A}$, —C(O)NR$^{20A}$R$^{20B}$, —C(O)NHNR$^{20A}$R$^{20B}$, —OR$^{20A}$, —NR$^{20A}$, —SO$_2$R$^{20B}$, —NR$^{20A}$C(O)R$^{20B}$, —NR$^{20A}$C(O)OR$^{20B}$, —NR$^{20A}$OR$^{20B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{21}$ is selected from hydrogen, halogen, —CX$^{21}_3$, —CHX$^{21}_2$, —CH$_2$X$^{21}$, —OCX$^{21}_3$, —OCH$_2$X$^{21}$, —OCHX$^{21}_2$, —CN, —SO$_{n21}$R$^{21A}$, —SO$_{v21}$NR$^{21A}$R$^{21B}$, —NHC(O)NR$^{21A}$R$^{21B}$, —N(O)$_{m21}$, —NR$^{21A}$R$^{21B}$, —NHNR$^{21A}$R$^{21B}$, —C(O)R$^{21A}$, —C(O)—OR$^{21A}$, —C(O)NR$^{21A}$R$^{21B}$, —C(O)NHNR$^{21A}$R$^{21B}$, —OR$^{21A}$, —NR$^{21A}$SO$_2$R$^{21B}$, —NR$^{21A}$C(O)R$^{21B}$, —NR$^{21A}$C(O)OR$^{21B}$, —NR$^{21A}$OR$^{21B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; R$^{20}$ and R$^{21}$ substituents may optionally be joined to form a substituted or unsubstituted cycloalkyl or heterocycloalkyl;

R$^{22}$ is selected from hydrogen, halogen, —CX$^{22}_3$, —CHX$^{22}_2$, —CH$_2$X$^{22}$, —OCX$^{22}_3$, —OCH$_2$X$^{22}$, —OCHX$^{22}_2$, —CN, —SO$_{n22}$R$^{22A}$, —SO$_{v22}$NR$^{22A}$R$^{22B}$, —NHC(O)NR$^{22A}$R$^{22B}$, —N(O)$_{m22}$, —NR$^{22A}$R$^{22B}$, —NHNR$^{22A}$R$^{22B}$, —C(O)R$^{22A}$, —C(O)—OR$^{22A}$, —C(O)NR$^{22A}$R$^{22B}$, —C(O)NHNR$^{22A}$R$^{22B}$, —OR$^{22A}$, —NR$^{22A}$SO$_2$R$^{22B}$, —NR$^{22A}$C(O)R$^{22B}$, —NR$^{22A}$C(O)OR$^{22B}$, —NR$^{22A}$OR$^{22B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{23}$ is selected from hydrogen, halogen, —CX$^{23}_3$, —CHX$^{23}_2$, —CH$_2$X$^{23}$, —OCX$^{23}_3$, —OCH$_2$X$^{23}$, —OCHX$^{23}_2$, —CN, —SO$_{n23}$R$^{23A}$, —SO$_{v23}$NR$^{23A}$R$^{23B}$, —NHC(O)NR$^{23A}$R$^{23B}$, —N(O)$_{m23}$, —NR$^{23A}$R$^{23B}$, —NHNR$^{23A}$R$^{23B}$, —C(O)R$^{23A}$, —C(O)—OR$^{23A}$, —C(O)NR$^{23A}$R$^{23B}$, —C(O)NHNR$^{23A}$R$^{23B}$, —OR$^{23A}$, —NR$^{23A}$SO$_2$R$^{23B}$, —NR$^{23A}$C(O)R$^{23B}$, —NR$^{23A}$C(O)OR$^{23B}$, —NR$^{23A}$OR$^{23B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{24}$ is selected from hydrogen, halogen, —CX$^{24}_3$, —CHX$^{24}_2$, —CH$_2$X$^{24}$, —OCX$^{24}_3$, —OCH$_2$X$^{24}$, —OCHX$^{24}_2$, —CN, —SO$_{n24}$R$^{24A}$, —SO$_{v24}$NR$^{24A}$R$^{24B}$, —NHC(O)NR$^{24A}$R$^{24B}$, —N(O)$_{m24}$, —NR$^{24A}$R$^{24B}$, —NHNR$^{24A}$R$^{24B}$, —C(O)R$^{24A}$, —C(O)—OR$^{24A}$, —C(O)NR$^{24A}$R$^{24B}$, —C(O)NHNR$^{24A}$R$^{24B}$, —OR$^{24A}$, —NR$^{24A}$SO$_2$R$^{24B}$, —NR$^{24A}$C(O)R$^{24B}$, —NR$^{24A}$C(O)OR$^{24B}$, —NR$^{24A}$OR$^{24B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{25}$ is selected from hydrogen, halogen, $-CX^{25}_3$, $-CHX^{25}_2$, $-CH_2X^{25}$, $-OCX^{25}_3$, $-OCH_2X^{25}$, $-OCHX^{25}_2$, $-CN$, $-SO_{n25}R^{25A}$, $-SO_{v25}NR^{25A}R^{25B}$, $-NHC(O)NR^{25A}R^{25B}$, $-N(O)_{m25}$, $-NR^{25A}R^{25B}$, $-NHNR^{25A}R^{25B}$, $-C(O)R^{25A}$, $-C(O)-OR^{25A}$, $-C(O)NR^{25A}R^{25B}$, $-C(O)NHNR^{25A}R^{25B}$, $-OR^{25A}$, $-NR^{25A}SO_2R^{25B}$, $-NR^{25A}C(O)R^{25B}$, $-NR^{25A}C(O)OR^{25B}$, $-NR^{25A}OR^{25B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{26}$ is selected from hydrogen, halogen, $-CX^{26}_3$, $-CHX^{26}_2$, $-CH_2X^{26}$, $-OCX^{26}_3$, $-OCH_2X^{26}$, $-OCHX^{26}_2$, $-CN$, $-SO_{n26}R^{26A}$, $-SO_{v26}NR^{26A}R^{26B}$, $-NHC(O)NR^{26A}R^{26B}$, $-N(O)_{m26}$, $-NR^{26A}R^{26B}$, $-NHNR^{26A}R^{26B}$, $-C(O)R^{26A}$, $-C(O)-OR^{26A}$, $-C(O)NR^{26A}R^{26B}$, $-C(O)NHNR^{26A}R^{26B}$, $-OR^{26A}$, $-NR^{26A}SO_2R^{26B}$, $-NR^{26A}C(O)R^{26B}$, $-NR^{26A}C(O)OR^{26B}$, $-NR^{26A}OR^{26B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{27}$ is selected from hydrogen, halogen, $-CX^{27}_3$, $-CHX^{27}_2$, $-CH_2X^{27}$, $-OCX^{27}_3$, $-OCH_2X^{27}$, $-OCHX^{27}_2$, $-CN$, $-SO_{n27}R^{27A}$, $-SO_{v27}NR^{27A}R^{27B}$, $-NHC(O)NR^{27A}R^{27B}$, $-N(O)_{m27}$, $-NR^{27A}R^{27B}$, $-NHNR^{27A}R^{27B}$, $-C(O)R^{27A}$, $-C(O)-OR^{27A}$, $-C(O)NR^{27A}R^{27B}$, $-C(O)NHNR^{27A}R^{27B}$, $-OR^{27A}$, $-NR^{27A}SO_2R^{27B}$, $-NR^{27A}C(O)R^{27B}$, $-NR^{27A}C(O)OR^{27B}$, $-NR^{27A}OR^{27B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{28}$ is selected from hydrogen, halogen, $-CX^{28}_3$, $-CHX^{28}_2$, $-CH_2X^{28}$, $-OCX^{28}_3$, $-OCH_2X^{28}$, $-OCHX^{28}_2$, $-CN$, $-SO_{n28}R^{28A}$, $-SO_{v28}NR^{28A}R^{28B}$, $-NHC(O)NR^{28A}R^{28B}$, $-N(O)_{m2}$, $-NR^{28A}R^{28B}$, $-NHNR^{28A}R^{28B}$, $-C(O)R^{28A}$, $-C(O)-OR^{28A}$, $-C(O)NR^{28A}R^{28B}$, $-C(O)NHNR^{28A}R^{28B}$, $-OR^{28A}$, $-NR^{28A}SO_2R^{28B}$, $-NR^{28A}C(O)R^{28B}$, $-NR^{28A}C(O)OR^{28B}$, $-NR^{28A}OR^{28B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{29}$ is selected from hydrogen, halogen, $-CX^{29}_3$, $-CHX^{29}_2$, $-CH_2X^{29}$, $-OCX^{29}_3$, $-OCH_2X^{29}$, $-OCHX^{29}_2$, $-CN$, $-SO_{n29}R^{29A}$, $-SO_{v29}NR^{29A}R^{29B}$, $-NHC(O)NR^{29A}R^{29B}$, $-N(O)_{m29}$, $-NR^{29A}R^{29B}$, $-NHNR^{29A}R^{29B}$, $-C(O)R^{29A}$, $-C(O)-OR^{29A}$, $-C(O)NR^{29A}R^{29B}$, $-C(O)NHNR^{29A}R^{29B}$, $-OR^{29A}$, $-NR^{29A}SO_2R^{29B}$, $-NR^{29A}C(O)R^{29B}$, $-NR^{29A}C(O)OR^{29B}$, $-NR^{29A}OR^{29B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{30}$ is selected from hydrogen, halogen, $-CX^{30}_3$, $-CHX^{30}_2$, $-CH_2X^{30}$, $-OCX^{30}_3$, $-OCH_2X^{30}$, $-OCHX^{30}_2$, $-CN$, $-SO_{n30}R^{30A}$, $-SO_{v30}NR^{30A}R^{30B}$, $-NHC(O)NR^{30A}R^{30B}$, $-N(O)_{m30}$, $-NR^{30A}R^{30B}$, $-NHNR^{30A}R^{30B}$, $-C(O)R^{30A}$, $-C(O)-OR^{30A}$, $-C(O)NR^{30A}R^{30B}$, $-C(O)NHNR^{30A}R^{30B}$, $-OR^{30A}$, $-NR^{30A}SO_2R^{30B}$, $-NR^{30A}C(O)R^{30B}$, $-NR^{30A}C(O)OR^{30B}$, $-NR^{30A}OR^{30B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{31}$ is selected from hydrogen, halogen, $-CX^{31}_3$, $-CHX^{31}_2$, $-CH_2X^{31}$, $-OCX^{31}_3$, $-OCH_2X^{31}$, $-OCHX^{31}_2$, $-CN$, $-SO_{n31}R^{31A}$, $-SO_{v31}NR^{31A}R^{31B}$, $-NHC(O)NR^{31A}R^{31B}$, $-N(O)_{m31}$, $-NR^{31A}R^{31B}$, $-NHNR^{31A}R^{31B}$, $-C(O)R^{31A}$, $-C(O)-OR^{31A}$, $-C(O)NR^{31A}R^{31B}$, $-C(O)NHNR^{31A}R^{31B}$, $-OR^{31A}$, $-NR^{31A}SO_2R^{31B}$, $-NR^{31A}C(O)R^{31B}$, $-NR^{31A}C(O)OR^{31B}$, $-NR^{31A}OR^{31B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{32}$ is selected from hydrogen, halogen, $-CX^{33}_3$, $-CHX^{32}_2$, $-CH_2X^{32}$, $-OCX^{33}_3$, $-OCH_2X^{32}$, $-OCHX^{32}_2$, $-CN$, $-SO_{n32}R^{32A}$, $-SO_{v32}NR^{32A}R^{32B}$, $-NHC(O)NR^{32A}R^{32B}$, $-N(O)_{m32}$, $-NR^{32A}R^{32B}$, $-NHNR^{32A}R^{32B}$, $-C(O)R^{32A}$, $-C(O)-OR^{32A}$, $-C(O)NR^{32A}R^{32B}$, $-C(O)NHNR^{32A}R^{32B}$, $-OR^{32A}$, $-NR^{32A}SO_2R^{32B}$, $-NR^{32A}C(O)R^{32B}$, $-NR^{32A}C(O)OR^{32B}$, $-NR^{32A}OR^{32B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{33}$ is selected from hydrogen, halogen, $-CX^{33}_3$, $-CHX^{33}_2$, $-CH_2X^{33}$, $-OCX^{33}_3$, $-OCH_2X^{33}$, $-OCHX^{33}_2$, $-CN$, $-SO_{n33}R^{33A}$, $-SO_{v33}NR^{33A}R^{33B}$, $-NHC(O)NR^{33A}R^{33B}$, $-N(O)_{m33}$, $-NR^{33A}R^{33B}$, $-NHNR^{33A}R^{33B}$, $-C(O)R^{33A}$, $-C(O)-OR^{33A}$, $-C(O)NR^{33A}R^{33B}$, $-C(O)NHNR^{33A}R^{33B}$, $-OR^{33A}$, $-NR^{33A}SO_2R^{33B}$, $-NR^{33A}C(O)R^{33B}$, $-NR^{33A}C(O)OR^{33B}$, $-NR^{33A}OR^{33B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{34}$ is selected from hydrogen, halogen, $-CX^{34}_3$, $-CHX^{34}_2$, $-CH_2X^{34}$, $-OCX^{34}_3$, $-OCH_2X^{34}$, $-OCHX^{34}_2$, $-CN$, $-SO_{n34}R^{34A}$, $-SO_{v34}NR^{34A}R^{34B}$, $-NHC(O)NR^{34A}R^{34B}$, $-N(O)_{m34}$, $-NR^{34A}R^{34B}$, $-NHNR^{34A}R^{34B}$, $-C(O)R^{34A}$, $-C(O)-OR^{34A}$, $-C(O)NR^{34A}R^{34B}$, $-C(O)NHNR^{34A}R^{34B}$, $-OR^{34A}$, $-NR^{34A}SO_2R^{34B}$, $-NR^{34A}C(O)R^{34B}$, $-NR^{34A}C(O)OR^{34B}$, $-NR^{34A}OR^{34B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{35}$ is selected from hydrogen, halogen, $-CX^{35}_3$, $-CHX^{35}_2$, $-CH_2X^{35}$, $-OCX^{35}_3$, $-OCH_2X^{35}$, —OCHX$^{35}_2$, —CN, —SO$_{n35}$R$^{35A}$, —SO$_{v35}$NR$^{35A}$R$^{35B}$, —NHC(O)NR$^{35A}$R$^{35B}$, —N(O)$_{m35}$, —NR$^{35A}$R$^{35B}$, —NHNR$^{35A}$R$^{35B}$, —C(O)R$^{35A}$, —C(O)—OR$^{35A}$, —C(O)NR$^{35A}$R$^{35B}$, —C(O)NHNR$^{35A}$R$^{35B}$, —OR$^{35A}$, —NR$^{35A}$SO$_2$R$^{35B}$, —NR$^{35A}$C(O)R$^{35B}$, —NR$^{35A}$C(O)OR$^{35B}$, —NR$^{35A}$OR$^{35B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

Each R$^{1A}$, R$^{1B}$, R$^{3A}$, R$^{3B}$, R$^{4A}$, R$^{4B}$, R$^{6A}$, R$^{6B}$, R$^{7A}$, R$^{7B}$, R$^{9A}$, R$^{9B}$, R$^{10A}$, R$^{10B}$, R$^{11A}$, R$^{11B}$, R$^{17A}$, R$^{17B}$, R$^{18A}$, R$^{18B}$, R$^{19A}$, R$^{19B}$, R$^{20A}$, R$^{20B}$, R$^{21A}$, R$^{21B}$, R$^{22A}$, R$^{22B}$, R$^{23A}$, R$^{23B}$, R$^{24A}$, R$^{24B}$, R$^{25A}$, R$^{25B}$, R$^{26A}$, R$^{26B}$, R$^{27A}$, R$^{27B}$, R$^{28A}$, R$^{28B}$, R$^{29A}$, R$^{29B}$, R$^{30A}$, R$^{30B}$, R$^{31A}$, R$^{31B}$, R$^{32A}$, R$^{32B}$, R$^{33A}$, R$^{33B}$, R$^{34A}$, R$^{34B}$, R$^{35A}$, R$^{35B}$ is independently selected from hydrogen, —CX$_3$, —CHX$_2$, —CH$_2$X, —C(O)OH, —C(O)NH$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$_3$, —OCHX$_2$, —OCH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{1A}$ and R$^{1B}$ substituents bonded to the same nitrogen atom may optionally be joined to form a substituted or unsubstituted heterocycloalkyl or substituted or unsubstituted heteroaryl; R$^{2A}$ and R$^{2B}$ substituents bonded to the same nitrogen atom may optionally be joined to form a substituted or unsubstituted heterocycloalkyl or substituted or unsubstituted heteroaryl; R$^{4A}$ and R$^{4B}$ substituents bonded to the same nitrogen atom may optionally be joined to form a substituted or unsubstituted heterocycloalkyl or substituted or unsubstituted heteroaryl; R$^{6A}$ and R$^{6B}$ substituents bonded to the same nitrogen atom may optionally be joined to form a substituted or unsubstituted heterocycloalkyl or substituted or unsubstituted heteroaryl; R$^{7A}$ and R$^{7B}$ substituents bonded to the same nitrogen atom may optionally be joined to form a substituted or unsubstituted heterocycloalkyl or substituted or unsubstituted heteroaryl; R$^{9A}$ and R$^{9B}$ substituents bonded to the same nitrogen atom may optionally be joined to form a substituted or unsubstituted heterocycloalkyl or substituted or unsubstituted heteroaryl; R$^{13A}$ and R$^{13B}$ substituents bonded to the same nitrogen atom may optionally be joined to form a substituted or unsubstituted heterocycloalkyl or substituted or unsubstituted heteroaryl; R$^{14A}$ and R$^{14B}$ substituents bonded to the same nitrogen atom may optionally be joined to form a substituted or unsubstituted heterocycloalkyl or substituted or unsubstituted heteroaryl; R$^{15A}$ and R$^{15B}$ substituents bonded to the same nitrogen atom may optionally be joined to form a substituted or unsubstituted heterocycloalkyl or substituted or unsubstituted heteroaryl; R$^{16A}$ and R$^{16B}$ substituents bonded to the same nitrogen atom may optionally be joined to form a substituted or unsubstituted heterocycloalkyl or substituted or unsubstituted heteroaryl; R$^{17A}$ and R$^{17B}$ substituents bonded to the same nitrogen atom may optionally be joined to form a substituted or unsubstituted heterocycloalkyl or substituted or unsubstituted heteroaryl; R$^{18A}$ and R$^{18B}$ substituents bonded to the same nitrogen atom may optionally be joined to form a substituted or unsubstituted heterocycloalkyl or substituted or unsubstituted heteroaryl; R$^{19A}$ and R$^{19B}$ substituents bonded to the same nitrogen atom may optionally be joined to form a substituted or unsubstituted heterocycloalkyl or substituted or unsubstituted heteroaryl; R$^{20A}$ and R$^{20B}$ substituents bonded to the same nitrogen atom may optionally be joined to form a substituted or unsubstituted heterocycloalkyl or substituted or unsubstituted heteroaryl; R$^{21A}$ and R$^{21B}$ substituents bonded to the same nitrogen atom may optionally be joined to form a substituted or unsubstituted heterocycloalkyl or substituted or unsubstituted heteroaryl; R$^{22A}$ and R$^{22B}$ substituents bonded to the same nitrogen atom may optionally be joined to form a substituted or unsubstituted heterocycloalkyl or substituted or unsubstituted heteroaryl; R$^{23A}$ and R$^{23B}$ substituents bonded to the same nitrogen atom may optionally be joined to form a substituted or unsubstituted heterocycloalkyl or substituted or unsubstituted heteroaryl; R$^{24A}$ and R$^{24B}$ substituents bonded to the same nitrogen atom may optionally be joined to form a substituted or unsubstituted heterocycloalkyl or substituted or unsubstituted heteroaryl; R$^{25A}$ and R$^{25B}$ substituents bonded to the same nitrogen atom may optionally be joined to form a substituted or unsubstituted heterocycloalkyl or substituted or unsubstituted heteroaryl; R$^{26A}$ and R$^{26B}$ substituents bonded to the same nitrogen atom may optionally be joined to form a substituted or unsubstituted heterocycloalkyl or substituted or unsubstituted heteroaryl; R$^{27A}$ and R$^{27B}$ substituents bonded to the same nitrogen atom may optionally be joined to form a substituted or unsubstituted heterocycloalkyl or substituted or unsubstituted heteroaryl; R$^{28A}$ and R$^{28B}$ substituents bonded to the same nitrogen atom may optionally be joined to form a substituted or unsubstituted heterocycloalkyl or substituted or unsubstituted heteroaryl; R$^{29A}$ and R$^{29B}$ substituents bonded to the same nitrogen atom may optionally be joined to form a substituted or unsubstituted heterocycloalkyl or substituted or unsubstituted heteroaryl; R$^{30A}$ and R$^{30B}$ substituents bonded to the same nitrogen atom may optionally be joined to form a substituted or unsubstituted heterocycloalkyl or substituted or unsubstituted heteroaryl;

Each m1, m3, m4, m6, m7, m9, m10, m11, m17, m18, m19, m20, m21, m22, m23, m24, m25, m26, m27, m28, m29, m30, m31, m32, m33, m34 and m35 is independently 1 or 2;

Each v1, v3, v4, v6, v7, v9, v10, v11, v17, v18, v19, v20, v21, v22, v23, v24, v25, v26, v27, v28, v29, v30, v31, v32, v33, v34 and v35 is independently 1 or 2;

Each n1, n3, n4, n6, n7, n9, n10, n11, n17, n18, n19, n20, n21, n22, n23, n24, n25, n26, n27, n28, n29, n30, n31, n32, n33, n34 and n35 is independently an integer from 0 to 2; and Each X$^1$, X$^3$, X$^4$, X$^6$, X$^7$, X$^9$, X$^{10}$, X$^{11}$, X$^{17}$, X$^{18}$, X$^{19}$, X$^{20}$, X$^{21}$, X$^{22}$, X$^{23}$, X$^{24}$, X$^{25}$, X$^{26}$, X$^{27}$, X$^{28}$, X$^{29}$, X$^{30}$, X$^{31}$, X$^{32}$, X$^{33}$, X$^{34}$, and X$^{35}$ is independently —Cl, —Br, —I or —F.

In one embodiment, ring B is optionally substituted with one or more substituent groups.

In one embodiment of compounds of Formula VII, ring B is selected from thienyl, furanyl, pyrrolyl, thiazolyl, oxazolyl, imidazolyl, pyrazolyl, isoxazolyl, triazolyl and isothiazolyl. In one embodiment, the thienyl, furanyl, pyrrolyl, thiazolyl, oxazolyl, imidazolyl, pyrazolyl, isoxazolyl, triazolyl and isothiazolyl rings are optionally substituted with one or more substituent groups.

In one embodiment of compounds of Formula VII, ring B is selected from phenyl, pyridyl, pyrazinyl, pyrimidinyl, pyridazinyl, and triazinyl. In one embodiment, the phenyl, pyridyl, pyrazinyl, pyrimidinyl, pyridazinyl, and triazinyl rings are optionally substituted with one or more substituent groups.

In one embodiment of compounds of Formula VII, ring B is selected from selected from

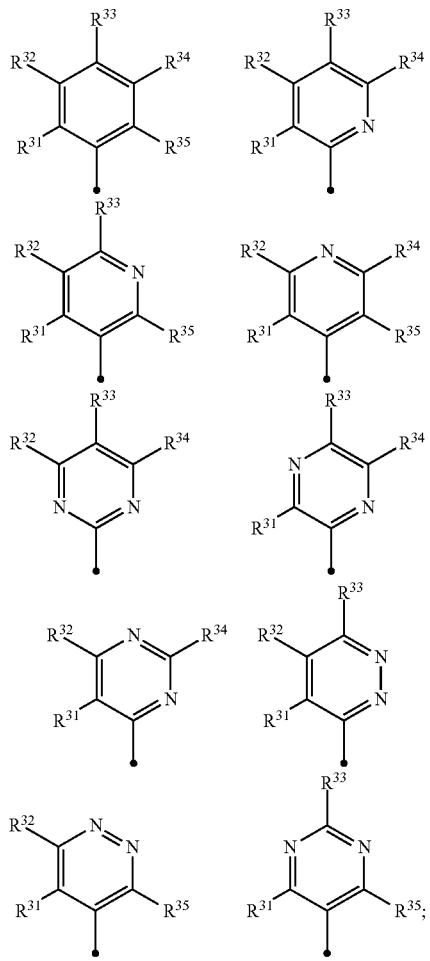

In one embodiment of compounds of Formula VII, ring B is selected from benzothienyl, benzothiazolyl, indolyl, benzimidazolyl, benzoxazolyl, benzofuryl, indazolyl and isolindolyl. In one embodiment, benzothienyl, benzothiazolyl, indolyl, benzimidazolyl, benzoxazolyl, benzofuryl, indazolyl and isolindolyl rings are optionally substituted with one or more substituent groups In one embodiment of compounds of Formula VII, ring B is selected from quinolyl, isoquinolyl, naphthpyridinyl, quinoxalinyl and quinazolinyl. In one embodiment, the quinolyl, isoquinolyl, naphthpyridinyl, quinoxalinyl and quinazolinyl rings are optionally substituted with one or more substituent groups In one embodiment of compounds of Formula VII, E is selected from —C(=O)CH=CH$_2$, —C(=O)-ethynyl, —C(=O)CH=CHCF$_3$, —C(=O)CH=CHCHF$_2$, —C(=O)CH=CHCH$_2$F, and —C(=O)CH$_2$Br.

The invention also relates to compounds of Formula VIII:

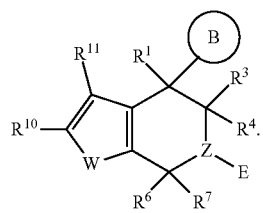

(VIII)

wherein

Z is N, or CR$^9$;

W is selected from NR$^{12}$, O, S, S=O, O=S=O, and Se;

ring B is selected from
 a) 5- or 6-membered cycloalkyl, saturated or partially saturated heterocyclyl,
 b) 5- or 6-membered aryl or heteroaryl,
 c) 9-, 10- or 11-membered fused partially saturated heterocyclyl,
 d) 9- or 10-membered fused heteroaryl,
 e) naphthyl, and
 f) 4-, 5- or 6-membered cycloalkenyl;

E is selected from an electrophilic moiety, selected from

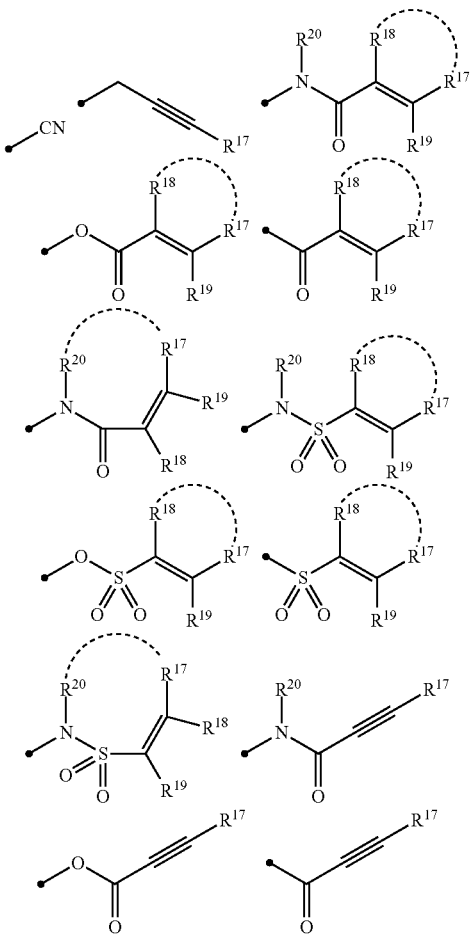

-continued

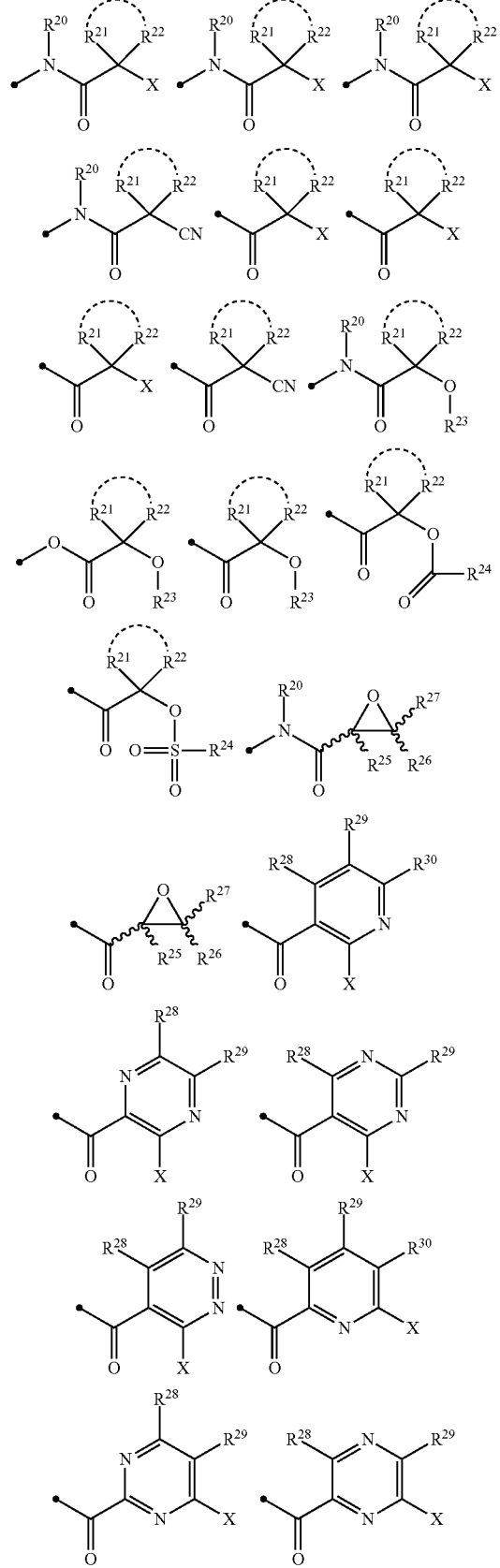
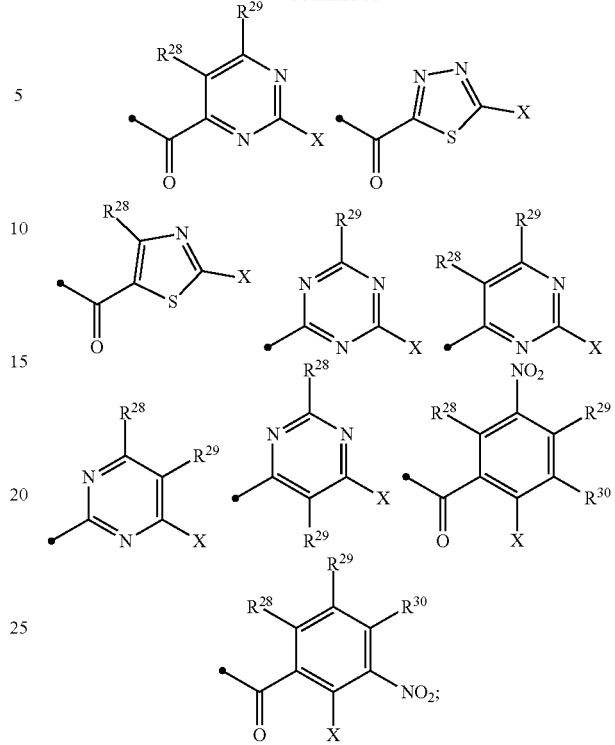

$R^1$ is selected from hydrogen, halogen, —CX$^1_3$, —CHX$^1_2$, —CH$_2$X$^1$, —OCX$^1_3$, —OCH$_2$X$^1$, —OCHX$^1_2$, —CN, —SO$_{n1}$R$^{1A}$, —SO$_{v1}$NR$^{1A}$R$^{1B}$, —NHC(O)NR$^{1A}$R$^{1B}$, —N(O)$_{m1}$, —NR$^{1A}$R$^{1B}$, —NHNR$^{1A}$R$^{1B}$, —C(O)R$^{1A}$, —C(O)—OR$^{1A}$, —C(O)NR$^{1A}$R$^{1B}$, —C(O)NHNR$^{1A}$R$^{1B}$, —OR$^{1A}$, —NR$^{1A}$SO$_2$R$^{1B}$, —NR$^{1A}$C(O)R$^{1B}$, —NR$^{1A}$C(O)OR$^{1B}$, —NR$^{1A}$OR$^{1B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, rand substituted or unsubstituted heteroaryl;

$R^3$ is selected from hydrogen, halogen, —CX$^3_3$, —CHX$^3_2$, —CH$_2$X$^3$, —OCX$^3_3$, —OCH$_2$X$^3$, —OCHX$^3_2$, —CN, —SO$_{n3}$R$^{3A}$, —SO$_{v3}$NR$^{3A}$R$^{3B}$, —NHC(O)NR$^{3A}$R$^{3B}$, —N(O)$_m$, —NR$^{3A}$R$^{3B}$, —NHNR$^{3A}$R$^{3B}$, —C(O)R$^{3A}$, —C(O)—OR$^{3A}$, —C(O)NR$^{3A}$R$^{3B}$, —OR$^{3A}$, —NR$^{3A}$SO$_2$R$^{3B}$, —NR$^{3A}$C(O)R$^{3B}$, —NR$^{3A}$C(O)OR$^{3B}$, —NR$^{3A}$OR$^{3B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^4$ is selected from hydrogen, halogen, —CX$^4_3$, —CHX$^4_2$, —CH$_2$X$^4$, —OCX$^4_3$, —OCH$_2$X$^4$, —OCHX$^4_2$, —CN, —SO$_{v4}$R$^{4A}$, —SO$_4$NR$^{4A}$R$^{4B}$, —NHC(O)NR$^{4A}$R$^{4B}$, —N(O)$_{m4}$, —NR$^{4A}$R$^{4B}$, —NHNR$^{4A}$R$^{4B}$, —C(O)R$^{4A}$, —C(O)—OR$^{4A}$, —C(O)NR$^{4A}$R$^{4B}$, —C(O)NHNR$^{4A}$R$^{4B}$, —OR$^{4A}$, —NR$^{4A}$SO$_2$R$^{4B}$, —NR$^{4A}$C(O)R$^{4B}$, —NR$^{4A}$C(O)OR$^{4B}$, —NR$^{4A}$OR$^{4B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; $R^3$ and $R^3$ substituents may optionally be joined to form a substituted or unsubstituted cycloalkyl or heterocycloalkyl;

$R^6$ is selected from hydrogen, halogen, $-CX^6_3$, $-CHX^6_2$, $-CH_2X^6$, $-OCX^6_3$, $-OCH_2X^6$, $-OCHX^6_2$, $-CN$, $-SO_{v6}R^{6A}$, $-SO_{v6}NR^{6A}R^{6B}$, $-NHC(O)NR^{6A}R^{6B}$, $-N(O)_{m6}$, $-NR^{6A}R^{6B}$, $-NHNR^{6A}R^{6B}$, $-C(O)R^{6A}$, $-C(O)-OR^{6A}$, $-C(O)NR^{6A}R^{6B}$, $-C(O)NHNR^{6A}R^{6B}$, $-OR^{6A}$, $-NR^{6A}SO_2R^{6B}$, $-NR^{6A}C(O)R^{6B}$, $-NR^{6A}C(O)OR^{6B}$, $-NR^{6A}OR^{6B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^7$ is selected from hydrogen, halogen, $-CX^7_3$, $-CHX^7_2$, $-CH_2X^7$, $-OCX^7_3$, $-OCH_2X^7$, $-OCHX^7_2$, $-CN$, $-SO_{n7}R^{7A}$, $-SO_{v7}NR^{7A}R^{7B}$, $-NHC(O)NR^{7A}R^{7B}$, $-N(O)_{m7}$, $-NR^{7A}R^{7B}$, $-NHNR^{7A}R^{7B}$, $-C(O)R^{7A}$, $-C(O)-OR^{7A}$, $-C(O)NR^{7A}R^{7B}$, $-C(O)NHNR^{7A}R^{7B}$, $-OR^{7A}$, $-NR^{7A}SO_2R^{7B}$, $-NR^{7A}C(O)R^{7B}$, $-NR^{7A}C(O)OR^{7B}$, $-NR^{7A}OR^{7B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^9$ is selected from hydrogen, halogen, $-CX^9_3$, $-CHX^9_2$, $-CH_2X^9$, $-OCX^9_3$, $-OCH_2X^9$, $-OCHX^9_2$, $-CN$, $-SO_{n9}R^{9A}$, $-SO_{v9}NR^{9A}R^{9B}$, $-NHC(O)NR^{9A}R^{9B}$, $-N(O)_{m9}$, $-NR^{9A}R^{9B}$, $-NHNR^{9A}R^{9B}$, $-C(O)R^{9A}$, $-C(O)-OR^{9A}$, $-C(O)NR^{9A}R^{9B}$, $-C(O)NHNR^{9A}R^{9B}$, $-OR^{9A}$, $-NR^{9A}SO_2R^{9B}$, $-NR^{9A}C(O)R^{9B}$, $-NR^{9A}C(O)OR^{9B}$, $-NR^{9A}OR^{9B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{10}$ is selected from hydrogen, halogen, $-CX^{10}_3$, $-CHX^{10}_2$, $-CH_2X^{10}$, $-OCX^{10}_3$, $-OCH_2X^{10}$, $-OCHX^{10}_2$, $-CN$, $-SO_{n10}R^{10A}$, $-SO_{v10}NR^{10A}R^{10B}$, $-NHC(O)NR^{10A}R^{10B}$, $-N(O)_{m10}$, $-NR^{10A}R^{10B}$, $-NHNR^{10A}R^{10B}$, $-C(O)R^{10A}$, $-C(O)-OR^{10A}$, $-C(O)NR^{10A}R^{10B}$, $-C(O)NHNR^{10A}R^{10B}$, $-OR^{10A}$, $-NR^{10A}SO_2R^{10B}$, $-NR^{10A}C(O)R^{10B}$, $-NR^{10A}C(O)OR^{10B}$, $-NR^{10A}OR^{10B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{11}$ is selected from hydrogen, halogen, $-CX^{11}_3$, $-CHX^{11}_2$, $-CH_2X^{11}$, $-OCX^{11}_3$, $-OCH_2X^{11}$, $-OCHX^{11}_2$, $-CN$, $-SO_{n11}R^{11A}$, $-SO_{v11}NR^{11A}R^{11B}$, $-NHC(O)NR^{11A}R^{11B}$, $-N(O)_{m11}$, $-NR^{11A}R^{11B}$, $-NHNR^{11A}R^{11B}$, $-C(O)R^{11A}$, $-C(O)-OR^{11A}$, $-C(O)NR^{11A}R^{11B}$, $-C(O)NHNR^{11A}R^{11B}$, $-OR^{11A}$, $-NR^{11A}SO_2R^{11B}$, $-NR^{11A}C(O)R^{11B}$, $-NR^{11A}C(O)OR^{11B}$, $-NR^{11A}OR^{11B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{12}$ is selected from hydrogen, halogen, $-CX^{12}_3$, $-CHX^{12}_2$, $-CH_2X^{12}$, $-OCX^{12}_3$, $-OCH_2X^{12}$, $-OCHX^{12}_2$, $-CN$, $-SO_{n12}R^{12A}$, $-SO_{v12}NR^{12A}R^{12B}$, $-NHC(O)NR^{12A}R^{12B}$, $-N(O)_{m12}$, $-NR^{12A}R^{12B}$, $-NHNR^{12A}R^{12B}$, $-C(O)R^{12A}$, $-C(O)-OR^{12A}$, $-C(O)NR^{12A}R^{12B}$, $-C(O)NHNR^{12A}R^{12B}$, $-OR^{12A}$, $-NR^{12A}SO_2R^{12B}$, $-NR^{12A}C(O)R^{12B}$, $-NR^{12A}C(O)OR^{12B}$, $-NR^{12A}OR^{12B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{17}$ is selected from hydrogen, halogen, $-CX^{17}_3$, $-CHX^{17}_2$, $-CH_2X^{17}$, $-OCX^{17}_3$, $-OCH_2X^{17}$, $-OCHX^{17}_2$, $-CN$, $-SO_{n17}R^{17A}$, $-SO_{v17}NR^{17A}R^{17B}$, $-NHC(O)NR^{17A}R^{17B}$, $-N(O)_{m17}$, $-NR^{17A}R^{17B}$, $-NHNR^{17A}R^{17B}$, $-C(O)R^{17A}$, $-C(O)-OR^{17A}$, $-C(O)NR^{17A}R^{17B}$, $-C(O)NHNR^{17A}R^{17B}$, $-OR^{17A}$, $-NR^{17A}SO_2R^{17B}$, $-NR^{17A}C(O)R^{17B}$, $-NR^{17A}C(O)OR^{17B}$, $-NR^{17A}OR^{17B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{18}$ is selected from hydrogen, halogen, $-CX^{18}_3$, $-CHX^{18}_2$, $-CH_2X^{18}$, $-OCX^{18}_3$, $-OCH_2X^{18}$, $-OCHX^{18}_2$, $-CN$, $-SO_{n18}R^{18A}$, $-SO_{v18}NR^{18A}R^{18B}$, $-NHC(O)NR^{18A}R^{18B}$, $-N(O)_{m18}$, $-NR^{18A}R^{18B}$, $-NHNR^{18A}R^{18B}$, $-C(O)R^{18A}$, $-C(O)-OR^{18A}$, $-C(O)NR^{18A}R^{18B}$, $-C(O)NHNR^{18A}R^{18B}$, $-OR^{18A}$, $-NR^{18A}SO_2R^{18B}$, $-NR^{18A}C(O)R^{18B}$, $-NR^{18A}C(O)OR^{18B}$, $-NR^{18A}OR^{18B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; $R^{16}$ and $R^{18}$ substituents may optionally be joined to form a substituted or unsubstituted cycloalkyl or heterocycloalkyl;

$R^{19}$ is selected from hydrogen, halogen, $-CX^{19}_3$, $-CHX^{19}_2$, $-CH_2X^{19}$, $-OCX^{19}_3$, $-OCH_2X^{19}$, $-OCHX^{19}_2$, $-CN$, $-SO_{n19}R^{19A}$, $-SO_{v19}NR^{19A}R^{19B}$, $-NHC(O)NR^{19A}R^{19B}$, $-N(O)_{m19}$, $-NR^{19A}R^{19B}$, $-NHNR^{19A}R^{19B}$, $-C(O)R^{19A}$, $-C(O)-OR^{19A}$, $-C(O)NR^{19A}R^{19B}$, $-C(O)NHNR^{19A}R^{19B}$, $-OR^{19A}$, $-NR^{19A}SO_2R^{19B}$, $-NR^{19A}C(O)R^{19B}$, $-NR^{19A}C(O)OR^{19B}$, $-NR^{19A}OR^{19B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; $R^{16}$ and $R^{19}$ substituents may optionally be joined to form a substituted or unsubstituted cycloalkyl or heterocycloalkyl;

$R^{20}$ is selected from hydrogen, halogen, $-CX^{20}_3$, $-CHX^{20}_2$, $-CH_2X^{20}$, $-OCX^{20}_3$, $-OCH_2X^{20}$, $-OCHX^{20}_2$, $-CN$, $-SO_{n20}R^{20A}$, $-SO_{v20}NR^{20A}R^{20B}$, $-NHC(O)NR^{20A}R^{20B}$, $-N(O)_{m20}$, $-NR^{20A}R^{20B}$, $-NHNR^{20A}R^{20B}$, $-C(O)R^{20A}$, $-C(O)-OR^{20A}$, $-C(O)NR^{20A}R^{20B}$, NHNR$^{20A}$R$^{20B}$, $-OR^{20A}$, $-NR^{20A}$, $-SO_2R^{20B}$, $-NR^{20A}C(O)R^{20B}$, $-NR^{20A}C(O)OR^{20B}$, $-NR^{20A}OR^{20B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{21}$ is selected from hydrogen, halogen, $-CX^{21}_3$, $-CHX^{21}_2$, $-CH_2X^{21}$, $-OCX^{21}_3$, $-OCH_2X^{21}$, $-OCHX^{21}_2$, $-CN$, $-SO_{n21}R^{21A}$, $-SO_{v21}NR^{21A}R^{21B}$, $-NHC(O)NR^{21A}R^{21B}$, $-N(O)_{m21}$, $-NR^{21A}R^{21B}$, $-NHNR^{21A}R^{21B}$, $-C(O)R^{21A}$, $-C(O)-OR^{21A}$, $-C(O)NR^{21A}R^{21B}$, $-C(O)NHNR^{21A}R^{21B}$, $-OR^{21A}$, $-NR^{21A}SO_2R^{21B}$, $-NR^{21A}C(O)R^{21B}$, $-NR^{21A}C(O)OR^{21B}$, $-NR^{21A}OR^{21B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; $R^{20}$ and $R^{21}$ substituents may optionally be joined to form a substituted or unsubstituted cycloalkyl or heterocycloalkyl;

$R^{22}$ is selected from hydrogen, halogen, $-CX^{22}_3$, $-CHX^{22}_2$, $-CH_2X^{22}$, $-OCX^{22}_3$, $-OCH_2X^{22}$, $-OCHX^{22}_2$, $-CN$, $-SO_{n22}R^{22A}$, $-SO_{v22}NR^{22A}R^{22B}$, $-NHC(O)NR^{22A}R^{22B}$, $-N(O)_{m22}$, $-NR^{22A}R^{22B}$, $-NHNR^{22A}R^{22B}$, $-C(O)R^{22A}$, $-C(O)-OR^{22A}$, $-C(O)NR^{22A}R^{22B}$, $-C(O)NHNR^{22A}R^{22B}$, $-OR^{22A}$, $-NR^{22A}SO_2R^{22B}$, $-NR^{22A}C(O)R^{22B}$, $-NR^{22A}C(O)OR^{22B}$, $-NR^{22A}OR^{22B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{23}$ is selected from hydrogen, halogen, $-CX^{23}_3$, $-CHX^{23}_2$, $-CH_2X^{23}$, $-OCX^{23}_3$, $-OCH_2X^{23}$, $-OCHX^{23}_2$, $-CN$, $-SO_{n23}R^{23A}$, $-SO_{v23}NR^{23A}R^{23B}$, $-NHC(O)NR^{23A}R^{23B}$, $-N(O)_{m23}$, $-NR^{23A}R^{23B}$, $-NHNR^{23A}R^{23B}$, $-C(O)R^{23A}$, $-C(O)-OR^{23A}$, $-C(O)NR^{23A}R^{23B}$, $-C(O)NHNR^{23A}R^{23B}$, $-OR^{23A}$, $-NR^{23A}SO_2R^{23B}$, $-NR^{23A}C(O)R^{23B}$, $-NR^{23A}C(O)OR^{23B}$, $-NR^{23A}OR^{23B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{24}$ is selected from hydrogen, halogen, $-CX^{24}_3$, $-CHX^{24}_2$, $-CH_2X^{24}$, $-OCX^{24}_3$, $-OCH_2X^{24}$, $-OCHX^{24}_2$, $-CN$, $-SO_{n24}R^{24A}$, $-SO_{v24}NR^{24A}R^{24B}$, $-NHC(O)NR^{24A}R^{24B}$, $-N(O)_{m24}$, $-NR^{24A}R^{24B}$, $-NHNR^{24A}R^{24B}$, $-C(O)R^{24A}$, $-C(O)-OR^{24A}$, $-C(O)NR^{24A}R^{24B}$, $-C(O)NHNR^{24A}R^{24B}$, $-OR^{24A}$, $-NR^{24A}SO_2R^{24B}$, $-NR^{24A}C(O)R^{24B}$, $-NR^{24A}C(O)OR^{24B}$, $-NR^{24A}OR^{24B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{25}$ is selected from hydrogen, halogen, $-CX^{25}_3$, $-CHX^{25}_2$, $-CH_2X^{25}$, $-OCX^{25}_3$, $-OCH_2X^{25}$, $-OCHX^{25}_2$, $-CN$, $-SO_{n25}R^{25A}$, $-SO_{v25}NR^{25A}R^{25B}$, $-NHC(O)NR^{25A}R^{25B}$, $-N(O)_{25}$, $-NR^{25A}R^{25B}$, $-NHNR^{25A}R^{25B}$, $-C(O)R^{25A}$, $-C(O)-OR^{25A}$, $-C(O)NR^{25A}R^{25B}$, $-C(O)NHNR^{25A}R^{25B}$, $-OR^{25A}$, $-NR^{25A}SO_2R^{25B}$, $-NR^{25A}C(O)R^{25B}$, $-NR^{25A}C(O)OR^{25B}$, $-NR^{25A}OR^{25B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{26}$ is selected from hydrogen, halogen, $-CX^{26}_3$, $-CHX^{26}_2$, $-CH_2X^{26}$, $-OCX^{26}_3$, $-OCH_2X^{26}$, $-OCHX^{26}_2$, $-CN$, $-SO_{n26}R^{26A}$, $-SO_{v26}NR^{26A}R^{26B}$, $-NHC(O)NR^{26A}R^{26B}$, $-N(O)_{m26}$, $-NR^{26A}R^{26B}$, $-NHNR^{26A}R^{26B}$, $-C(O)R^{26A}$, $-C(O)-OR^{26A}$, $-C(O)NR^{26A}R^{26B}$, $-C(O)NHNR^{26A}R^{26B}$, $-OR^{26A}$, $-NR^{26A}SO_2R^{26B}$, $-NR^{26A}C(O)R^{26B}$, $-NR^{26A}C(O)OR^{26B}$, $-NR^{26A}OR^{26B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{27}$ is selected from hydrogen, halogen, $-CX^{27}_3$, $-CHX^{27}_2$, $-CH_2X^{27}$, $-OCX^{27}_3$, $-OCH_2X^{27}$, $-OCHX^{27}_2$, $-CN$, $-SO_{n27}R^{27A}$, $-SO_{v27}NR^{27A}R^{27B}$, $-NHC(O)NR^{27A}R^{27B}$, $-N(O)_{m27}$, $-NR^{27A}R^{27B}$, $-NHNR^{27A}R^{27B}$, $-C(O)R^{27A}$, $-C(O)-OR^{27A}$, $-C(O)NR^{27A}R^{27B}$, $-C(O)NHNR^{27A}R^{27B}$, $-OR^{27A}$, $-NR^{27A}SO_2R^{27B}$, $-NR^{27A}C(O)R^{27B}$, $-NR^{27A}C(O)OR^{27B}$, $-NR^{27A}OR^{27B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{28}$ is selected from hydrogen, halogen, $-CX^{28}_3$, $-CHX^{28}_2$, $-CH_2X^{28}$, $-OCX^{28}_3$, $-OCH_2X^{28}$, $-OCHX^{28}_2$, $-CN$, $-SO_{n28}R^{28A}$, $-SO_{v28}NR^{28A}R^{28B}$, $-NHC(O)NR^{28A}R^{28B}$, $-N(O)_{m28}$, $-NR^{28A}R^{28B}$, $-NHNR^{28A}R^{28B}$, $-C(O)R^{28A}$, $-C(O)-OR^{28A}$, $-C(O)NR^{28A}R^{28B}$, $-C(O)NHNR^{28A}R^{28B}$, $-OR^{28A}$, $-NR^{28A}SO_2R^{28B}$, $-NR^{28A}C(O)R^{28B}$, $-NR^{28A}C(O)OR^{28B}$, $-NR^{28A}OR^{28B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted and unsubstituted heteroaryl;

$R^{29}$ is selected from hydrogen, halogen, $-CX^{29}_3$, $-CHX^{29}_2$, $-CH_2X^{29}$, $-OCX^{29}_3$, $-OCH_2X^{29}$, $-OCHX^{29}_2$, $-CN$, $-SO_{n29}R^{29A}$, $-SO_{v29}NR^{29A}R^{29B}$, $-NHC(O)NR^{29A}R^{29B}$, $-N(O)_{m29}$, $-NR^{29A}R^{29B}$, $-NHNR^{29A}R^{29B}$, $-C(O)R^{29A}$, $-C(O)-OR^{29A}$, $-C(O)NR^{29A}R^{29B}$, $-C(O)NHNR^{29A}R^{29B}$, $-OR^{29A}$, $-NR^{29A}SO_2R^{29B}$, $-NR^{29A}C(O)R^{29B}$, $-NR^{29A}C(O)OR^{29B}$, $-NR^{29A}OR^{29B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{30}$ is selected from hydrogen, halogen, $-CX^{30}_3$, $-CHX^{30}_2$, $-CH_2X^{30}$, $-OCX^{30}_3$, $-OCH_2X^{30}$, $-OCHX^{30}_2$, $-CN$, $-SO_{n30}R^{30A}$, $-SO_{v30}NR^{30A}R^{30B}$, $-NHC(O)NR^{30A}R^{30B}$, $-N(O)_{m30}$, $-NR^{30A}R^{30B}$, $-NHNR^{30A}R^{30B}$, $-C(O)R^{30A}$, $-C(O)-OR^{30A}$, $-C(O)NR^{30A}R^{30B}$, $-C(O)NHNR^{30A}R^{30B}$, $-OR^{30A}$, $-NR^{30A}SO_2R^{30B}$, $-NR^{30A}C(O)R^{30B}$, $-NR^{30A}C(O)OR^{30B}$, $-NR^{30A}OR^{30B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{31}$ is selected from hydrogen, halogen, —$CX^{31}_3$, —$CHX^{31}_2$, —$CH_2X^{31}$, —$OCX^{31}_3$, —$OCH_2X^{31}$, —$OCHX^{31}_2$, —CN, —$SO_{n31}R^{31A}$, —$SO_{v31}NR^{31A}R^{31B}$, —NHC(O)NR$^{31A}R^{31B}$, —N(O)$_{m31}$, —$NR^{31A}R^{31B}$, —$NHNR^{31A}R^{31B}$, —C(O)R$^{31A}$, —C(O)—OR$^{31A}$, —C(O)NR$^{31A}R^{31B}$, —C(O)NHNR$^{31A}R^{31B}$, —OR$^{31A}$, —NR$^{31A}SO_2R^{31B}$, —NR$^{31A}$C(O)R$^{31B}$, —NR$^{31A}$C(O)OR$^{31B}$, —NR$^{31A}$OR$^{31B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{32}$ is selected from hydrogen, halogen, —$CX^{33}_3$, —$CHX^{32}_2$, —$CH_2X^{32}$, —$OCX^{33}_3$, —$OCH_2X^{32}$, —$OCHX^{32}_2$, —CN, —$SO_{n32}R^{32A}$, —$SO_{v32}NR^{32A}R^{32B}$, —NHC(O)NR$^{32A}R^{32B}$, —N(O)$_{m32}$, —$NR^{32A}R^{32B}$, —$NHNR^{32A}R^{32B}$, —C(O)R$^{32A}$, —C(O)—OR$^{32A}$, —C(O)NR$^{32A}R^{32B}$, —C(O)NHNR$^{32A}R^{32B}$, —OR$^{32A}$, —NR$^{32A}SO_2R^{32B}$, —NR$^{32A}$C(O)R$^{32B}$, —NR$^{32A}$C(O)OR$^{32B}$, —NR$^{32A}$OR$^{32B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted and unsubstituted heteroaryl;

$R^{33}$ is selected from hydrogen, halogen, —$CX^{33}_3$, —$CHX^{33}_2$, —$CH_2X^{33}$, —$OCX^{33}_3$, —$OCH_2X^{33}$, —$OCHX^{33}_2$, —CN, —$SO_{n33}R^{33A}$, —$SO_{v33}NR^{33A}R^{33B}$, —NHC(O)NR$^{33A}R^{33B}$, —N(O)$_{m33}$, —$NR^{33A}R^{33B}$, —$NHNR^{33A}R^{33B}$, —C(O)R$^{33A}$, —C(O)—OR$^{33A}$, —C(O)NR$^{33A}R^{33B}$, —C(O)NHNR$^{33A}R^{33B}$, —OR$^{33A}$, —NR$^{33A}SO_2R^{33B}$, —NR$^{33A}$C(O)R$^{33B}$, —NR$^{33A}$C(O)OR$^{33B}$, —NR$^{33A}$OR$^{33B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{34}$ is selected from hydrogen, halogen, —$CX^{34}_3$, —$CHX^{34}_2$, —$CH_2X^{34}$, —$OCX^{34}_3$, —$OCH_2X^{34}$, —$OCHX^{34}_2$, —CN, —$SO_{n34}R^{34A}$, —$SO_{v34}NR^{34A}R^{34B}$, —NHC(O)NR$^{34A}R^{34B}$, —N(O)$_{m34}$, —$NR^{34A}R^{34B}$, —$NHNR^{34A}R^{34B}$, —C(O)R$^{34A}$, —C(O)—OR$^{34A}$, —C(O)NR$^{34A}R^{34B}$, —C(O)NHNR$^{34A}R^{34B}$, —OR$^{34A}$, —NR$^{34A}SO_2R^{34B}$, —NR$^{34A}$C(O)R$^{34B}$, —NR$^{34A}$C(O)OR$^{34B}$, —NR$^{34A}$OR$^{34B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{35}$ is selected from hydrogen, halogen, —$CX^{35}_3$, —$CHX^{35}_2$, —$CH_2X^{35}$, —$OCX^{35}_3$, —$OCH_2X^{35}$, —$OCHX^{35}_2$, —CN, —$SO_{v35}R^{35A}$, —$SO_{v35}NR^{35A}R^{35B}$, —NHC(O)NR$^{35A}R^{35B}$, —N(O)$_{m35}$, —$NR^{35A}R^{35B}$, —$NHNR^{35A}R^{35B}$, —C(O)R$^{35A}$, —C(O)—OR$^{35A}$, —C(O)NR$^{35A}R^{35B}$, —C(O)NHNR$^{35A}R^{35B}$, —OR$^{35A}$, —NR$^{35A}SO_2R^{35B}$, —NR$^{35A}$C(O)R$^{35B}$, —NR$^{35A}$C(O)OR$^{35B}$, —NR$^{35A}$OR$^{35B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

Each $R^{1A}$, $R^{1B}$, $R^{3A}$, $R^{3B}$, $R^{4A}$, $R^{4B}$, $R^{6A}$, $R^{6B}$, $R^{7A}$, $R^{7B}$, $R^{9A}$, $R^{9B}$, $R^{10A}$, $R^{10B}$, $R^{11A}$, $R^{11B}$, $R^{17A}$, $R^{17B}$, $R^{18A}$, $R^{18B}$, $R^{19A}$, $R^{19B}$, $R^{20A}$, $R^{20B}$, $R^{21A}$, $R^{21B}$, $R^{22A}$, $R^{22B}$, $R^{23A}$, $R^{23B}$, $R^{24A}$, $R^{24B}$, $R^{25A}$, $R^{25B}$, $R^{26A}$, $R^{26B}$, $R^{27A}$, $R^{27B}$, $R^{28A}$, $R^{28B}$, $R^{29A}$, $R^{29B}$, $R^{30A}$, $R^{30B}$, $R^{31A}$, $R^{31B}$, $R^{32A}$, $R^{32B}$, $R^{33A}$, $R^{33B}$, $R^{34A}$, $R^{34B}$, $R^{35A}$, $R^{35B}$ is independently selected from hydrogen, —$CX_3$, —$CHX_2$, —$CH_2X$, —C(O)OH, —C(O)NH$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$_3$, —OCHX$_2$, —OCH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{1A}$ and $R^{1B}$ substituents bonded to the same nitrogen atom may optionally be joined to form a substituted or unsubstituted heterocycloalkyl or substituted or unsubstituted heteroaryl; $R^{2A}$ and $R^{2B}$ substituents bonded to the same nitrogen atom may optionally be joined to form a substituted or unsubstituted heterocycloalkyl or substituted or unsubstituted heteroaryl; $R^{4A}$ and $R^{4B}$ substituents bonded to the same nitrogen atom may optionally be joined to form a substituted or unsubstituted heterocycloalkyl or substituted or unsubstituted heteroaryl; $R^{6A}$ and $R^{6B}$ substituents bonded to the same nitrogen atom may optionally be joined to form a substituted or unsubstituted heterocycloalkyl or substituted or unsubstituted heteroaryl; $R^{7A}$ and $R^{1B}$ substituents bonded to the same nitrogen atom may optionally be joined to form a substituted or unsubstituted heterocycloalkyl or substituted or unsubstituted heteroaryl; $R^{9A}$ and $R^{9B}$ substituents bonded to the same nitrogen atom may optionally be joined to form a substituted or unsubstituted heterocycloalkyl or substituted or unsubstituted heteroaryl; $R^{13A}$ and $R^{13B}$ substituents bonded to the same nitrogen atom may optionally be joined to form a substituted or unsubstituted heterocycloalkyl or substituted or unsubstituted heteroaryl; $R^{14A}$ and $R^{14B}$ substituents bonded to the same nitrogen atom may optionally be joined to form a substituted or unsubstituted heterocycloalkyl or substituted or unsubstituted heteroaryl; $R^{15A}$ and $R^{15B}$ substituents bonded to the same nitrogen atom may optionally be joined to form a substituted or unsubstituted heterocycloalkyl or substituted or unsubstituted heteroaryl; $R^{16A}$ and $R^{16B}$ substituents bonded to the same nitrogen atom may optionally be joined to form a substituted or unsubstituted heterocycloalkyl or substituted or unsubstituted heteroaryl; $R^{17A}$ and $R^{17B}$ substituents bonded to the same nitrogen atom may optionally be joined to form a substituted or unsubstituted heterocycloalkyl or substituted or unsubstituted heteroaryl; $R^{18A}$ and $R^{18B}$ substituents bonded to the same nitrogen atom may optionally be joined to form a substituted or unsubstituted heterocycloalkyl or substituted or unsubstituted heteroaryl; $R^{19A}$ and $R^{19B}$ substituents bonded to the same nitrogen atom may optionally be joined to form a substituted or unsubstituted heterocycloalkyl or substituted or unsubstituted heteroaryl; $R^{20A}$ and $R^{20B}$, substituents bonded to the same nitrogen atom may optionally be joined to form a substituted or unsubstituted heterocycloalkyl or substituted or unsubstituted heteroaryl; $R^{21A}$ and $R^{21B}$ substituents bonded to the same nitrogen atom may optionally be joined to form a substituted or unsubstituted heterocycloalkyl or substituted or unsubstituted heteroaryl; $R^{22A}$ and $R^{22B}$ substituents bonded to the same nitrogen atom may optionally be joined to form a substituted or unsubstituted heterocycloalkyl or substituted or unsubstituted heteroaryl; $R^{23A}$ and $R^{23B}$ substituents bonded to the same nitrogen atom may optionally be joined to form a substituted or unsubstituted heterocycloalkyl or substituted or unsubstituted heteroaryl; $R^{24A}$ and $R^{24B}$ substituents bonded to the same nitrogen atom may optionally be joined to form a substituted or unsubstituted heterocycloalkyl or substituted or unsubstituted heteroaryl; $R^{25A}$ and $R^{25B}$ substituents bonded to the same nitrogen atom may optionally be joined to form a substituted or unsubstituted heterocycloalkyl or substituted or unsubstituted heteroaryl; $R^{26A}$ and $R^{26B}$ substituents bonded to the same nitrogen atom may optionally be joined to form a substituted or unsubstituted heterocycloalkyl or substituted or unsubstituted heteroaryl; $R^{27A}$ and $R^{27B}$ substituents bonded to the same nitrogen atom may optionally be joined to form a substituted or unsubstituted heterocycloalkyl or substituted or unsubstituted heteroaryl; $R^{28A}$ and $R^{28B}$ substituents bonded to the same nitrogen atom may optionally be joined to form a substituted or unsubstituted heterocycloalkyl or substituted or unsubstituted heteroaryl; $R^{29A}$ and $R^{29B}$ substituents bonded to the same nitrogen atom may optionally be joined to form a substituted or unsubstituted heterocycloalkyl or substituted or unsubstituted heteroaryl; $R^{30A}$ and $R^{30B}$ substituents bonded to the same nitrogen atom may optionally be joined to form a substituted or unsubstituted heterocycloalkyl or substituted or unsubstituted heteroaryl;

Each m1, m3, m4, m6, m7, m9, m10, m11, m17, m18, m19, m20, m21, m22, m23, m24, m25, m26, m27, m28, m29, m30, m31, m32, m33, m34 and m35 is independently 1 or 2;

Each v1, v3, v4, v6, v7, v9, v10, v11, v17, v18, v19, v20, v21, v22, v23, v24, v25, v26, v27, v28, v29, v30, v31, v32, v33, v34 and v35 is independently 1 or 2;

Each n1, n3, n4, n6, n7, n9, n10, n11, n17, n18, n19, n20, n21, n22, n23, n24, n25, n26, n27, n28, n29, n30, n31, n32, n33, n34 and n35 is independently an integer from 0 to 2; and Each $X^1$, $X^3$, $X^4$, $X^6$, $X^7$, $X^9$, $X^{10}$, $X^{11}$, $X^{17}$, $X^{18}$, $X^9$, $X^{20}$, $X^{21}$, $X^{22}$, $X^{23}$, $X^{24}$, $X^{25}$, $X^{26}$, $X^{27}$, $X^{28}$, $X^{29}$, $X^{30}$, $X^{31}$, $X^{32}$, $X^{33}$, $X^{34}$, and $X^{35}$ is independently —Cl, —Br, —I or —F.

In one embodiment, ring B is optionally substituted with one or more substituent groups.

In one embodiment of compounds of Formula VIII, ring B is selected from thienyl, furanyl, pyrrolyl, thiazolyl, oxazolyl, imidazolyl, pyrazolyl, isoxazolyl, triazolyl and isothiazolyl. In one embodiment, the thienyl, furanyl, pyrrolyl, thiazolyl, oxazolyl, imidazolyl, pyrazolyl, isoxazolyl, triazolyl and isothiazolyl rings are optionally substituted with one or more substituent groups.

In one embodiment of compounds of Formula VIII, ring B is selected from phenyl, pyridyl, pyrazinyl, pyrimidinyl, pyridazinyl, and triazinyl. In one embodiment, the phenyl, pyridyl, pyrazinyl, pyrimidinyl, pyridazinyl, and triazinyl rings are optionally substituted with one or more substituent groups.

In one embodiment of compounds of Formula VIII, ring B is selected from selected from

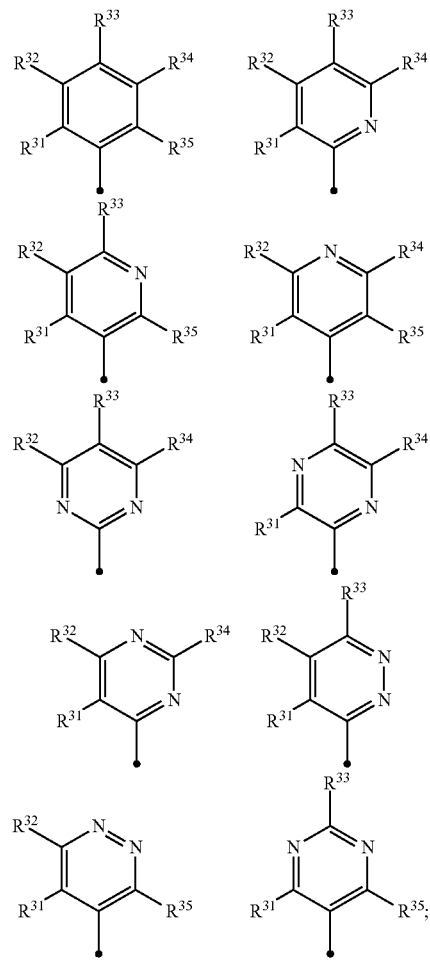

In one embodiment of compounds of Formula VIII, ring B is selected from benzothienyl, benzothiazolyl, indolyl, benzimidazolyl, benzoxazolyl, benzofuryl, indazolyl and isolindolyl. In one embodiment, the benzothienyl, benzothiazolyl, indolyl, benzimidazolyl, benzoxazolyl, benzofuryl, indazolyl and isolindolyl rings are optionally substituted with one or more substituent groups.

In one embodiment of compounds of Formula VIII, ring B is selected from quinolyl, isoquinolyl, naphthpyridinyl, quinoxalinyl and quinazolinyl. In one embodiment, the quinolyl, isoquinolyl, naphthpyridinyl, quinoxalinyl and quinazolinyl rings are optionally substituted with one or more substituent groups.

In one embodiment of compounds of Formula VIII, E is selected from —C(=O)CH=CH$_2$, —C(=O)-ethynyl, —C(=O)CH=CHCF$_3$, —C(=O)CH=CHCHF$_2$, —C(=O)CH=CHCH$_2$F, and —C(=O)CH$_2$Br.

In one embodiment, W is S.

One embodiment relates to compounds of Formula IX:

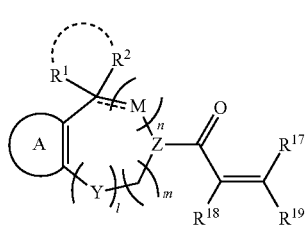

(IX)

wherein
= is a single bond or double bond.
l, m, n are independently an integer from 0 to 2.
M is selected from $CR^3R^4$, $-NR^5$, $C=O$, $O$, $S=O$, $O=S=O$, and $S$.
Y is selected from $CR^6R^7$, $NR$, $C=O$, $O$, $S=O$, $O=S=O$, and $S$.
Z is $CR^9$, or N.
ring A is selected from
  a) 5- or 6-membered partially saturated heterocyclyl,
  b) 5- or 6-membered aryl or heteroaryl,
  c) 9-, 10- or 11-membered fused partially saturated heterocyclyl,
  d) 9- or 10-membered fused heteroaryl,
  e) naphthyl, and
  f) 4-, 5- or 6-membered cycloalkenyl;
$R^1$ is selected from hydrogen, halogen, $-CX^1_3$, $-CHX^1_2$, $-CH_2X^1$, $-OCX^1_3$, $-OCH_2X^1$, $-OCHX^1_2$, $-CN$, $-SO_{n1}R^{1A}$, $-SO_{v1}NR^{1A}R^{1B}$, $-NHC(O)NR^{1A}R^{1B}$, $-N(O)_{m1}$, $-NR^{1A}R^{1B}$, $-NHNR^{1A}R^{1B}$, $-C(O)R^{1A}$, $-C(O)-OR^{1A}$, $-C(O)NR^{1A}R^{1B}$, $-C(O)NHNR^{1A}R^{1B}$, $-OR^{1A}$, $-NR^{1A}SO_2R^{1B}$, $-NR^{1A}C(O)R^{1B}$, $-NR^{1A}C(O)OR^{1B}$, $-NR^{1A}OR^{1B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;
$R^2$ is selected from hydrogen, halogen, $-CX^2_3$, $-CHX^2_2$, $-CH_2X^2$, $-OCX^2_3$, $-OCH_2X^2$, $-OCHX^2_2$, $-CN$, $-SO_{n2}R^{2A}$, $-SO_{v2}NR^{2A}R^{2B}$, $-NHC(O)NR^{2A}R^{2B}$, $-N(O)_{m2}$, $-NR^{2A}R^{2B}$, $-NHNR^{2A}R^{2B}$, $-C(O)R^{2A}$, $-C(O)-OR^{2A}$, $-C(O)NR^{2A}R^{2B}$, $-C(O)NHNR^{2A}R^{2B}$, $-OR^{2A}$, $-NR^{2A}SO_2R^{2B}$, $-NR^{2A}C(O)R^{2B}$, $-NR^{2A}C(O)OR^{2B}$, $-NR^{2A}OR^{2B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; $R^1$ and $R^2$ substituents may optionally be joined to form a substituted or unsubstituted cycloalkyl or heterocycloalkyl;
$R^3$ is selected from hydrogen, halogen, $-CX^3_3$, $-CHX^3_2$, $-CH_2X^3$, $-OCX^3_3$, $-OCH_2X^3$, $-OCHX^3_2$, $-CN$, $-SO_{3R3A}$, $-SO_{v3}NR^{3A}R^{3B}$, $-NHC(O)NR^{3A}R^{3B}$, $-N(O)_{m3}$, $-NR^{3A}R^{3B}$, $-NHNR^{3A}R^{3B}$, $-C(O)R^{3A}$, $-C(O)-OR^{3A}$, $-C(O)NR^{3A}R^{3B}$, $-OR^{3A}$, $-NR^{3A}SO_2R^{3B}$, $-NR^{3A}C(O)R^{3B}$, $-NR^{3A}C(O)OR^{3B}$, $-NR^{3A}OR^{3B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^4$ is selected from hydrogen, halogen, $-CX^4_3$, $-CHX^4_2$, $-CH_2X^4$, $-OCX^4_3$, $-OCH_2X^4$, $-OCHX^4_2$, $-CN$, $-SO_{n4}R^{4A}$, $-SO_{v4}NR^{4A}R^{4B}$, $-NHC(O)NR^{4A}R^{4B}$, $-N(O)_{m4}$, $-NR^{4A}R^{4B}$, $-NHNR^{4A}R^{4B}$, $-C(O)R^{4A}$, $-C(O)-OR^{4A}$, $-C(O)NR^{4A}R^{4B}$, $-C(O)NHNR^{4A}R^{4B}$, $-OR^{4A}$, $-NR^{4A}SO_2R^{4B}$, $-NR^{4A}C(O)R^{4B}$, $-NR^{4A}C(O)OR^{4B}$, $-NR^{4A}OR^{4B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; $R^3$ and $R^3$ substituents may optionally be joined to form a substituted or unsubstituted cycloalkyl or heterocycloalkyl;
$R^5$ is selected from hydrogen, halogen, $-CX^5_3$, $-CHX^5_2$, $-CH_2X^5$, $-OCX^5_3$, $-OCH_2X^5$, $-OCHX^5_2$, $-CN$, $-SO_5R^{5A}$, $-SO_{v5}NR^{5A}R^{5B}$, $-NHC(O)NR^{5A}R^{5B}$, $-N(O)_{m5}$, $-NR^{5A}R^{5B}$, $-NHNR^{5A}R^{5B}$, $-C(O)R^{5A}$, $-C(O)-OR^{5A}$, $-C(O)NR^{5A}R^{5B}$, $-C(O)NHNR^{5A}R^{5B}$, $-OR^{5A}$, $-NR^{5A}SO_2R^{5B}$, $-NR^{5A}C(O)R^{5B}$, $-NR^{5A}C(O)OR^{5B}$, $-NR^{5A}OR^{5B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;
$R^6$ is selected from hydrogen, halogen, $-CX^6_3$, $-CHX^6_2$, $-CH_2X^6$, $-OCX^6_3$, $-OCH_2X^6$, $-OCHX^6_2$, $-CN$, $-SO_{v6}R^{6A}$, $-SO_6NR^{6A}R^{6B}$, $-NHC(O)NR^{6A}R^{6B}$, $-N(O)_{m6}$, $-NR^{6A}R^{6B}$, $-NHNR^{6A}R^{6B}$, $-C(O)R^{6A}$, $-C(O)-OR^{6A}$, $-C(O)NR^{6A}R^{6B}$, $-C(O)NHNR^{6A}R^{6B}$, $-OR^{6A}$, $-NR^{6A}SO_2R^{6B}$, $-NR^{6A}C(O)R^{6B}$, $-NR^{6A}C(O)OR^{6B}$, $-NR^{6A}OR^{6B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;
$R^7$ is selected from hydrogen, halogen, $-CX^7_3$, $-CHX^7_2$, $-CH_2X^7$, $-OCX^7_3$, $-OCH_2X^7$, $-OCHX^7_2$, $-CN$, $-SO_7R^{7A}$, $-SO_{v7}NR^{7A}R^{7B}$, $-NHC(O)NR^{7A}R^{7B}$, $-N(O)_{m7}$, $-NR^{7A}R^{7B}$, $-NHNR^{7A}R^{7B}$, $-C(O)R^{7A}$, $-C(O)-OR^{7A}$, $-C(O)NR^{7A}R^{7B}$, $-C(O)NHNR^{7A}R^{7B}$, $-OR^{7A}$, $-NR^{7A}SO_2R^{7B}$, $-NR^{7A}C(O)R^{7B}$, $-NR^{7A}C(O)OR^{7B}$, $-NR^{7A}OR^{7B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;
$R^8$ is selected from hydrogen, halogen, $-CX^8_3$, $-CHX^8_2$, $-CH_2X^8$, $-OCX^8_3$, $-OCH_2X^8$, $-OCHX^8_2$, $-CN$, $-SO_{v8}R^{8A}$, $-SO_8NR^{8A}R^{8B}$, $-NHC(O)NR^{8A}R^{8B}$, $-N(O)_{m8}$, $-NR^{8A}R^{7B}$, $-NHNR^{8A}R^{8B}$, $-C(O)R^{8A}$, $-C(O)-OR^{8A}$, $-C(O)NR^{8A}R^{8B}$, $-C(O)NHNR^{8A}R^{8B}$, $-OR^{8A}$, $-NR^{8A}SO_2R^{8B}$, $-NR^{8A}C(O)R^{8B}$, $-NR^{8A}C(O)OR^{8B}$, $-NR^{8A}OR^{8B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;
$R^9$ is selected from hydrogen, halogen, $-CX^9_3$, $-CHX^9_2$, $-CH_2X^9$, $-OCX^9_3$, $-OCH_2X^9$, $-OCHX^9_2$, $-CN$, $-SO_{v9}R^{9A}$, $-SO_9NR^{9A}R^{9B}$, $-NHC(O)NR^{9A}R^{9B}$, $-N(O)_{m9}$, $-NR^{9A}R^{9B}$, $-NHNR^{9A}R^{9B}$, $-C(O)R^{9A}$, $-C(O)-$ $NR^{9A}R^{9B}$, —C(O)NHNR$^{9A}R^{9B}$, —OR$^{9A}$, —NR$^{9A}$SO$_2$R$^{9B}$, —NR$^{9A}$C(O)R$^{9B}$, —NR$^{9A}$C(O)OR$^{9B}$, —NR$^{9A}$OR$^{9B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{10}$ is selected from hydrogen, halogen, —CX$^{10}_3$, —CHX$^{10}_2$, —CH$_2$X$^{10}$, —OCX$^{10}_3$, —OCH$_2$X$^{10}$, —OCHX$^{10}_2$, —CN, —SO$_{n10}$R$^{10A}$, —SO$_{v10}$NR$^{10A}$R$^{10B}$, —NHC(O)NR$^{10A}$R$^{10B}$, —N(O)$_{m10}$, —NR$^{10A}$R$^{10B}$, —NHNR$^{10A}$R$^{10B}$, —C(O)R$^{10A}$, —C(O)—OR$^{10A}$, —C(O)NR$^{10A}$R$^{10B}$, —C(O)NHNR$^{10A}$R$^{10B}$, —OR$^{10A}$, —NR$^{10A}$SO$_2$R$^{10B}$, —NR$^{10A}$C(O)R$^{10B}$, —NR$^{10A}$C(O)OR$^{10B}$, —NR$^{10A}$OR$^{10B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{11}$ is selected from hydrogen, halogen, —CX$^{11}_3$, —CHX$^{11}_2$, —CH$_2$X$^{11}$, —OCX$^{11}_3$, —OCH$_2$X$^{11}$, —OCHX$^{11}_2$, —CN, —SO$_{n11}$R$^{11A}$, —SO$_{v11}$NR$^{11A}$R$^{11B}$, —NHC(O)NR$^{11A}$R$^{11B}$, —N(O)$_{m11}$, —NR$^{11A}$R$^{11B}$, —NHNR$^{11A}$R$^{11B}$, —C(O)R$^{11A}$, —C(O)—OR$^{11A}$, —C(O)NR$^{11A}$R$^{11B}$, —C(O)NHNR$^{11A}$R$^{11B}$, —OR$^{11A}$, —NR$^{11A}$SO$_2$R$^{11B}$, —NR$^{11A}$C(O)R$^{11B}$, —NR$^{11A}$C(O)OR$^{11B}$, —NR$^{11A}$OR$^{11B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{12}$ is selected from hydrogen, halogen, —CX$^{12}_3$, —CHX$^{12}_2$, —CH$_2$X$^{12}$, —OCX$^{12}_3$, —OCH$_2$X$^{12}$, —OCHX$^{12}_2$, —CN, —SO$_{n12}$R$^{12A}$, —SO$_{v12}$NR$^{12A}$R$^{12B}$, —NHC(O)NR$^{12A}$R$^{12B}$, —N(O)$_{m12}$, —NR$^{12A}$R$^{12B}$, —NHNR$^{12A}$R$^{12B}$, —C(O)R$^{12A}$, —C(O)—OR$^{12A}$, —C(O)NR$^{12A}$R$^{12B}$, —C(O)NHNR$^{12A}$R$^{12B}$, —OR$^{12A}$, —NR$^{12A}$SO$_2$R$^{12B}$, —NR$^{12A}$C(O)R$^{12B}$, —NR$^{12A}$C(O)OR$^{12B}$, —NR$^{12A}$OR$^{12B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{13}$ is selected from hydrogen, halogen, —CX$^{13}_3$, —CHX$^{13}_2$, —CH$_2$X$^{13}$, —OCX$^{13}_3$, —OCH$_2$X$^{13}$, —OCHX$^{13}_2$, —CN, —SO$_{n13}$R$^{13A}$, —SO$_{v13}$NR$^{13A}$R$^{13B}$, —NHC(O)NR$^{13A}$R$^{13B}$, —N(O)$_{m13}$, —NR$^{13A}$R$^{13B}$, —NHNR$^{13A}$R$^{13B}$, —C(O)R$^{13A}$, —C(O)—OR$^{13A}$, —C(O)NR$^{13A}$R$^{13B}$, —C(O)NHNR$^{13A}$R$^{13B}$, —OR$^{13A}$, —NR$^{13A}$SO$_2$R$^{13B}$, —NR$^{13A}$C(O)R$^{13B}$, —NR$^{13A}$C(O)OR$^{13B}$, —NR$^{13A}$OR$^{13B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{14}$ is selected from hydrogen, halogen, —CX$^{14}_3$, —CHX$^{14}_2$, —CH$_2$X$^{14}$, —OCX$^{14}_3$, —OCH$_2$X$^{14}$, —OCHX$^{14}_2$, —CN, —SO$_{n14}$R$^{14A}$, —SO$_{v14}$NR$^{14A}$R$^{14B}$, —NHC(O)NR$^{14A}$R$^{14B}$, —N(O)$_{m14}$, —NR$^{14A}$R$^{14B}$, —NHNR$^{14A}$R$^{14B}$, —C(O)R$^{14A}$, —C(O)—OR$^{14A}$, —C(O)NR$^{14A}$R$^{14B}$, —C(O)NHNR$^{14A}$R$^{14B}$, —OR$^{14A}$, —NR$^{14A}$SO$_2$R$^{14B}$, —NR$^{14A}$C(O)R$^{14B}$, —NR$^{14A}$C(O)OR$^{14B}$, —NR$^{14A}$OR$^{14B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{15}$ is selected from hydrogen, halogen, —CX$^{15}_3$, —CHX$^{5}_2$, —CH$_2$X$^{15}$, —OCX$^{15}_3$, —OCH$_2$X$^{1}$, —OCHX$^{15}_2$, —CN, —SO$_{n5}$R$^{15A}$ SO$_{v15}$NR$^{15A}$R$^{15B}$, —NHC(O)NR$^{15A}$R$^{15B}$, —N(O)$_{m15}$, —NR$^{15A}$R$^{15B}$, —NHNR$^{15A}$R$^{15B}$, —C(O)R$^{15A}$, —C(O)—OR$^{15A}$, —C(O)NR$^{15A}$R$^{15B}$, —C(O)NHNR$^{15A}$R$^{15B}$, —OR$^{15A}$, —NR$^{15A}$SO$_2$R$^{15B}$, —NR$^{15A}$C(O)R$^{15B}$, —NR$^{15A}$C(O)OR$^{15B}$, —NR$^{15A}$OR$^{15B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{17}$ is selected from hydrogen, halogen, —CX$^{17}_3$, —CHX$^{17}_2$, —CH$_2$X$^{17}$, —OCX$^{17}_3$, —OCH$_2$X$^{17}$, —OCHX$^{17}_2$, —CN, —SO$_{n17}$R$^{17A}$, —SO$_{v17}$NR$^{17A}$R$^{17B}$, —NHC(O)NR$^{17A}$R$^{17B}$, —N(O)$_{m17}$, —NR$^{17A}$R$^{17B}$, —NHNR$^{17A}$R$^{17B}$, —C(O)R$^{17A}$, —C(O)—OR$^{17A}$, —C(O)NR$^{17A}$R$^{17B}$, —C(O)NHNR$^{17A}$R$^{17B}$, —OR$^{17A}$, —NR$^{17A}$SO$_2$R$^{17B}$, —NR$^{17A}$C(O)R$^{17B}$, —NR$^{17A}$C(O)OR$^{17B}$, —NR$^{17A}$OR$^{17B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{18}$ is selected from hydrogen, halogen, —CX$^{18}_3$, —CHX$^{18}_2$, —CH$_2$X$^{18}$, —OCX$^{18}_3$, —OCH$_2$X$^{18}$, —OCHX$^{18}_2$, —CN, —SO$_{n18}$R$^{18A}$, —SO$_{v18}$NR$^{18A}$R$^{18B}$, —NHC(O)NR$^{18A}$R$^{18B}$, —N(O)$_{m18}$, —NR$^{18A}$R$^{18B}$, —NHNR$^{18A}$R$^{18B}$, —C(O)R$^{18A}$, —C(O)—OR$^{18A}$, —C(O)NR$^{18A}$R$^{18B}$, —C(O)NHNR$^{18A}$R$^{18B}$, —OR$^{18A}$, —NR$^{18A}$SO$_2$R$^{18B}$, —NR$^{18A}$C(O)R$^{18B}$, —NR$^{18A}$C(O)OR$^{18B}$, —NR$^{18A}$OR$^{18B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; $R^{17}$ and $R^{18}$ substituents may optionally be joined to form a substituted or unsubstituted cycloalkyl or heterocycloalkyl;

$R^{19}$ is selected from hydrogen, halogen, —CX$^{19}_3$, —CHX$^{19}_2$, —CH$_2$X$^{19}$, —OCX$^{19}_3$, —OCH$_2$X$^{19}$, —OCHX$^{19}_2$, —CN, —SO$_{n19}$R$^{19A}$, —SO$_{v19}$NR$^{19A}$R$^{19B}$, —NHC(O)NR$^{19A}$R$^{19B}$, —N(O)$_{m19}$, —NR$^{19A}$R$^{19B}$, —NHNR$^{19A}$R$^{19B}$, —C(O)R$^{19A}$, —C(O)—OR$^{19A}$, —C(O)NR$^{19A}$R$^{19B}$, —C(O)NHNR$^{19A}$R$^{19B}$, —OR$^{19A}$, —NR$^{19A}$SO$_2$R$^{19B}$, —NR$^{19A}$C(O)R$^{19B}$, —NR$^{19A}$C(O)OR$^{19B}$, —NR$^{19A}$OR$^{19B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

Each $R^{1A}$, $R^{1B}$, $R^{2A}$, $R^{2B}$, $R^{3A}$, $R^{3B}$, $R^{4A}$, $R^{4B}$, $R^{5A}$, $R^{5B}$, $R^{6A}$, $R^{6B}$, $R^{7A}$, $R^{7B}$, $R^{8A}$, $R^{8B}$, $R^{9A}$, $R^{9B}$, $R^{10A}$, $R^{10B}$, $R^{11A}$, $R^{11B}$, $R^{12A}$, $R^{12B}$, $R^{13A}$, $R^{13B}$, $R^{14A}$, $R^{14B}$, $R^{15A}$, $R^{15B}$, $R^{17A}$, $R^{17B}$, $R^{18A}$, $R^{18B}$, $R^{19A}$, $R^{19B}$ is independently selected from hydrogen, —CX$_3$, —CHX$_2$, —CH$_2$X, —C(O)OH, —C(O)NH$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$_3$, —OCHX$_2$, —OCH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{1A}$ and R$^{1B}$ substituents bonded to the same nitrogen atom may optionally be joined to form a substituted or unsubstituted heterocycloalkyl or substituted or unsubstituted heteroaryl; R$^{2A}$ and R$^{2B}$ substituents bonded to the same nitrogen atom may optionally be joined to form a substituted or unsubstituted heterocycloalkyl or substituted or unsubstituted heteroaryl; R$^{4A}$ and R$^{4B}$ substituents bonded to the same nitrogen atom may optionally be joined to form a substituted or unsubstituted heterocycloalkyl or substituted or unsubstituted heteroaryl; R$^{5A}$ and R$^{5B}$ substituents bonded to the same nitrogen atom may optionally be joined to form a substituted or unsubstituted heterocycloalkyl or substituted or unsubstituted heteroaryl; R$^{6A}$ and R$^{6B}$ substituents bonded to the same nitrogen atom may optionally be joined to form a substituted or unsubstituted heterocycloalkyl or substituted or unsubstituted heteroaryl; R$^{7A}$ and R$^{1B}$ substituents bonded to the same nitrogen atom may optionally be joined to form a substituted or unsubstituted heterocycloalkyl or substituted or unsubstituted heteroaryl; R$^{8A}$ and R$^{8B}$ substituents bonded to the same nitrogen atom may optionally be joined to form a substituted or unsubstituted heterocycloalkyl or substituted or unsubstituted heteroaryl; R$^{9A}$ and R$^{9B}$ substituents bonded to the same nitrogen atom may optionally be joined to form a substituted or unsubstituted heterocycloalkyl or substituted or unsubstituted heteroaryl; R$^{10A}$ and R$^{10B}$ substituents bonded to the same nitrogen atom may optionally be joined to form a substituted or unsubstituted heterocycloalkyl or substituted or unsubstituted heteroaryl; R$^{11A}$ and R$^{11B}$ substituents bonded to the same nitrogen atom may optionally be joined to form a substituted or unsubstituted heterocycloalkyl or substituted or unsubstituted heteroaryl; R$^{13A}$ and R$^{13B}$ substituents bonded to the same nitrogen atom may optionally be joined to form a substituted or unsubstituted heterocycloalkyl or substituted or unsubstituted heteroaryl; R$^{14A}$ and R$^{14B}$ substituents bonded to the same nitrogen atom may optionally be joined to form a substituted or unsubstituted heterocycloalkyl or substituted or unsubstituted heteroaryl; R$^{15A}$ and R$^{15B}$ substituents bonded to the same nitrogen atom may optionally be joined to form a substituted or unsubstituted heterocycloalkyl or substituted or unsubstituted heteroaryl; R$^{17A}$ and R$^{17B}$, substituents bonded to the same nitrogen atom may optionally be joined to form a substituted or unsubstituted heterocycloalkyl or substituted or unsubstituted heteroaryl; R$^{18A}$ and R$^{18B}$ substituents bonded to the same nitrogen atom may optionally be joined to form a substituted or unsubstituted heterocycloalkyl or substituted or unsubstituted heteroaryl; R$^{19A}$ and R$^{19B}$ substituents bonded to the same nitrogen atom may optionally be joined to form a substituted or unsubstituted heterocycloalkyl or substituted or unsubstituted heteroaryl;

Each m, m1, m2, m3, m4, m5, m6, m7, m8, m9, m10, m11, m12, m13, m14, m15, m17, m18, and m19 are independently 1 or 2;

Each v1, v2, v3, v4, v5, v6, v7, v8, v9, v10, v11, v12, v13, v14, v15, v16, v17, v18, v19, are independently 1 or 2;

Each n, n1, n2, n3, n4, n5, n6, n7, n8, n9, n10, n11, n12, n13, n14, n15, n17, n18, n19, are independently an integer from 0 to 2 and Each X, X$^1$, X$^2$, X$^3$, X$^4$, X$^5$, X$^6$, X$^7$, X$^8$, X$^9$, X$^{10}$, X$^{11}$, X$^{12}$, X$^{13}$, X$^{14}$, X$^{15}$, X$^{17}$, X$^{18}$, X$^{19}$, are independently —Cl, —Br, —I or —F.

Chemical entities of the present disclosure include those described generally for formula I, above, and are further illustrated by the classes, subclasses, and species disclosed herein. It will be appreciated that preferred subsets described for each variable herein can be used for any of the structural subsets as well.

In an embodiment, a family of compounds consists of compounds provided in Table 1:

TABLE 1

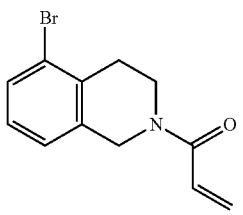

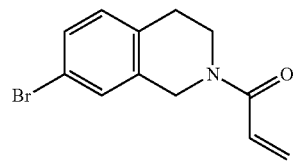

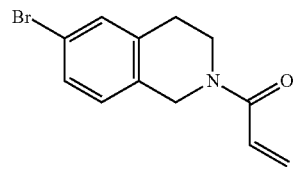

TABLE 1-continued
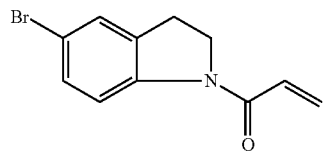
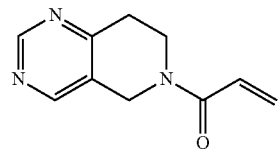
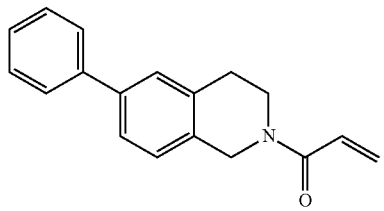 [SMILES: C=CC(=O)N1CCc2cc(-c3ccccc3)ccc2C1]
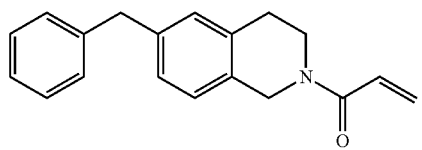 [SMILES: C=CC(=O)N1CCc2cc(Cc3ccccc3)ccc2C1]
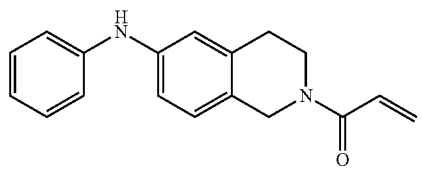 [SMILES: C=CC(=O)N1CCc2cc(Nc3ccccc3)ccc2C1]
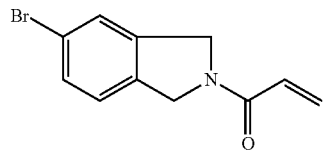
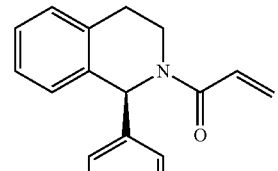
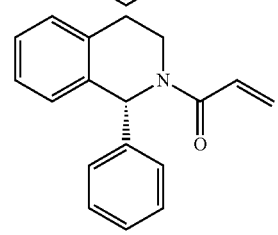

TABLE 1-continued
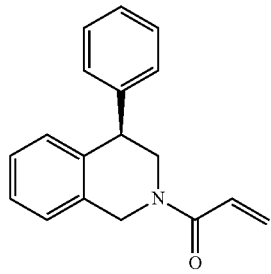 [SMILES: C=CC(=O)N1Cc2ccccc2[C@@H](c2ccccc2)C1]
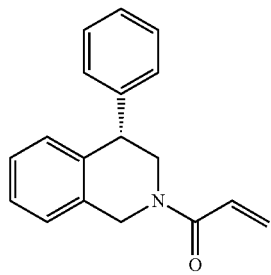 [SMILES: C=CC(=O)N1Cc2ccccc2[C@H](c2ccccc2)C1]
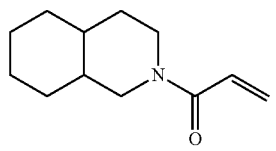
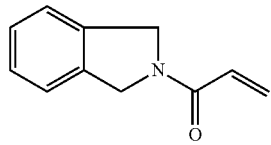
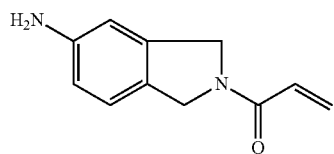
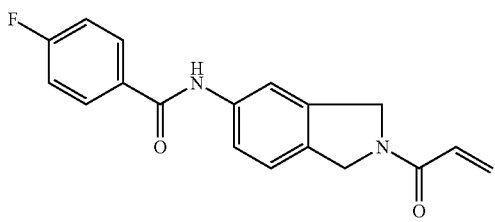
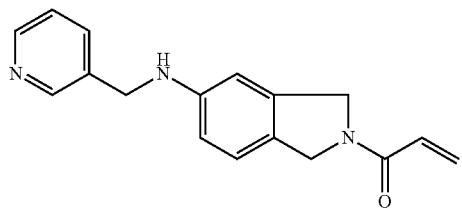 [SMILES: C=CC(=O)N1Cc2ccc(NCc3cccnc3)cc2C1]

TABLE 1-continued
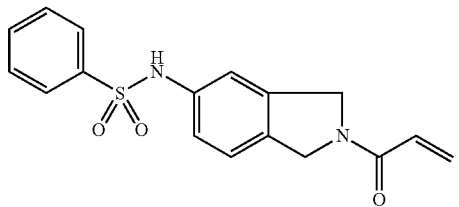 [SMILES: C=CC(=O)N1Cc2ccc(NS(=O)(=O)c3ccccc3)cc2C1]
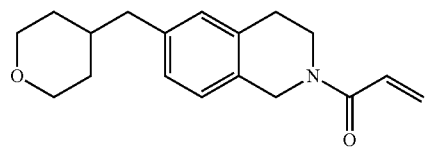 [SMILES: C=CC(=O)N1CCc2cc(CC3CCOCC3)ccc2C1]
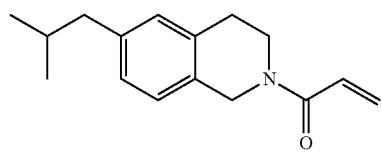 [SMILES: C=CC(=O)N1CCc2cc(CC(C)C)ccc2C1]
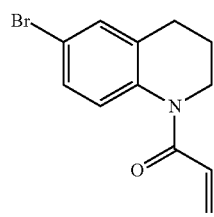
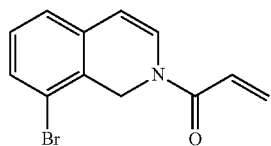
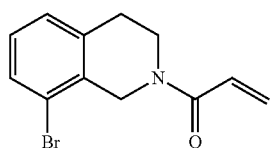
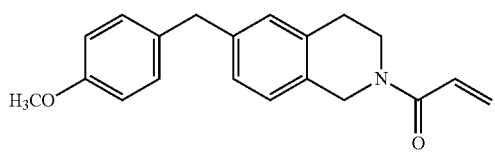 [SMILES: C=CC(=O)N1CCc2cc(Cc3ccc(OC)cc3)ccc2C1]
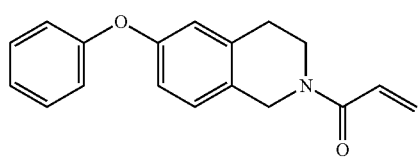 [SMILES: C=CC(=O)N1CCc2cc(Oc3ccccc3)ccc2C1]
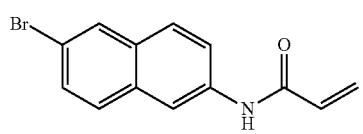 [SMILES: C=CC(=O)Nc1ccc2cc(Br)ccc2c1]

TABLE 1-continued
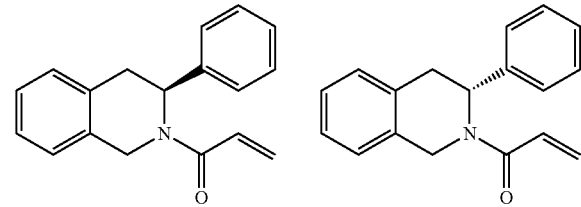
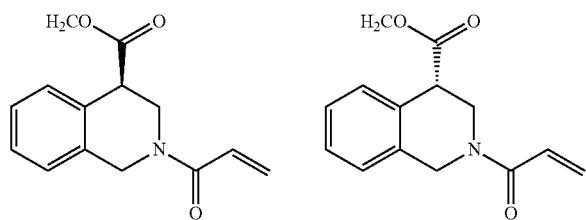
No entry
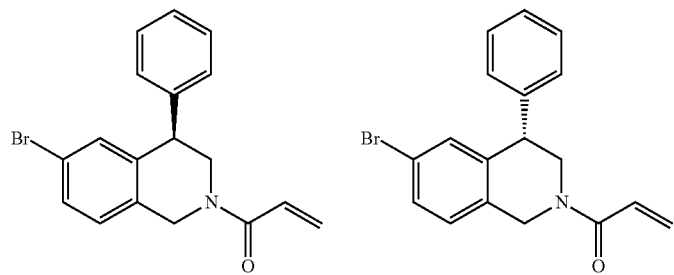 [SMILES: C=CC(=O)N1Cc2ccc(Br)cc2[C@@H](c2ccccc2)C1 ; C=CC(=O)N1Cc2ccc(Br)cc2[C@H](c2ccccc2)C1]
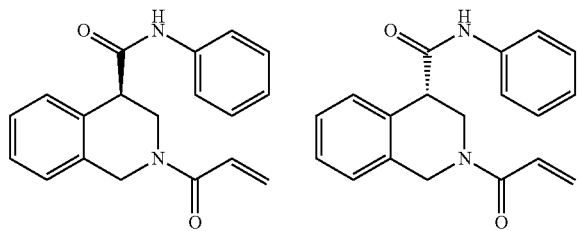
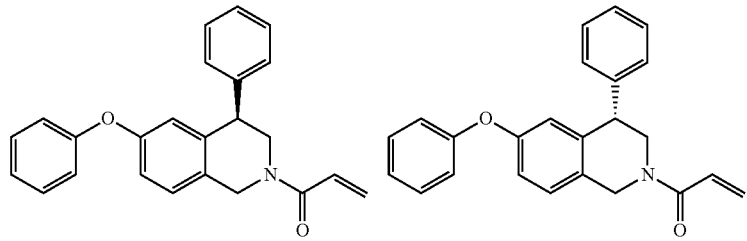
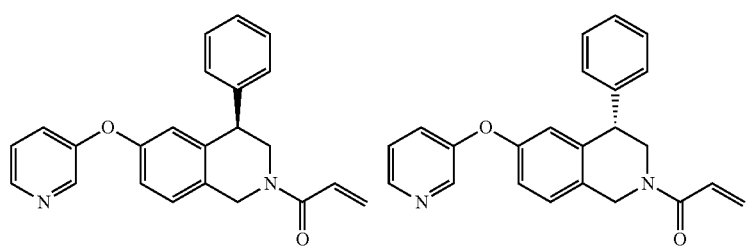

TABLE 1-continued
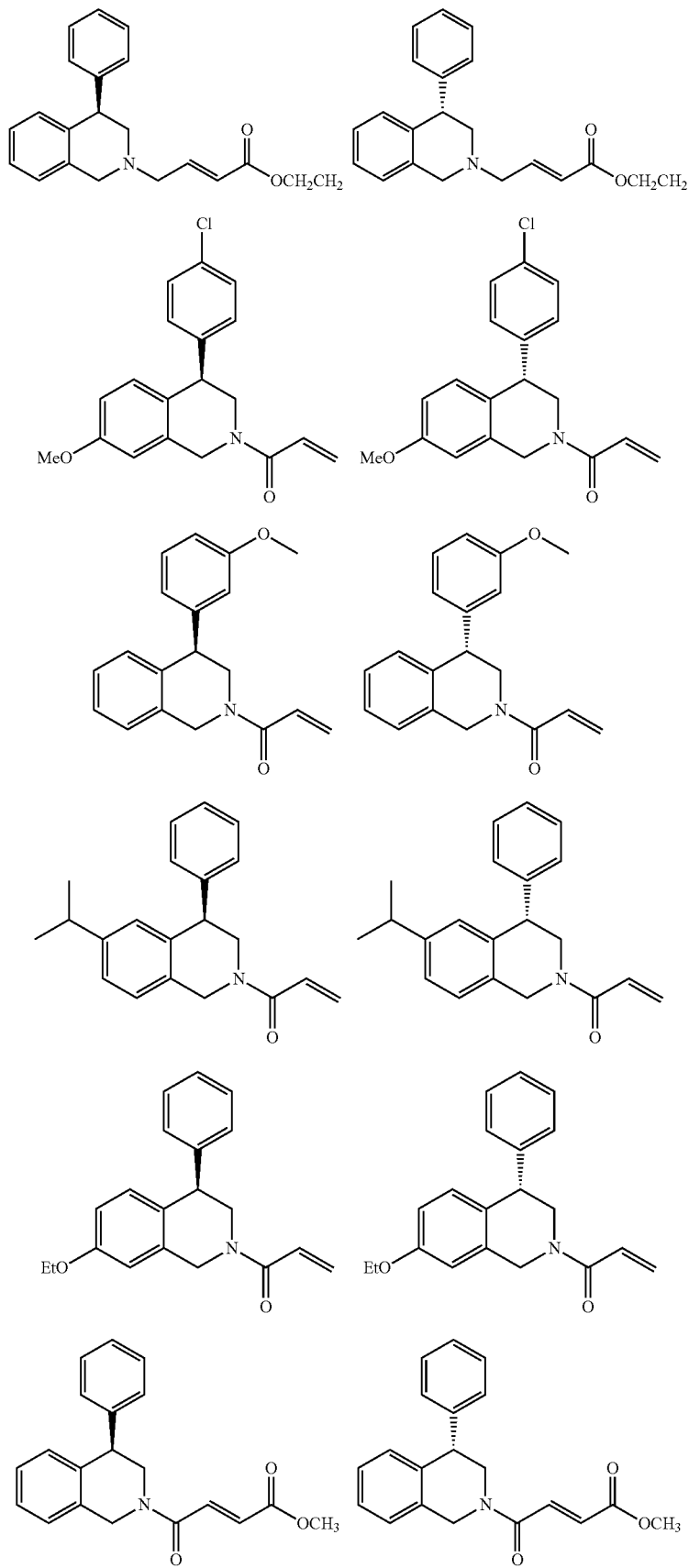

TABLE 1-continued
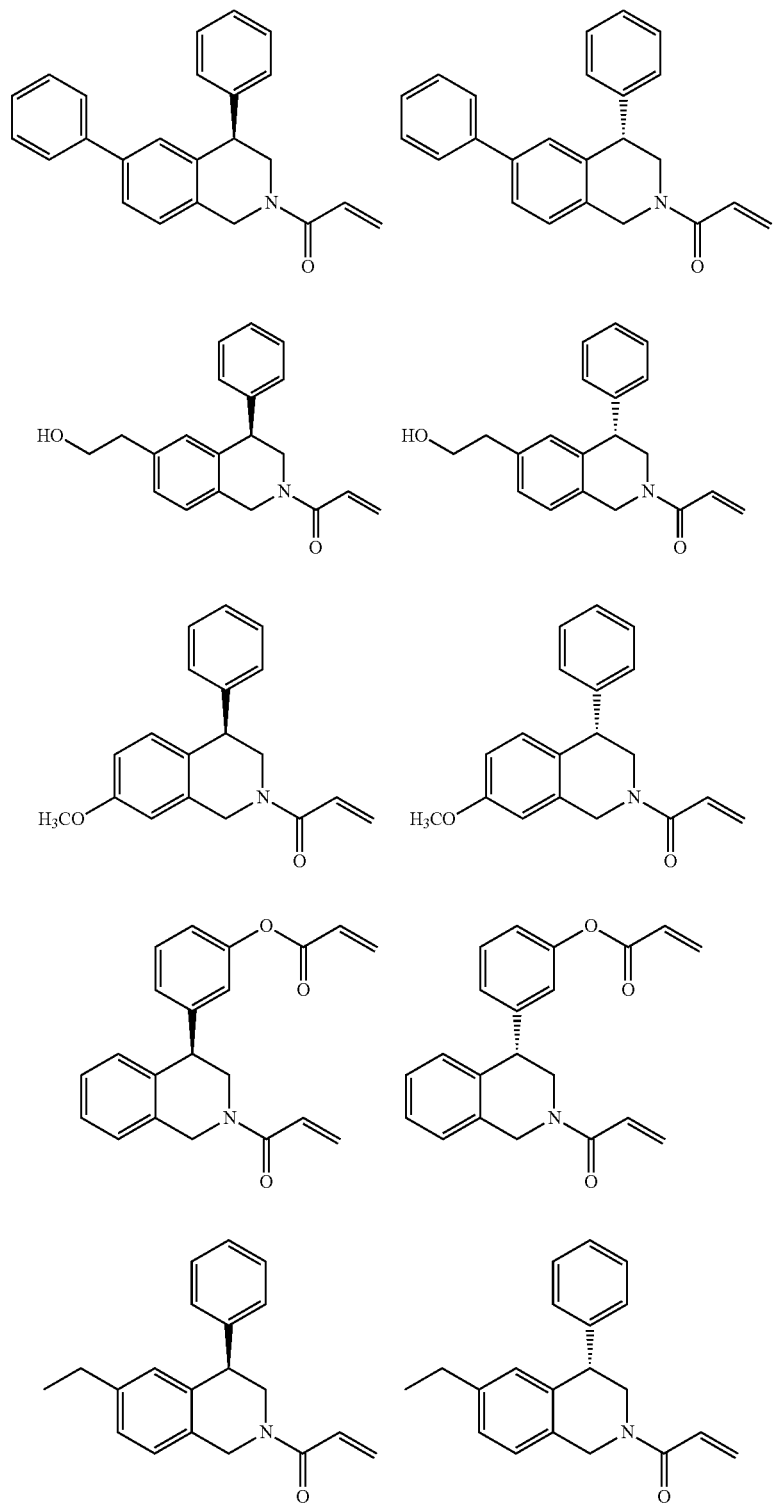

TABLE 1-continued
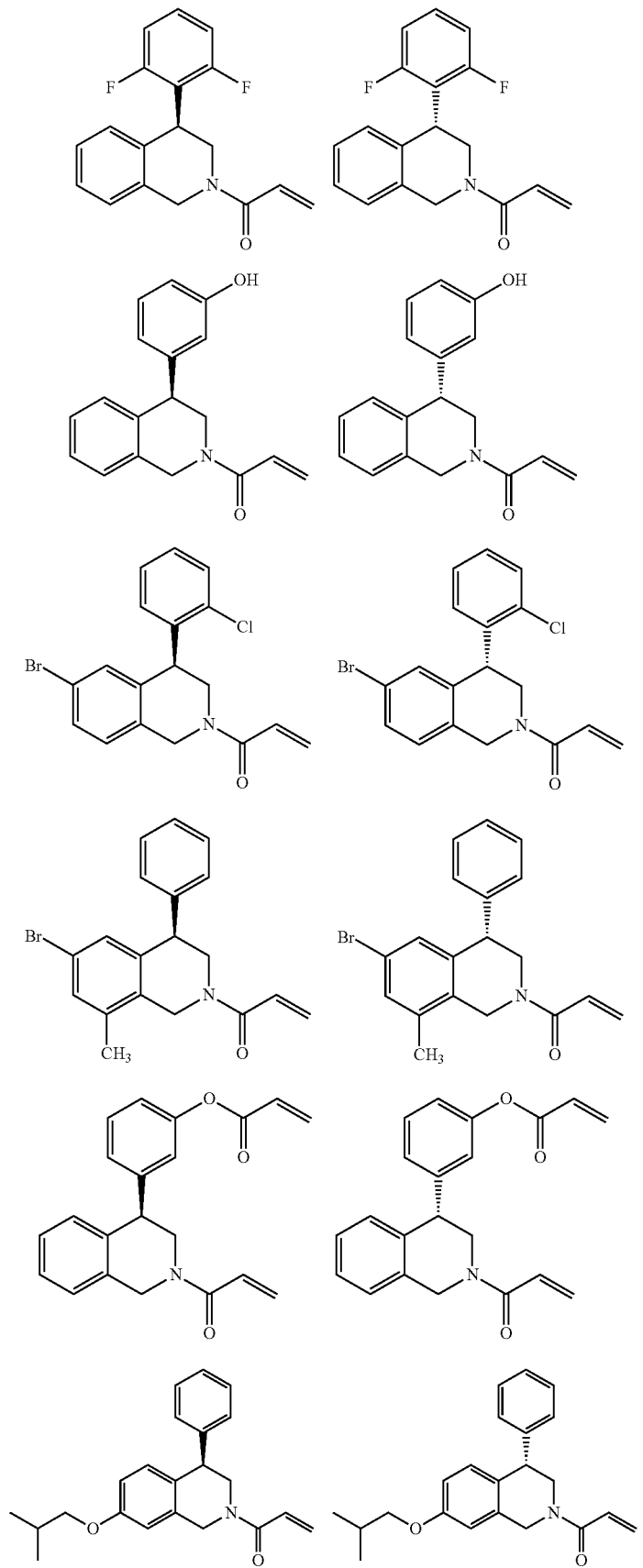

TABLE 1-continued
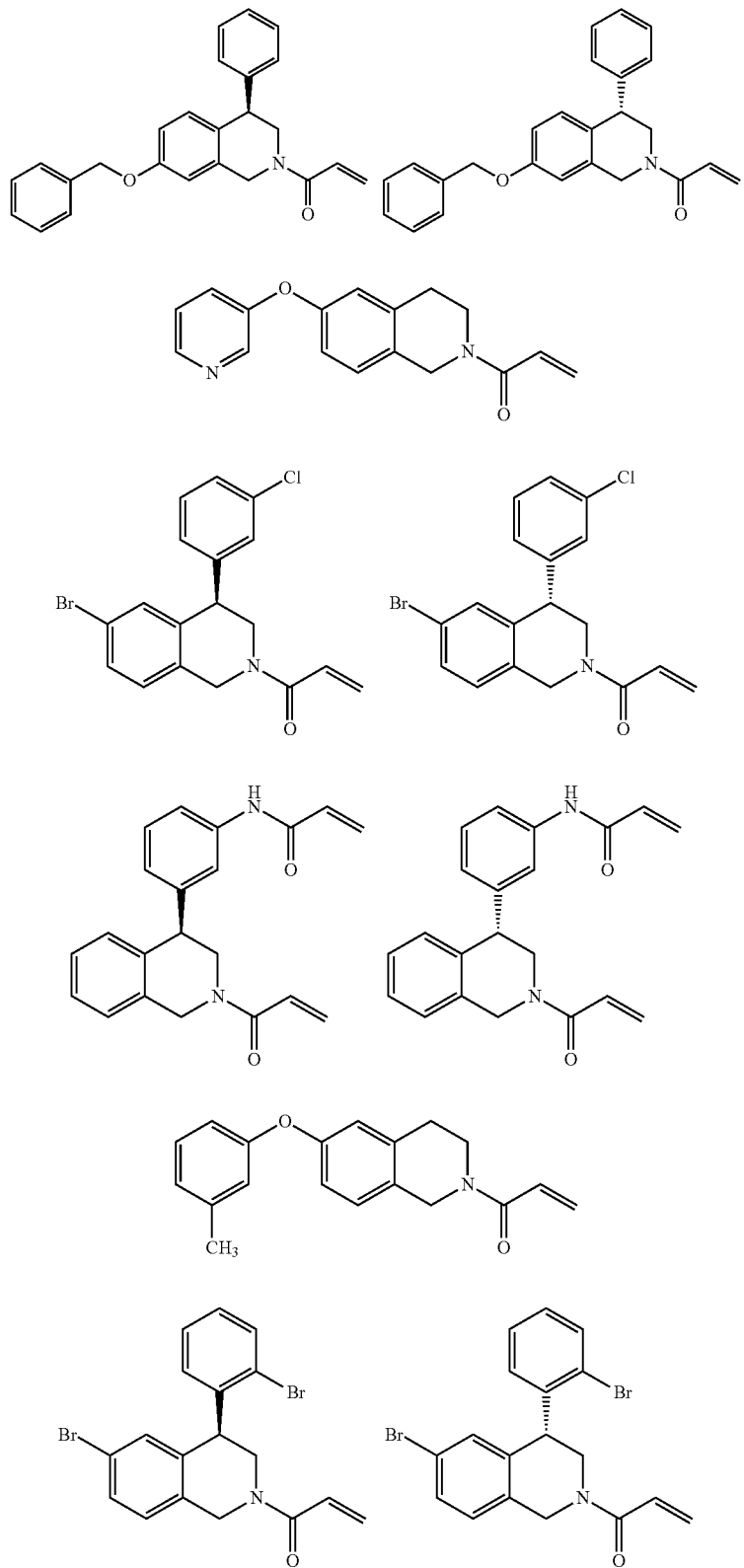

TABLE 1-continued
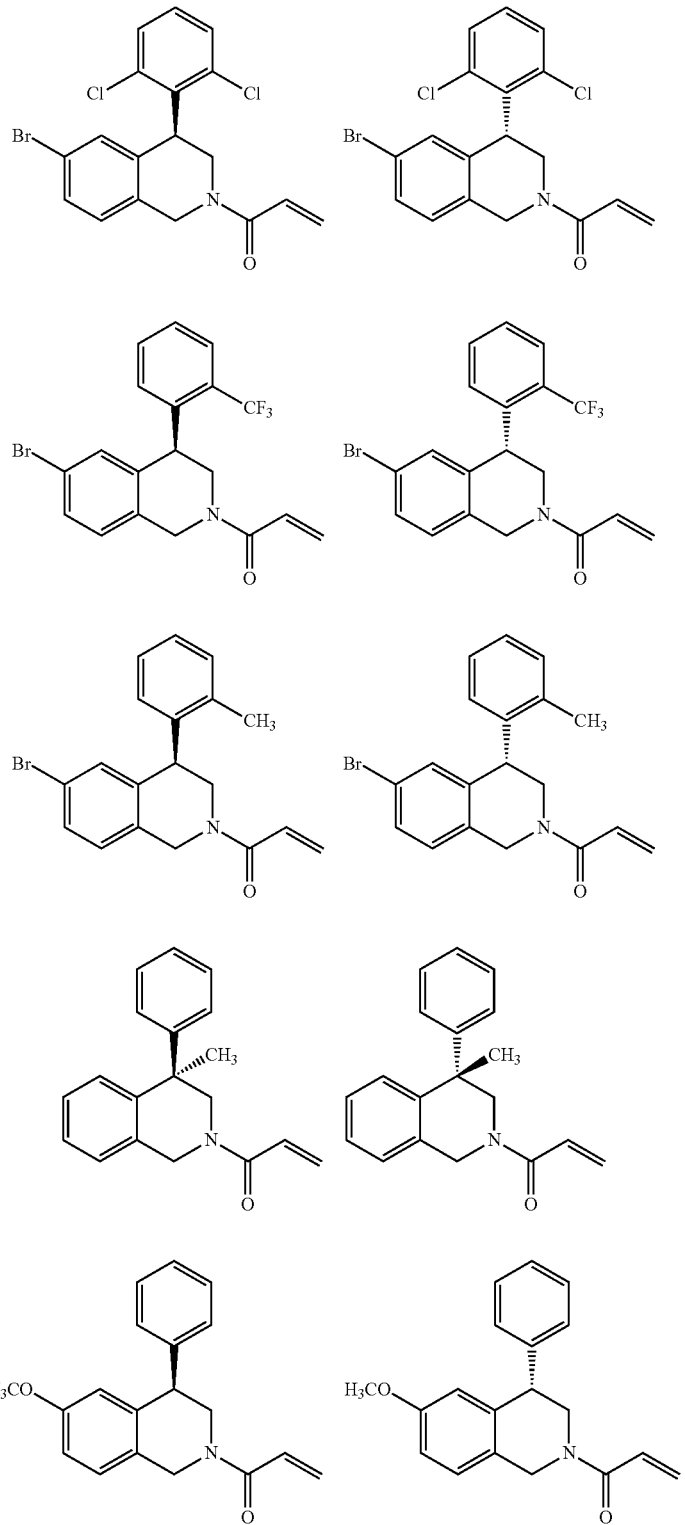

TABLE 1-continued
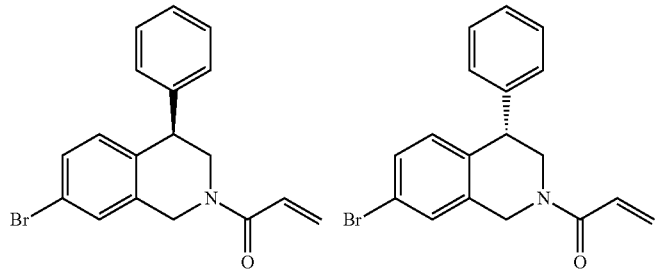
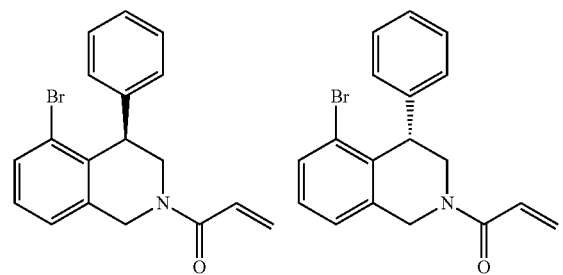
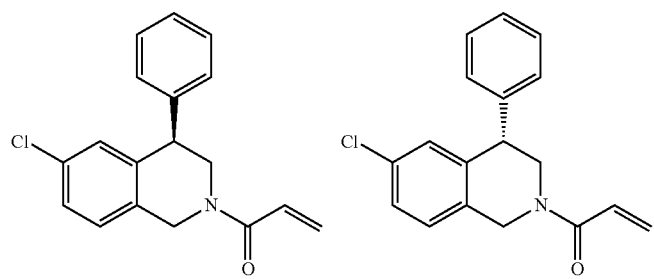 [SMILES: C=CC(=O)N1Cc2ccc(Cl)cc2[C@@H](c2ccccc2)C1 ; C=CC(=O)N1Cc2ccc(Cl)cc2[C@H](c2ccccc2)C1]
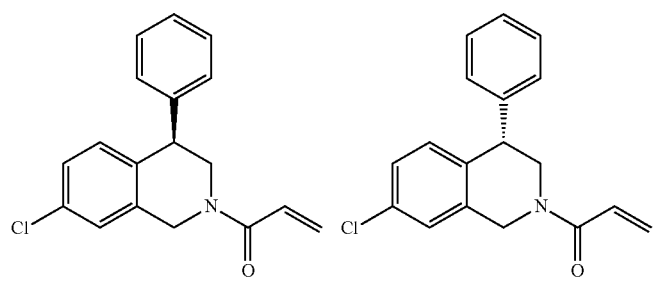
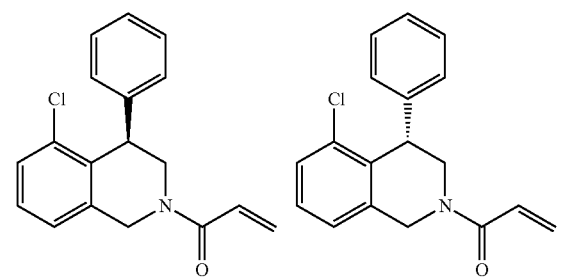

TABLE 1-continued
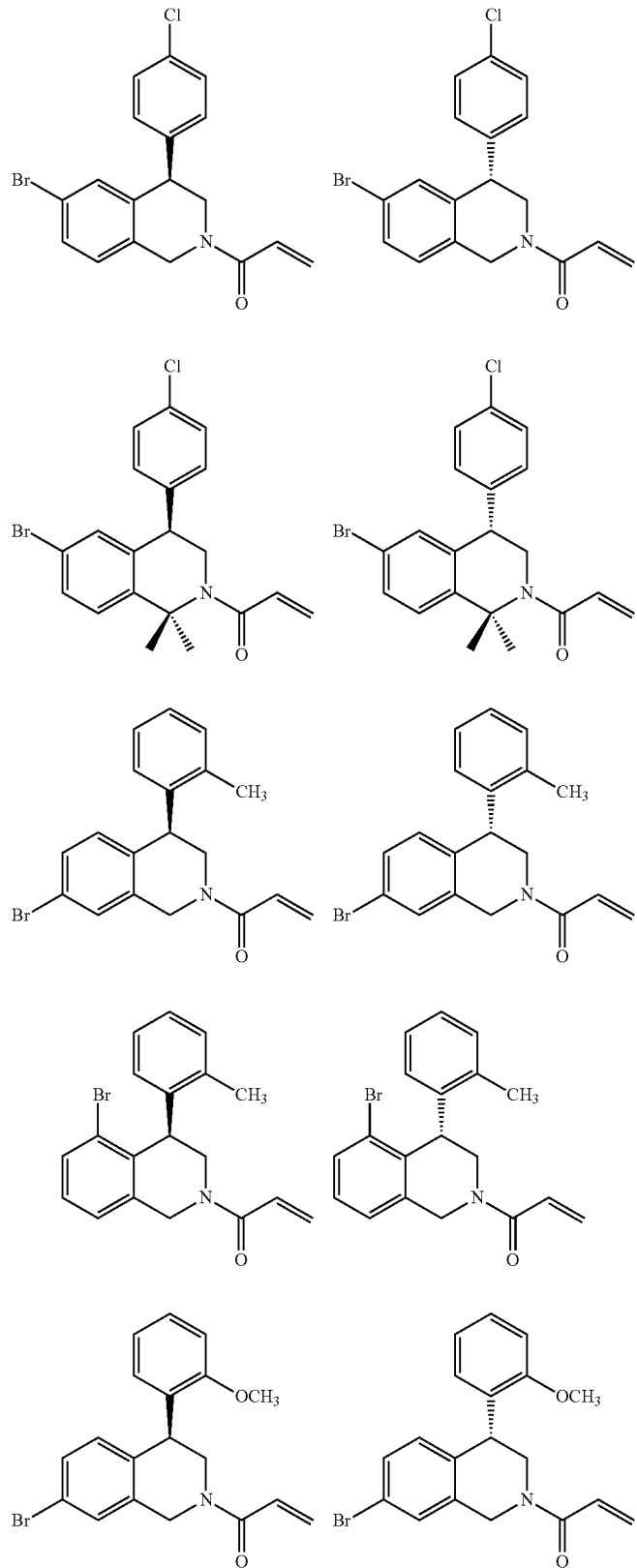

TABLE 1-continued
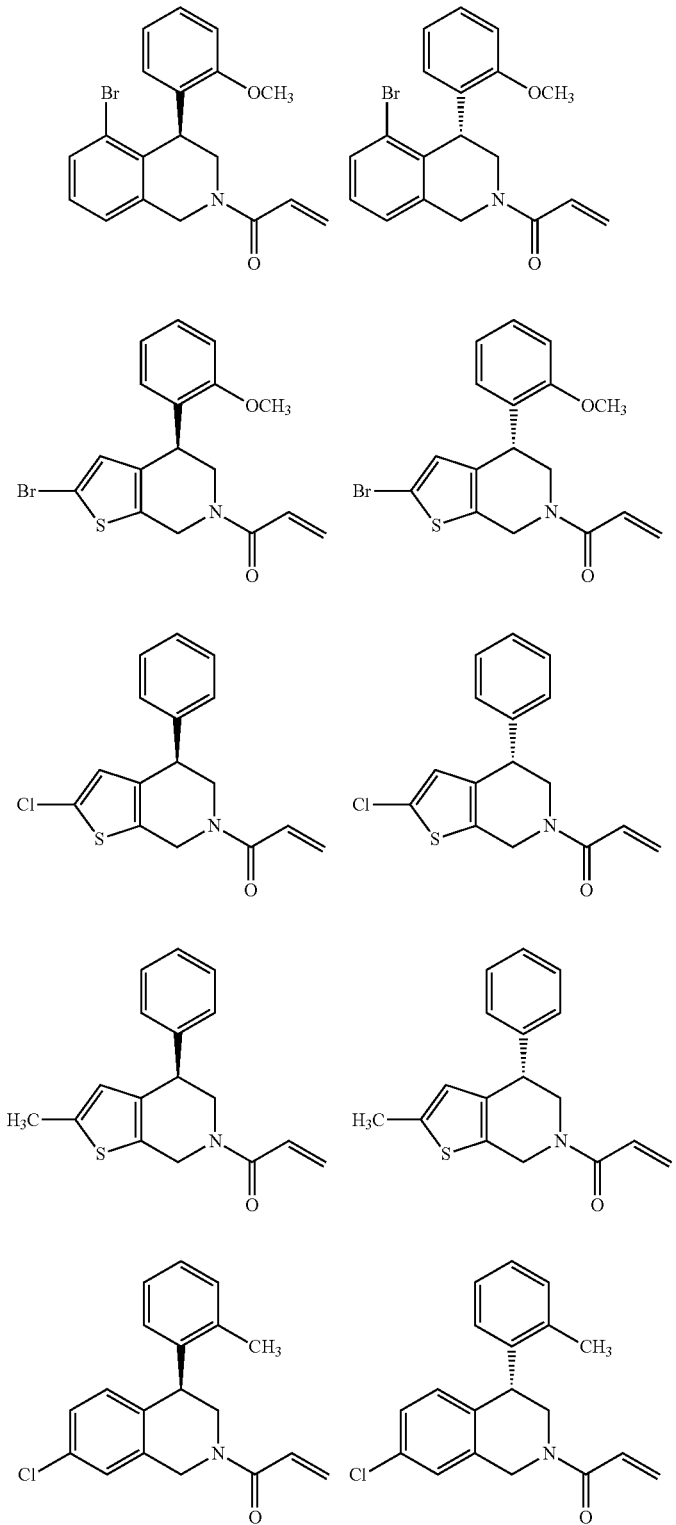

TABLE 1-continued
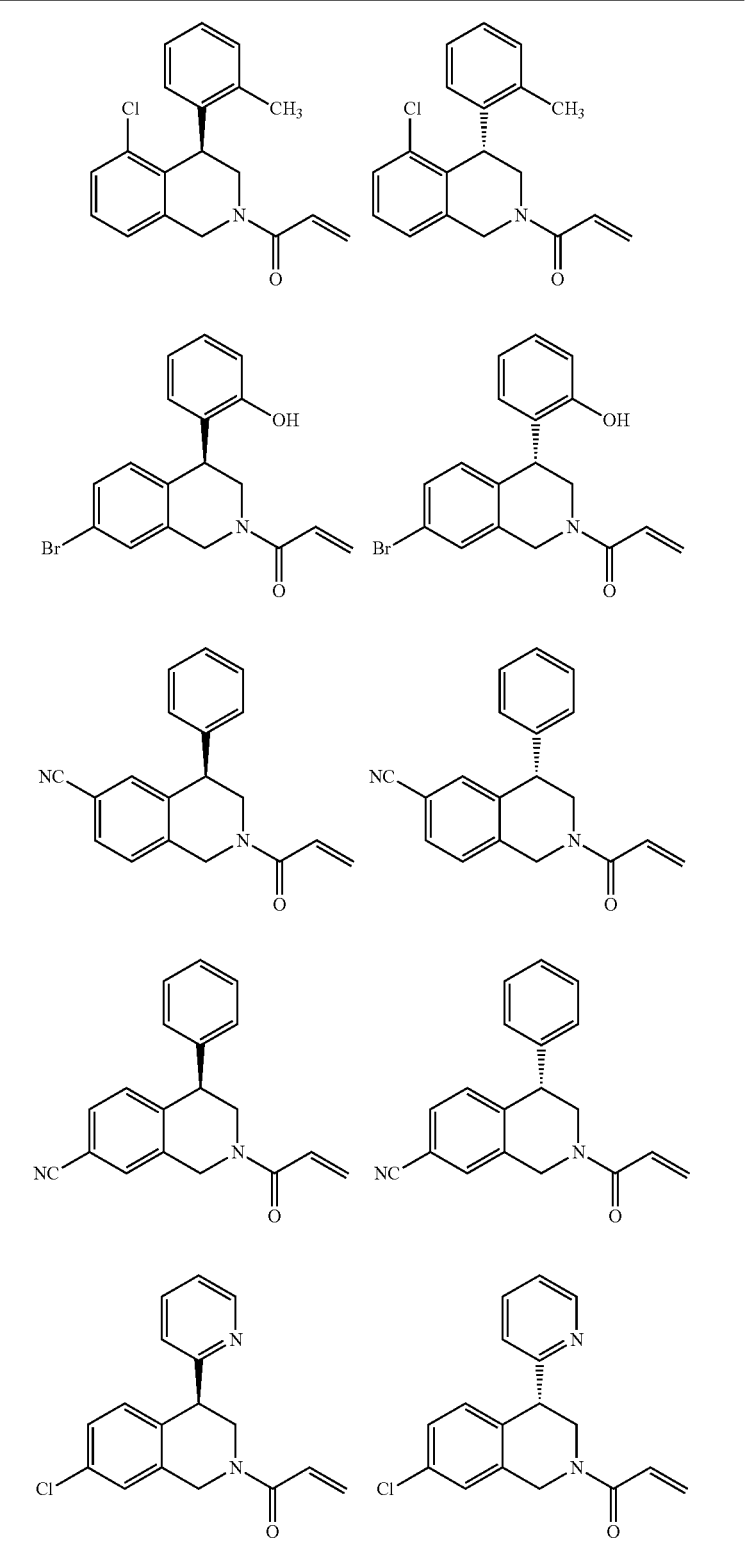

TABLE 1-continued
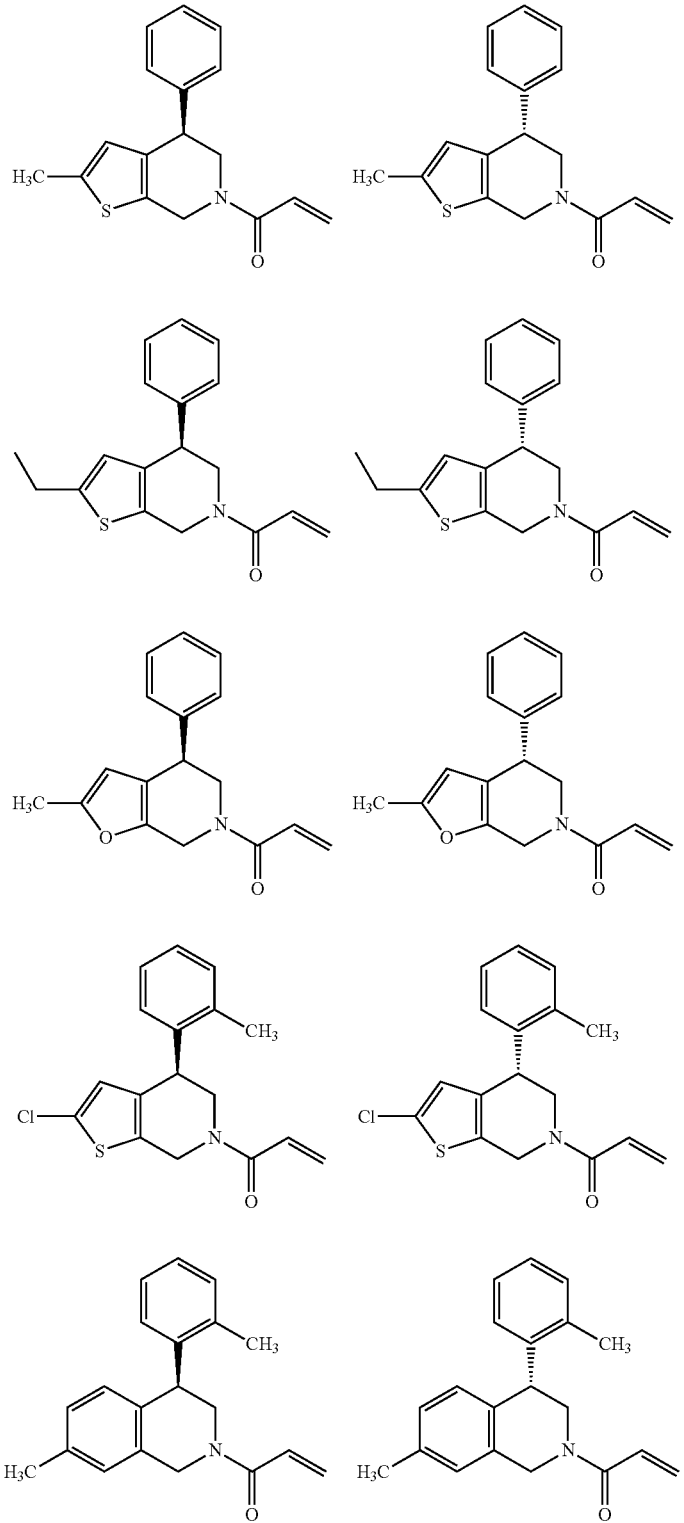

TABLE 1-continued
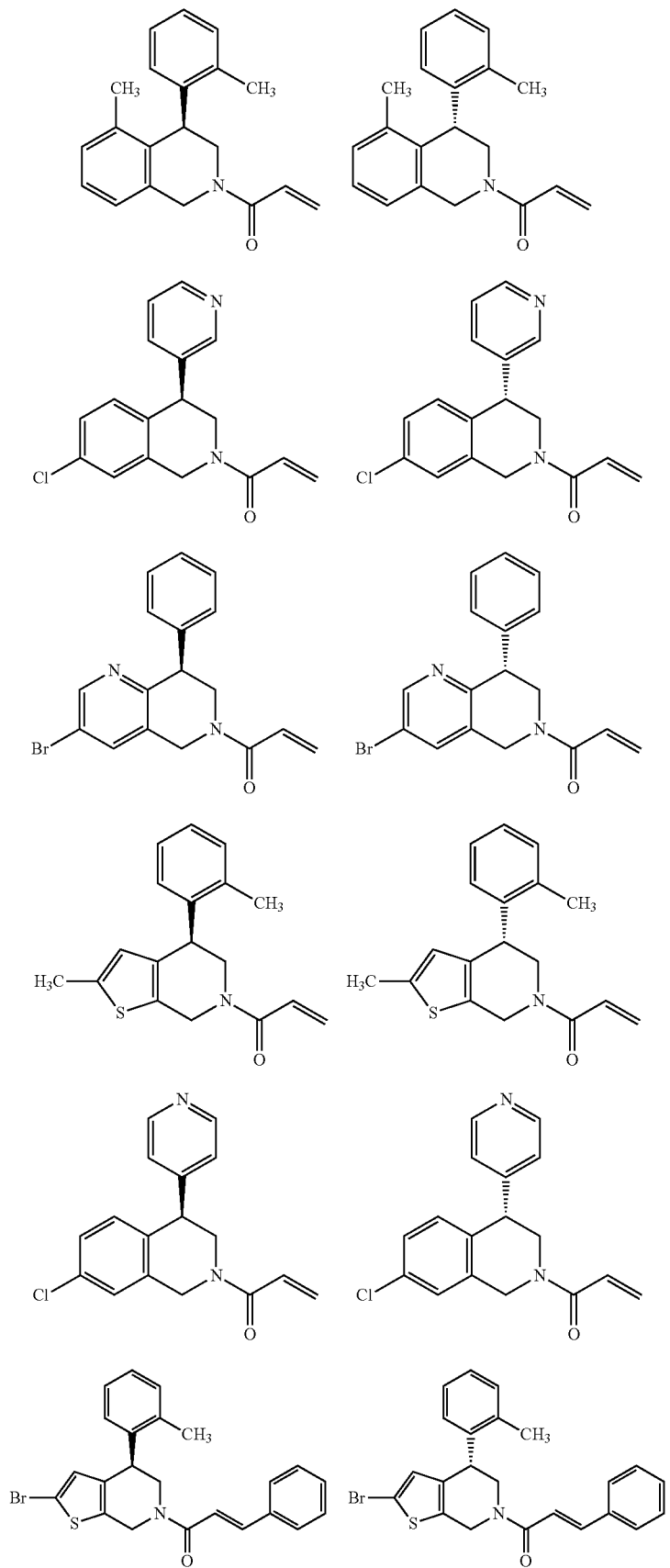

TABLE 1-continued
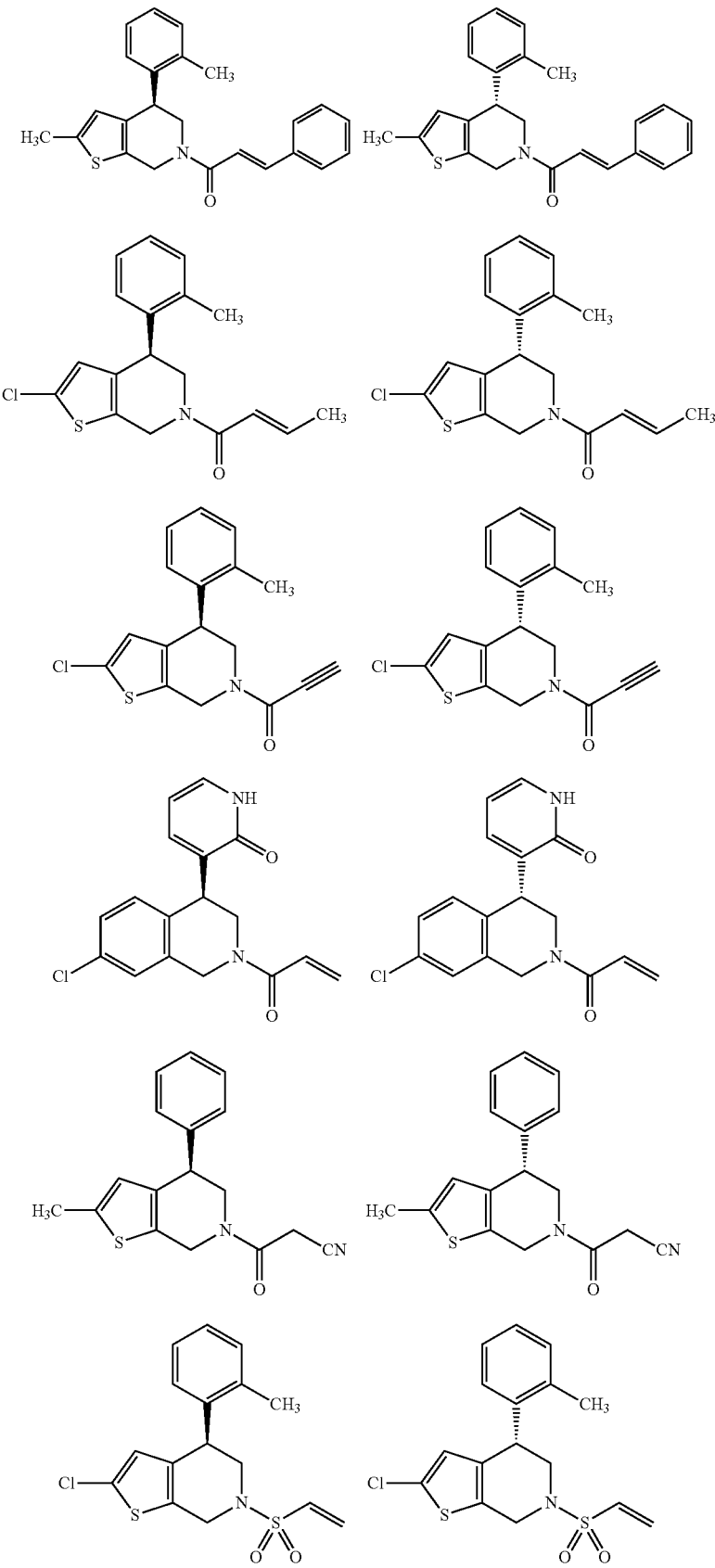

TABLE 1-continued
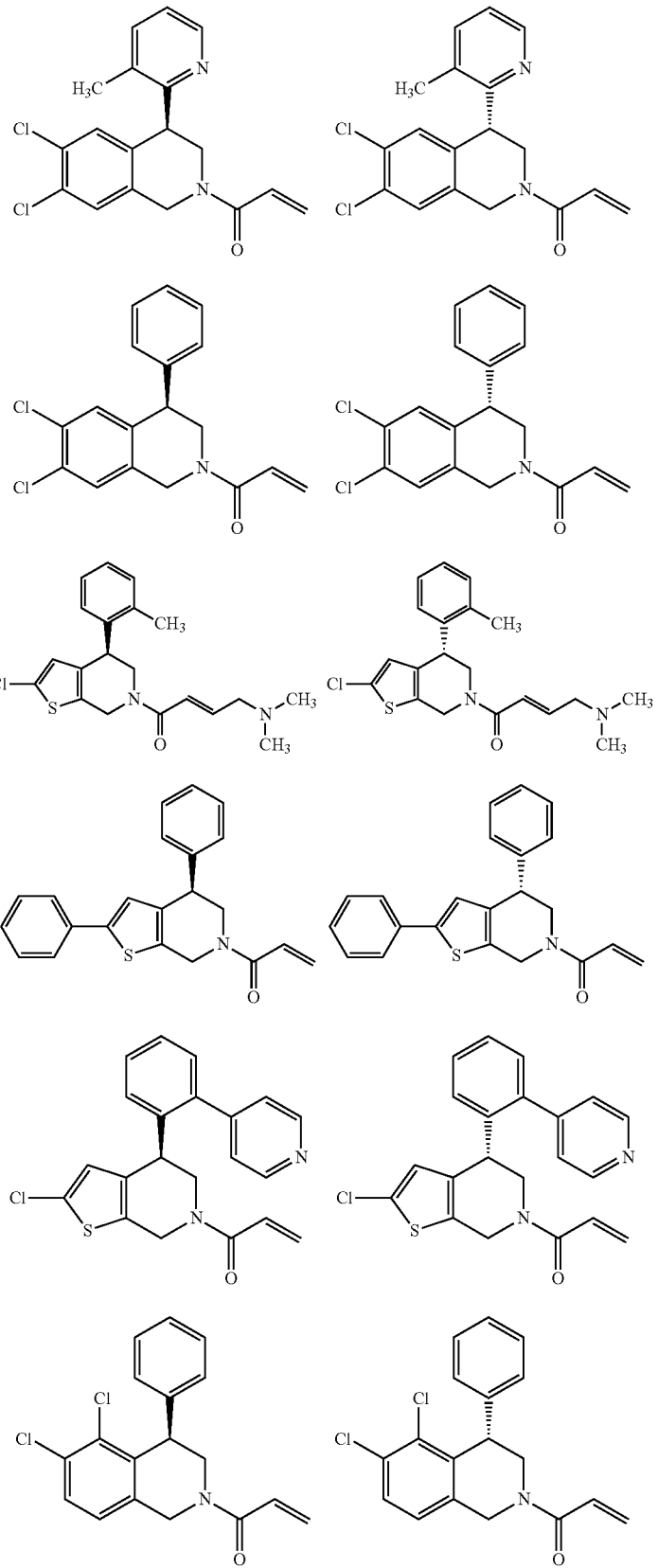

TABLE 1-continued
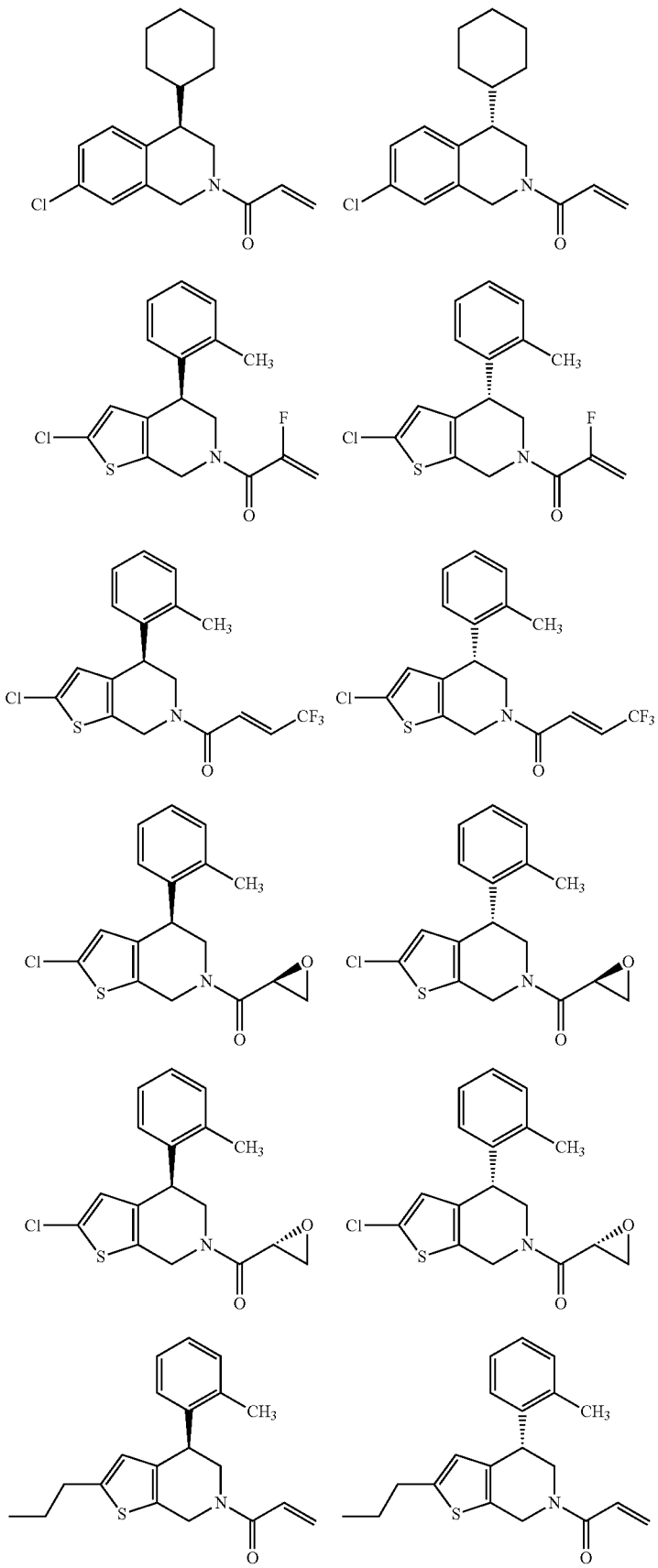

TABLE 1-continued
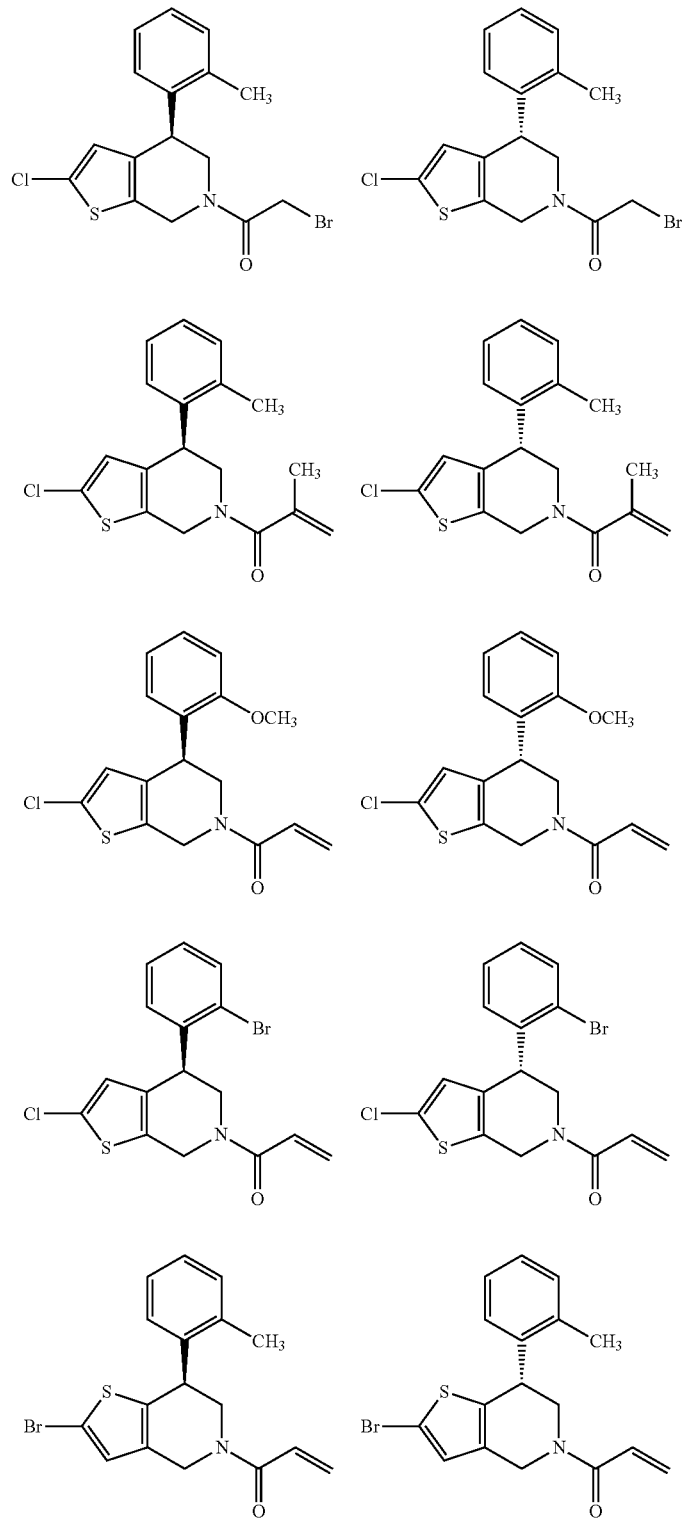

TABLE 1-continued
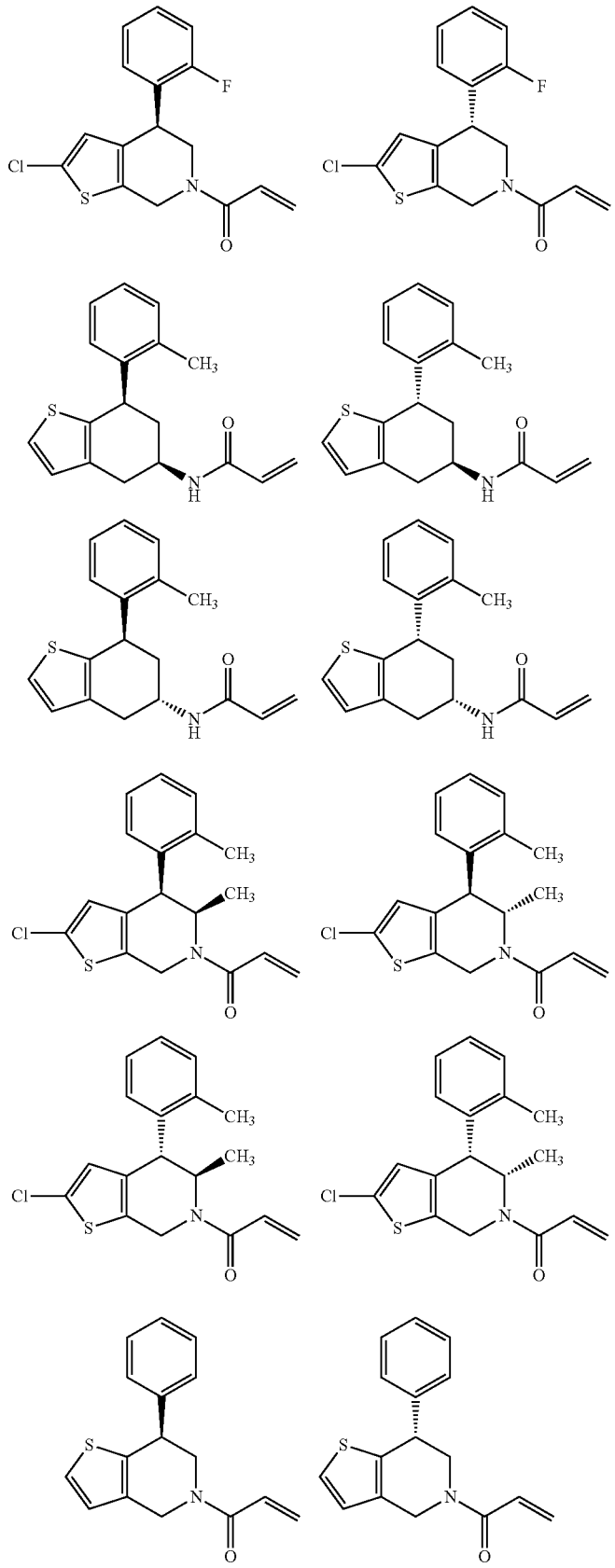

TABLE 1-continued
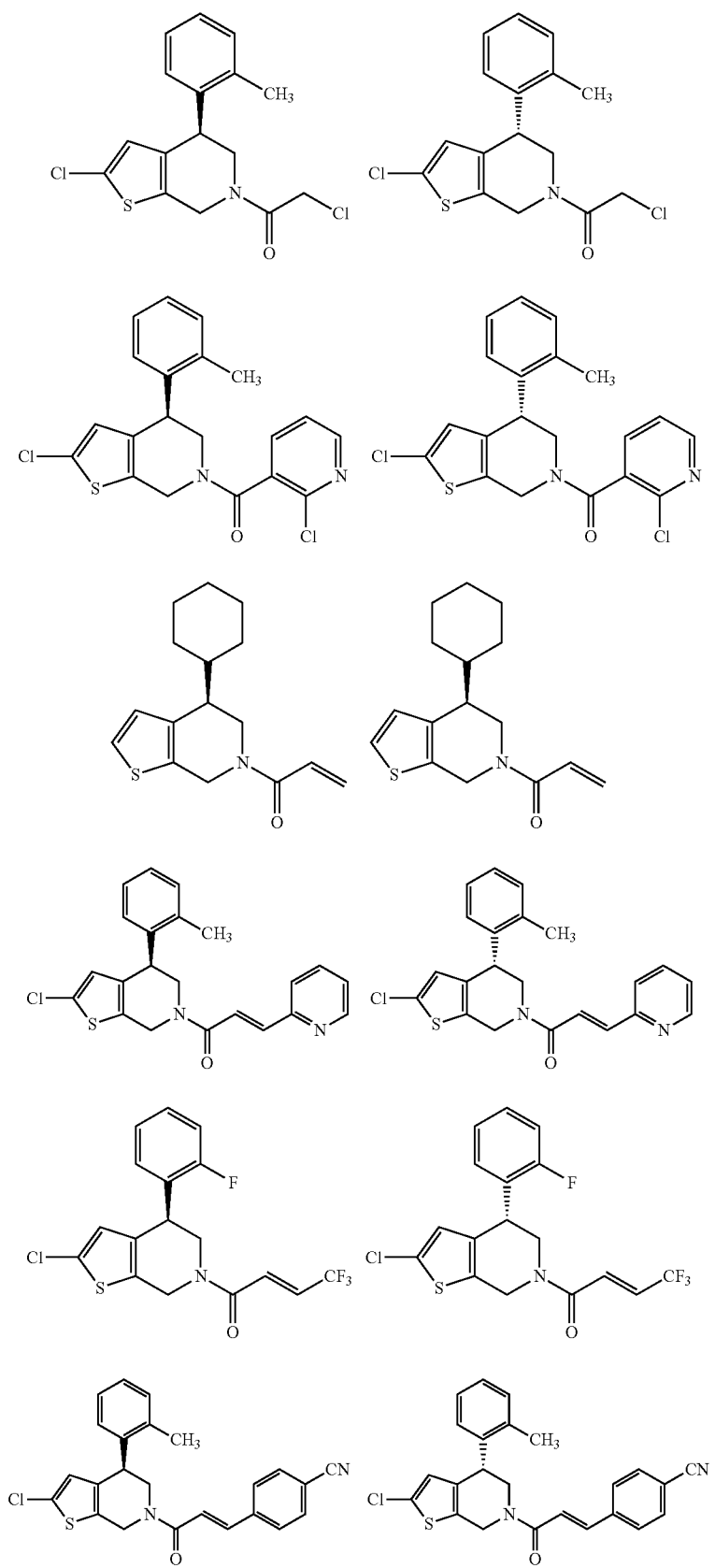

TABLE 1-continued
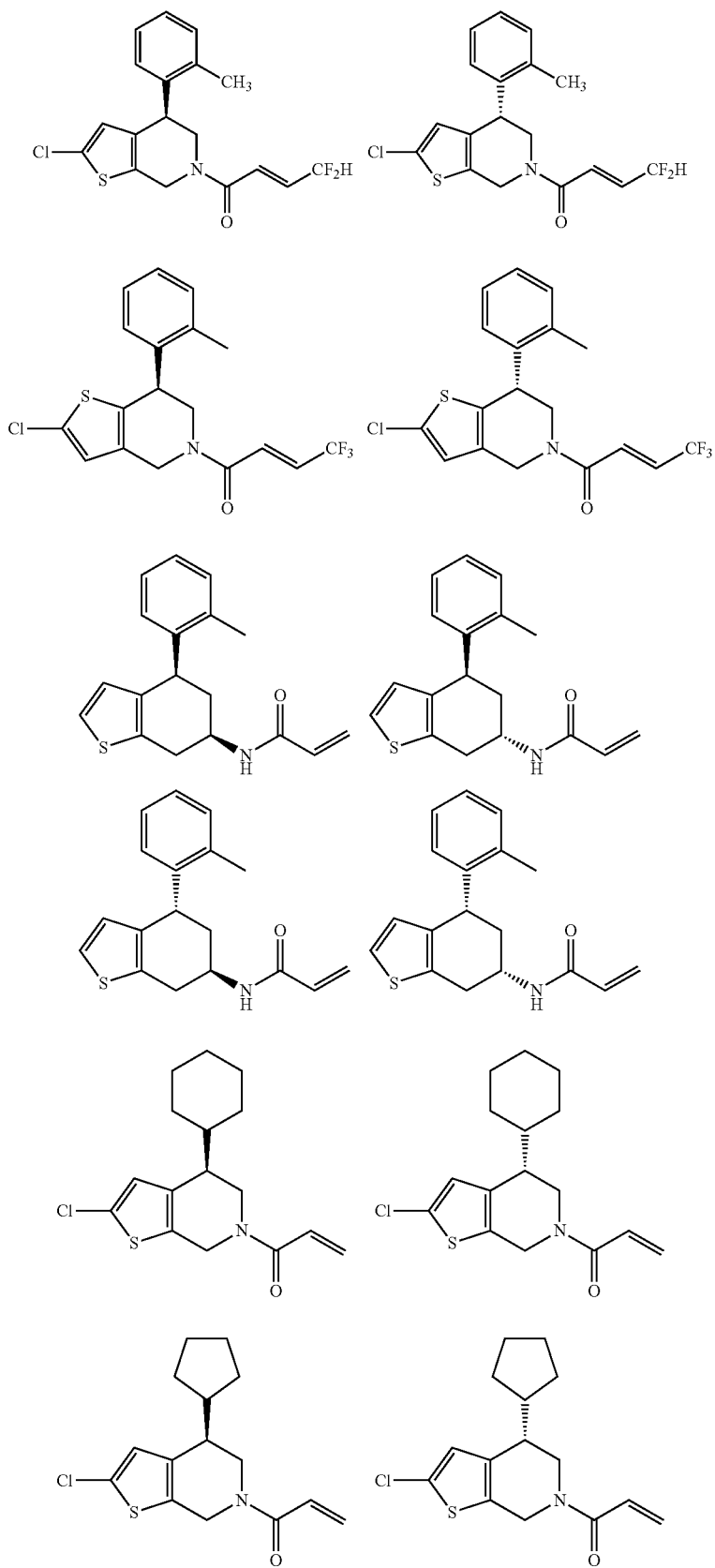

TABLE 1-continued
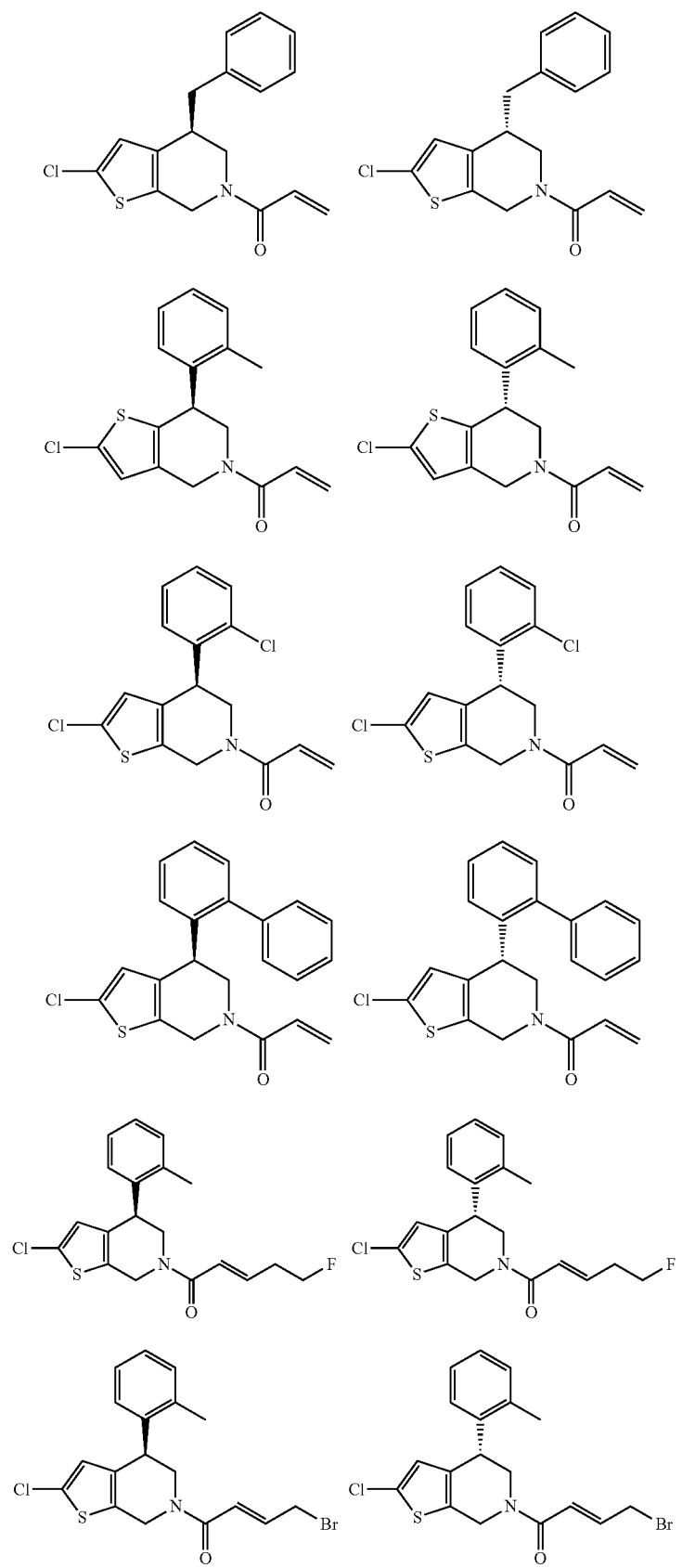

TABLE 1-continued
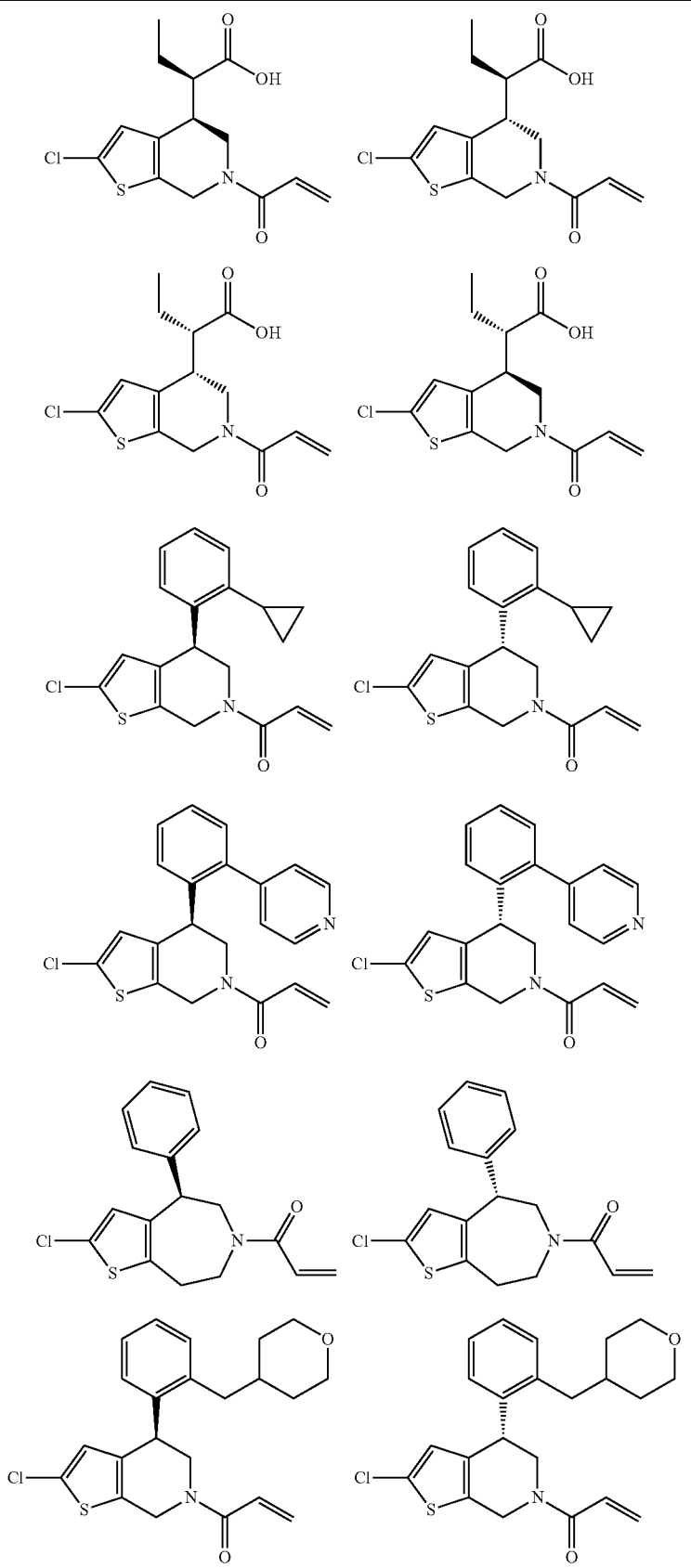

TABLE 1-continued
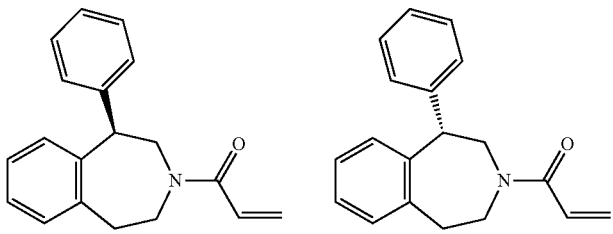
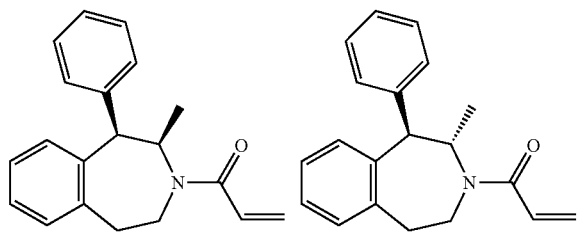
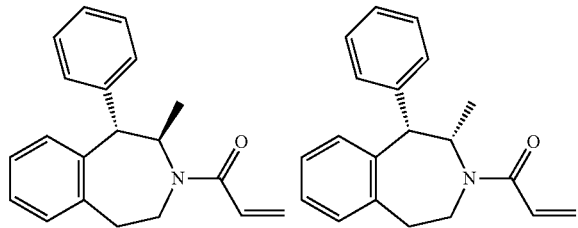
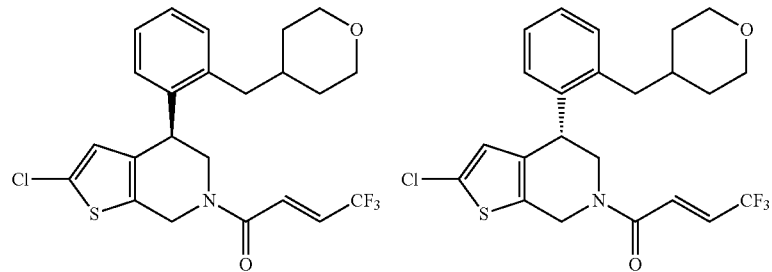 [SMILES: O=C(/C=C/C(F)(F)F)N1Cc2sc(Cl)cc2[C@@H](c2ccccc2CC2CCOCC2)C1 ; O=C(/C=C/C(F)(F)F)N1Cc2sc(Cl)cc2[C@H](c2ccccc2CC2CCOCC2)C1]
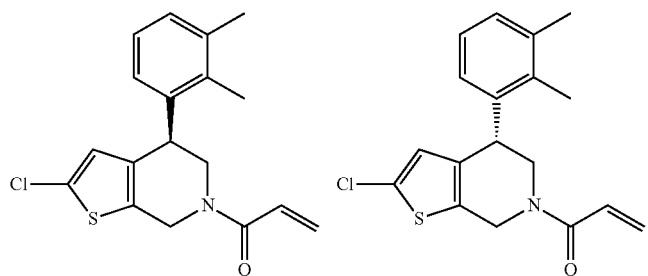
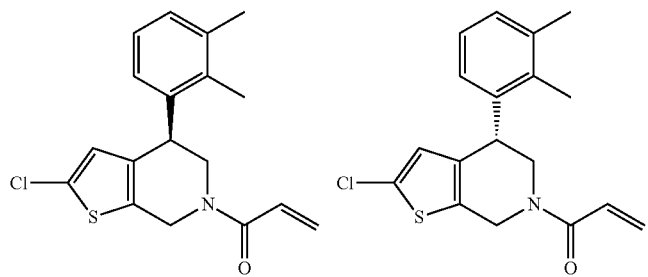

TABLE 1-continued
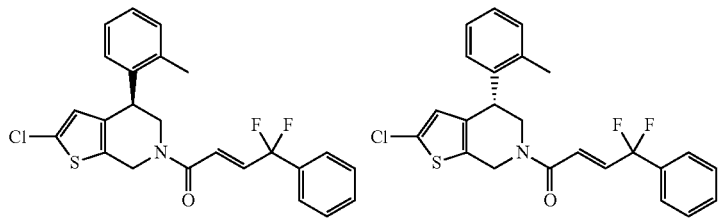
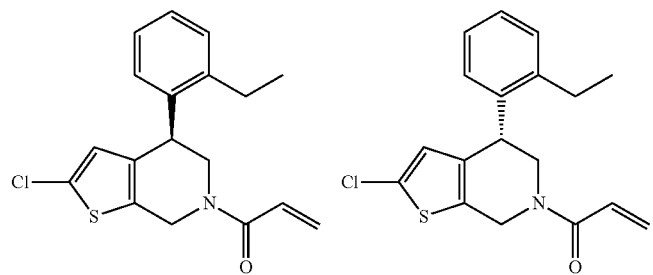
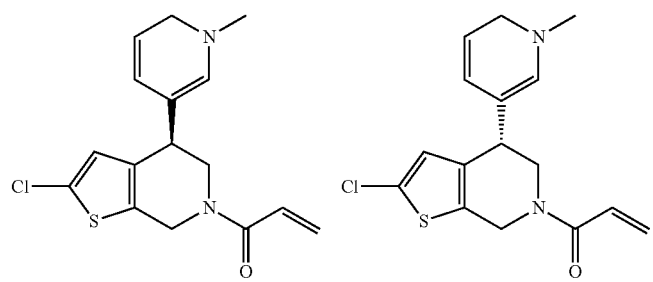
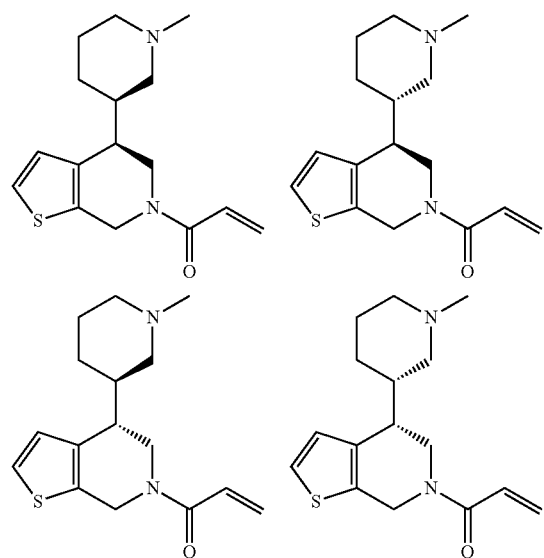

TABLE 1-continued
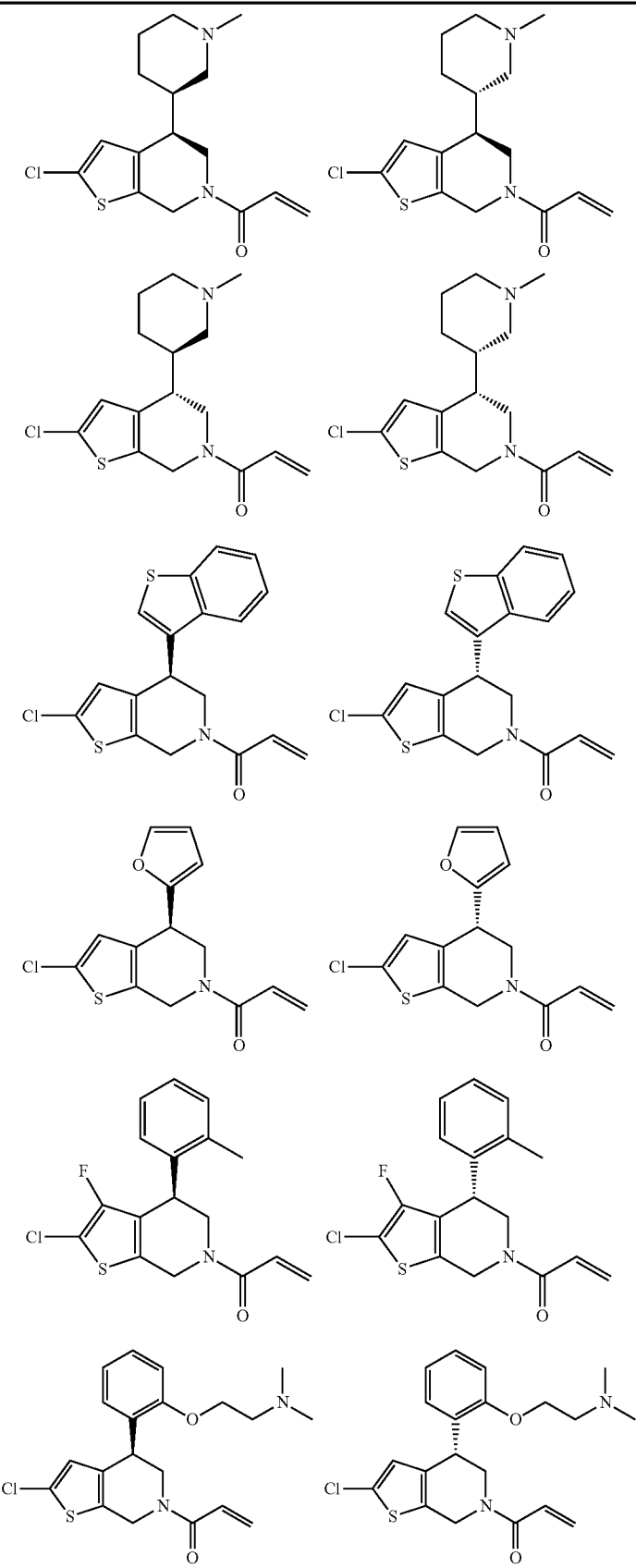

TABLE 1-continued
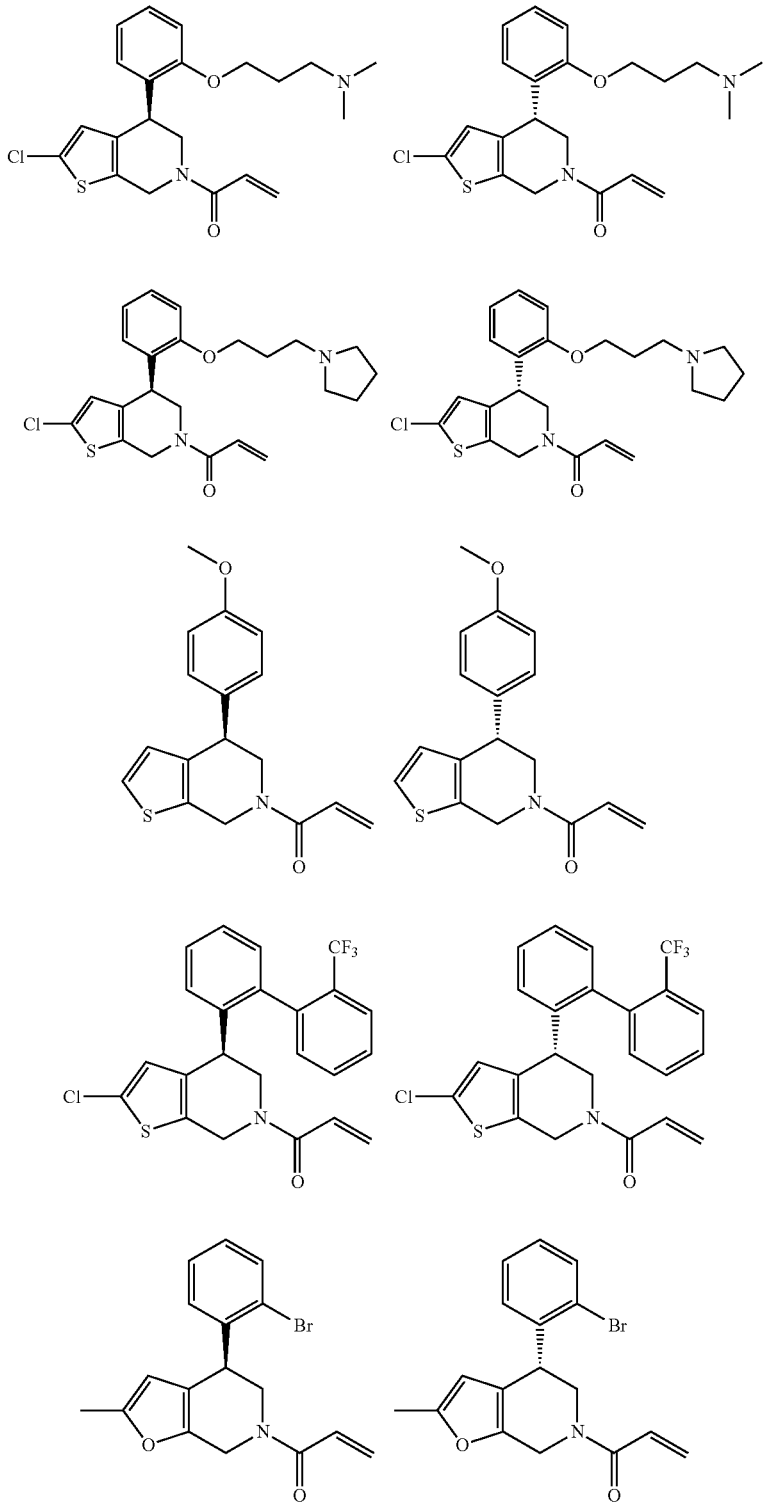

TABLE 1-continued

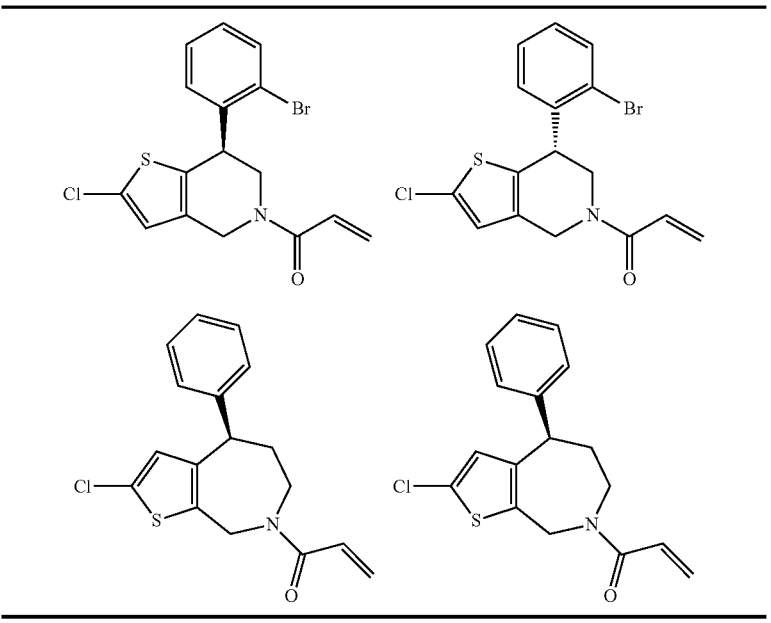

- 1-(6-bromo-4-(2-chlorophenyl)-3,4-dihydroisoquinolin-2 (1H)-yl)prop-2-en-1-one;
- 1-(2-chloro-4-(o-tolyl)-4,7-dihydrothieno[2,3-c]pyridin-6(5H)-yl)prop-2-en-1-one;
- (E)-1-(2-chloro-4-(o tolyl)-4,7-dihydrothieno[2,3-c]pyridin-6(5H)-yl)-4,4,4-trifluorobut-2-en-1-one;
- 2-chloro-1-(2-chloro-4-(o-tolyl)-4,7-dihydrothieno[2,3-c]pyridin-6(5H)-yl)ethan-1-one;
- (E)-1-(2-chloro-4-(o-tolyl)-4,7-dihydrothieno[2,3-c]pyridin-6(5H)-yl)-4,4-difluorobut-2-en-1-one;
- (E)-1-(2-chloro-4-(o-tolyl)-4,7-dihydrothieno[2,3-c]pyridin-6(5H)-yl)-4-fluorobut-2-en-1-one;
- N-(4-(o-tolyl)-4,5,6,7-tetrahydrobenzo[b]thiophen-6-yl)acrylamide;
- 1-(4-([1,1'-biphenyl]-2-yl)-2-chloro-4,7-dihydrothieno[2,3-c]pyridin-6(5H)-yl)prop-2-en-1-one;
- (E)-4-bromo-1-(2-chloro-4-(o-tolyl)-4,7-dihydrothieno[2,3-c]pyridin-6(5H)-yl)but-2-en-1-one;
- (E)-1-(2-chloro-4-(o-tolyl)-4,7-dihydrothieno[2,3-c]pyridin-6(5H)-yl)-4-(dimethylamino)but-2-en-1-one;
- 1-(7-chloro-4-(pyridin-2-yl)-3,4-dihydroisoquinolin-2(1H)-yl)prop-2-en-1-one;
- 1-(3-bromo-8-phenyl-7,8-dihydro-1,6-naphthyridin-6(5H)-yl)prop-2-en-1-one;
- 1-(2-chloro-4-cyclohexyl-4,7-dihydrothieno[2,3-c]pyridin-6(5H)-yl)prop-2-en-1-one;
- 1-(4-methyl-4-phenyl-3,4-dihydroisoquinolin-2(1H)-yl)prop-2-en-1-one;
- 1-(6-ethyl-4-phenyl-3,4-dihydroisoquinolin-2(1H)-yl)prop-2-en-1-one;
- 3-(2-acryloyl-7-chloro-1,2,3,4-tetrahydroisoquinolin-4-yl)pyridin-2(1H)-one;
- 1-(7-isobutoxy-4-phenyl-3,4-dihydroisoquinolin-2(1H)-yl)prop-2-en-1-one; and
- 1-(2-chloro-5-methyl-4-phenyl-4,7-dihydrothieno[2,3-c]pyridin-6(5H)-yl)prop-2-en-1-one.

In some embodiments, the compound is covalently attached to an E1 cysteine amino acid corresponding to Cys30 of Uba2 subunit 2. In embodiments, E contains an electrophilic moiety. In embodiments, the electron-withdrawing moieties are sufficiently electron withdrawing to allow the compound to covalently bind to an E1 cysteine amino acid corresponding to Cys30 of Uba2 subunit 2.

Method of Inhibition

Without wishing to be bound by any particular theory, it is believed that administration of a provided compound to a patient having an E1 cysteine amino acid, more specifically Cys30 of Uba2 subunit 2. In embodiments, the compound covalently binds to an E1 cysteine amino acid corresponding to Cys30 of Uba2 subunit 2; and forms a complex of formula X:

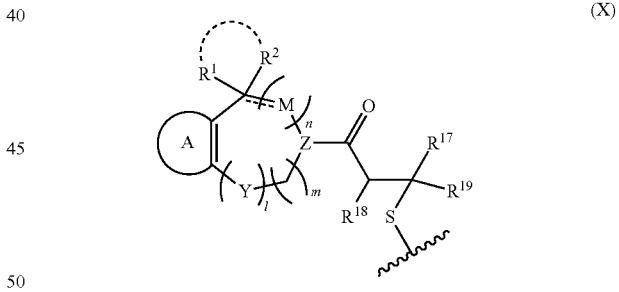

(X)

Wherein ~~~ represents the protein; and ring A, M, Z, l, m, n, Y, $R^1$, $R^2$, $R^{17}$, $R^{18}$ and $R^{19}$ are defined above.

In embodiments, the method includes allowing the compound to covalently bind an E1 enzyme. In embodiments, the method includes allowing the compound to covalently bind an E1 cysteine amino acid corresponding to Cys30 of Uba2 subunit 2. In embodiments, the method includes allowing the E1 cysteine amino acid to bind to carbon attached to $R^{17}$ and $R^{18}$.

In an aspect is provided a method of inhibiting cell proliferation, the method including contacting the cell with a compound described herein. In embodiments, the method includes contacting the cell with an effective amount of the compound. In embodiments, the compound is administered at a rate approximately equal to the half-life of an E1 enzyme.

In an aspect is provided a method of inhibiting an E1 enzyme, the method including contacting an E1 enzyme with a compound described herein, thereby inhibiting the E1 enzyme. In embodiments, the method includes allowing the compound to covalently bind the E1 enzyme. In embodiments, the method includes allowing the compound to covalently bind an E1 cysteine amino acid corresponding to Cys30 of Uba2 subunit 2. In embodiments, the method includes allowing the E1 cysteine amino acid to bind to carbon attached to $R^{17}$ and $R^{19}$.

In an aspect is provided a pharmaceutical composition including a compound described herein, or pharmaceutically acceptable salt thereof, and a pharmaceutically acceptable excipient.

In an aspect is provided a method of treating cancer, the method including administering to a subject in need thereof an effective amount of a compound described herein.

In an aspect is provided a method of inhibiting cell proliferation, the method including contacting the cell with a compound described herein.

One embodiment of the invention relates to a method of treating a disease related to E1 or SUMOylation, the method including administering to a subject in need thereof an effective amount of a compound described herein.

The compounds of the present invention, or the pharmaceutically acceptable salts thereof, may also be administered in combination with one or more additional pharmaceutically active compounds/agents, in a particular embodiment, the additional pharmaceutically active agent is an agent that can be used to treat a cancer. For example, an additional pharmaceutically active agent can be selected from antineoplastic agents, anti-angiogenic agents, chemotherapeutic agents and peptidal cancer therapy agents, in yet another embodiment, the antineoplastic agents are selected from antibiotic-type agents, alkylating agents, antimetabolite agents, hormonal agents, immunological agents, interferon-type agents, kinase inhibitors, miscellaneous agents and combinations thereof. It is noted that the additional pharmaceutically active compounds/agents may be traditional small organic chemical molecule or can be macromolecules such as proteins, antibodies, peptibodies, DNA, RNA or fragments of such macromolecules.

Examples of specific pharmaceutically active agents that can be used in combination with one or more compounds of the present invention include: atezolizumab, pembrolizumab, ipilimumab, methotrexate; tamoxifen; fluorouracil; 5-fluorouracil; hydroxyurea; mercaptopurine: cispiatin; carboplatin; daunorubicin; doxorubicin; etoposide; vinblastine; vincristine; pacitaxei; thioguanine; idarubicin; dactinomycin; matinib; gemcitabine; altretamine; asparaginase; bleomycin; capecitabine; carmustine; cladisat. aq. NaCl solution; cyclophosphamine; cytarabine; decarazine; docetaxel; idarubicin; ifosfamide; irinotecan; fludarabine; mitosmycin; mitoxane; mitoxantrone; topotecan; vinoreibine; adriamycin; mithram; miquimod; alemtuzmab; exemestane; bevacizumab; cetuximab; azacitidine; clofarabine; decitabine; desatinib; dexrazoxane; docetaxel; epirubicin; oxaliplatin; erlotinib; raloxifene; fulvestrant; letrozole; gefitinib; gemtuzumab; trastuzumab; gefitinib; ixabepilone; lapatinib; lenalidomide; aminolevulinic acid; temozolomide; nelarabine; sorafenib; nilotinib; pegaspargase; pemetrexed; rituximab; dasatinib; thalidomide; bexarotene; temsirolimus; bortezomib; vorinostat; capecitabine; zoledronic acid; anastrozole; sunitinib; aprepitant and nelarabine, or a pharmaceutically acceptable salt thereof.

Other examples of anti-cancer agents include, but are not limited to, MEK (e.g. MEK1, MEK2, or MEK1 and MEK2) inhibitors (e.g. XL518, CI-1040, PD035901, selumetinib/ AZD6244, GSK1120212/trametinib, GDC-0973, ARRY-162, ARRY-300, AZD8330, PD0325901, U0126, P)98059, TAK-733, PD318088, AS703026, BAY 869766), alkylating agents (e.g., cyclophosphamide, ifosfamide, chlorambucil, busulfan, melphalan, mechlorethanine, uramustine, thiotepa, nitrosoureas, nitrogen mustards (e.g., mechloroethamine, cyclophosphanide, chlorambucil, meiphalan), ethyleninine and mnethylmelanines (e.g., hexanethlynelanine, thiotepa), alkyl sulfonates (e.g., busulfan), nitrosoureas (e.g., carmustine, lomusitne, semustine, streptozocin), triazenes (decarbazine)), anti-metabolites (e.g, 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g. mercaptopurine, thioguanine, pentostatin), etc.), plant alkaloids (e.g, vincristine, vinblastine, vinorelbine, vindesine, podophyllotoxin, paclitaxel, docetaxel, etc.), topoisomerase inhibitors (e.g, irinotecan, topotecan, amsacrine, etoposide (VP 16), etoposide phosphate, teniposide, etc.), antitumor antibiotics (e.g, doxorubicin, adriamnycin, daunorubicin, epirubicin, actinornycin, bleomnycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubiein, doxorubicin, bleomnycin), enzymes (e.g., L-asparaginase), inhibitors of mitogen-activated protein kinase signaling (e.g. U0126, PD98059, PD 184352, PD0325901, ARRY-142886, SB239063, SP600125, BAY 43-9006, wortnannin, or LY294002, Syk inhibitors, mnTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, matinib (Gleevec®), geldanamycin, 17-N-Allylamino-17-Demethoxygeldananycin (17-AAG), flavopiridol, LY294002, bortezonib, trastuzurnab, BAY 11-7082, PKC412, PD184352, 20-epi-1, 25 dihydroxyvitanin D3; 5-ethynyluracil; abiraterone; aclarubicin; acvlfulvene; adecypenol; adozelesin; aldesleukin: ALL-TK antagonists: altretamine; ambamustine; amidox; amifostine; aminolevulinic acid; ainrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives: balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropitimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4 combretastatin analogue; conagenin; crambescidin 816 crisnatol; cryptophycin 8; cryptophycin A derivatives; curacin A; cyclopentanthraquinones; cycloplatam; ecpemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spironustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunonnicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfan; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levanisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MTF inhibitor; mifepristone; miltefosine; mirimostim; mismatched double stranded RNA; mitoguazone; mitolactol; mitomycin analogues; mitonafide; nitotoxin fibroblast growth factor-saporin; nitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitruillyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritreximn placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethlerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfmosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor: translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate: aminoglutethimide; amsacrine; anastrozole; anthranycin; asparaginase; asperlin; azacitidine; azetepa; azotonycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride: carzelesin; cedefigol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflomithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin II (including recombinant interleukin II, or rlL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lonustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; nitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamvcin; plomestane; porfimer sodium; porfiromycin; prednimustine; procarbazine hydrochloride; puromycin; puromyein hydrochloride; pyrazofurin; riboprine; rogletimide; safmigol; safrgol hydrochloride; semustine; simtrazene; sparfosate sodium; sparsomycin; spirogernaniurn hydrochloride; spiromustine; spiroplatin; streptonigrin; streptozocin; sulofenur; talisomycin; tecogalan sodium; tegafir; teloxantrone hydrochloride; temoporfin; teniposide; teroxirone; testolactone; thiamiprine; thioguanine; thiotepa; tiazofurin; tirapazanine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincnstine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2. Spongistatin 3, Spongistatin 4, Spongistatin 5, Spongistatin 6, Spongistatin 7, Spongistatin 8, and Spongistatin 9). Cemadotin hydrochloride (i.e LET-1 03793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B. 21-aninoepothilone B (i.e. BMS-310705), 21-hydroxy epothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-1 12378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF i.e. ILX-651 and LU-223651), SAH-49960 (Lillv/Novartis), SDZ-268970 (Lilly/Novartis), AM-97 (Armad/Kyowa Hakko), AM-132 (Arnad), AM-138 (Armad/Kyowa Hakko), IDN-5005 (Indena), Cryptophycin 52 (i.e. LY-355703), AC-7739 (Ajinomoto, i.e. AVE-8063A and CS-39.HCl), AC-7700 (Ajinomoto, i.e. AVE-8062, AVE-8062A, CS-39-L-Ser.HCl, and RPR-258062A), Vitilevuanide, Tubulysin A, Canadensol, Centaureidin (i.e. NSC-106969), T-138067 (Tularik. i.e. T-67, TL-138067 and TI-138067). COBRA-1 (Parker Hughes Institute, i.e. DDE-261 and WHI-261), H10 (Kansas State ETniversity), H16 (Kansas State University). Oncocidin A1 (i.e. BTO-956 and DIME), DDE-313 (Parker Hughes Institute), Fijianolide B, Lauliralide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569). Narcosine (also known as NSC-5366), Nascapine, D-24851 (Asta Medica), A-105972 (Abbott), Heriasterlin, 3-BAABU (Cytoskeleton/Mt. Sinai School of Medicine, i.e. MF-191), TMPN (Arizona State University), Vanadocene acetyl acetonate, T-138026 (Tularik), Monsatrol, inanocine (i.e NSC-698666), 3-IAABE (Cytoskeleton/Mt. Sinai School of Medicine), A-204197 (Abbott), T-607 (Tuiarik, i.e. T-900607), RPR-1 15781 (Aventis), Eleutherobins (such as desmethyleleutherobin, Desaetvleleutherobin, lsoeleutherobin A, and Z-Eleutherobin), Caribacoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (−)-Phenylahistin (i.e. NSCL-96F037), D-68838 (Asta Medica), D-68836 (Asta Medica), Myoseverin B. D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR—OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guerin (BCG), levamisole, interleukin-2, alpha-interferon, etc.), monoclonal antibodies (e.g., anti-CD20, anti-HER2, anti-CD52, anti-ILA-DR- and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmnunotherapy (e.g. anti-CD20 monoclonal antibody conjugated to $^{1u}$In, $^{90}$Y, or $^{131}$I, etc.), triptolide, homoharringtonine, dactinonycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, geflitinib, EGFR inhibitors, epidermal growth factor receptor (EGFR)-targeted therapy ortherapeutic (e.g. gefitinib (Iressa™), erlotinib (Tarceva™), cetuximab (Erbitux™), lapatinib (Tykerb™), panitunumab (Vectibix™), vandetamib (Caprelsa™), afatinib/B1BW2992, CI-1033/canertinib, neratinib/HI1-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

The compound of the present invention may also be used in combination with radiation therapy, hormone therapy, surgery and immunotherapy, which therapies are well known to those skilled in the art.

Since one aspect of the present invention contemplates the treatment of the disease/conditions with a combination of pharmaceutically active compounds that may be administered separately, the invention further relates to combining separate pharmaceutical compositions in kit form. The kit comprises two separate pharmaceutical compositions: the compound of the present invention, and a second pharmaceutical compound. The kit comprises a container for containing the separate compositions such as a divided bottle or a divided foil packet. Additional examples of containers include syringes, boxes and bags. Typically, the kit comprises directions for the use of the separate components. The kit form is particularly advantageous when the separate components are preferably administered in different dosage forms (e.g., oral and parenteral), are administered at different dosage intervals, or when titration of the individual components of the combination is desired by the prescribing physician or veterinarian.

Definitions

The abbreviations used herein have their conventional meaning within the chemical and biological arts. The chemical structures and formulae set forth herein are constructed according to the standard rules of chemical valency known in the chemical arts. As used herein, the following definitions shall apply unless otherwise indicated.

The term "alkyl," by itself or as part of another substituent, means, unless otherwise stated, a straight (i.e., unbranched) or branched carbon chain (or carbon), or combination thereof, which may be fully saturated, mono- or polyunsaturated and can include mono-, di- and multivalent radicals, having the number of carbon atoms designated (i.e., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —$CH_2CH_2CH_2CH_2$—. The term "alkenylene," by itself or as part of another substituent, means, unless otherwise stated, a divalent radical derived from an alkene.

The term "heteroalkyl," by itself or in combination with another term, means, unless otherwise stated, a stable straight or branched chain, or combinations thereof, including at least one carbon atom and at least one heteroatom (e.g., O, N, P, S, B, As, or Si), and wherein the nitrogen and sulfur atoms may optionally be oxidized, and the nitrogen heteroatom may optionally be quaternized. The heteroatom(s) (e.g., O, N, P, S, B, As, or Si) may be placed at any interior position of the heteroalkyl group or at the position at which the alkyl group is attached to the remainder of the molecule. Heteroalkyl is an uncyclized chain. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CHO—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$.

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'.

The terms "cycloalkyl" and "heterocycloalkyl," by themselves or in combination with other terms, mean, unless otherwise stated, cyclic versions of "alkyl" and "heteroalkyl," respectively. Cycloalkyl and heterocycloalkyl are not aromatic. Additionally, for heterocycloalkyl, a heteroatom can occupy the position at which the heterocycle is attached to the remainder of the molecule. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A heteroaryl group can be attached to the remainder of the molecule through a carbon or heteroatom. An "arylene" and a "heteroarylene," alone or as part of another substituent, mean a divalent radical derived from an aryl and heteroaryl, respectively.

Spirocyclic rings are two or more rings wherein adjacent rings are attached through a single atom. The individual rings within spirocyclic rings may be identical or different. Individual rings in spirocyclic rings may be substituted or unsubstituted and may have different substituents from other individual rings within a set of spirocyclic rings. Possible substituents for individual rings within spirocyclic rings are the possible substituents for the same ring when not part of spirocyclic rings (e.g. substituents for cycloalkyl or heterocycloalkyl rings). Spirocylic rings may be substituted or unsubstituted cycloalkyl, substituted or unsubstituted cycloalkylene, substituted or unsubstituted heterocycloalkyl or substituted or unsubstituted heterocycloalkylene and individual rings within a spirocyclic ring group may be any of the immediately previous list, including having all rings of one type (e.g. all rings being substituted heterocycloalkylene wherein each ring may be the same or different substituted heterocycloalkylene). When referring to a spirocyclic ring system, heterocyclic spirocyclic rings means a spirocyclic rings wherein at least one ring is a heterocyclic ring and wherein each ring may be a different ring. When referring to a spirocyclic ring system, substituted spirocyclic rings means that at least one ring is substituted and each substituent may optionally be different.

The symbol "~~~" denotes the point of attachment of a chemical moiety to the remainder of a molecule or chemical formula.

The term "oxo," as used herein, means an oxygen that is double bonded to a carbon atom.

The term "alkylarylene" as an arylene moiety covalently bonded to an alkylene moiety (also referred to herein as an alkylene linker). In embodiments, the alkylarylene group has the formula:

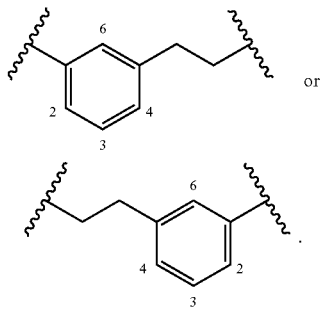

Each of the above terms (e.g., "alkyl," "heteroalkyl," "cycloalkyl," "heterocycloalkyl," "aryl," and "heteroaryl") includes both substituted and unsubstituted forms of the indicated radical.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR" ", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —NR'SO$_2$R", —NR'C(O)R", —NR'C(O)—OR", —NR'OR", in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound described herein includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR" ", —NR—C(NR'R")=NR'", —S(O)R', —S(O)$_2$R', —S(O)$_2$NR'R", —NRSO$_2$R', —NR'NR"R'", —ONR'R", —NR'C(O)NR"NR'"R"", —CN, —NO$_2$, —R', —N$_3$, —CH(Ph)$_2$, fluoro(C$_1$-C$_4$)alkoxy, and fluoro(C$_1$-C$_4$)alkyl, —NR'SO$_2$R", —NR'C(O)R", —NR'C(O)—OR", —NR'OR", in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound described herein includes more than one R group, for example, each of the R groups is independently selected as are each R', R", R'", and R"" groups when more than one of these groups is present.

Substituents for rings (e.g. cycloalkyl, heterocycloalkyl, aryl, heteroaryl, cycloalkylene, heterocycloalkylene, arylene, or heteroarylene) may be depicted as substituents on the ring rather than on a specific atom of a ring (commonly referred to as a floating substituent). In such a case, the substituent may be attached to any of the ring atoms (obeying the rules of chemical valency) and in the case of fused rings or spirocyclic rings, a substituent depicted as associated with one member of the fused rings or spirocyclic rings (a floating substituent on a single ring), may be a substituent on any of the fused rings or spirocyclic rings (a floating substituent on multiple rings). When a substituent is attached to a ring, but not a specific atom (a floating substituent), and a subscript for the substituent is an integer greater than one, the multiple substituents may be on the same atom, same ring, different atoms, different fused rings, different spirocyclic rings, and each substituent may optionally be different. Where a point of attachment of a ring to the remainder of a molecule is not limited to a single atom (a floating substituent), the attachment point may be any atom of the ring and in the case of a fused ring or spirocyclic ring, any atom of any of the fused rings or spirocyclic rings while obeying the rules of chemical valency. Where a ring, fused rings, or spirocyclic rings contain one or more ring heteroatoms and the ring, fused rings, or spirocyclic rings are shown with one more floating substituents (including, but not limited to, points of attachment to the remainder of the molecule), the floating substituents may be bonded to the heteroatoms. Where the ring heteroatoms are shown bound to one or more hydrogens (e.g. a ring nitrogen with two bonds to ring atoms and a third bond to a hydrogen) in the structure or formula with the floating substituent, when the heteroatom is bonded to the floating substituent, the substituent will be understood to replace the hydrogen, while obeying the rules of chemical valency.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

As used herein, the terms "heteroatom" or "ring heteroatom" are meant to include oxygen (O), nitrogen (N), sulfur (S), phosphorus (P), Boron (B), and silicon (Si).

A "substituent group," as used herein, means a group selected from the following moieties:

(A) halogen, oxo, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$F, —OCH$_2$I, —N$_3$, unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_5$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered), and (B) alkyl (e.g., $C_1$-$C_{20}$, $C_1$-$C_{12}$, $C_1$-$C_5$, $C_1$-$C_6$, $C_1$-$C_4$, or $C_1$-$C_2$), heteroalkyl (e.g., 2 to 20 membered, 2 to 12 membered, 2 to 8 membered, 2 to 6 membered, 4 to 6 membered, 2 to 3 membered, or 4 to 5 membered), cycloalkyl (e.g., $C_3$-$C_{10}$, $C_3$-$C_5$, $C_3$-$C_6$, $C_4$-$C_6$, or $C_5$-$C_6$), heterocycloalkyl (e.g., 3 to 10 membered, 3 to 8 membered, 3 to 6 membered, 4 to 6 membered, 4 to 5 membered, or 5 to 6 membered), aryl (e.g., $C_6$-$C_{12}$, $C_6$-$C_{10}$, or phenyl), or heteroaryl (e.g., 5 to 12 membered, 5 to 10 membered, 5 to 9 membered, or 5 to 6 membered), substituted with at least one substituent selected from:

(i) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$F, —OCH$_2$I, —N$_3$, unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_5$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered), and (ii) alkyl (e.g., $C_1$-$C_{20}$, $C_1$-$C_{12}$, $C_1$-$C_5$, $C_1$-$C_6$, $C_1$-$C_4$, or $C_1$-$C_2$), heteroalkyl (e.g., 2 to 20 membered, 2 to 12 membered, 2 to 8 membered, 2 to 6 membered, 4 to 6 membered, 2 to 3 membered, or 4 to 5 membered), cycloalkyl (e.g., $C_3$-$C_{10}$, $C_3$-$C_5$, $C_3$-$C_6$, $C_4$-$C_6$, or $C_5$-$C_6$), heterocycloalkyl (e.g., 3 to 10 membered, 3 to 8 membered, 3 to 6 membered, 4 to 6 membered, 4 to 5 membered, or 5 to 6 membered), aryl (e.g., $C_6$-$C_{12}$, $C_6$-$C_{10}$, or phenyl), or heteroaryl (e.g., 5 to 12 membered, 5 to 10 membered, 5 to 9 membered, or 5 to 6 membered), substituted with at least one substituent selected from:

(a) oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —S O$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$F, —OCH$_2$I, —N$_3$, unsubstituted alkyl (e.g., $C_1$-$C_{20}$, $C_1$-$C_{12}$, $C_1$-$C_5$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_5$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered), and (b) alkyl (e.g., $C_1$-$C_{20}$, $C_1$-$C_{12}$, $C_1$-$C_5$, $C_1$-$C_6$, $C_1$-$C_4$, or $C_1$-$C_2$), heteroalkyl (e.g., 2 to 20 membered, 2 to 12 membered, 2 to 8 membered, 2 to 6 membered, 4 to 6 membered, 2 to 3 membered, or 4 to 5 membered), cycloalkyl (e.g., $C_3$-$C_{10}$, $C_3$-$C_5$, $C_3$-$C_6$, $C_4$-$C_6$, or $C_5$-$C_6$), heterocycloalkyl (e.g., 3 to 10 membered, 3 to 6 membered, 4 to 6 membered, 4 to 5 membered, or 5 to 6 membered), aryl (e.g., $C_6$-$C_{12}$, $C_6$-$C_{10}$, or phenyl), or heteroaryl (e.g., 5 to 12 membered, 5 to 10 membered, 5 to 9 membered, or 5 to 6 membered), substituted with at least one substituent selected from: oxo, halogen, —CCl$_3$, —CBr$_3$, —CF$_3$, —CI$_3$, —CHCl$_2$, —CHBr$_2$, —CHF$_2$, —CHI$_2$, —CH$_2$Cl, —CH$_2$Br, —CH$_2$F, —CH$_2$I, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC(O)NHNH$_2$, —NHC(O)NH$_2$, —NHSO$_2$H, —NHC(O)H, —NHC(O)OH, —NHOH, —OCCl$_3$, —OCF$_3$, —OCBr$_3$, —OCI$_3$, —OCHCl$_2$, —OCHBr$_2$, —OCHI$_2$, —OCHF$_2$, —OCH$_2$Cl, —OCH$_2$Br, —OCH$_2$F, —OCH$_2$I, —N$_3$, unsubstituted alkyl (e.g., $C_1$-$C_{20}$, $C_1$-$C_{12}$, $C_1$-$C_8$, $C_1$-$C_6$, $C_1$-$C_4$, or $C_1$-$C_2$), unsubstituted heteroalkyl (e.g., 2 to 20 membered, 2 to 12 membered, 2 to 8 membered, 2 to 6 membered, 4 to 6 membered, 2 to 3 membered, or 4 to 5 membered), unsubstituted cycloalkyl (e.g., $C_3$-$C_{10}$, $C_3$-$C_5$, $C_3$-$C_6$, $C_4$-$C_6$, or $C_5$-$C_6$), unsubstituted heterocycloalkyl (e.g., 3 to 10 membered, 3 to 8 membered, 3 to 6 membered, 4 to 6 membered, 4 to 5 membered, or 5 to 6 membered), unsubstituted aryl (e.g., $C_6$-$C_{12}$, $C_6$-$C_{10}$, or phenyl), or unsubstituted heteroaryl (e.g., 5 to 12 membered, 5 to 10 membered, 5 to 9 membered, or 5 to 6 membered).

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_5$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_5$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_5$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_5$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_5$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_5$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is unsubstituted (e.g., is an unsubstituted alkyl, unsubstituted heteroalkyl, unsubstituted cycloalkyl, unsubstituted heterocycloalkyl, unsubstituted aryl, unsubstituted heteroaryl, unsubstituted alkylene, unsubstituted heteroalkylene, unsubstituted cycloalkylene, unsubstituted heterocycloalkylene, unsubstituted arylene, and/or unsubstituted heteroarylene, respectively). In embodiments, a substituted or unsubstituted moiety (e.g., substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, substituted or unsubstituted alkylene, substituted or unsubstituted heteroalkylene, substituted or unsubstituted cycloalkylene, substituted or unsubstituted heterocycloalkylene, substituted or unsubstituted arylene, and/or substituted or unsubstituted heteroarylene) is substituted (e.g., is a substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene, respectively).

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, wherein if the substituted moiety is substituted with a plurality of substituent groups, each substituent group may optionally be different. In embodiments, if the substituted moiety is substituted with a plurality of substituent groups, each substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one size-limited substituent group, wherein if the substituted moiety is substituted with a plurality of size-limited substituent groups, each size-limited substituent group may optionally be different. In embodiments, if the substituted moiety is substituted with a plurality of size-limited substituent groups, each size-limited substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one lower substituent group, wherein if the substituted moiety is substituted with a plurality of lower substituent groups, each lower substituent group may optionally be different. In embodiments, if the substituted moiety is substituted with a plurality of lower substituent groups, each lower substituent group is different.

In embodiments, a substituted moiety (e.g., substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene) is substituted with at least one substituent group, size-limited substituent group, or lower substituent group; wherein if the substituted moiety is substituted with a plurality of groups selected from substituent groups, size-limited substituent groups, and lower substituent groups; each substituent group, size-limited substituent group, and/or lower substituent group may optionally be different. In embodiments, if the substituted moiety is substituted with a plurality of groups selected from substituent groups, size-limited substituent groups, and lower substituent groups; each substituent group, size-limited substituent group, and/or lower substituent group is different.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those that are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

When a disclosed chemical entity has at least one chiral center, the present disclosure encompasses one enantiomer of inhibitor free from the corresponding optical isomer, a racemic mixture of the inhibitor, and mixtures enriched in one enantiomer relative to its corresponding optical isomer. When a mixture is enriched in one enantiomer relative to its optical isomers, the mixture contains, for example, an enantiomeric excess of at least 50%, 75% 90%, 95%, 99%, or 99.5%.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this is selected from invention. Other examples of isotopes suitable for inclusion in the compounds of the invention include, but are not limited to, isotopes of chlorine, such as $^{38}$Cl, fluorine, such as $^{18}$F iodine, such as $^{123}$I and $^{125}$I, nitrogen, such as $^{13}$N and $^{15}$N, oxygen, such as $^{15}$O, $^{17}$O and $^{ls}$O, phosphorus, such as $^{32}$P, and sulphur, such as $^{35}$S.

It should be noted that throughout the application that alternatives are written in Markush groups, for example, each amino acid position that contains more than one possible amino acid. It is specifically contemplated that each member of the Markush group should be considered separately, thereby comprising another embodiment, and the Markush group is not to be read as a single unit.

The terms "a" or "an," as used in herein means one or more. In addition, the phrase "substituted with a[n]," as used herein, means the specified group may be substituted with one or more of any or all of the named substituents. The phrase "optionally substituted" is used interchangeably with the phrase "substituted or unsubstituted." In general, the term "substituted," whether preceded by the term "optionally" or not, means that a hydrogen radical of the designated moiety is replaced with the radical of a specified substituent, provided that the substitution results in a stable or chemically feasible chemical entity. The term "substitutable," when used in reference to a designated atom, means that attached to the atom is a hydrogen radical, which hydrogen atom can be replaced with the radical of a suitable substituent. Unless otherwise indicated, an "optionally substituted" group may have a substituent at each substitutable position of the group, and when more than one position in any given structure may be substituted with more than one substituent selected from a specified group, the substituent may be either the same or different at every position. Combinations of substituents envisioned by this disclosure are, for instance, those that result in the formation of stable or chemically feasible chemical entities. The phrase "one or more substituents," as used herein, refers to a number of substituents that equals from one to the maximum number of substituents possible based on the number of available bonding sites, provided that the conditions of stability and chemical feasibility are met. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls.

Moreover, where a moiety is substituted with an R substituent, the group may be referred to as "R-substituted." Where a moiety is R-substituted, the moiety is substituted with at least one R substituent and each R substituent is optionally different. Where a particular R group is present in the description of a chemical genus (such as Formula (I)), a Roman alphabetic symbol may be used to distinguish each appearance of that particular R group. For example, where multiple $R^{13}$ substituents are present, each $R^{13}$ substituent may be distinguished as $R^{13A}$, $R^{13B}$, $R^{13C}$, $R^{13D}$ etc., wherein each of $R^{13A}$, $R^{13B}$, $R^{13C}$, $R^{13D}$, etc. is defined within the scope of the definition of $R^{13}$ and optionally differently.

The term "pharmaceutically acceptable salts" is meant to include salts of the active compounds that are prepared with relatively nontoxic acids or bases, depending on the particular substituents found on the compounds described herein. Non-limiting examples of such salts include hydrochlorides, hydrobromides, phosphates, sulfates, methanesulfonates, nitrates, maleates, acetates, citrates, fumarates, proprionates, tartrates (e.g., (+)-tartrates, (−)-tartrates, or mixtures thereof including racemic mixtures), succinates, benzoates, and salts with amino acids such as glutamic acid, and quaternary ammonium salts (e.g. methyl iodide, ethyl iodide, and the like). These salts may be prepared by methods known to those skilled in the art. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The neutral forms of the compounds are preferably regenerated by contacting the salt with a base or acid and isolating the parent compound in the conventional manner. The parent form of the compound may differ from the various salt forms in certain physical properties, such as solubility in polar solvents.

In addition to salt forms, the present invention provides compounds, which are in a prodrug form. Prodrugs of the compounds described herein are those compounds that readily undergo chemical changes under physiological conditions to provide the compounds of the present invention. Prodrugs of the compounds described herein may be converted in vivo after administration. Additionally, prodrugs can be converted to the compounds of the present invention by chemical or biochemical methods in an ex vivo environment, such as, for example, when contacted with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture. The term "contacting"

may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

The terms "disease" or "condition" refer to a state of being or health status of a patient or subject capable of being treated with the compounds or methods provided herein. The disease may be a cancer. The term "cancer" refers to a cellular disorder characterized by uncontrolled or disregulated cell proliferation, decreased cellular differentiation, inappropriate ability to invade surrounding tissue, and/or ability to establish new growth at ectopic sites. The term "cancer" includes, but is not limited to, solid tumors and bloodborne tumors (hematologic malignancies). The term "cancer" further encompasses primary and metastatic cancers. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma. As used herein, the term "cancer" refers to all types of cancer, neoplasm or malignant tumors found in mammals (e.g. humans), including leukemia, carcinomas and sarcomas. The term "leukemia" refers broadly to progressive, malignant diseases of the blood-forming organs and is generally characterized by a distorted proliferation and development of leukocytes and their precursors in the blood and bone marrow. The term "sarcoma" generally refers to a tumor which is made up of a substance like the embryonic connective tissue and is generally composed of closely packed cells embedded in a fibrillar or homogeneous substance. The term "melanoma" is taken to mean a tumor arising from the melanocytic system of the skin and other organs.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatinifori carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

The terms "treating", or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing.

"Patient" or "subject in need thereof" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

A "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom (s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses.

Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal) compatible with the preparation. Parenteral administration includes, e.g., intravenous, intramuscular, intraarteriole, intradermal, subcutaneous, intraperitoneal, intraventricular, and intracranial. Other modes of delivery include, but are not limited to, the use of liposomal formulations, intravenous infusion, transdermal patches, etc.

"Co-administer" it is meant that a composition described herein is administered at the same time, just prior to, or just after the administration of one or more additional therapies. The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present invention can be delivered transdermally, by a topical route, or formulated as applicator sticks, solutions, suspensions, emulsions, gels, creams, ointments, pastes, jellies, paints, powders, and aerosols.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

The term "modulator" refers to a composition that increases or decreases the level of a target molecule or the function of a target molecule or the physical state of the target of the molecule.

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

The term "associated" or "associated with" in the context of a substance or substance activity or function associated with a disease (e.g. a protein associated disease) means that the disease (e.g. cancer) is caused by (in whole or in part), or a symptom of the disease is caused by (in whole or in part) the substance or substance activity or function.

The term "aberrant" as used herein refers to different from normal. When used to describe enzymatic activity or protein function, aberrant refers to activity or function that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propogated to other signaling pathway components.

The present invention comprises a method of treating cancer with a therapeutically effective amount of a compound of any of Formulas II-IX.

In certain embodiments, a compound of any of Formulas I-IX is administered at a rate approximately equal to the half-life of an E1 enzyme.

The present invention comprises a method of treating cancer with a therapeutically-effective amount of a compound of

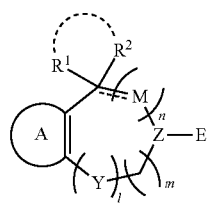

(I)

wherein
  ═ is selected from a single bond or double bond;
  l, m, and n are independently an integer from 0 to 2;
  M is selected from $CR^3R^4$, $-NR^5$, C═O, O, S═O, O═S═O, and S;
  Y is selected from $CR^6R^7$, NR, C═O, O, S═O, O═S═O, and S;
  Z is $CR^9$, or N;
  ring A is selected from
    a) 5- or 6-membered partially saturated heterocyclyl,
    b) 5- or 6-membered aryl or heteroaryl,
    c) 9-, 10- or 11-membered fused partially saturated heterocyclyl,
    d) 9- or 10-membered fused heteroaryl,
    e) naphthyl, and
    f) 4-, 5- or 6-membered cycloalkenyl; and E, $R^1$ through $R^{30}$ are as described above for Formula I;
  Each $R^{1A}$, $R^{1B}$, $R^{2A}$, $R^{2B}$, $R^{3A}$, $R^{3B}$, $R^{4A}$, $R^{4B}$, $R^{5A}$, $R^{5B}$, $R^{6A}$, $R^{6B}$, $R^{7A}$, $R^{7B}$, $R^{8A}$, $R^{8B}$, $R^{9A}$, $R^{9B}$, $R^{10A}$, $R^{10B}$, $R^{11A}$, $R^{11B}$, $R^{12A}$, $R^{12B}$, $R^{13A}$, $R^{13B}$, $R^{14A}$, $R^{14B}$, $R^{15A}$, $R^{15B}$, $R^{16A}$, $R^{16B}$, $R^{17A}$, $R^{17B}$, $R^{18A}$, $R^{18B}$, $R^{19A}$, $R^{19B}$, $R^{20A}$, $R^{20B}$, $R^{21A}$, $R^{21B}$, $R^{22A}$, $R^{22B}$, $R^{23A}$, $R^{23B}$, $R^{24A}$, $R^{24B}$, $R^{25A}$, $R^{25B}$, $R^{26A}$, $R^{26B}$, $R^{27A}$, $R^{27B}$, $R^{28A}$, $R^{28B}$, $R^{29A}$, $R^{29B}$, $R^{30A}$, $R^{30B}$ is independently selected from hydrogen, $-CX_3$, $-CHX_2$, $-CH_2X$, $-C(O)OH$, $-C(O)NH_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC$═$(O)NHNH_2$, $-NHC$═$(O)NH_2$, $-NHSO_2H$, $-NHC$═$(O)H$, $-NHC(O)OH$, $-NHOH$, $-OCX_3$, $-OCHX_2$, $-OCH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;
  $R^{1A}$ and $R^{1B}$ substituents bonded to the same nitrogen atom may optionally be joined to form a substituted or unsubstituted heterocycloalkyl or substituted or unsubstituted heteroaryl;
  $R^{2A}$ and $R^{2B}$ substituents bonded to the same nitrogen atom may optionally be joined to form a substituted or unsubstituted heterocycloalkyl or substituted or unsubstituted heteroaryl;
  $R^{4A}$ and $R^{4B}$ substituents bonded to the same nitrogen atom may optionally be joined to form a substituted or unsubstituted heterocycloalkyl or substituted or unsubstituted heteroaryl;
  $R^{5A}$ and $R^{5B}$ substituents bonded to the same nitrogen atom may optionally be joined to form a substituted or unsubstituted heterocycloalkyl or substituted or unsubstituted heteroaryl;
  $R^{6A}$ and $R^{6B}$ substituents bonded to the same nitrogen atom may optionally be joined to form a substituted or unsubstituted heterocycloalkyl or substituted or unsubstituted heteroaryl;
  $R^{7A}$ and $R^{7B}$ substituents bonded to the same nitrogen atom may optionally be joined to form a substituted or unsubstituted heterocycloalkyl or substituted or unsubstituted heteroaryl;
  $R^{8A}$ and $R^{8B}$ substituents bonded to the same nitrogen atom may optionally be joined to form a substituted or unsubstituted heterocycloalkyl or substituted or unsubstituted heteroaryl;
  $R^{9A}$ and $R^{9B}$ substituents bonded to the same nitrogen atom may optionally be joined to form a substituted or unsubstituted heterocycloalkyl or substituted or unsubstituted heteroaryl;
  $R^{10A}$ and $R^{10B}$ substituents bonded to the same nitrogen atom may optionally be joined to form a substituted or unsubstituted heterocycloalkyl or substituted or unsubstituted heteroaryl;
  $R^{11A}$ and $R^{11B}$ substituents bonded to the same nitrogen atom may optionally be joined to form a substituted or unsubstituted heterocycloalkyl or substituted or unsubstituted heteroaryl;
  $R^{12A}$ and $R^{12B}$ substituents bonded to the same nitrogen atom may optionally be joined to form a substituted or unsubstituted heterocycloalkyl or substituted or unsubstituted heteroaryl;
  $R^{13A}$ and $R^{13B}$ substituents bonded to the same nitrogen atom may optionally be joined to form a substituted or unsubstituted heterocycloalkyl or substituted or unsubstituted heteroaryl;
  $R^{14A}$ and $R^{14B}$ substituents bonded to the same nitrogen atom may optionally be joined to form a substituted or unsubstituted heterocycloalkyl or substituted or unsubstituted heteroaryl;
  $R^{15A}$ and $R^{15B}$ substituents bonded to the same nitrogen atom may optionally be joined to form a substituted or unsubstituted heterocycloalkyl or substituted or unsubstituted heteroaryl;
  $R^{16A}$ and $R^{16B}$ substituents bonded to the same nitrogen atom may optionally be joined to form a substituted or unsubstituted heterocycloalkyl or substituted or unsubstituted heteroaryl;
  $R^{17A}$ and $R^{17B}$ substituents bonded to the same nitrogen atom may optionally be joined to form a substituted or unsubstituted heterocycloalkyl or substituted or unsubstituted heteroaryl;
  $R^{18A}$ and $R^{18B}$ substituents bonded to the same nitrogen atom may optionally be joined to form a substituted or unsubstituted heterocycloalkyl or substituted or unsubstituted heteroaryl;
  $R^{19A}$ and $R^{19B}$ substituents bonded to the same nitrogen atom may optionally be joined to form a substituted or unsubstituted heterocycloalkyl or substituted or unsubstituted heteroaryl;
  $R^{20A}$ and $R^{20B}$, substituents bonded to the same nitrogen atom may optionally be joined to form a substituted or unsubstituted heterocycloalkyl or substituted or unsubstituted heteroaryl;

R$^{21A}$ and R$^{21B}$ substituents bonded to the same nitrogen atom may optionally be joined to form a substituted or unsubstituted heterocycloalkyl or substituted or unsubstituted heteroaryl;

R$^{22A}$ and R$^{22B}$ substituents bonded to the same nitrogen atom may optionally be joined to form a substituted or unsubstituted heterocycloalkyl or substituted or unsubstituted heteroaryl;

R$^{23A}$ and R$^{23B}$ substituents bonded to the same nitrogen atom may optionally be joined to form a substituted or unsubstituted heterocycloalkyl or substituted or unsubstituted heteroaryl;

R$^{24A}$ and R$^{24B}$ substituents bonded to the same nitrogen atom may optionally be joined to form a substituted or unsubstituted heterocycloalkyl or substituted or unsubstituted heteroaryl;

R$^{25A}$ and R$^{25B}$ substituents bonded to the same nitrogen atom may optionally be joined to form a substituted or unsubstituted heterocycloalkyl or substituted or unsubstituted heteroaryl;

R$^{26A}$ and R$^{26B}$ substituents bonded to the same nitrogen atom may optionally be joined to form a substituted or unsubstituted heterocycloalkyl or substituted or unsubstituted heteroaryl;

R$^{27A}$ and R$^{27B}$ substituents bonded to the same nitrogen atom may optionally be joined to form a substituted or unsubstituted heterocycloalkyl or substituted or unsubstituted heteroaryl;

R$^{28A}$ and R$^{28B}$ substituents bonded to the same nitrogen atom may optionally be joined to form a substituted or unsubstituted heterocycloalkyl or substituted or unsubstituted heteroaryl;

R$^{29A}$ and R$^{29B}$ substituents bonded to the same nitrogen atom may optionally be joined to form a substituted or unsubstituted heterocycloalkyl or substituted or unsubstituted heteroaryl;

R$^{30A}$ and R$^{30B}$ substituents bonded to the same nitrogen atom may optionally be joined to form a substituted or unsubstituted heterocycloalkyl or substituted or unsubstituted heteroaryl;

Each m1, m2, m3, m4, m5, m6, m7, m8, m9, m10, m11, m12, m13, m14, m15, m16, m17, m18, m19, m20, m21, m22, m23, m24, m25, m26, m27, m28, m29, and m30 are independently 1 or 2;

Each v1, v2, v3, v4, v5, v6, v7, v8, v9, v10, v11, v12, v13, v14, v15, v16, v17, v18, v19, v20, v21, v22, v23, v24, v25, v26, v27, v28, v29 and v30 are independently 1 or 2;

Each n1, n2, n3, n4, n5, n6, n7, n8, n9, n10, n11, n12, n13, n14, n15, n16, n17, n18, n19, n20, n21, n22, n23, n24, n25, n26, n27, n28, n29 and n30 are independently an integer from 0 to 2; and Each X, X$^1$, X$^2$, X$^3$, X$^4$, X$^5$, X$^6$, X$^7$, X$^8$, X$^9$, X$^{10}$, X$^{11}$, X$^{12}$, X$^{13}$, X$^{14}$, X$^{15}$, X$^{16}$, X$^{17}$, X$^{18}$, X$^{19}$, X$^{20}$, X$^{21}$, X$^{22}$, X$^{23}$, X$^{24}$, X$^{25}$, X$^{26}$, X$^{27}$, X$^{28}$, X$^{29}$ and X$^{30}$ are independently —Cl, —Br, —I or —F; provided R$^1$ is not 4-amino-1H-pyrazolo[3,4-d]pyrimidin-1-yl when R$^2$, R$^6$, R$^7$, R$^{13}$, R$^{14}$, R$^5$ and R$^{16}$ are H, ring A is phenyl and E is ethenylcarbonyl.

The present invention comprises a method of inhibiting E1 with a therapeutically-effective amount of a compound of

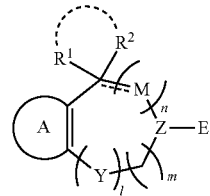

(I)

wherein $=$ is selected from a single bond or double bond;

l, m, and n are independently an integer from 0 to 2;

M is selected from CR$^3$R$^4$, —NR$^5$, C=O, O, S=O, O=S=O, and S;

Y is selected from CR$^6$R$^7$, —NR$^8$, C=O, O, S=O, O=S=O, and S;

Z is CR$^9$, or N;

ring A is selected from
 a) 5- or 6-membered partially saturated heterocyclyl,
 b) 5- or 6-membered aryl or heteroaryl,
 c) 9-, 10- or 11-membered fused partially saturated heterocyclyl,
 d) 9- or 10-membered fused heteroaryl,
 e) naphthyl, and
 f) 4-, 5- or 6-membered cycloalkenyl; and E, R$^1$ through R$^{30}$ are as described above for Formula I;

Each R$^{1A}$, R$^{1B}$, R$^{2A}$, R$^{2B}$, R$^{3A}$, R$^{3B}$, R$^{4A}$, R$^{4B}$, R$^{5A}$, R$^{5B}$, R$^{6A}$, R$^{6B}$, R$^{7A}$, R$^{7B}$, WA, R$^{8B}$, R$^{9A}$, R$^{9B}$, R$^{10A}$, R$^{10B}$, R$^{11A}$, R$^{11B}$, R$^{12A}$, R$^{12B}$, R$^{13A}$, R$^{13B}$, R$^{14A}$, R$^{14B}$, R$^{15A}$, R$^{15B}$, R$^{16A}$, R$^{16B}$, R$^{17A}$, R$^{17B}$, R$^{18A}$, R$^{18B}$, R$^{19A}$, R$^{19B}$, R$^{20A}$, R$^{20B}$, R$^{21A}$, R$^{21B}$, R$^{22A}$, R$^{22B}$, R$^{23A}$, R$^{23B}$, R$^{24A}$, R$^{24B}$, R$^{25A}$, R$^{25B}$, R$^{26A}$, R$^{26B}$, R$^{27A}$, R$^{27B}$, R$^{28A}$, R$^{28B}$, R$^{29A}$, R$^{29B}$, R$^{30A}$, R$^{30B}$ is independently selected from hydrogen, —CX$_3$, —CHX$_2$, —CH$_2$X, —C(O)OH, —C(O)NH$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O) NHNH$_2$, —NHC=(O)NH$_2$, —NHSO$_2$H, —NHC= (O)H, —NHC(O)OH, —NHOH, —OCX$_3$, —OCHX$_2$, —OCH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{1A}$ and R$^{1B}$ substituents bonded to the same nitrogen atom may optionally be joined to form a substituted or unsubstituted heterocycloalkyl or substituted or unsubstituted heteroaryl;

R$^{2A}$ and R$^{2B}$ substituents bonded to the same nitrogen atom may optionally be joined to form a substituted or unsubstituted heterocycloalkyl or substituted or unsubstituted heteroaryl;

R$^{4A}$ and R$^{4B}$ substituents bonded to the same nitrogen atom may optionally be joined to form a substituted or unsubstituted heterocycloalkyl or substituted or unsubstituted heteroaryl;

R$^{5A}$ and R$^{5B}$ substituents bonded to the same nitrogen atom may optionally be joined to form a substituted or unsubstituted heterocycloalkyl or substituted or unsubstituted heteroaryl;

R$^{6A}$ and R$^{6B}$ substituents bonded to the same nitrogen atom may optionally be joined to form a substituted or unsubstituted heterocycloalkyl or substituted or unsubstituted heteroaryl;

$R^{7A}$ and $R^{7B}$ substituents bonded to the same nitrogen atom may optionally be joined to form a substituted or unsubstituted heterocycloalkyl or substituted or unsubstituted heteroaryl;

$R^{8A}$ and $R^{8B}$ substituents bonded to the same nitrogen atom may optionally be joined to form a substituted or unsubstituted heterocycloalkyl or substituted or unsubstituted heteroaryl;

$R^{9A}$ and $R^{9B}$ substituents bonded to the same nitrogen atom may optionally be joined to form a substituted or unsubstituted heterocycloalkyl or substituted or unsubstituted heteroaryl;

$R^{10A}$ and $R^{10B}$ substituents bonded to the same nitrogen atom may optionally be joined to form a substituted or unsubstituted heterocycloalkyl or substituted or unsubstituted heteroaryl;

$R^{11A}$ and $R^{11B}$ substituents bonded to the same nitrogen atom may optionally be joined to form a substituted or unsubstituted heterocycloalkyl or substituted or unsubstituted heteroaryl;

$R^{12A}$ and $R^{12B}$ substituents bonded to the same nitrogen atom may optionally be joined to form a substituted or unsubstituted heterocycloalkyl or substituted or unsubstituted heteroaryl;

$R^{13A}$ and $R^{13B}$ substituents bonded to the same nitrogen atom may optionally be joined to form a substituted or unsubstituted heterocycloalkyl or substituted or unsubstituted heteroaryl;

$R^{14A}$ and $R^{14B}$ substituents bonded to the same nitrogen atom may optionally be joined to form a substituted or unsubstituted heterocycloalkyl or substituted or unsubstituted heteroaryl;

$R^{15A}$ and $R^{15B}$ substituents bonded to the same nitrogen atom may optionally be joined to form a substituted or unsubstituted heterocycloalkyl or substituted or unsubstituted heteroaryl;

$R^{16A}$ and $R^{16B}$ substituents bonded to the same nitrogen atom may optionally be joined to form a substituted or unsubstituted heterocycloalkyl or substituted or unsubstituted heteroaryl;

$R^{17A}$ and $R^{17B}$ substituents bonded to the same nitrogen atom may optionally be joined to form a substituted or unsubstituted heterocycloalkyl or substituted or unsubstituted heteroaryl;

$R^{18A}$ and $R^{18B}$ substituents bonded to the same nitrogen atom may optionally be joined to form a substituted or unsubstituted heterocycloalkyl or substituted or unsubstituted heteroaryl;

$R^{19A}$ and $R^{19B}$ substituents bonded to the same nitrogen atom may optionally be joined to form a substituted or unsubstituted heterocycloalkyl or substituted or unsubstituted heteroaryl;

$R^{20A}$ and $R^{20B}$, substituents bonded to the same nitrogen atom may optionally be joined to form a substituted or unsubstituted heterocycloalkyl or substituted or unsubstituted heteroaryl;

$R^{21A}$ and $R^{21B}$ substituents bonded to the same nitrogen atom may optionally be joined to form a substituted or unsubstituted heterocycloalkyl or substituted or unsubstituted heteroaryl;

$R^{22A}$ and $R^{22B}$ substituents bonded to the same nitrogen atom may optionally be joined to form a substituted or unsubstituted heterocycloalkyl or substituted or unsubstituted heteroaryl;

$R^{23A}$ and $R^{23B}$ substituents bonded to the same nitrogen atom may optionally be joined to form a substituted or unsubstituted heterocycloalkyl or substituted or unsubstituted heteroaryl;

$R^{24A}$ and $R^{24B}$ substituents bonded to the same nitrogen atom may optionally be joined to form a substituted or unsubstituted heterocycloalkyl or substituted or unsubstituted heteroaryl;

$R^{25A}$ and $R^{25B}$ substituents bonded to the same nitrogen atom may optionally be joined to form a substituted or unsubstituted heterocycloalkyl or substituted or unsubstituted heteroaryl;

$R^{26A}$ and $R^{26B}$ substituents bonded to the same nitrogen atom may optionally be joined to form a substituted or unsubstituted heterocycloalkyl or substituted or unsubstituted heteroaryl;

$R^{27A}$ and $R^{27B}$ substituents bonded to the same nitrogen atom may optionally be joined to form a substituted or unsubstituted heterocycloalkyl or substituted or unsubstituted heteroaryl;

$R^{28A}$ and $R^{28B}$ substituents bonded to the same nitrogen atom may optionally be joined to form a substituted or unsubstituted heterocycloalkyl or substituted or unsubstituted heteroaryl;

$R^{29A}$ and $R^{29B}$ substituents bonded to the same nitrogen atom may optionally be joined to form a substituted or unsubstituted heterocycloalkyl or substituted or unsubstituted heteroaryl;

$R^{30A}$ and $R^{30B}$ substituents bonded to the same nitrogen atom may optionally be joined to form a substituted or unsubstituted heterocycloalkyl or substituted or unsubstituted heteroaryl;

Each m1, m2, m3, m4, m5, m6, m7, m8, m9, m10, m11, m12, m13, m14, m15, m16, m17, m18, m19, m20, m21, m22, m23, m24, m25, m26, m27, m28, m29, and m30 are independently 1 or 2;

Each v1, v2, v3, v4, v5, v6, v7, v8, v9, v10, v11, v12, v13, v14, v15, v16, v17, v18, v19, v20, v21, v22, v23, v24, v25, v26, v27, v28, v29 and v30 are independently 1 or 2;

Each n1, n2, n3, n4, n5, n6, n7, n8, n9, n10, n11, n12, n13, n14, n15, n16, n17, n18, n19, n20, n21, n22, n23, n24, n25, n26, n27, n28, n29 and n30 are independently an integer from 0 to 2; and Each X, $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, $X^{16}$, $X^{17}$, $X^{18}$, $X^{19}$, $X^{20}$, $X^{21}$, $X^{22}$, $X^{23}$, $X^{24}$, $X^{25}$, $X^{26}$, $X^{27}$, $X^{28}$, $X^{29}$ and $X^{30}$ are independently —Cl, —Br, —I or —F.

In embodiments, the compound is covalently attached to an E1 cysteine amino acid corresponding to Cys30 of Uba2 subunit 2. In embodiments, E contains an electrophilic moiety. In embodiments, the electron-withdrawing moieties are sufficiently electron withdrawing to allow the compound to covalently bind to an E1 cysteine amino acid corresponding to Cys30 of Uba2 subunit 2. In embodiments, the compound covalently binds to an E1 cysteine amino acid corresponding to Cys30 of Uba2 subunit 2; and forms a complex of formula X:

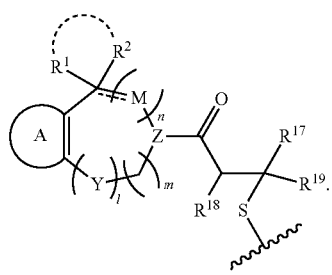

In a certain embodiment, the method includes allowing the compound to covalently bind an E1 enzyme.

In embodiments, the method includes allowing the compound to covalently bind an E1 cysteine amino acid corresponding to Cys30 of Uba2 subunit 2. In embodiments, the method includes allowing the E1 cysteine amino acid to bind to carbon attached to $R^{17}$ and $R^{18}$.

In an aspect is provided a method of inhibiting cell proliferation, the method including contacting the cell with a compound described herein. In embodiments, the method includes contacting the cell with an effective amount of the compound. In embodiments, the compound is administered at a rate approximately equal to the half-life of an E1 enzyme.

In an aspect is provided a method of inhibiting an E1 enzyme, the method including contacting an E1 enzyme with a compound described herein, thereby inhibiting the E1 enzyme. In embodiments, the method includes allowing the compound to covalently bind the E1 enzyme. In embodiments, the method includes allowing the compound to covalently bind an E1 cysteine amino acid corresponding to Cys30 of Uba2 subunit 2. In embodiments, the method includes allowing the E1 cysteine amino acid to bind to carbon attached to $R^{17}$ and $R^{19}$.

General Synthetic Schemes

The compounds of this invention can be synthesized according to the following procedures of Schemes I-VII, wherein the Substituents are as defined for Formulas I-IX, above, except where further noted. The Schemes reflect preparation of compounds where ring A of Formula I is phenyl, however similar reactions are known to one skilled in the art for the full scope of the definition of ring A.

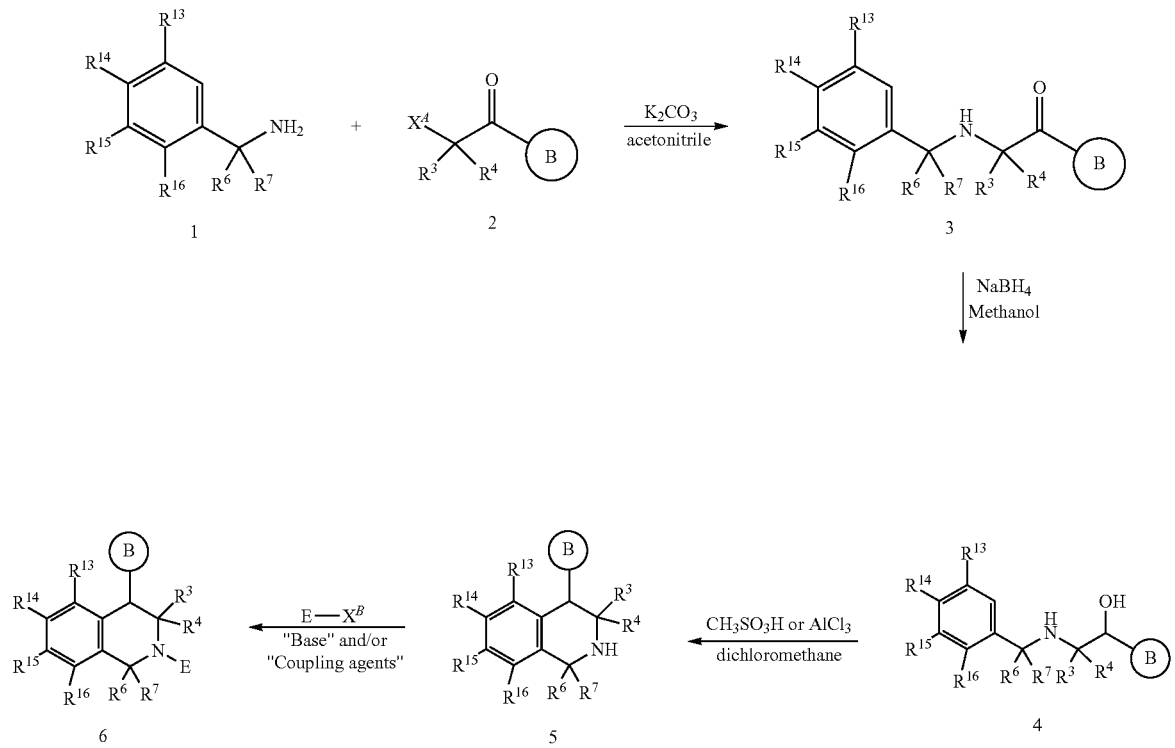

The compounds of Formula I-IX can be synthesized according to Scheme I. In step A, amine compound 1 can react with compound 2 (wherein $X^4$=F, Cl, Br, I) to form ketone intermediate 3, which will further react with a ketone-reducing agent such as $NaBH_4$ to give compound 4. Compound 4 will undergo cyclization in the presence of an acid to give compound 5. Compound 5 will be converted to compound 6 (Formula V, $R^1$=H, ring B is aryl or heteroaryl) by reacting with E-$X^B$ using reaction including alkylation, acylation and sulfonylation ($X^B$ is F, Cl, Br, I, OMs, OTs, CHO, COOH, COCl, —$SO_2Cl$).

Scheme II:

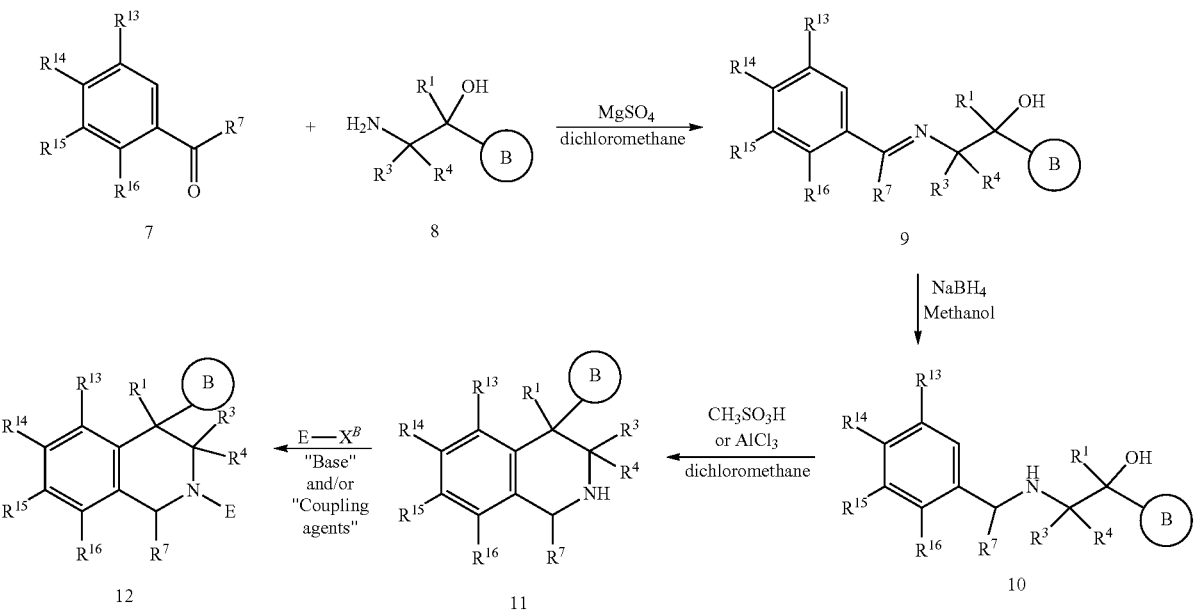

The compounds of Formula I-IX can also be synthesized according to Scheme II. In step A, carbonyl compound 7 can react with amine compound 8 to form mine intermediate 9, which will further react with a reducing agent such as NaBH$_4$ to give compound 10. Compound 10 will undergo cyclization in the presence of an acid to give compound 11. Compound 11 will be converted to compound 12 (Formula V, R$^6$=H, ring B is aryl or heteroaryl) by reacting with E-X$^B$ using reaction including alkylation, acylation and sulfonylation (X$^B$ is F, Cl, Br, I, OMs, OTs, CHO, COOH, COCl, —SO$_2$Cl).

The compounds of Formula I-IX can also be synthesized according to Scheme III. In step A, compound 13 (X$^B$=F, Cl, Br, OH) can react with amine compound 14 to form amide intermediate 15, which will further react with a reducing agent such as LiAlH$_4$ to give amine compound 16. Compound 16 will undergo cyclization in the presence of an acid to give compound 17. Compound 17 will be converted to compound 18 (Formula V, R$^6$=H, R$^7$=H, ring B is aryl or heteroaryl) by reacting with E-X$^B$ using reaction including alkylation, acylation and sulfonylation (X$^A$ is F, Cl, Br, I, OMs, OTs, CHO, COOH, COCl, —SO$_2$Cl).

Scheme III:

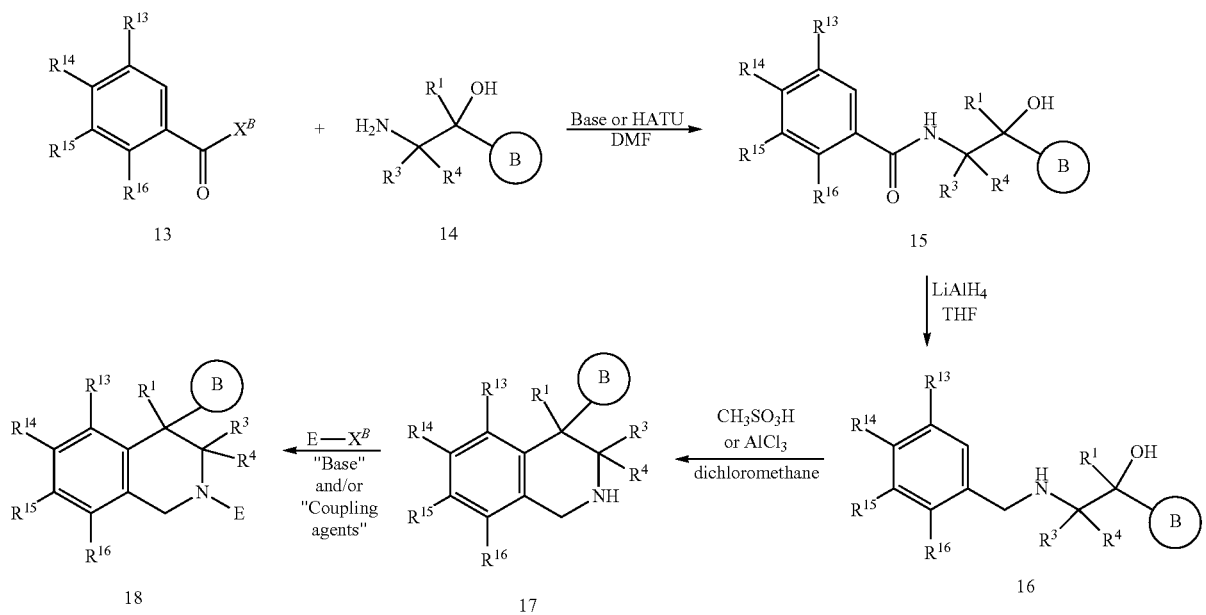

Scheme IV:

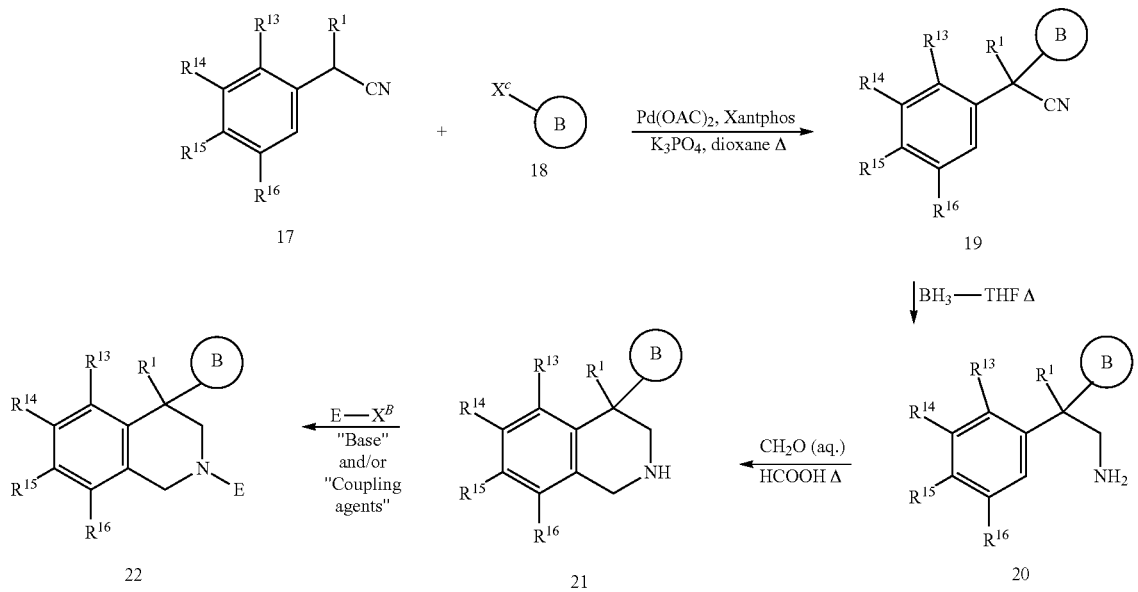

The compounds of Formula I-IX can also be synthesized according to Scheme IV. In step A, nitrile compound 17 can react with compound 18 ($X^c$=Cl, Br, I, ring B=aryl, heteroaryl) to form intermediate 19, which will further react with a reducing agent such as $BH_3$ to give amine compound 20. Compound 20 will undergo cyclization with formaldehyde to give compound 21. Compound 21 will be converted to compound 22 (Formula V, $R^3$=H, $R^4$=H, R=H, $R^7$=H, ring B is aryl or heteroaryl) by reacting with E-$X^B$ using reaction including alkylation, acylation and sulfonylation ($X^A$ is F, Cl, Br, I, OMs, OTs, CHO, COOH, COCl, —$SO_2Cl$).

The compounds of Formula I-IX can also be synthesized according to Scheme V. In step A, nitrile compound 17 can react with compound 22 ($X^D$=F, Cl, Br, I) to form intermediate 23, which will further react with a reducing agent such as $BH_3$ to give amine compound 24. Compound 24 will undergo cyclization with formaldehyde to give compound 25. Compound 25 will be converted to compound 26 (Formula III, $R^3$=H, $R^4$=H, $R^6$=H, $R^7$=H) by reacting with E-$X^B$ using reaction including alkylation, acylation and sulfonylation ($X^A$ is F, Cl, Br, I, OMs, OTs, CHO, COOH, COCl, —$SO_2Cl$).

Scheme V:

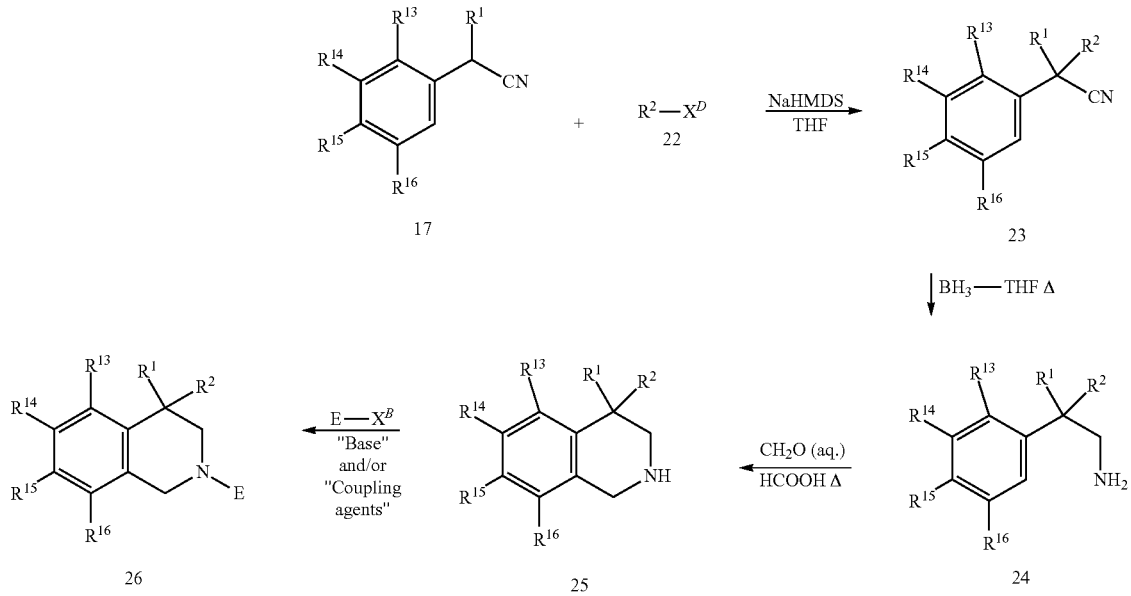

Scheme VI:

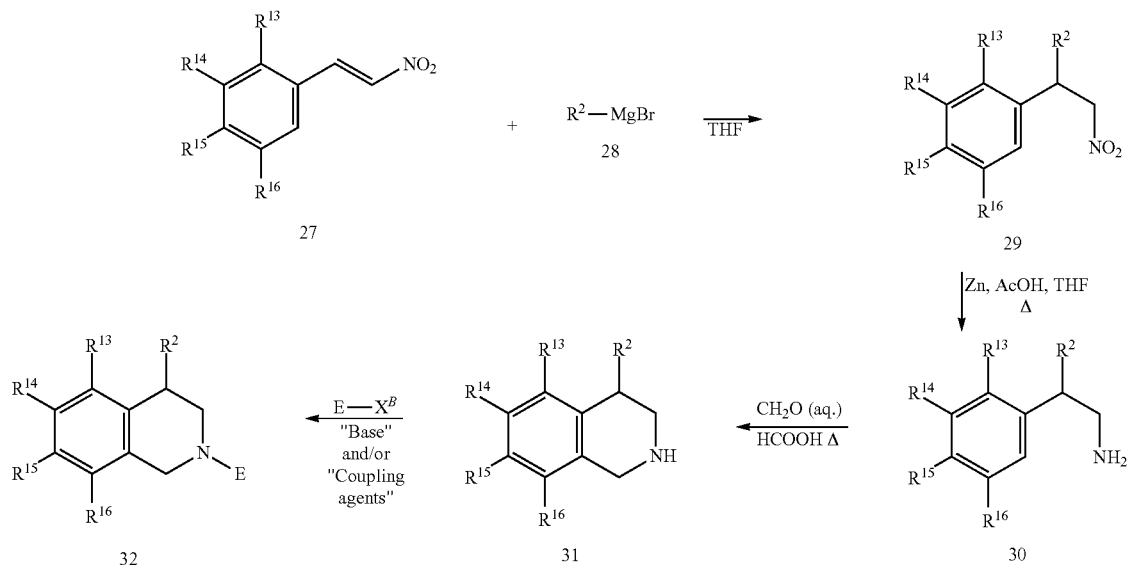

The compounds of Formula I-IX can also be synthesized according to Scheme VI. In step A, vinyl nitro compound 27 can react with compound 28 to form intermediate 29, which will further react with a reducing agent such as Zinc/acetic acid to give amine compound 30. Compound 30 will undergo cyclization with formaldehyde to give compound 31. Compound 31 will be converted to compound 32 (Formula III, $R^1$=H, $R^3$=H, $R^4$=H, R=H, $R^7$=H) by reacting with E-$X^B$ using reaction including alkylation, acylation and sulfonylation ($X^A$ is F, Cl, Br, I, OMs, OTs, CHO, COOH, COCl, —$SO_2Cl$).

The compounds of Formula I-IX can also be synthesized according to Scheme VII. In step A, acid compound 33 is converted to ketone 34. 34 will then condense with aldehyde 35 (ring B is aryl or heteroaryl) to give compound 36. Compound 36 will undergo cyclization to give compound 37. Compound 37 will be reductively aminated to compound 38. Compound 38 will be converted to compound 39 (Formula V, $R^1$=H, $R^3$=H, $R^4$=H, $R^6$=H, $R^7$=H, Z=CH) by reacting with E-$X^B$ using reaction including alkylation, acylation and sulfonylation ($X^A$ is F, Cl, Br, I, OMs, OTs, CHO, COOH, COCl, —$SO_2Cl$).

Scheme VII:

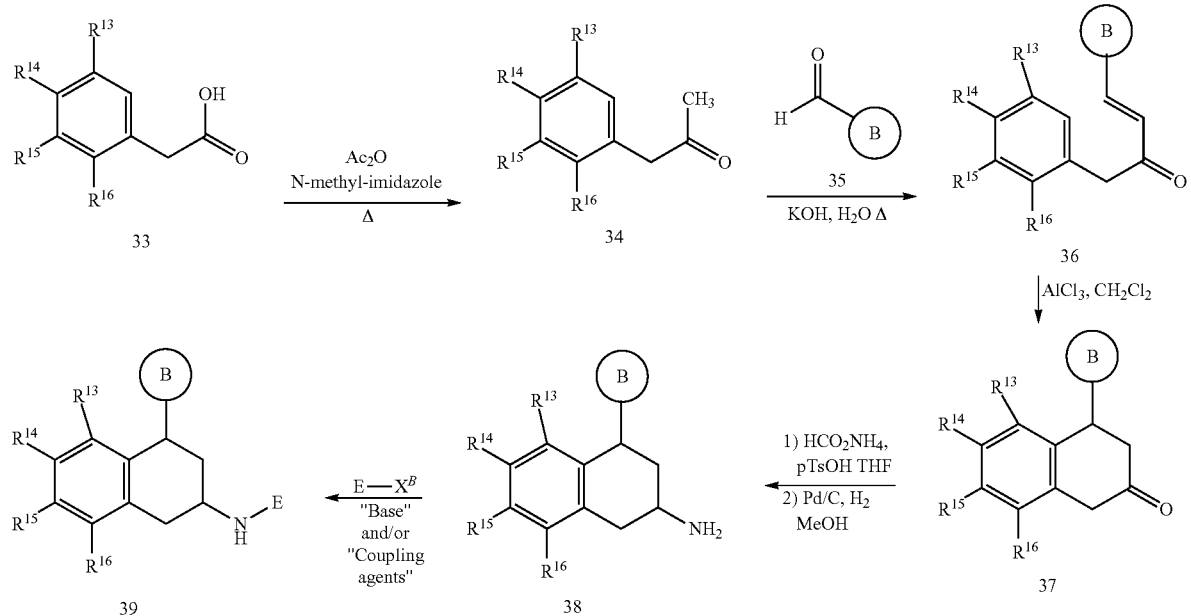

EXAMPLES

Example 1

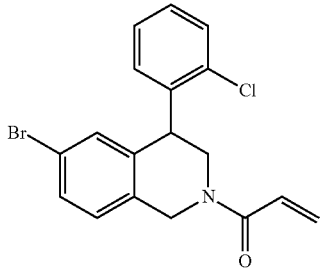 [SMILES: C=CC(=O)N1Cc2ccc(Br)cc2C(c2ccccc2Cl)C1]

1-(6-bromo-4-(2-chlorophenyl)-3,4-dihydroisoquinolin-2(1H)-yl)prop-2-en-1-one

Step A—Preparation of 2-((4-bromobenzyl)amino)-1-(2-chlorophenyl)ethan-1-one

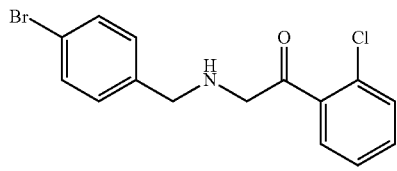 [SMILES: O=C(CNCc1ccc(Br)cc1)c1ccccc1Cl]

To a mixture of (4-bromophenyl)methanamine (20 mmol), potassium carbonate (60 mmol) in acetonitrile (50 mL) was added 2-bromo-1-(2-chlorophenyl)ethan-1-one (20 mmol) under argon. After two hours, the mixture was filtered and the filtrate was concentrated in vacuo to give a crude mixture that was used directly for next step without further purification. MS (ES+): 338.0, 339.9 (M+H).

Step B—Preparation of 2-((4-bromobenzyl)amino)-1-(2-chlorophenyl)ethan-1-ol

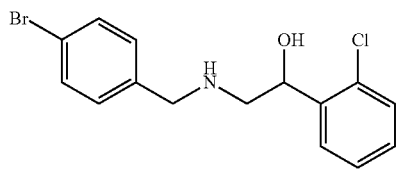 [SMILES: OC(CNCc1ccc(Br)cc1)c1ccccc1Cl]

To a mixture of 2-((4-bromobenzyl)amino)-1-(2-chlorophenyl)ethan-1-one (20 mmol) in methanol (50 mL) was added sodium borohydride (20 mmol). After one hour, the mixture was concentrated in vacuo and the residue was extracted between ethyl acetate and saturated sodium bicarbonate aqueous solution. The organic layer was dried over anhydrous magnesium sulfate and then concentrated in vacuo. The crude mixture was purified via flash chromatography to give 2.3 g (7.1 mmol) of the desired product. MS (ES+): 339.7, 341.7 (M+H).

Step C—Preparation of 6-bromo-4-(2-chlorophenyl)-1,2,3,4-tetrahydroisoquinoline

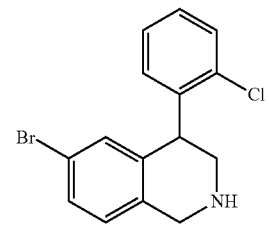 [SMILES: Clc1ccccc1C1CNCc2ccc(Br)cc21]

To a mixture of 2-((4-bromobenzyl)amino)-1-(2-chlorophenyl)ethan-1-ol (7 mmol) in dichloromethane (30 mL) was added methanesulfonic acid (35 mmol), and the mixture was heated at 70° C. for two hours. The mixture was cooled to 0° C. and quenched with saturated sodium bicarbonate aqueous solution saturated until pH>8. The mixture then extracted with ethyl acetate. The organic layer was dried over anhydrous magnesium sulfate and then concentrated in vacuo. The crude mixture was purified via flash chromatography to give 0.6 g (7.1 mmol) of the desired product. MS (ES+): 321.8, 323.8 (M+H).

Step D—Preparation of 1-(6-bromo-4-(2-chlorophenyl)-3,4-dihydroisoquinolin-2(1H)-yl)prop-2-en-1-one To a mixture of 6-bromo-4-(2-chlorophenyl)-1,2,3,4-tetrahydroisoquinoline (0.25 mmol), N,N-diisopropylethylamine (0.75 mmol) in dichloromethane (3 mL) was added acryloyl chloride (0.25 mmol). After 5 min, the mixture was quenched with saturated sodium bicarbonate aqueous solution and then extracted with ethyl acetate. The organic layer was dried over anhydrous magnesium sulfate and then concentrated in vacuo. The crude mixture was purified with preparative thin-layer chromatography to give 80 mg (0.21 mmol) of the desired product. MS (ES+): 375.8, 377.8 (M+H).

Example 2

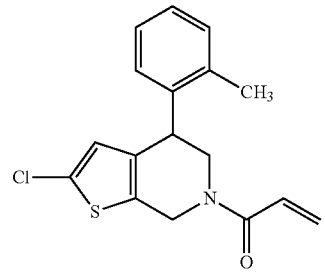 [SMILES: C=CC(=O)N1Cc2sc(Cl)cc2C(c2ccccc2C)C1]

1-(2-chloro-4-(o-tolyl)-4,7-dihydrothieno[2,3-c]pyridin-6(5H)-yl)prop-2-en-1-one Step A—Preparation of (E)-2-(((5-chlorothiophen-2-yl)methyl)imino)-1-(o-tolyl)ethan-1-ol

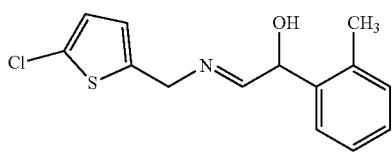 [SMILES: Cc1ccccc1C(O)/C=N/Cc1ccc(Cl)s1]

To a mixture of 5-chlorothiophene-2-carbaldehyde (1.65 mmol), 2-amino-1-(o-tolyl)ethan-1-ol (1.65 mmol) in dichloromethane (20 mL) was added anhydrous magnesium sulfate (6 mmol). The mixture was heated at 50° C. under argon for 3 hours. The mixture was filtered and the filtrate was concentrated in vacuo to give a crude mixture that was used directly for next step without further purification. MS (ES+): 279.8, 281.8 (M+H).

Step B—Preparation of 2-(((5-chlorothiophen-2-yl)methyl)amino)-1-(o-tolyl)ethan-1-ol

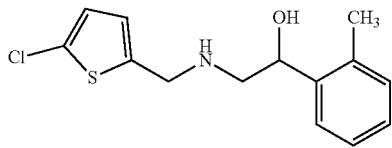 [SMILES: Cc1ccccc1C(O)CNCc1ccc(Cl)s1]

To a mixture of (E)-2-(((5-chlorothiophen-2-yl)methyl)imino)-1-(o-tolyl)ethan-1-ol (1.65 mmol) in methanol (30 mL) was added sodium borohydride (1.65 mmol). After one hour, the mixture was concentrated in vacuo and the residue was extracted between ethyl acetate and saturated sodium bicarbonate aqueous solution. The organic layer was dried over anhydrous magnesium sulfate and then concentrated in vacuo. The crude mixture was purified via flash chromatography to give 400 mg (1.42 mmol) of the desired product. MS (ES+): 282.0, 284.0 (M+H).

Step C—Preparation of 2-chloro-4-(o-tolyl)-4,5,6,7-tetrahydrothieno[2,3-c]pyridine

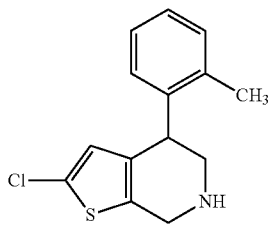 [SMILES: Cc1ccccc1C1CNCc2sc(Cl)cc21]

To a mixture of 2-(((5-chlorothiophen-2-yl)methyl)amino)-1-(o-tolyl)ethan-1-ol (1.42 mmol) in dichloromethane (10 mL) was added methanesulfonic acid (10 mmol), and the mixture was heated at 90° C. for two hours. The mixture was cooled to 0° C. and quenched with saturated sodium bicarbonate aqueous solution saturated until pH>8. The mixture then extracted with ethyl acetate. The organic layer was dried over anhydrous magnesium sulfate and then concentrated in vacuo. The crude mixture was purified via flash chromatography to give 0.16 g (0.6 mmol) of the desired product. MS (ES+): 263.8, 265.8 (M+H).

Step D—Preparation of 1-(2-chloro-4-(o-tolyl)-4,7-dihydrothieno[2,3-c]pyridin-6(5H)-yl)prop-2-en-1-one To a mixture of 2-chloro-4-(o-tolyl)-4,5,6,7-tetrahydrothieno[2,3-c]pyridine (0.38 mmol), N,N-diisopropylethylamine (0.114 mmol) in dichloromethane (3 mL) was added acryloyl chloride (0.38 mmol). After 5 min, the mixture was quenched with saturated sodium bicarbonate aqueous solution and then extracted with ethyl acetate. The organic layer was dried with anhydrous magnesium sulfate and then concentrated in vacuo. The crude mixture was purified by preparative thin-layer chromatography to give 30 mg (0.1 mmol) of the desired product. MS (ES+): 318.0, 320.0 (M+H).

Example 3

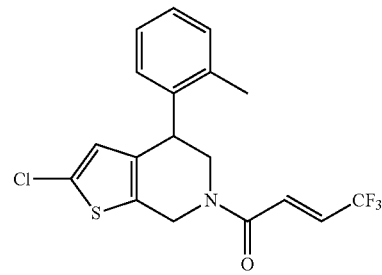 [SMILES: Cc1ccccc1C1CN(C(=O)/C=C/C(F)(F)F)Cc2sc(Cl)cc21]

(E)-1-(2-chloro-4-(o-tolyl)-4,7-dihydrothieno[2,3-c]pyridin-6(5H)-yl)-4,4,4-trifluorobut-2-en-1-one 4,4,4-Trifluorocrotonic acid (11.0 mg, 0.08 mmol), DIPEA (0.26 mL, 0.15 mmol), and HATU (43.0 mg, 0.11 mmol) was added to a round bottom flask and dissolved in dichloromethane (2 mL). The mixture was stirred at r.t. for 15 min. 2-chloro-4-(o-tolyl)-4,5,6,7-tetrahydrothieno[2,3-c]pyridine (20.0 mg, 0.08 mmol) was added to the mixture and stirred for 3 h. The mixture was diluted with dichloromethane (5 mL) and was then washed with sat. $NH_4Cl$ solution (5 mL) and the organic layer was separated. The organic liquor was then washed with sat. $NaHCO_3$ solution (5 mL), separated, dried over $MgSO_4$, and concentrated in vacuo. The crude oil was then dissolved in dichloromethane (1 mL) and purified by prep TLC (30% ethyl acetate/hexanes) to give the final product as a white solid (19 mg). LC-MS Calcd for $C_{18}H_{16}ClF_3NOS$ 386.84 $[M+H]^+$, found 386.1 $[M+H]^+$.

Example 4

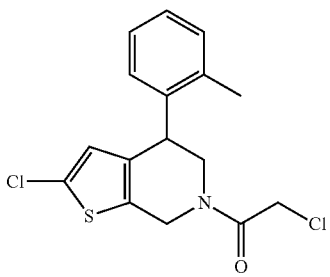 [SMILES: Cc1ccccc1C1CN(C(=O)CCl)Cc2sc(Cl)cc21]

2-chloro-1-(2-chloro-4-(o-tolyl)-4,7-dihydrothieno[2,3-c]pyridin-6(5H)-yl)ethan-1-one 2-Chloro-4-(o-tolyl)-4,5,6,7-tetrahydrothieno[2,3-c]pyridine (20 mg, 0.08 mmol) and DIPEA (0.26 mL, 0.19 mmol) was dissolved in dichloromethane (2 mL) and stirred at 0° C. Chloroacetylchloride (0.07 mL, 0.152 mmol) was added to the mixture dropwise and stirred for 10 min. The mixture was then diluted with ethyl acetate (5 mL) and washed with sat. NaHCO$_3$ solution (5 mL). The organic layer was then separated, dried over MgSO$_4$, and concentrated in vacuo. The crude oil was diluted in dichloromethane (1 mL) and purified by prep TLC (40% ethyl acetate/Hexanes) to give the final product as a yellow oil (45 mg). LC-MS Calcd for C$_{16}$H$_{15}$Cl$_2$NOSNa 363.26 [M+Na]$^+$, found 363.7 [M+Na]$^+$.

Example 5

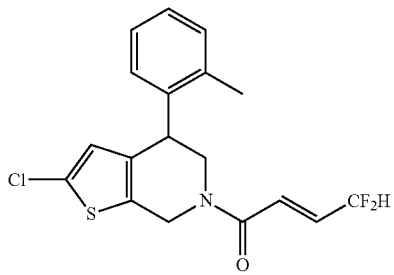 [SMILES: Cc1ccccc1C1CN(C(=O)/C=C/C(F)F)Cc2sc(Cl)cc21]

(E)-1(2-chloro-4-(o-tolyl)-4,7-dihydrothieno[2,3-c]pyridin-6(5H)-yl)-4,4-difluorobut-2-en-1-one Step A—Preparation of (E)-4,4-difluorobut-2-enoic Acid

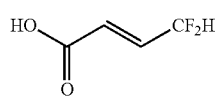

Ethyl (E)-4,4-difluorobut-2-enoate (258 mg, 2.11 mmol) was stirred in a 10% NaOH solution (3 mL) at 50° C. for 16 h. 0.5 N HCl solution was added the mixture until a pH of 1 was achieved. The mixture was then extracted with ethyl acetate (5×5 mL). The organic liquor was dried over MgSO$_4$ and concentrated in vacuo to give a yellow oil, (227 mg). The crude product was then used in the next reaction without purification.

Step B—Preparation of (E)-1-(2-chloro-4-(o-tolyl)-4,7-dihydrothieno[2,3-c]pyridin-6(5H)-yl)-4,4-difluorobut-2-en-1-one (E)-4,4-difluorobut-2-enoic acid (10.0 mg, 0.08 mmol), HATU (43.0, 0.11 mmol), and DIPEA (0.26 mL, 1.49 mmol) was dissolved in 2 mL of dichloromethane. The mixture was stirred at r.t. for 15 min. The amine 17-117 was added to the mixture and stirred at r.t. for 2 h. Upon completion, the mixture was diluted with ethyl acetate (5 mL) washed with 0.5 N HCl (5 mL) and separated. The organic layer was then dried over MgSO$_4$ and concentrated in vacuo. The crude oil was then dissolved in dichloromethane (1 mL) and purified by prep TLC (40% ethyl acetate/hexanes) to give the final product as a clear oil (18 mg). LC-MS Calcd for C$_{18}$H$_{16}$ClF$_2$NOSNa 390.84 [M+Na]$^+$, found 389.8 [M+Na]$^+$.

Example 6

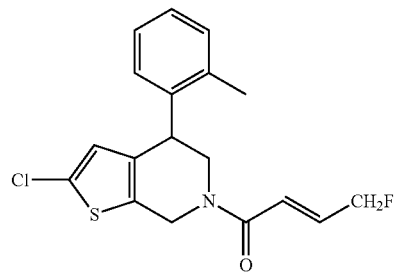

(E)-1-(2-chloro-4-(o-tolyl)-4,7-dihydrothieno[2,3-c]pyridin-6(5H)-yl)-4-fluorobut-2-en-1-one Step A—Preparation of ethyl (E)-4-fluorobut-2-enoate

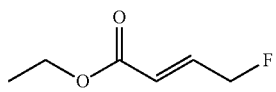

Ethyl-4-bromocrotonate (500 mg, 2.59 mmol) and AgF (990 mg, 7.77 mmol) was dissolved in MeCN (5 mL) and stirred in the dark at RT for 24 h. The mixture was filtered through a Celite pad and washed with dichloromethane. The organic liquor was concentrated in vacuo and used in the next reaction without further purification.

Step B—Preparation of (E)-4-fluorobut-2-enoic Acid

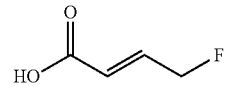

The crude ethyl (E)-4-fluorobut-2-enoate was dissolved in methanol (5 mL) and KOH (290 mg, 5.18 mmol) was added to the mixture and stirred for 16 h. 0.5 N HCl was added to the mixture until a pH of 3 was achieved. The mixture was then extracted with ethyl acetate (5×10 mL), separated, and dried over MgSO$_4$. The organic liquor was then concentrated in vacuo to give the crude product as a yellow oil (380 mg). The product was used in the next reaction without further purification.

Step C—Preparation of (E)-1-(2-chloro-4-(o-tolyl)-4,7-dihydrothieno[2,3-c]pyridin-6(5H)-yl)-4-fluorobut-2-en-1-one The crude (E)-4-fluorobut-2-enoic acid (7.99 mg, 0.08 mmol), DIPEA (0.26 mL, 0.15 mmol), and HATU (43.0 mg, 0.11 mmol) was dissolved in dichloromethane (2 mL) and stirred for 10 min. The amine 17-117 (20.0 mg, 0.08 mmol) was added to the mixture and stirred at r.t. for 3 h. The mixture was diluted with dichloromethane (5 mL) and washed with 0.5 N HCl (5 mL). The organic layer was separated and then washed with sat. NaHCO$_3$ solution (5 mL). The organic layer was separated, dried over MgSO$_4$ and concentrated in vacuo. The crude product was then dissolved in dichloromethane (1 mL) and purified by prep TLC (40% ethyl acetate/hexanes) to give both the product (6.34 mg). LC-MS Calcd for C$_{18}$H$_{17}$ClFNOS 349.85 [M]$^+$, found 349.8 [M]$^+$.

Example 7

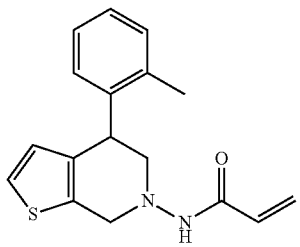 [SMILES: C=CC(=O)NN1Cc2sccc2C(c2ccccc2C)C1]

N-(4-(o-tolyl)-4,5,6,7-tetrahydrobenzo[b]thiophen-6-yl)acrylamide

Step A—Preparation of 1-(thiophen-2-yl)propan-2-one

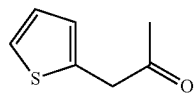

2-(Thiophen-2-yl)acetic acid (1.00 g, 9.79), Ac$_2$O (5.15 mL, 39.2 mmol), and N-methylimidazole (0.78 mL, 9.79 mmol), was stirred at 50° C. for 1 h. Upon completion, 10% KOH solution was added to the mixture. The mixture was extracted with ethyl acetate (15 mL) and separated. The organic layer was then washed with sat. NH$_4$Cl solution (20 mL) and separated. The organic layer was then washed with sat. NaHCO$_3$ solution (20 mL), separated, dried over MgSO$_4$, and concentrated in vacuo. The crude oil was used in the next reaction without further purification.

Step B—Preparation of (E)-1-(thiophen-2-yl)-4-(o-tolyl)but-3-en-2-one

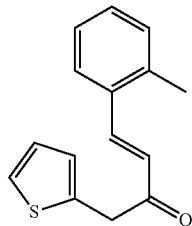 [SMILES: Cc1ccccc1/C=C/C(=O)Cc1cccs1]

2-methylbenzaldehyde (1.25 mL, 10.8 mmol) and KOH (82.0 mg, 1.47 mmol) was added to 40 mL of water and heated to 60° C. 1-(thiophen-2-yl)propan-2-one was added to the mixture dropwise and stirred for 16 h. The reaction was then quenched with sat. NH$_4$Cl solution (20 mL) and extracted with ethyl acetate (20 mL). The organic layer was separated and washed with sat. NaHCO$_3$ solution (10 mL). The organic layer was separated, dried over MgSO$_4$, and concentrated in vacuo. The crude product was purified by silica flash column chromatography (0-20% ethyl acetate/hexanes) to give the product as a yellow oil (504 mg). LC-MS Calcd for C$_{15}$H$_{14}$OSNa 265.34 [M+Na]$^+$, found 264.9 [M+Na]$^+$.

Step C—Preparation of 4-(o-tolyl)-4,7-dihydrobenzo[b]thiophen-6(5H-one

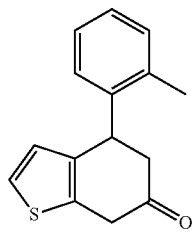 [SMILES: Cc1ccccc1C1CC(=O)Cc2sccc21]

(E)-1-(Thiophen-2-yl)-4-(o-tolyl)but-3-en-2-one (0.83 g, 3.40 mmol) was dissolved in dichloromethane (150 mL). AlCl$_3$ (6.00 g, 44.9 mmol) was added to the mixture and stirred for 2 h. The mixture was then quenched with sat. Rochelle's salt solution. The mixture was separated, further extracted with dichloromethane (2×50 mL) and dried over MgSO$_4$. The organic layer was concentrated in vacuo and purified by silica column flash chromatography (0-40% ethyl acetate/hexanes) to give the product as a yellow solid. LC-MS Calcd for C$_{15}$H$_{14}$OSNa 265.34 [M+Na]$^+$, found 267.0 [M+Na]$^+$.

Step D—Preparation of 4-(o-tolyl)-4,5,6,7-tetrahydrobenzo[b]thiophen-6-amine

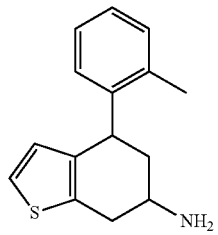 [SMILES: Cc1ccccc1C1CC(N)Cc2sccc21]

4-(o-Tolyl)-4,7-dihydrobenzo[b]thiophen-6(5H)-one (177 mg, 0.73 mmol) was dissolved in a dichloromethane:methanol mixture (2:1, 15 mL). Ammonium formate (164 mg, 2.92 mmol), p-TsOH (12.5 mg, 0.07 mmol), and mol sieves were added to the mixture and stirred for 14 h. NaBH$_4$ (55.3 mg, 1.46 mmol) was added to the mixture slowly and stirred for 1 h. 1 N HCl (3 mL) was added the mixture. The mixture was then extracted with ethyl acetate (20 mL) and separated. The organic layer was then washed with a sat. NaHCO$_3$ solution (20 mL), separated, and dried over MgSO$_4$. The organic liquor was then concentrated in vacuo and purified by silica flash column chromatography to give the product as a yellow oil (72 mg). LC-MS Calcd for $C_{15}H_{17}NSNa$ 266.37 [M+Na]$^+$, found 266.9 [M+Na]$^+$.

Step E—Preparation of N-(4-(o-tolyl)-4,5,6,7-tetrahydrobenzo[b]thiophen-6-yl)acrylamide 4-(o-Tolyl)-4,5,6,7-tetrahydrobenzo[b]thiophen-6-amine (20 mg, 0.08 mmol) and DIPEA (0.04 mL, 0.25 mmol) was dissolved in dichloromethane (1 mL). Acryloyl chloride (0.01 mL, 0.12 mmol) was added to the mixture dropwise and stirred for 10 min. The mixture was then diluted with dichloromethane (5 mL) and washed with sat. NaHCO$_3$ solution (5 mL). The organic layer was then separated, dried over MgSO$_4$, and concentrated in vacuo. The crude oil was diluted in dichloromethane (1 mL) and purified by prep TLC (50% ethyl acetate/hexanes) to give the final product as a yellow oil (3.5 mg). LC-MS Calcd for $C_{18}H_{19}NOS$ 297.42 [M]$^+$, found 297.2 [M]$^+$.

Example 8

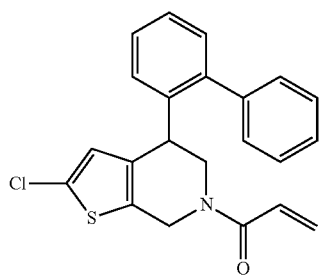 [SMILES: C=CC(=O)N1Cc2sc(Cl)cc2C(c2ccccc2-c2ccccc2)C1]

1-(4-([1,1'-biphenyl]-2-yl)-2-chloro-4,7-dihydrothieno[2,3-c]pyridin-6(5H)-yl)prop-2-en-1-one

Step A—Preparation of Boc-protected 2-amino-1-(2-bromophenyl)ethan-1-one

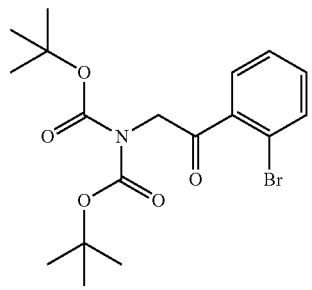 [SMILES: CC(C)(C)OC(=O)N(CC(=O)c1ccccc1Br)C(=O)OC(C)(C)C]

To a mixture of di-tert-butyl iminodicarboxylate (3.9 g, 18 mmol) in dry DMF (25 mL) was added NaH (1 g, 60% oil suspension) and the resulting mixture was stirred under argon for 2 hours. 2-bromo-1-(2-bromophenyl)ethan-1-one (5 g, 18 mmol) in DMF (25 mL) was added and the mixture was stirred under argon overnight. The mixture was quenched with 200 mL saturated NH$_4$Cl solution (aq.) and then extracted with ethyl acetate (200 mL). The organic layer was washed with brine, then dried over MgSO$_4$. After concentration in vacuo, flash chromatography was used to isolate 4.4 g of the desired product.

Step B—Preparation of Boc-protected 1-([1,1'-biphenyl]-2-yl)-2-aminoethan-1-one

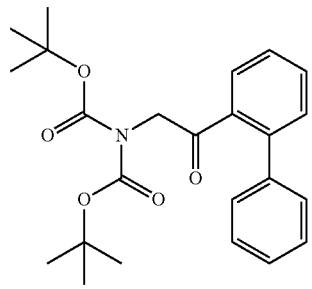 [SMILES: CC(C)(C)OC(=O)N(CC(=O)c1ccccc1-c1ccccc1)C(=O)OC(C)(C)C]

Boc-protected 2-amino-1-(2-bromophenyl)ethan-1-one (828 mg, 2 mmol), phenylboronic acid (268 mg, 2.2 mmol), K$_3$PO$_4$ (1.4 g, 6.6 mmol) and PdCl$_2$(dppf) (74 mg, 0.1 mmol) were mixed in dioxane (30 mL) and DI water (10 mL) and the mixture was heated at 90° C. under argon overnight. The mixture was then concentrated and purified by flash chromatography to give 690 mg yellow oil.

Step C—Preparation of 1-([1,1'-biphenyl]-2-yl)-2-aminoethan-1-one

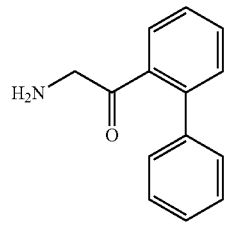 [SMILES: NCC(=O)c1ccccc1-c1ccccc1]

Boc-protected 1-([1,1'-biphenyl]-2-yl)-2-aminoethan-1-one (690 mg, 3.3 mmol) was dissolved in 14 mL dichloromethane, then 6 mL TFA was added and the mixture was stirred at room temperature for 10 min. The mixture was concentrated under high vacuum and the resulting crude product was used directly for next step.

Step D—Preparation of 1-([1,1'-biphenyl]-2-yl)-2-aminoethan-1-ol

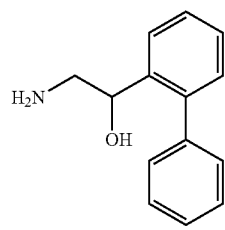 [SMILES: NCC(O)c1ccccc1-c1ccccc1]

1-([1,1'-Biphenyl]-2-yl)-2-aminoethan-1-one (3.3 mol) was dissolved in methanol (5 mL), then NaBH$_4$ (123 mg, 3.3 mol) was added and the mixture was left at room temperature for 30 min. After removal of the solvent, the mixture was partitioned between ethyl acetate (30 mL) and saturated NaHCO$_3$ solution (30 mL, aq.). The organic phase was dried over MgSO$_4$ and then concentrated. Flash chromatography on silica gel yielded 100 mg of the title compound as a light yellow oil. MS (ES+): 214.0, 215.1 (M+H).

Step E—Preparation of (E)-1-([1,1'-biphenyl]-2-yl)-2-(((5-chlorothiophen-2-yl)methylene)amino)ethan-1-ol

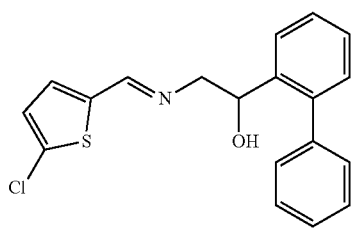 [SMILES: OC(C/N=C/c1ccc(Cl)s1)c1ccccc1-c1ccccc1]

1-([1,1'-Biphenyl]-2-yl)-2-aminoethan-1-ol (100 mg, 0.47 mmol), 5-chlorothiophene-2-carbaldehyde (70 mg, 0.47 mmol), MgSO$_4$ (240 mg, 2 mmol) were mixed in dichloromethane and heated at 50° C. for 3 hours. The mixture was then filtered and the filtrate was concentrated in vacuo to give a crude product.

Step F—Preparation of 1-([1,1'-biphenyl]-2-yl)-2-(((5-chlorothiophen-2-yl)methyl)amino)ethan-1-ol

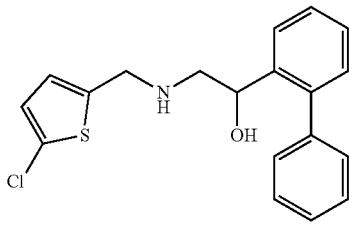 [SMILES: OC(CNCc1ccc(Cl)s1)c1ccccc1-c1ccccc1]

(E)-1-([1,1'-Biphenyl]-2-yl)-2-(((5-chlorothiophen-2-yl)methylene)amino)ethan-1-ol (0.47 mmol) was dissolved in methanol (20 mL), then sodium borohydride (0.47 mmol) was added, and the mixture was left at room temperature for 30 min. After removal of the solvent, the mixture was partitioned between ethyl acetate (30 mL) and saturated NaHCO$_3$ solution (30 mL, aq.). The organic phase was dried over MgSO$_4$ and then concentrated. Flash chromatography on silica gel yielded 22 mg of the title as white solid. MS (ES+): 343.9, 346.0 (M+H).

Step G—Preparation of 4-([1,1'-biphenyl]-2-yl)-2-chloro-4,5,6,7-tetrahydrothieno[2,3-c]pyridine

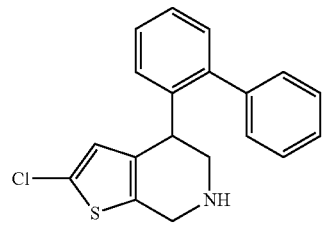 [SMILES: Clc1cc2c(s1)CNCC2c1ccccc1-c1ccccc1]

1-([1,1'-Biphenyl]-2-yl)-2-(((5-chlorothiophen-2-yl)methyl)amino)ethan-1-ol (0.064 mmol) was mixed with methanesulfonic acid (0.45 mmol), and the mixture was heated at 80° C. for two hours. The mixture was cooled to 0° C. and quenched with saturated sodium bicarbonate aqueous solution saturated until pH>8. The mixture then extracted with ethyl acetate. The organic layer was dried with anhydrous magnesium sulfate and then concentrated in vacuo. The crude mixture was purified with preparative TLC to give 8 mg (0.025 mmol) of the desired product. MS (ES+): 325.8, 327.8 (M+H).

Step H—Preparation of 1-(4-([1,1'-biphenyl]-2-yl)-2-chloro-4,7-dihydrothieno[2,3-c]pyridin-6(5H)-yl)prop-2-en-1-one To a mixture of 4-([1,1'-biphenyl]-2-yl)-2-chloro-4,5,6,7-tetrahydrothieno[2,3-c]pyridine (6 mg, 0.018 mmol), N,N-diisopropylethylamine (7 mg, 0.055 mmol) in dichloromethane (3 mL) was added acryloyl chloride (1.6 mg, 0.018 mmol). After 5 min, the mixture was quenched with saturated sodium bicarbonate aqueous solution and then extracted with ethyl acetate. The organic layer was dried over anhydrous magnesium sulfate and then concentrated in vacuo. The crude mixture was purified via preparative thin-layer chromatography to give 2 mg (0.005 mmol) of the desired product. MS (ES+): 379.8, 381.8 (M+H).

Example 9

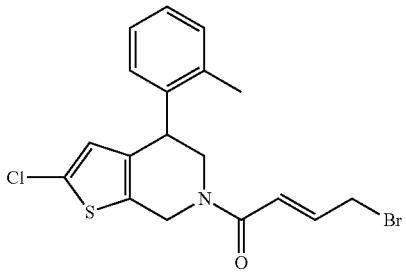 [SMILES: Cc1ccccc1C1CN(C(=O)/C=C/CBr)Cc2sc(Cl)cc21]

(E)-4-bromo-1-(2-chloro-4-(o-tolyl)-4,7-dihydrothieno[2,3-c]pyridin-6(5H)-yl)but-2-en-1-one Step A—Preparation of (E)-4-bromobut-2-enoic Acid

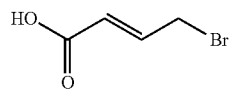

At 0° C., ethyl-4-bromocrotonate (300 m g, 1.55 mmol) and LiOH—H$_2$O (65 mg, 1.55 mmol) was mixed in THF (10 mL) and DI water (10 mL) for 2 hours, then 1N HCl was added to the mixture until a pH of 1 was achieved. The mixture was then extracted with ethyl acetate (5×10 mL), separated, and dried over MgSO$_4$. The organic liquor was then concentrated in vacuo to give the crude product as a yellow oil (200 mg, 1.2 mmol). The product was used in the next reaction without further purification. MS (ES−): 163.0, 165.0 (M−H).

Step B—Preparation of (E)-4-bromobut-2-enoyl Chloride

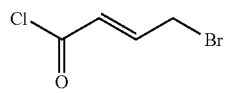

The crude of (E)-4-bromobut-2-enoic acid (200 mg, 1.2 mmol), was dissolved in SOCl$_2$ (5 mL) heated to reflux for 2 hours. The mixture was concentrated in vacuo and the crude product was used directly for next step.

Step C—Preparation of (E)-4-bromo-1-(2-chloro-4-(o-tolyl)-4,7-dihydrothieno[2,3-c]pyridin-6(5H)-yl)but-2-en-1-one At 0° C., the crude (E)-4-bromobut-2-enoyl chloride (1.2 mmol) was added to a mixture of 2-chloro-4-(o-tolyl)-4,5,6,7-tetrahydrothieno[2,3-c]pyridine (30 mg, 0.114 mmol),
DIPEA (88 mg, 0.684 mmol) in dichloromethane (3 mL) and DMF (2 mL). The mixture was sonicated for 20 min and then partitioned between ethyl acetate (25 mL) and brine (25 mL). The organic layer was dried over MgSO$_4$ and then concentrated. Preparative TLC was used to isolate 10 mg of desired product.

Example 10

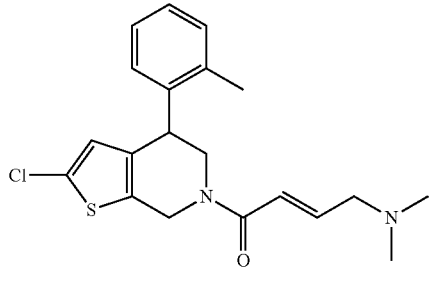 [SMILES: Cc1ccccc1C1CN(C(=O)/C=C/CN(C)C)Cc2sc(Cl)cc21]

(E)-1-(2-chloro-4-(o-tolyl)-4,7-dihydrothieno[2,3-c]pyridin-6(5H)-yl)-4-(dimethylamino)but-2-en-1-one At 0° C., (E)-4-bromo-1-(2-chloro-4-(o-tolyl)-4,7-dihydrothieno[2,3-c]pyridin-6(5H)-yl)but-2-en-1-one (10 m g, 0.024 mmol) was mixed with THF (1 mL), then 1 mL of 2 M dimethylamine in THF was added. After 30 min, the mixture was concentrated in vacuo to give the crude product, which was purified by preparative-TLC to give 6 mg of desired product. The product was used in the next reaction without further purification. MS (ES+): 374.8, 376.8 (M+H).

Example 11

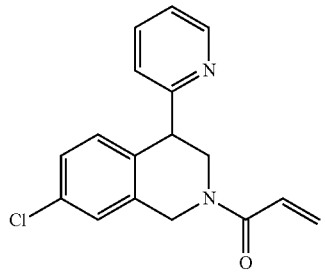 [SMILES: C=CC(=O)N1Cc2cc(Cl)ccc2C(c2ccccn2)C1]

1-(7-chloro-4-(pyridin-2-yl)-3,4-dihydroisoquinolin-2(1H)-yl)prop-2-en-1-one

Step A—Preparation of 2-(4-chlorophenyl)-2-(pyridin-2-yl)acetonitrile

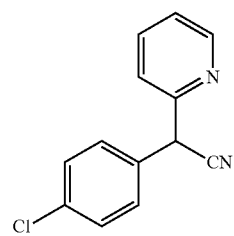 [SMILES: N#CC(c1ccc(Cl)cc1)c1ccccn1]

Potassium tert-butoxide (2.94 g, 26.2 mmol) was added in one portion to a solution of 2-(4-chlorophenyl)acetonitrile (3.97 g, 26.2 mmol) in DMSO (15 mL). Next, 2-Bromopyridine (1 mL, 10.5 mmol) was added and the vial sealed and heated in a 94° C. heat block for 16 hours. After cooling to room temperature, the reaction was poured into water. The pH of the solution was adjusted to pH=7 with the addition of 10% HCl aq. solution and was extracted with ethyl acetate. The combined organics were washed with water, brine, dried over sodium sulfate, filtered and concentrated. The crude product was purified via column chromatography with 4:1 hexanes/ethyl acetate as eluent to provide the title compound. MS (ES+): 229.1 (M+H).

Step B—Preparation of 2-(4-chlorophenyl)-2-(pyridin-2-yl)ethan-1-amine

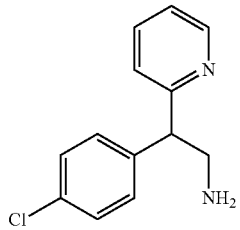 [SMILES: NCC(c1ccc(Cl)cc1)c1ccccn1]

Cobalt(II) chloride hexahydrate (2.62 g, 11.0 mmol) was added to a solution of 2-(4-chlorophenyl)-2-(pyridin-2-yl)acetonitrile (4.2 g, 18.4 mmol) in 2:1 THF/water (90 mL) in one portion. The resulting clear solution was cooled in an ice bath for 15 minutes before sodium borohydride (695 mg, 18.4 mmol) was added in one portion. After the initial vigorous reaction, the ice bath was removed and stirred at room temperature. After 20 minutes, an additional portion of sodium borohydride (695 mg, 18.4 mmol) was added and the reaction stirred 20 additional minutes until complete as judged by LC/MS analysis. The reaction was placed in an ice bath and quenched by careful addition of 10% HCl until pH<3. After stirring at room temperature 1 hr., the solution was washed 1× with ethyl acetate and the separated organic layer back extracted 1×10% HCl. The pH of the combined aqueous solutions was adjusted to pH>10 with the addition of solid sodium carbonate and extracted with dichloromethane. The combined dichloromethane extracts were washed with brine, dried over sodium sulfate, filtered, and concentrated to afford the intermediate amine titled above. MS (ES+): 232.9 (M+H).

Step C—Preparation of methyl (2-(4-chlorophenyl)-2-(pyridin-2-yl)ethyl)carbamate

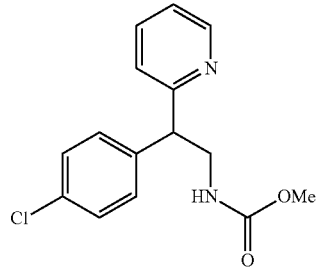 [SMILES: COC(=O)NCC(c1ccc(Cl)cc1)c1ccccn1]

The crude amine product from STEP B above was dissolved in 100 mL of dichloromethane and cooled in an ice bath for 10 minutes before DIPEA (6.4 mL, 36.7 mmol) was added followed by methyl chloroformate (1.4 mL, 18.1 mmol). After 15 min., the reaction was quenched by the addition of saturated $NaHCO_{3\ (aq)}$ and diluted with ethyl acetate. The layers were separated, and the aqueous layer extracted with ethyl acetate. The combined organic extracts were washed with saturated $NH_4Cl_{(aq)}$, brine, dried over sodium sulfate, filtered, and concentrated. The product was purified by filtering through a plug of silica gel with ethyl acetate to afford the titled compound.

Step D—Preparation of methyl 7-chloro-4-(pyridin-2-yl)-3,4-dihydroisoquinoline-2(1H)-carboxylate

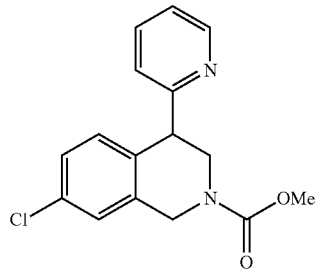 [SMILES: COC(=O)N1Cc2cc(Cl)ccc2C(c2ccccn2)C1]

A screw cap vial was charged with methyl (2-(4-chlorophenyl)-2-(pyridin-2-yl)ethyl)carbamate (300 mg, 1.03 mmol), paraformaldehyde (235 mg, 7.83 mmol), sulfuric acid (0.78 mL) and acetic acid (3.1 mL). The resulting solution was stirred over 48 h before being poured into ice water. The solution was neutralized with solid sodium carbonate and extracted with 2× ethyl acetate and 1× dichloromethane. The combined organic extracts were washed with brine, dried over sodium sulfate, filtered, and concentrated. The crude product was purified by column chromatography with 1:1 ethyl acetate/hexanes to 2:1 ethyl acetate/hexanes to afford the desired product methyl 7-chloro-4-(pyridin-2-yl)-3,4-dihydroisoquinoline-2(1H)-carboxylate. MS (ES+): 303.2 (M+H).

Step E—Preparation of 1-(7-Chloro-4-(pyridin-2-yl)-3,4-dihydroisoquinolin-2(1H)-yl)prop-2-en-1-one

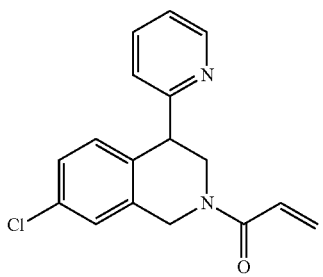 [SMILES: C=CC(=O)N1Cc2cc(Cl)ccc2C(c2ccccn2)C1]

Methyl 7-chloro-4-(pyridin-2-yl)-3,4-dihydroisoquinoline-2(1H)-carboxylate (208 mg, 0.69 mmol) was refluxed in 6 N $HCl_{(aq)}$ 5 mL for 14 hours. Concentrated HCl (2 mL) was added and the reaction refluxed 5 additional hours. The reaction was allowed to cool to room temperature, neutralized by the addition of solid sodium carbonate, and extracted 2× ethyl acetate and 1× dichloromethane. The combined organic extracts were washed with brine, dried over sodium sulfate, filtered, and concentrated. The crude product was taken up in dichloromethane (3 mL) and cooled in an ice bath. DIPEA (0.30 mL, 1.7 mmol) and acryloyl chloride (0.060 mL, 0.74 mmol) were added and the reaction was stirred 30 minutes before being quenched with sat. NaHCO₃ (aq) solution and extracted with ethyl acetate. The combined organic extracts were washed with brine, dried over sodium sulfate, filtered, and concentrated. The crude product was purified twice by PTLC with 5% methanol in ethyl acetate as the eluent followed by 5% methanol in dichloromethane as the eluent for the second purification to afford the titled product 1-(7-Chloro-4-(pyridin-2-yl)-3,4-dihydroisoquinolin-2(1H)-yl)prop-2-en-1-one. MS (ES+): 298.9 (M+H).

Example 12

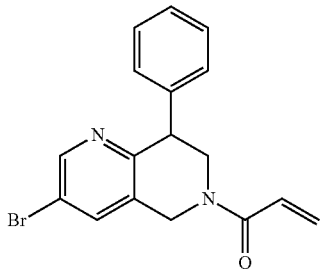

1-(3-bromo-8-phenyl-7,8-dihydro-1,6-naphthyridin-6(5H)-yl)prop-2-en-1-one

Step A—Preparation of 5-Bromo-2-(cyano(phenyl)methyl)nicotinonitrile

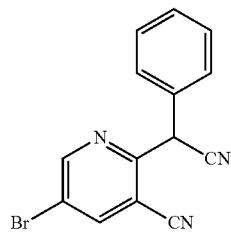 [SMILES: N#Cc1cc(Br)cnc1C(C#N)c1ccccc1]

A screw cap vial was charged with 5-bromo-2-chloronicotinonitrile (0.5 g, 2.30 mmol), 2-phenylacetonitrile (0.650 mL, 5.63 mmol), and cesium carbonate (1.5 g, 4.60 mmol). MeCN was added (10 mL) and the vial was sealed and heated in a heat block set at 60° C. overnight. After cooling to room temperature, the reaction was poured into water and neutralized with 10% HCl₍aq₎ to a pH of 7 and extracted repeatedly with ethyl acetate. The combined organic extracts were washed with brine, dried over sodium sulfate, filtered, and concentrated. The crude product was purified by silica gel chromatography with a 0-25% gradient of ethyl acetate/hexanes. The product was further recrystallized with ethyl acetate and hexanes to afford the title product was a white crystalline product. MS (ES+): 297.9, 299.9 (M+H).

Step B—Preparation of 3-Bromo-8-phenyl-5,6,7,8-tetrahydro-1,6-naphthyridine

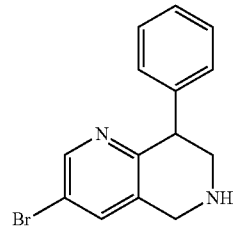 [SMILES: Brc1cnc2c(c1)CNCC2c1ccccc1]

To a solution of 5-bromo-2-(cyano(phenyl)methyl)nicotinonitrile (0.200 g, 0.67 mmol) in THF (3.4 mL) cooled to 0° C. in an ice bath was added diisobutylaluminium hydride as a 1.0 M solution in THF (2.7 mL, 2.7 mmol). The reaction was allowed to warm to room temperature and stirred. An additional portion of diisobutylaluminium hydride solution was added (2.0 mL, 2.0 mmol) and the reaction was stirred. The reaction was quenched by the addition of a saturated aqueous solution of Rochelle salt. Solid NaOH was added to adjust the pH to >11 followed by dilution with ethyl acetate and the biphasic mixture was stirred until two clear solutions were observed. The layers were separated, and the aqueous layer extracted 3× ethyl acetate. The combined organic extracts were washed with brine, dried over sodium sulfate, filtered, and concentrated. The crude product was used directly for the next reaction. MS (ES+): 301.9, 303.8 (M+H).

Step C—Preparation of 1-(3-bromo-8-phenyl-7,8-dihydro-1,6-naphthyridin-6(5H)-yl)prop-2-en-1-one The crude product from STEP B above was taken up in dichloromethane (3 mL) and cooled to 0° C. DIPEA (0.250 mL, 1.44 mmol) followed by acryloyl chloride (0.053 ml, 6.7 mmol) were added and the solution stirred 30 minutes before being quenched with sat. NaHCO₃ (aq) solution and extracted with ethyl acetate. The combined organic extracts were washed with brine, dried over sodium sulfate, filtered, and concentrated. The crude product was purified by PTLC with a 2:1 ethyl acetate/Hexanes mixture as eluent. The product was then further purified by PTLC with 20:1 dichloromethane/methanol as eluent to afford the title product 1-(3-bromo-8-phenyl-7,8-dihydro-1,6-naphthyridin-6(5H)-yl)prop-2-en-1-one. MS (ES+): 342.7, 344.7 (M+H).

Example 13

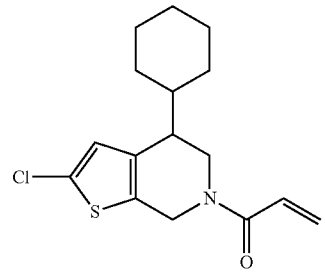 [SMILES: C=CC(=O)N1Cc2sc(Cl)cc2C(C2CCCCC2)C1]

1-(2-chloro-4-cyclohexyl-4,7-dihydrothieno[2,3-c]
pyridin-6(5H)-yl)prop-2-en-1-one Step A—Preparation of
2-cyclohexyl-2-(thiophen-3-yl)acetonitrile

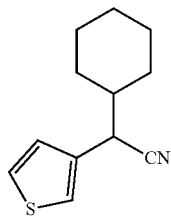 [SMILES: N#CC(c1ccsc1)C1CCCCC1]

A solution of 3-thiopheneacetonitrile (1 mL, 9.4 mmol) in THF (40 mL) was cooled for 15 minutes in a −78° C. acetone/dry ice bath before a 1 M solution of NaHMDS in THF (9.4 mL, 9.4 mmol) was slowly added. The resulting solution was stirred 45 minutes before iodocyclohexane (1.5 mL, 11.6 mmol) was added to the dark orange solution. The reaction was stirred 10 minutes before allowing to warm to 0° C. After 1 hr. at this temperature the reaction was quenched with saturated aqueous ammonium chloride and diluted with water and ethyl acetate. The layers were separated, and the aqueous layer extracted 3× ethyl acetate. The combined organic extracts were washed with brine, dried over sodium sulfate, filtered, and concentrated. The crude product was purified by silica gel chromatography using 0-15% ethyl acetate in hexanes gradient to afford the titled product 2-cyclohexyl-2-(thiophen-3-yl)acetonitrile.

Step B—Preparation of
2-cyclohexyl-2-(thiophen-3-yl)ethan-1-amine

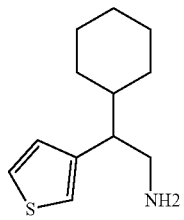 [SMILES: NCC(c1ccsc1)C1CCCCC1]

A 1 M solution of borane in THF (12 mL, 12 mmol) was added to a solution of 2-cyclohexyl-2-(thiophen-3-yl)acetonitrile (1.23 g, 6 mmol) in THF (30 mL) under argon atmosphere. The reaction was heated to 55° C. overnight before allowing to cool to room temperature. The reaction was placed in an ice bath for 10 minutes before 1 M KOH aqueous solution was slowly added. The mixture was stirred 15 minutes and then extracted with ethyl acetate. The combined organic layers were extracted with 10% aqueous HCl. The combined HCl aqueous extracts was adjusted to pH>10 with 1 N KOH aqueous solution and extracted with ethyl acetate. The combined organic extracts were washed with brine, dried over sodium sulfate, filtered, and concentrated to afford the desired product which was used without further purification. MS (ES+): 210.1 (M+H).

Step C—Preparation of 4-cyclohexyl-4,5,6,7-tetra-
hydrothieno[2,3-c]pyridine

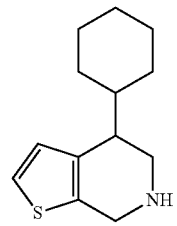 [SMILES: c1cc2c(s1)CNCC2C1CCCCC1]

A mixture of 2-cyclohexyl-2-(thiophen-3-yl)ethan-1-amine (0.170 g, 0.83 mmol), 37% aqueous formaldehyde (0.528 mL, 7.1 mmol) acetic acid (0.3 mL) and conc. HCl (5 uL) were heated to 80° C. for 15 minutes. The solution was allowed to cool to room temperature before pouring into aqueous sodium carbonate solution and was extracted with ethyl acetate. The combined organic extracts were washed with brine, dried over sodium sulfate, filtered, and concentrated to afford the desired product which was used without further purification. MS (ES+): 221.9 (M+H).

Step D—Preparation of 1-(4-cyclohexyl-4,7-dihy-
drothieno[2,3-c]pyridin-6(5H)-yl)prop-2-en-1-one

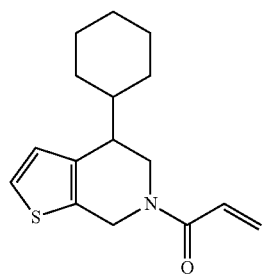 [SMILES: C=CC(=O)N1Cc2sccc2C(C2CCCCC2)C1]

The crude product from the previous reaction was taken up in dichloromethane (3 mL) and cooled to 0° C. DIPEA (0.300 mL, 1.73 mmol) followed by acryloyl chloride (0.080 ml, 1.01 mmol) were added and the solution stirred 30 minutes before being quenched with sat. NaHCO$_3$ $_{(aq)}$ solution and extracted with ethyl acetate. The combined organic extracts were washed with brine, dried over sodium sulfate, filtered, and concentrated. The crude product was purified by silica gel chromatography using a gradient of 0-40% ethyl acetate in hexanes to afford the desired product 1-(4-cyclohexyl-4,7-dihydrothieno[2,3-c]pyridin-6(5H)-yl)prop-2-en-1-one. MS (ES+): 275.9 (M+H).

Step E—Preparation of 1-(2-chloro-4-cyclohexyl-4,
7-dihydrothieno[2,3-c]pyridin-6(5H)-yl)prop-2-en-1-
one A solution of 1-(4-cyclohexyl-4,7-dihydrothieno[2,3-c] pyridin-6(5H)-yl)prop-2-en-1-one (26 mg, 0.094 mmol) and N-chlorosuccinimide (15 mg, 0.113 mmol) in DMF was heated in a 55° C. heat block for 15 minutes. After cooling to room temperature, the reaction was poured into water and extracted with ethyl acetate. The combined organic extracts were washed with brine, dried over sodium sulfate, filtered, and concentrated. The crude product was purified by PTLC with a 2.5:1 hexanes/ethyl acetate mixture as eluent to afford 1-(2-chloro-4-cyclohexyl-4,7-dihydrothieno[2,3-c]pyridin-6(5H)-yl)prop-2-en-1-one. MS (ES+): 309.9 (M+H).

Example 14

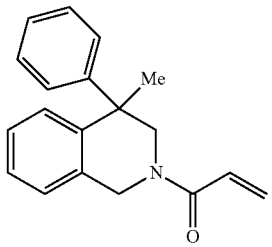 [SMILES: C=CC(=O)N1Cc2ccccc2C(C)(c2ccccc2)C1]

1-(4-methyl-4-phenyl-3,4-dihydroisoquinolin-2(1H)-yl)prop-2-en-1-one

Step A—Preparation of 2,2-diphenylpropanenitrile

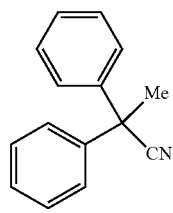 [SMILES: CC(C#N)(c1ccccc1)c1ccccc1]

A solution of diphenylacetonitrile (2 g, 10.4 mmol) in THF (50 mL) was cooled in an ice bath for 15 minutes. Next, 1 M solution of NaHMDS in THF (12.5 mL, 12.5 mmol) was added and the solution stirred 30 minutes before methyl iodide (0.777 mL, 12.5 mmol) was added and the solution was stirred overnight while coming to room temperature. The reaction was partitioned between ethyl acetate and water. The aqueous solution was extracted with ethyl acetate. The combined organic extracts were washed with saturated aqueous ammonium chloride solution, brine, dried over sodium sulfate, filtered, and concentrated. The crude product was purified by silica gel chromatography using an eluent of 1:20 ethyl acetate in hexane to afford the desired product 2,2-diphenylpropanenitrile.

Step B—Preparation of 2,2-diphenylpropan-1-amine

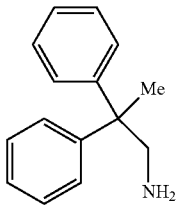 [SMILES: CC(CN)(c1ccccc1)c1ccccc1]

A 1 M solution of borane in THF (9.7 mL, 9.7 mmol) was added to a solution of 2,2-diphenylpropanenitrile (1.0 g, 4.82 mmol) in THF (24 mL) under argon atmosphere. The reaction was heated to 55° C. overnight before allowing to cool to room temperature. The reaction was placed in an ice bath for 10 minutes before 10% sodium carbonate aqueous solution was slowly added. The mixture was stirred 15 minutes and then extracted with ethyl acetate. The combined organic extracts were washed with brine, dried over sodium sulfate, filtered, and concentrated to afford the desired product which was used without further purification. MS (ES+): 212.1 (M+H).

Step C—Preparation of N-(2,2-diphenylpropyl)-2,2,2-trifluoroacetamide

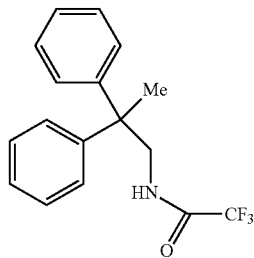 [SMILES: CC(CNC(=O)C(F)(F)F)(c1ccccc1)c1ccccc1]

A solution of 2,2-diphenylpropan-1-amine (1.0 g, 4.82 mmol) as described above in dichloromethane (25 mL) was cooled to 0° C. Triethylamine (1.34 mL, 9.61 mmol) followed by trifluoroacetic anhydride (0.884 mL, 6.27 mmol) were added and the solution stirred 30 minutes at room temperature before being quenched with sat. NaHCO$_3$ $_{(aq)}$ solution and extracted with ethyl acetate. The combined organic extracts were washed with saturated ammonium chloride aqueous solution, brine, dried over sodium sulfate, filtered, and concentrated. The product was purified by silica gel chromatography with 20:1 hexanes/ethyl acetate as eluent to afford N-(2,2-diphenylpropyl)-2,2,2-trifluoroacetamide. MS (ES+): 307.9 (M+H).

Step D—Preparation of 2,2,2-trifluoro-1-(4-methyl-4-phenyl-3,4-dihydroisoquinolin-2(1H)-yl)ethan-1-one

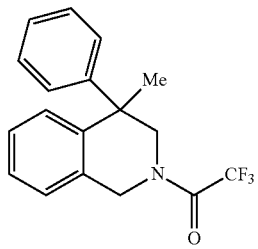 [SMILES: CC1(c2ccccc2)CN(C(=O)C(F)(F)F)Cc2ccccc21]

Paraformaldehyde (86 mg, 2.9 mmol) was added portion wise to a solution of N-(2,2-diphenylpropyl)-2,2,2-trifluoroacetamide (590 mg, 1.92 mmol) in a 4:1 mixture of AcOH and H$_2$SO$_4$ (7.5 mL). The solution was stirred at room temperature until complete as judged by LC/MS analysis. The reaction was poured into ice water and extracted with ethyl acetate. The combined organic extracts were washed with brine, dried over sodium sulfate, filtered, and concentrated. The crude product was purified by column chromatography to afford the desired product 2,2,2-trifluoro-1-(4-methyl-4-phenyl-3,4-dihydroisoquinolin-2(1H)-yl)ethan-1-one. MS (ES+): 319.9 (M+H).

Step E—Preparation of 4-methyl-4-phenyl-1,2,3,4-tetrahydroisoquinoline

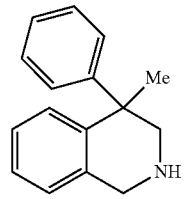 [SMILES: CC1(c2ccccc2)CNCc2ccccc21]

Potassium hydroxide (0.215 g, 3.8 mmol) was added to a solution of 2,2,2-trifluoro-1-(4-methyl-4-phenyl-3,4-dihydroisoquinolin-2(1H)-yl)ethan-1-one (0.340 g, 1.1 mmol) in methanol (7.5 mL) and water (1.5 mL) and the resulting solution stirred for 2 d. The methanol was removed in vacuo and the pH of the solution adjusted to pH<2 with 10% HCl aq solution. The aqueous solution was washed 1×MTBE and the organic layer was back extracted 1×10% aq HCl. The pH of the combined aqueous extracts was adjusted to pH of >11 with solid NaOH and extracted with dichloromethane. The combined organic extracts were washed with brine, dried over sodium sulfate, filtered, and concentrated to give 4-methyl-4-phenyl-1,2,3,4-tetrahydroisoquinoline. MS (ES+): 224.2 (M+H).

Step F—Preparation of 1-(4-methyl-4-phenyl-3,4-dihydroisoquinolin-2(1H)-yl)prop-2-en-1-one

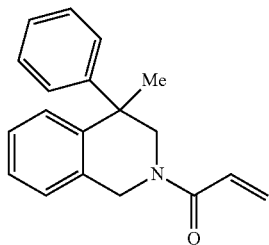 [SMILES: C=CC(=O)N1Cc2ccccc2C(C)(c2ccccc2)C1]

To a solution of 4-methyl-4-phenyl-1,2,3,4-tetrahydroisoquinoline (202 mg, 0.90 mmol) in dichloromethane (4 mL) cooled in an ice bath was added DIPEA (0.30 mL, 1.7 mmol) and acryloyl chloride (0.060 mL, 0.74 mmol) and the reaction was stirred 30 minutes before being quenched with sat. NaHCO$_3$ $_{(aq)}$ solution and extracted with ethyl acetate. The combined organic extracts were washed with brine, dried over sodium sulfate, filtered, and concentrated. The crude product was purified by PTLC with 1.5/1 hexanes in ethyl acetate as the eluent to give the titled compound 1-(4-methyl-4-phenyl-3,4-dihydroisoquinolin-2(1H)-yl)prop-2-en-1-one. MS (ES+): 277.9 (M+H).

Example 15

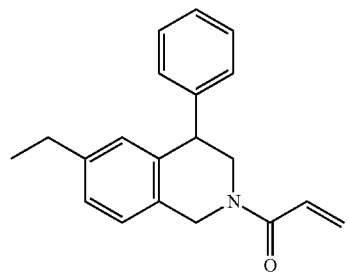 [SMILES: C=CC(=O)N1Cc2ccc(CC)cc2C(c2ccccc2)C1]

1-(6-ethyl-4-phenyl-3,4-dihydroisoquinolin-2(1H)-yl)prop-2-en-1-one

Step A—Preparation of benzyl 6-bromo-4-phenyl-3,4-dihydroisoquinoline-2(1H)-carboxylate

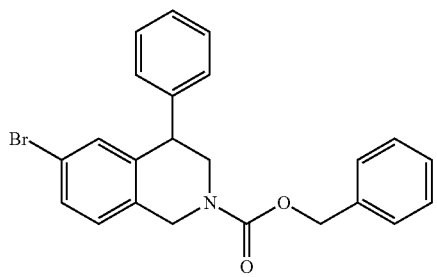 [SMILES: O=C(OCc1ccccc1)N1Cc2ccc(Br)cc2C(c2ccccc2)C1]

To a solution of 6-Bromo-4-phenyl-1,2,3,4-tetrahydroisoquinoline (7.5 g, 26.0 mmol), prepared according to methods described by Chennamanenia, N. K.; Arifb, J.; Frederick, S. B.; Gelb, M. H. *Bioorganic & Medicinal Chemistry Letters* 19 (2009) pp. 6582-6584 starting from 2-amino-1-phenylethan-1-ol and 4-bromobenzaldehyde, in dichloromethane (120 mL) was added triethylamine (7.25 mL, 52.0 mmol) and the solution was cooled in an ice bath for 15 minutes. CBz-Cl (3.67 mL, 26.0 mmol) was added slowly and the solution was stirred at 0° C. for 1 hr. before saturated aqueous sodium bicarbonate was added. The reaction was diluted with water and ethyl acetate and the layers were separated. The aqueous layer was extracted with ethyl acetate and the combined organic extracts were washed with brine, dried over sodium sulfate, filtered, and concentrated. The crude product was purified by column chromatography to afford benzyl 6-bromo-4-phenyl-3,4-dihydroisoquinoline-2(1H)-carboxylate. MS (ES+): 422.0, 423.9 (M+H).

Step B—Preparation of benzyl 6-ethyl-4-phenyl-3,4-dihydroisoquinoline-2(1H)-carboxylate

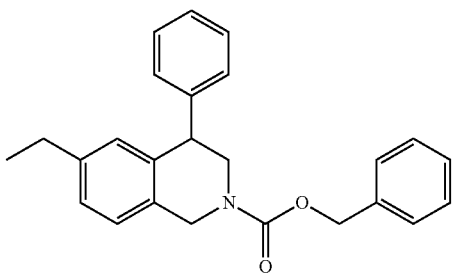 [SMILES: CCc1ccc2c(c1)C(c1ccccc1)CN(C(=O)OCc1ccccc1)C2]

Ethylmagnesium bromide, 3 M solution in THF (0.474 mL, 1.42 mmol) was added to zinc chloride, 1.9 M solution in 2-MeTHF (1.25 mL, 2.38 mmol) and the solution was stirred 30 minutes at room temperature. In a separate vial, benzyl 6-bromo-4-phenyl-3,4-dihydroisoquinoline-2(1H)-carboxylate (0.200 mg, 0.47 mmol) and (1,1'-Bis(diphenylphosphino)ferrocene)palladium(II) dichloride (17 mg, 0.023 mmol) were charged and the vial was evacuated and flushed with argon two times. THF was added and the vial was again evacuated and flushed with argon two times. Next, the ethyl zinc chloride solution prepared above was added and the vial was heated in a 90° C. heat block overnight. The reaction was allowed to cool to room temperature and partitioned between water and ethyl acetate and separated. The organic layer was washed with 10% aq HCl and the pH of the combined aqueous layers was adjusted to pH=7 with sodium carbonate. The aqueous layer was extracted with ethyl acetate. The combined organic extracts were washed with brine, dried over sodium sulfate, filtered, and concentrated. The crude product was purified by column chromatography to afford benzyl 6-ethyl-4-phenyl-3,4-dihydroisoquinoline-2(1H)-carboxylate.

Step C—Preparation of 6-ethyl-4-phenyl-1,2,3,4-tetrahydroisoquinoline

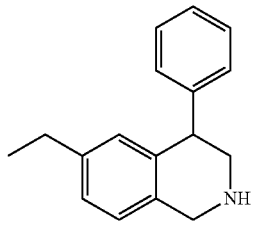 [SMILES: CCc1ccc2c(c1)C(c1ccccc1)CNC2]

Palladium hydroxide (4 mg, 0.03 mmol) was added to a solution of benzyl 6-ethyl-4-phenyl-3,4-dihydroisoquinoline-2(1H)-carboxylate (110 mg, 0.30 mmol) in 1:1 ethanol/ethyl acetate (1.5 mL). The reaction flask was evacuated and flushed with argon three times and then evacuated and flushed with a balloon of hydrogen gas. The reaction was stirred under a balloon of hydrogen until complete by LC/MS and then purged with argon. The reaction was filtered through a celite pad with ethyl acetate and concentrated to afford the desired product 6-ethyl-4-phenyl-1,2,3,4-tetrahydroisoquinoline. MS (ES+): 238.1 (M+H).

Step D—Preparation of 1-(6-ethyl-4-phenyl-3,4-dihydroisoquinolin-2(1H)-yl)prop-2-en-1-one The crude material from the previous reaction was taken up in dichloromethane (2 mL) and cooled in an ice bath. DIPEA (0.15 mL, 0.85 mmol) followed by acryloyl chloride (0.030 mL, 0.36 mmol) was added and the reaction was stirred 30 minutes before being quenched with sat. NaHCO₃ (aq) solution and extracted with ethyl acetate. The combined organic extracts were washed with brine, dried over sodium sulfate, filtered, and concentrated. The crude product was purified by PTLC to give the titled compound 1-(6-ethyl-4-phenyl-3,4-dihydroisoquinolin-2(1H)-yl)prop-2-en-1-one. MS (ES+): 291.9 (M+H).

Example 16

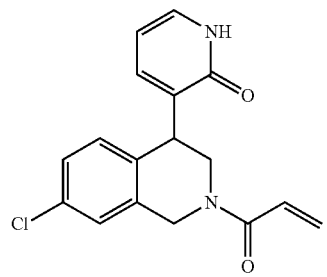 [SMILES: C=CC(=O)N1Cc2cc(Cl)ccc2C(c2ccc[nH]c2=O)C1]

3-(2-acryloyl-7-chloro-1,2,3,4-tetrahydroisoquinolin-4-yl)pyridin-2(1H)-one

Step A—Preparation of 2-(4-chlorophenyl)-2-(2-methoxypyridin-3-yl)acetonitrile

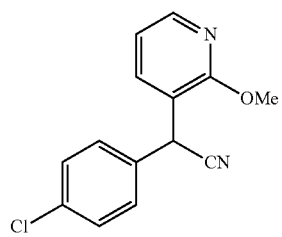 [SMILES: COc1ncccc1C(C#N)c1ccc(Cl)cc1]

A screw cap 20 ml vial with a pressure relief cap was charged with 2-(4-chlorophenyl)acetonitrile (1 g, 6.60 mmol), 3-bromo-2-methoxypyridine (0.829 g, 4.41 mmol), sodium tert-butoxide (1.26 g, 13.1 mmol), palladium(II) acetate (49 mg, 0.22 mmol), and Xantphos (153 mg, 0.264 mmol). The vial was evacuated and flushed with argon three times. Dioxane (10 mL) was added and the vial was again evacuated and flushed with argon three times and then placed in a heat block preheated to 96° C. and stirred overnight. The reaction was allowed to cool to room temperature and poured into water. The pH of the solution was adjusted to pH=7 with 10% HCl and extracted with ethyl acetate. The combined organic extracts were washed with brine, dried over sodium sulfate, filtered, and concentrated. The crude product was purified by silica gel column chromatography with 0-25% ethyl acetate/hexanes as the gradient to afford the title compound. MS (ES+): 258.8 (M+H).

Step B—Preparation of 2-(4-chlorophenyl)-2-(2-methoxypyridin-3-yl)ethan-1-amine

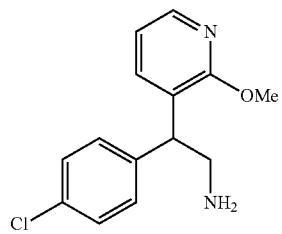 [SMILES: COc1ncccc1C(CN)c1ccc(Cl)cc1]

Cobalt (II) chloride hexahydrate (1.27 g, 5.3 mmol) was added to a solution of 2-(4-chlorophenyl)-2-(2-methoxypyridin-3-yl)acetonitrile (4.2 g, 8.9 mmol) in 2:1 THF/water (60 mL) in one portion. The resulting clear solution was cooled in an ice bath for 15 minutes before sodium borohydride (832 mg, 22.0 mmol) was added in one portion. After the initial vigorous reaction, the ice bath was removed and stirred at room temperature. After 20 minutes, an additional portion of sodium borohydride (832 mg, 22.0 mmol) was added and the reaction stirred 30 additional minutes until complete as judged by LC/MS analysis. The reaction was placed in an ice bath and quenched by careful addition of 10% HCl until pH<3. After stirring at room temperature 1 hr., the solution was washed 1× with ethyl acetate and the separated organic layer back extracted 1×10% HCl. The pH of the combined aqueous solutions was adjusted to pH>10 with the addition of solid sodium carbonate and extracted with ethyl acetate. The combined ethyl acetate extracts were washed with brine, dried over sodium sulfate, filtered, and concentrated to afford the title compound. MS (ES+): 262.8 (M+H).

Step C—Preparation of methyl (2-(4-chlorophenyl)-2-(2-methoxypyridin-3-yl)ethyl)carbamate

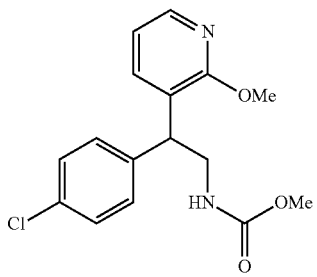 [SMILES: COC(=O)NCC(c1ccc(Cl)cc1)c1cccnc1OC]

The product from the previous step was taken up in dichloromethane (40 mL) and cooled in an ice bath for 10 minutes before DIPEA (3.8 mL, 21.8 mmol) was added followed by methyl chloroformate (1.4 mL, 8.80 mmol). After 15 min., the reaction was quenched by the addition of saturated NaHCO$_{3(aq)}$ and diluted with ethyl acetate. The layers were separated, and the aqueous layer extracted with ethyl acetate. The combined organic extracts were washed with saturated NH$_4$Cl$_{(aq)}$, brine, dried over sodium sulfate, filtered, and concentrated. The crude product was purified by silica gel column chromatography with 0-40% ethyl acetate/hexanes as the gradient to afford the title compound. MS (ES+): 320.9 (M+H).

Step D—Preparation of methyl 7-chloro-4-(2-methoxypyridin-3-yl)-3,4-dihydroisoquinoline-2(1H)-carboxylate

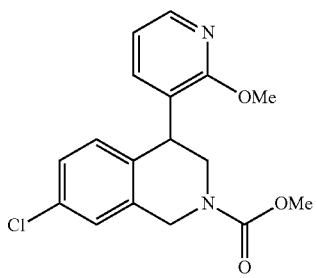 [SMILES: COC(=O)N1Cc2cc(Cl)ccc2C(c2cccnc2OC)C1]

Paraformaldehyde (84 mg, 2.8 mmol) was added portion wise to a solution of methyl (2-(4-chlorophenyl)-2-(2-methoxypyridin-3-yl)ethyl)carbamate (893 mg, 2.78 mmol) in a 4:1 mixture of AcOH and H$_2$SO$_4$ (10 mL). The solution was stirred at room temperature overnight and then heated in a 55° C. heat block for 1 hr. until complete as judged by LC/MS analysis. The reaction was poured into ice water, neutralized to a pH=7 with solid sodium carbonate, and extracted with ethyl acetate. The combined organic extracts were washed with brine, dried over sodium sulfate, filtered, and concentrated. The crude product was purified by column chromatography to afford the desired product methyl 7-chloro-4-(2-methoxypyridin-3-yl)-3,4-dihydroisoquinoline-2(1H)-carboxylate. MS (ES+): 332.9 (M+H).

Step E—Preparation of 3-(2-acryloyl-7-chloro-1,2,3,4-tetrahydroisoquinolin-4-yl)pyridin-2(1H)-one Methyl 7-chloro-4-(2-methoxypyridin-3-yl)-3,4-dihydroisoquinoline-2(1H)-carboxylate (0.20 g, 0.6 mmol) was refluxed in 48% aq. HBr (4 mL) overnight. The reaction was concentrated and dichloromethane (4 mL) and DIPEA (0.630 mL, 3.6 mmol) were added. The resulting solution was cooled in an ice bath for 10 minutes before acryloyl chloride (0.050 mL, 0.63 mmol) was added. The reaction was stirred 30 minutes before being quenched with sat. NaHCO$_3$ $_{(aq)}$ solution and extracted with ethyl acetate. The combined organic extracts were washed with brine, dried over sodium sulfate, filtered, and concentrated. The crude product was purified by PTLC with 5% methanol in ethyl acetate as the eluent to afford the titled product 3-(2-acryloyl-7-chloro-1,2,3,4-tetrahydroisoquinolin-4-yl)pyridin-2(1H)-one. MS (ES+): 314.8 (M+H).

Example 17

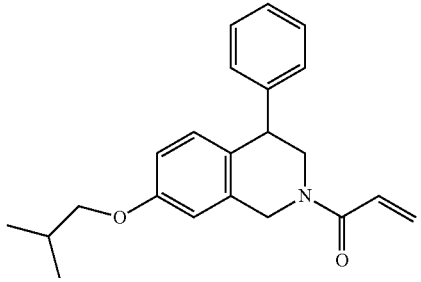 [SMILES: C=CC(=O)N1Cc2cc(OCC(C)C)ccc2C(c2ccccc2)C1]

1-(7-isobutoxy-4-phenyl-3,4-dihydroisoquinolin-2(1H)-yl)prop-2-en-1-one

Step A—Preparation of 2-((4-methoxybenzyl)amino)-1-phenylethan-1-ol

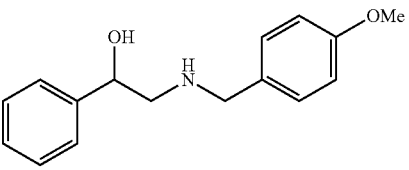 [SMILES: COc1ccc(CNCC(O)c2ccccc2)cc1]

A mixture of 2-amino-1-phenylethan-1-ol (4.5 g, 32.8 mmol), p-anisaldehyde (4.4 mL, 36.2 mmol), and triethylamine (5.0 mL, 3.59 mmol) was stirred in methanol (125 mL) for 14 hours. The solution was cooled in an ice water bath and sodium borohydride (2.5 g, 6.61 mmol) was added and the reaction was stirred 3.5 hours while warming to room temperature. Saturated aqueous sodium bicarbonate was added and the reaction was diluted with water and ethyl acetate and the layers were separated. The aqueous layer was extracted with ethyl acetate and the combined organic extracts were washed with brine, dried over sodium sulfate, filtered, and concentrated. The crude product was purified by column chromatography using 1:1 hexanes/ethyl acetate to 20% methanol in ethyl acetate as eluent to afford 2-((4-methoxybenzyl)amino)-1-phenylethan-1-ol. MS (ES+): 258.0 (M+H).

Step B—Preparation of 7-methoxy-4-phenyl-1,2,3,4-tetrahydroisoquinoline

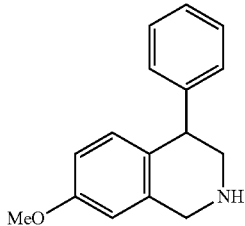 [SMILES: COc1ccc2c(c1)CNCC2c1ccccc1]

A solution of 2-((4-methoxybenzyl)amino)-1-phenylethan-1-ol (3.0 g, 11.7 mmol) in dichloromethane (78 mL) was slowly added via an addition funnel to a slurry of aluminum trichloride (4.7 g, 35.0 mmol) in dichloromethane (78 mL) at room temperature. After 3 hours stirring an additional portion of aluminum trichloride (1.0 g, 7.5 mmol) was added and reaction was stirred. The reaction was poured into ice water and stirred, the pH of the aqueous layer was adjusted to pH>10 with 1 N NaOH. Solid Rochelle's salt was added, and the biphasic mixture was stirred until two clear layers were present. The layers were separated, and the aqueous layer was extracted with dichloromethane and the combined organic extracts were washed with brine, dried over magnesium sulfate, filtered, and concentrated to afford 7-methoxy-4-phenyl-1,2,3,4-tetrahydroisoquinoline which was used directly in the next reaction.

Step C—Preparation of 4-phenyl-1,2,3,4-tetrahydroisoquinolin-7-ol

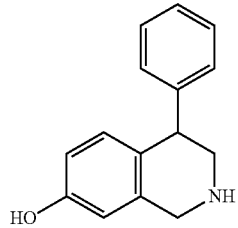

Boron tribromide (1.67 mL, 1.67 mmol) as a 1 M solution in dichloromethane was added to a solution of 7-methoxy-4-phenyl-1,2,3,4-tetrahydroisoquinoline (200 mg, 0.836 mmol) in dichloromethane (3 mL) cooled in an ice bath. The reaction was stirred for 2 hrs. before being quenched with ice water. The pH of the aqueous layer was adjusted to pH=7 with solid sodium carbonate and separated. The aqueous layer was extracted with dichloromethane and the combined organic extracts were washed with brine, dried over magnesium sulfate, filtered, and concentrated to afford 4-phenyl-1,2,3,4-tetrahydroisoquinolin-7-ol. MS (ES+): 226.0 (M+H).

Step D—Preparation of tert-butyl 7-hydroxy-4-phenyl-3,4-dihydroisoquinoline-2(1H)-carboxylate

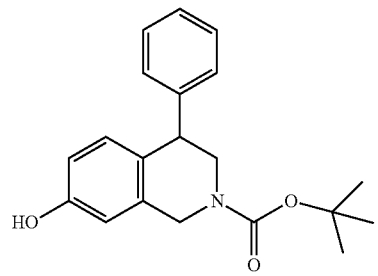 [SMILES: CC(C)(C)OC(=O)N1Cc2cc(O)ccc2C(c2ccccc2)C1]

Boc-anhydride (3.1 g, 14.2 mmol) was added to a solution of 4-phenyl-1,2,3,4-tetrahydroisoquinolin-7-ol (3.2 g, 14.2 mmol) in methanol (100 mL) with triethylamine (2.0 mL, 14.32 mmol) at room temperature and the solution was stirred 2 hours. Saturated aqueous ammonium chloride was added and the methanol was removed in vacuo. Ethyl acetate and water were added and the layers were separated. The aqueous layer was extracted with ethyl acetate and the combined organic extracts were washed with brine, dried over sodium sulfate, filtered, and concentrated. The crude product was purified by column chromatography using 4:1 hexanes/ethyl acetate to afford tert-butyl 7-hydroxy-4-phenyl-3,4-dihydroisoquinoline-2(1H)-carboxylate as a white crystalline solid.

Step E—Preparation of tert-butyl 7-isobutoxy-4-phenyl-3,4-dihydroisoquinoline-2(1H)-carboxylate

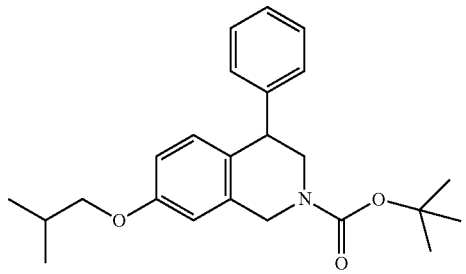 [SMILES: CC(C)COc1ccc2c(c1)CN(C(=O)OC(C)(C)C)CC2c1ccccc1]

A mixture of tert-butyl 7-hydroxy-4-phenyl-3,4-dihydroisoquinoline-2(1H)-carboxylate (100 mg, 0.31 mmol), 1-iodo-2-methylpropane (0.088 mL, 0.77 mmol), and cesium carbonate (300 mg, 0.92 mmol) was stirred at room temperature in MeCN (2 mL) and then heated overnight in a 60° C. heat block. The reaction was allowed to cool to room temperature, filtered, and concentrated. The crude residue was partitioned between ethyl acetate and water. The layers were separated and the aqueous layer was extracted with ethyl acetate and the combined organic extracts were washed with brine, dried over sodium sulfate, filtered, and concentrated. The crude product was purified by silica gel column chromatography using 4:1 hexanes/ethyl acetate to afford tert-butyl 7-isobutoxy-4-phenyl-3,4-dihydroisoquinoline-2(1H)-carboxylate. MS (ES+): 404.0 (M+Na).

Step F—Preparation of tert-butyl 7-isobutoxy-4-phenyl-1,2,3,4-tetrahydroisoquinoline

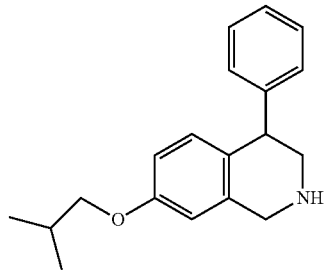 [SMILES: CC(C)COc1ccc2c(c1)CNCC2c1ccccc1]

tert-Butyl 7-isobutoxy-4-phenyl-3,4-dihydroisoquinoline-2(1H)-carboxylate (70 mg, 0.18 mmol) was stirred in a 2:1 mixture of dichloromethane and TFA (3 mL) until the reaction was complete as judged by LC/MS. The reaction mixture was concentrated to afford the intermediate product 7-isobutoxy-4-phenyl-1,2,3,4-tetrahydroisoquinoline as the TFA salt which was used directly in the next reaction. MS (ES+): 282.0 (M+H).

Step G—Preparation of 1-(7-isobutoxy-4-phenyl-3,4-dihydroisoquinolin-2(1H)-yl)prop-2-en-1-one The crude product from the previous step was dissolved in dichloromethane (2 mL) and the solution was cooled in an ice water bath. Acryloyl chloride (0.015 mL, 0.19 mmol) and diisopropylethylamine (0.070 mL, 0.40 mol) were added and the reaction was stirred 30 minutes before being quenched with sat. NaHCO$_3$ $_{(aq)}$ solution and extracted with ethyl acetate. The combined organic extracts were washed with brine, dried over sodium sulfate, filtered, and concentrated. The crude product was purified by PTLC with 2:1 hexanes in ethyl acetate as the eluent to afford the titled product 1-(7-isobutoxy-4-phenyl-3,4-dihydroisoquinolin-2(1H)-yl)prop-2-en-1-one. MS (ES+): 336.0 (M+H).

Example 18

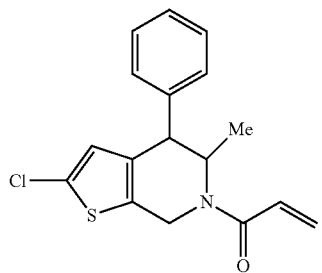 [SMILES: C=CC(=O)N1Cc2sc(Cl)cc2C(c2ccccc2)C1C]

1-(2-chloro-5-methyl-4-phenyl-4,7-dihydrothieno[2,3-c]pyridin-6(5H)-yl)prop-2-en-1-one 1-(2-chloro-5-methyl-4-phenyl-4,7-dihydrothieno[2,3-c]pyridin-6(5H)-yl)prop-2-en-1-one was prepared as a single diastereomer according to the general procedure for the preparation of 1-(2-chloro-4-(o-tolyl)-4,7-dihydrothieno[2,3-c]pyridin-6(5H)-yl)prop-2-en-1-one as described in EXAMPLE 2 starting from racemic 2-amino-1-phenylpropan-1-ol. MS (ES+): 318.0 (M+H).

Example 19

When incubating such compounds with the activating enzymes (E1) of ubiquitin, SUMO, Nedd8, Urm1, ISG15 or Atg7, it forms covalent adducts with the specific Cys residue as depicted below. For the compounds provided herein including embodiments thereof, a covalent adduct may be formed with a cysteine amino acid corresponding to a Cys residue highlighted and in bold from Uba1, Uba2, Uba3, Uba4, Uba7 or Atg7 as shown in the sequence alignment below.

```
Uba1 (ubiquitin)
                                      (SEQ ID NO: 1)
LVGAGAIGCELLK Uba2 (SUMO)
                                      (SEQ ID NO: 2)
VVGAGGIGCELLK Uba3 (Nedd8)
                                      (SEQ ID NO: 3)
VIGAGGIGCELLK Uba4 (Urm1)
                                      (SEQ ID NO: 4)
IVGCGGLGCPLAQ Uba7 (ISG15)
                                      (SEQ ID NO: 5)
LVGAGAIGCELLK Atg7 (Atg8, Atg12)
                                      (SEQ ID NO: 6)
LLGAGTLGCNVAR
```

Compounds are evaluated for their inhibitory effect on activating enzymes (E1) of ubiquitin, SUMO, Nedd8, Urm1, ISG15 or Atg7 using previously reported methods and protocols. One example is in: Allosteric inhibition of ubiquitin-like modifications by a class of inhibitor of SUMO-activating enzyme. Cell Chemical Biology, 26, 1-11, 2019. PMID: 28051857. The results are provided in Table 2.

Compounds are tested in the following manner. The compound and SUMO E1 are incubated for a predetermined amount of time. UBC9, SUMO1, and ATP are added to the E1-compound mixture and incubated at 37° C. The reaction is quenched with Laemmli Buffer. The UBC9-SUMO1 conjugation is analyzed via SDS gel electrophoresis. The percent inhibition is measured by the intensity of the UBC9-SUMO1 band compared to the no compound control. Activities are listed as compound concentration (uM), preincubation time of E1 with compound (min), and percent inhibition of adduct formation (%). Activities are listed as compound concentration (uM), preincubation time of E1 with compound (min), and percent inhibition of adduct formation (%).

TABLE 2
Compounds and Biological Activity.
| # | Structure | SUMO E1 | Atg7 |
|---|---|---|---|
| 1 | 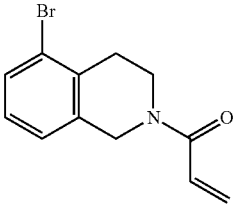 | 25 uM 55 min 50% | 25uM 60 min <1% |
| 2 | 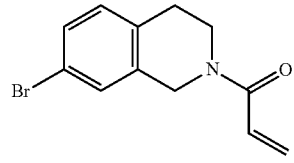 | 25 uM 55 min 50% | 25 uM 60 min <1% |
| 3 | 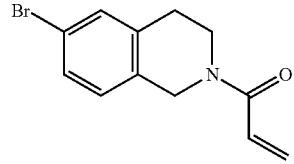 | 25 uM 60 min 70% | 25 uM 60 min <1% |
| 4 | 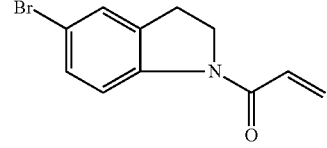 | 25 uM 30 min 10% | 25 uM 60 min <1% |
| 5 | 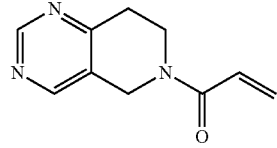 | 25 uM 30 min 10% | 25 uM 60 min <1% |
| 6 | 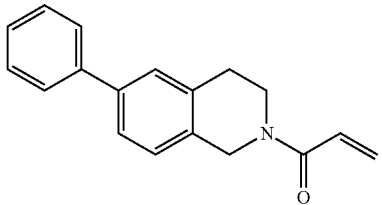 [SMILES: C=CC(=O)N1CCc2cc(-c3ccccc3)ccc2C1] | 25 uM 30 min <1% | 25 uM 60 min <1% |
| 7 | 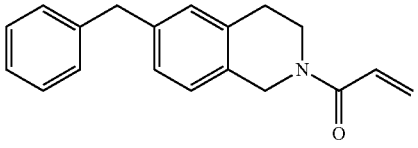 [SMILES: C=CC(=O)N1CCc2cc(Cc3ccccc3)ccc2C1] | 25 uM 30 min 20% | 25 uM 60 min <1% |
| 8 | 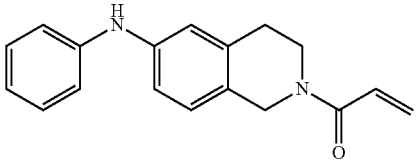 [SMILES: C=CC(=O)N1CCc2cc(Nc3ccccc3)ccc2C1] | 25 uM 60 min <1% | 25 uM 60 mimn <1% |

TABLE 2-continued

Compounds and Biological Activity.

| # | Structure | SUMO E1 | Atg7 |
|---|---|---|---|
| 9 | 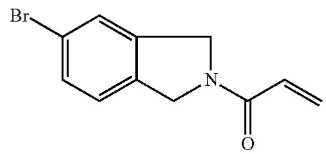 | 25 uM 60 min <1% | 25 uM 60 min <1% |
| 10 | 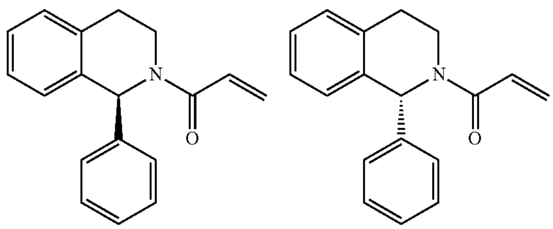 | 25 uM 60 min <1% | 25 uM 60 min <1% |
| 11 | 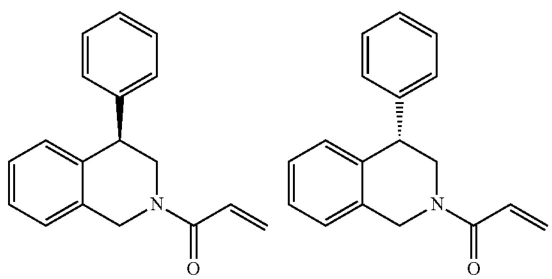 | 10uM 60 min 90% | 25 uM 60 min <1% |
| 12 | 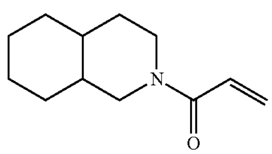 | 25 uM 60 min <1% | 25 uM 60 min <1% |
| 13 | 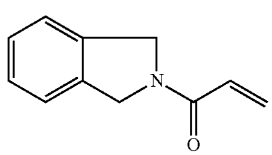 | 25 uM 60 min <1% | 25 uM 60 min <1% |
| 14 | 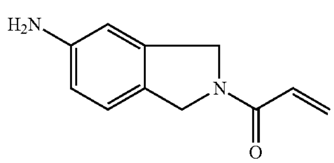 | 25 uM 60 min <1% | 25 uM 60 min <1% |
| 15 | 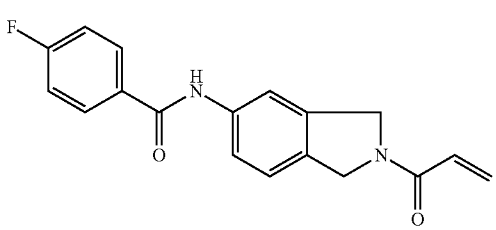 [SMILES: C=CC(=O)N1Cc2ccc(NC(=O)c3ccc(F)cc3)cc2C1] | 25 uM 60 min <1% | 25 uM 60 min <1% |

TABLE 2-continued

Compounds and Biological Activity.

| # | Structure | SUMO E1 | Atg7 |
|---|---|---|---|
| 16 | 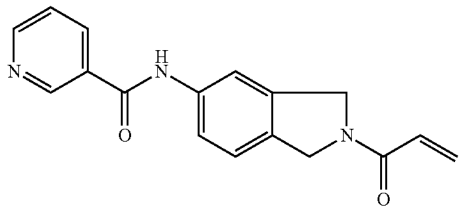 [SMILES: C=CC(=O)N1Cc2ccc(NC(=O)c3cccnc3)cc2C1] | 25 uM 60 min 20% | 25 uM 60 min <1% |
| 17 | 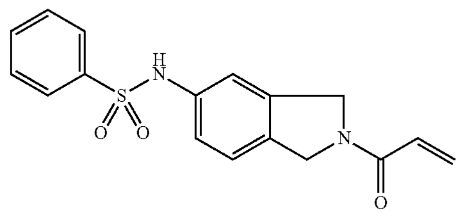 [SMILES: C=CC(=O)N1Cc2ccc(NS(=O)(=O)c3ccccc3)cc2C1] | 25 uM 60 min 20% | 25 uM 60 min <1% |
| 18 | 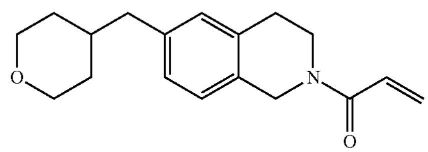 [SMILES: C=CC(=O)N1CCc2cc(CC3CCOCC3)ccc2C1] | 25 uM 60 min <1% | 25 uM 60 min 95% |
| 19 | 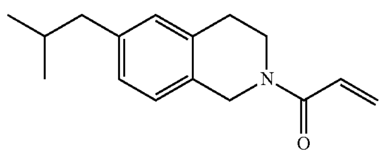 [SMILES: C=CC(=O)N1CCc2cc(CC(C)C)ccc2C1] | 25 uM 60 min 40% | 25 uM 60 min <1% |
| 20 | 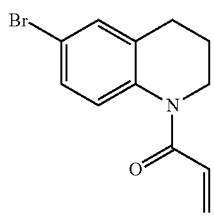 | 25 uM 60 min <1% | 25 uM 60 min <1% |
| 21 | 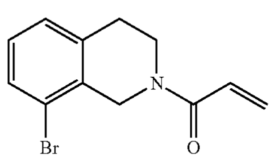 | 25 uM 60 min <1% | 25 uM 60 min <1% |
| 22 | 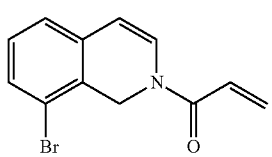 | 25 uM 60 min 95% | 25 uM 60 min <1% |
| 23 | 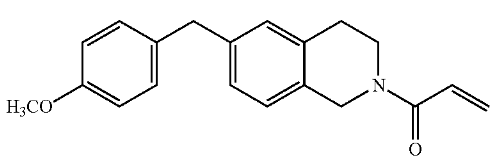 [SMILES: C=CC(=O)N1CCc2cc(Cc3ccc(OC)cc3)ccc2C1] | 25 uM 60 min <1% | 25 uM 60 min <1% |

TABLE 2-continued

Compounds and Biological Activity.

| # | Structure | SUMO E1 | Atg7 |
|---|---|---|---|
| 24 | 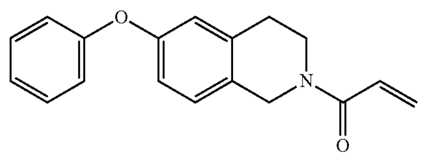 [SMILES: C=CC(=O)N1CCc2cc(Oc3ccccc3)ccc2C1] | 25 uM 60 min 50% | 25 uM 60 min <1% |
| 25 | 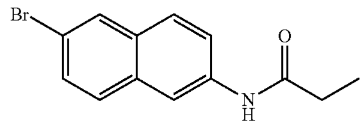 [SMILES: CCC(=O)Nc1ccc2cc(Br)ccc2c1] | 25 uM 60 min <1% | 25 uM 60 min <1% |
| 26 | 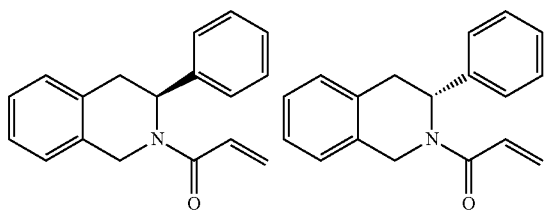 | 25 uM 60 min 10% | 25 uM 60 min <1% |
| 27 | 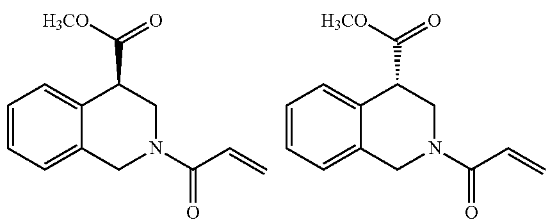 | 25 uM 60 min <1% | 25 uM 60 min <1% |
| 28 | 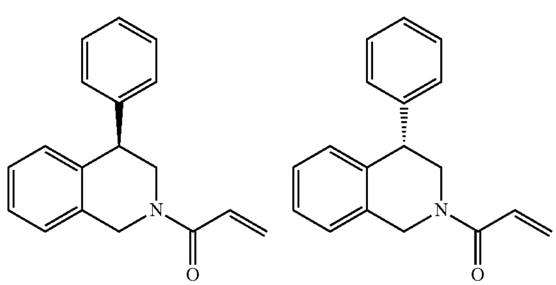 | 25 uM 60 min <1% | 25 uM 60 min <1% |
| 29 | 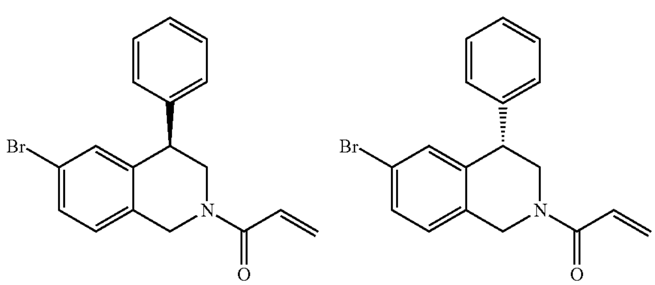 [SMILES: C=CC(=O)N1Cc2ccc(Br)cc2[C@@H](c2ccccc2)C1 ; C=CC(=O)N1Cc2ccc(Br)cc2[C@H](c2ccccc2)C1] | 25 uM 60 min 90% | 25 uM 60 min <1% |
| 30 | 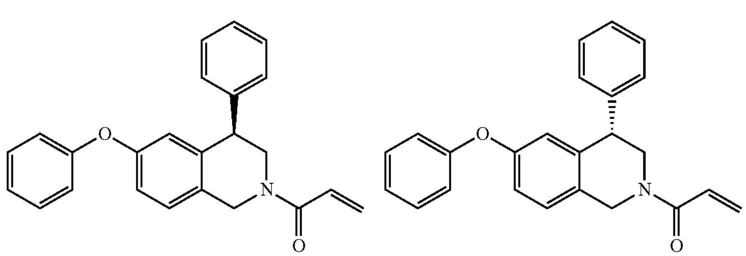 | 25 uM 60 min <1% | 25 uM 60 min <1% |

TABLE 2-continued

Compounds and Biological Activity.

| # | Structure | SUMO E1 | Atg7 |
|---|---|---|---|
| 31 | 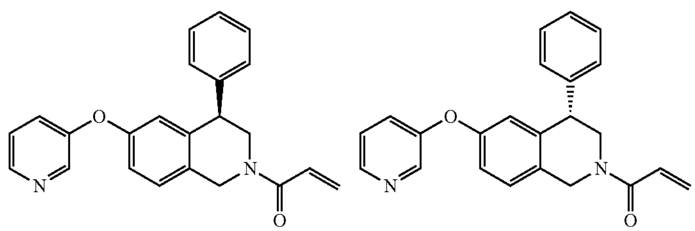 | 25 uM 60 min <1% | 25 uM 60 min <1% |
| 32 | 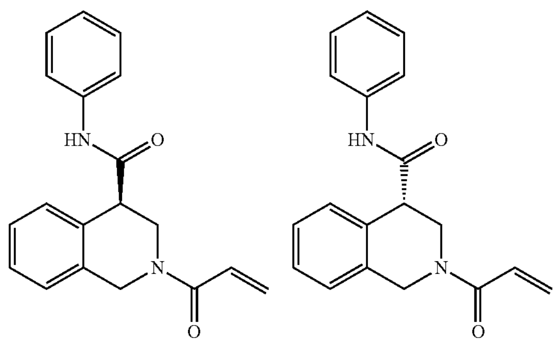 | 25 uM 60 min <1% | 25 uM 60 min <1% |
| 33 | 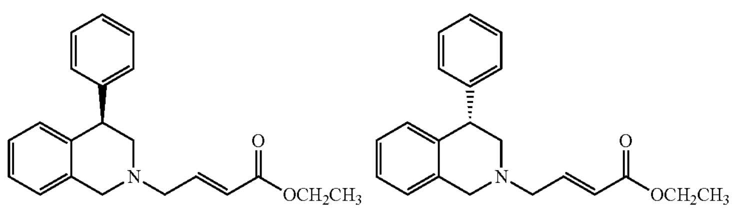 [SMILES: CCOC(=O)/C=C/CN1Cc2ccccc2[C@@H](c2ccccc2)C1 ; CCOC(=O)/C=C/CN1Cc2ccccc2[C@H](c2ccccc2)C1] | 25 uM 60 min <1% | No entry |
| 34 | 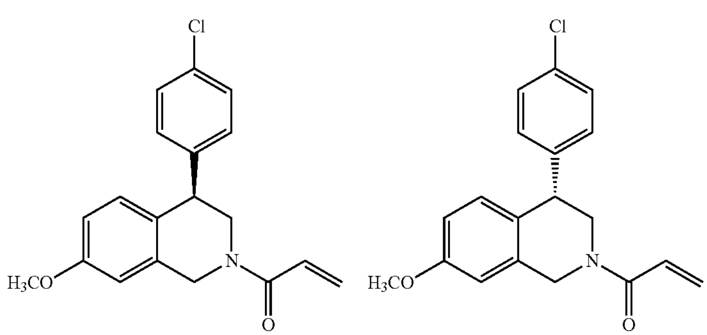 [SMILES: C=CC(=O)N1Cc2cc(OC)ccc2[C@@H](c2ccc(Cl)cc2)C1 ; C=CC(=O)N1Cc2cc(OC)ccc2[C@H](c2ccc(Cl)cc2)C1] | 25 uM 60 min <1% | 25 uM 60 min <1% |
| 35 | 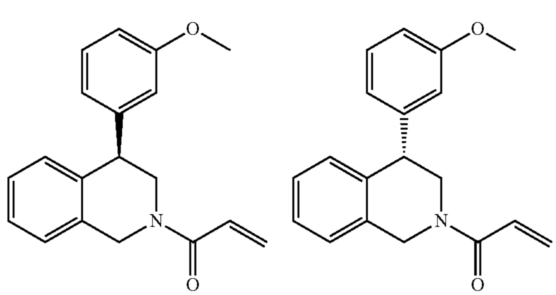 | 25 uM 60 min <1% | 25 uM 60 min <1% |

TABLE 2-continued

Compounds and Biological Activity.

| # | Structure | SUMO E1 | Atg7 |
|---|---|---|---|
| 36 | | 25 uM 60 min 40% | 25 uM 60 min <1% |
| 37 | | 25 uM 60 min 40% | 25 uM 60 min <1% |
| 38 | | 25 uM 60 min <1% | 25 uM 60 min <1% |
| 39 | | 25 uM 60 min <1% | 25 uM 60 min <1% |
| 40 | | 25 uM 60 min <1% | 25 uM 60 min <1% |

TABLE 2-continued

Compounds and Biological Activity.

| # | Structure | SUMO E1 | Atg7 |
|---|---|---|---|
| 41 | | 25 uM 60 min <1% | 25 uM 60 min <1% |
| 42 | | 25 uM 60 min <1% | 25 uM 60 min <1% |
| 43 | | 25 uM 60 min <1% | 25 uM 60 min <1% |
| 44 | | 18 uM 30 min 50% | No entry |
| 45 | | 25 uM 60 min <1% | 25 uM 60 min <1% |

TABLE 2-continued

Compounds and Biological Activity.

| # | Structure | SUMO E1 | Atg7 |
|---|---|---|---|
| 46 | | 9 uM<br>30 min<br>50% | 25 uM<br>60 min<br><1% |
| 47 | | 25 uM<br>60 min<br><1% | 25 uM<br>60 min<br><1% |
| 48 | | 25 uM<br>60 min<br>30% | 25 uM<br>60 min<br><1% |
| 49 | | 25 uM<br>60 min<br><1% | 25 uM<br>60 min<br><1% |
| 50 | | 10 uM<br>60 min<br>50% | No entry |

TABLE 2-continued

Compounds and Biological Activity.

| # | Structure | SUMO E1 | Atg7 |
|---|-----------|---------|------|
| 51 | | 25 uM 60 min 50% | 25 uM 60 min <1% |
| 52 | | 25 uM 60 min 50% | 25 uM 60 min <1% |
| 53 | 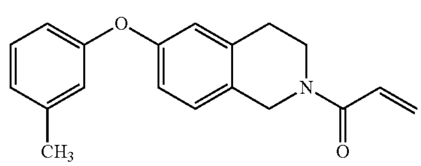 [SMILES: C=CC(=O)N1CCc2cc(Oc3cccc(C)c3)ccc2C1] | 25 uM 60 min <1% | 25 uM 60 min <1% |
| 54 | 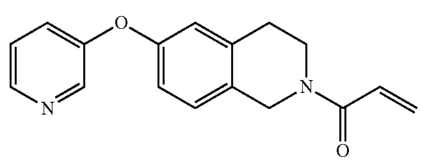 [SMILES: C=CC(=O)N1CCc2cc(Oc3cccnc3)ccc2C1] | 25 uM 60 min 10% | 25 uM 60 min <1% |
| 55 | | 25 uM 60 min 50% | 25 uM 60 min <1% |
| 56 | | 25 uM 60 min <1% | 25 uM 60 min <1% |

TABLE 2-continued
Compounds and Biological Activity.
| # | Structure | SUMO E1 | Atg7 |
|---|-----------|---------|------|
| 57 | 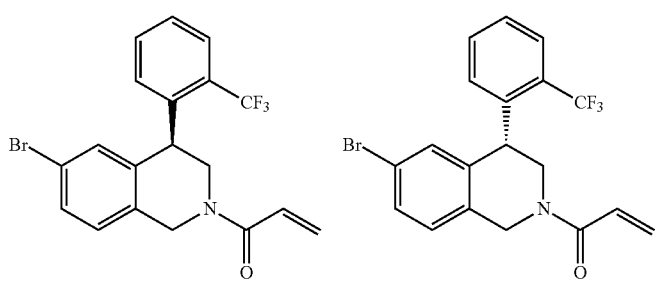 [SMILES: C=CC(=O)N1Cc2ccc(Br)cc2[C@@H](c2ccccc2C(F)(F)F)C1 ; C=CC(=O)N1Cc2ccc(Br)cc2[C@H](c2ccccc2C(F)(F)F)C1] | 25 uM 60 min 90% | 25 uM 60 min <1% |
| 58 | 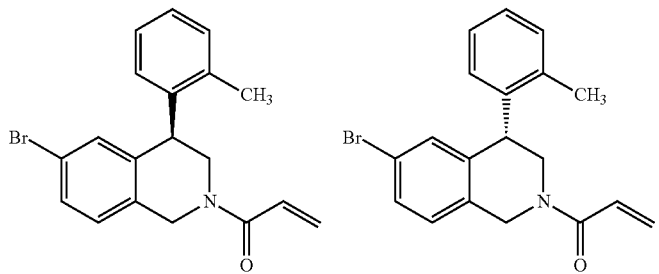 [SMILES: C=CC(=O)N1Cc2ccc(Br)cc2[C@@H](c2ccccc2C)C1 ; C=CC(=O)N1Cc2ccc(Br)cc2[C@H](c2ccccc2C)C1] | 25 uM 60 min 95% | 25 uM 60 min <1% |
| 59 | 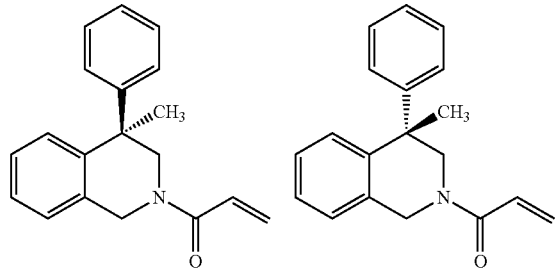 | 25 uM 60 min 40% | 25 uM 60 min <1% |
| 60 | 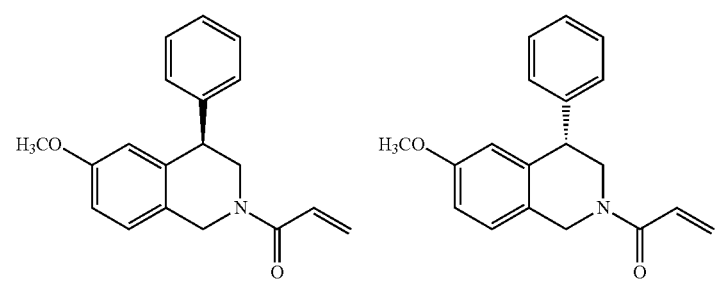 [SMILES: C=CC(=O)N1Cc2ccc(OC)cc2[C@@H](c2ccccc2)C1 ; C=CC(=O)N1Cc2ccc(OC)cc2[C@H](c2ccccc2)C1] | 25 uM 60 min 40% | 25 uM 60 min <1% |
| 61 | 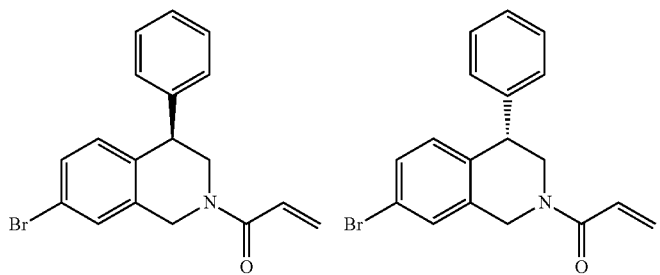 | 10 uM 60 min 100% | 25 uM 60 min <1% |

TABLE 2-continued

Compounds and Biological Activity.

| # | Structure | SUMO E1 | Atg7 |
|---|---|---|---|
| 62 | | 25 uM 60 min 5% | 25 uM 60 min <1% |
| 63 | | 10 uM 60 min 50% | 25 uM 60 min <1% |
| 64 | | 10 uM 60 min 100% | 25 uM 60 min <1% |
| 65 | | 25 uM 60 min 10% | 25 uM 60 min <1% |
| 66 | | 25 uM 60 min <1% | 25 uM 60 min <1% |

TABLE 2-continued

Compounds and Biological Activity.

| # | Structure | SUMO E1 | Atg7 |
|---|---|---|---|
| 67 | | 25 uM 60 min <1% | 25 uM 60 min <1% |
| 68 | | 10 uM 60 min 100% | 25 uM 60 min <1% |
| 69 | | 10 uM 60 min 60% | 25 uM 60 min <1% |
| 70 | | 10 uM 60 min 60% | 25 uM 60 min <1% |
| 71 | | 25 uM 60 min 20% | 25 uM 60 min <1% |

TABLE 2-continued

Compounds and Biological Activity.

| # | Structure | SUMO E1 | Atg7 |
|---|---|---|---|
| 72 | 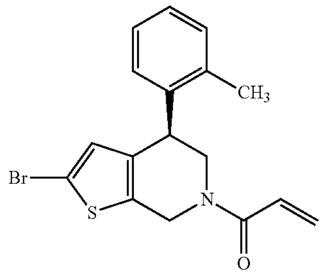 | 10 uM 60 min 100% | 25 uM 60 min <1% |
| 73 | 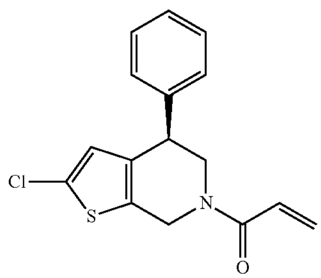 | 10 uM 60 min 100% | 25 uM 60 min <1% |
| 74 | 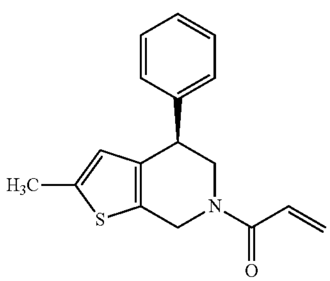 | 25 uM 60 min 10% | 25 uM 60 min <1% |
| 75 | 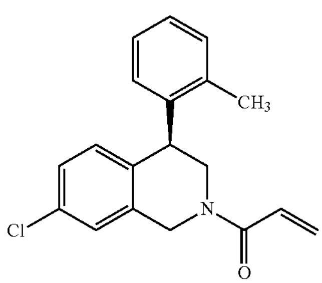 | 10 uM 60 min 100% | 25 uM 60 min <1% |
| 76 | 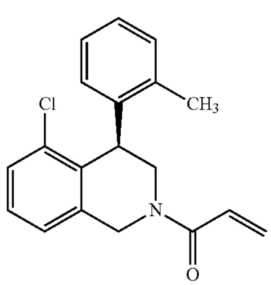 | 25 uM 60 min <1% | 25 uM 60 min <1% |

TABLE 2-continued

Compounds and Biological Activity.

| # | Structure | SUMO E1 | Atg7 |
|---|---|---|---|
| 77 | | 25 uM 60 min 20% | 25 uM 60 min 30% |
| 78 | | 25 uM 60 min <1% | 25 uM 60 min <1% |
| 79 | | 25 uM 60 min <1% | 25 uM 60 min <1% |
| 80 | | 25 uM 30 min 50% | 25 uM 60 min <1% |
| 81 | | 10 uM 30 min 30% | 25 uM 60 min <1% |

TABLE 2-continued

Compounds and Biological Activity.

| # | Structure | SUMO E1 | Atg7 |
|---|---|---|---|
| 82 | | 10 uM 30 min 10% | 25 uM 60 min <1% |
| 83 | | 10 uM 30 min <1% | 25 uM 60 min <1% |
| 84 | | 2.5 uM 30 min 90% | 25 uM 60 min <1% |
| 85 | | 10 uM 30 min 100% | 25 uM 60 min <1% |
| 86 | | 10 uM 30 min <1% | 25 uM 60 min <1% |

TABLE 2-continued

Compounds and Biological Activity.

| # | Structure | SUMO E1 | Atg7 |
|---|---|---|---|
| 87 | | 9 uM<br>30 min<br><1% | 25 uM<br>60 min<br><1% |
| 88 | | 9 uM<br>30 min<br><1% | 25 uM<br>60 min<br><1% |
| 89 | | 9 uM<br>30 min<br>95% | 25 uM<br>60 min<br><1% |
| 90 | | 25 uM<br>60 min<br><1% | 25 uM<br>60 min<br><1% |
| 91 | | 9 uM<br>30 min<br><1% | 25 uM<br>60 min<br><1% |

TABLE 2-continued

Compounds and Biological Activity.

| # | Structure | SUMO E1 | Atg7 |
|---|---|---|---|
| 92 | 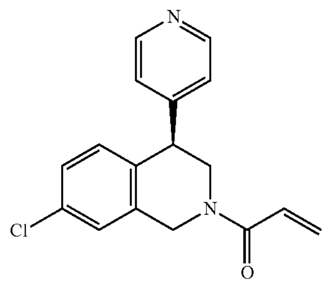 | 20 uM 60 min 10% | 25 uM 60 min <1% |
| 93 | 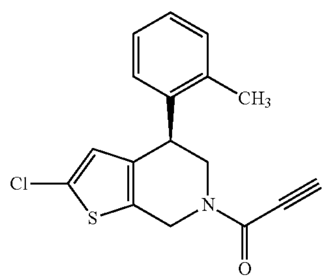 | 9 uM 30 min 95% | 25 uM 60 min 100% |
| 94 | 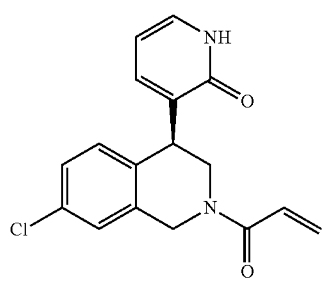 | 9 uM 30 min <1% | 25 uM 60 min <1% |
| 95 | 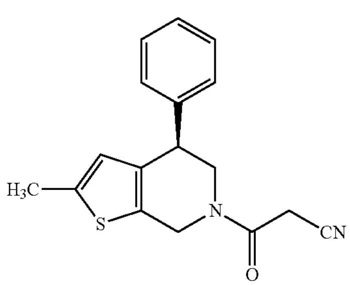 | 9 uM 30 min <1% | 25 uM 60 min <1% |
| 96 | 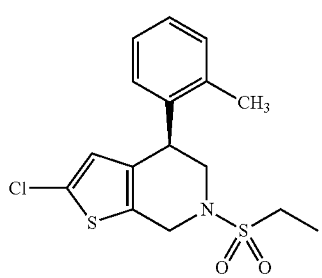 | 9 uM 30 min <1% | 25 uM 60 min 90% |

TABLE 2-continued

Compounds and Biological Activity.

| # | Structure | SUMO E1 | Atg7 |
|---|---|---|---|
| 97 | 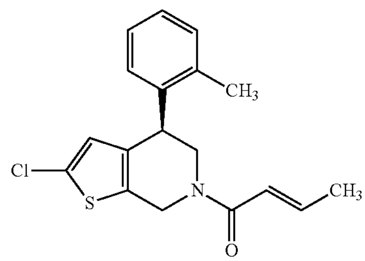 | 9 uM 30 min <1% | 25 uM 60 min <1% |
| 98 | 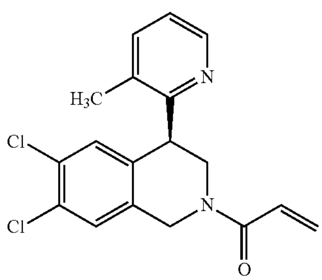 | 9 uM 30 min <1% | 25 uM 60 min <1% |
| 99 | 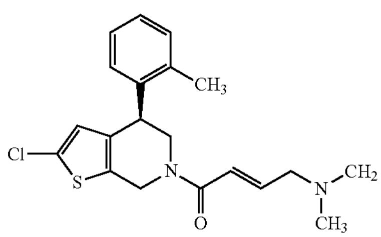 | 9 uM 20 min <1% | 25 uM 60 min <1% |
| 100 | 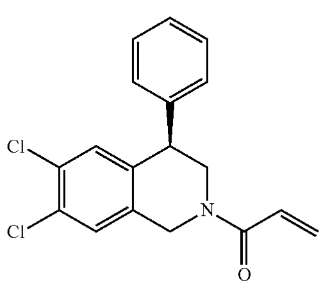 | 3 uM 15 min 30% | 25 uM 60 min <1% |
| 101 | 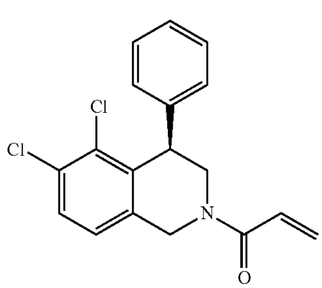 | 3 uM 15 min 30% | 25 uM 60 min <1% |

TABLE 2-continued

Compounds and Biological Activity.

| # | Structure | SUMO E1 | Atg7 |
|---|---|---|---|
| 102 | | 9 uM<br>30 min<br>40% | 25 uM<br>60 min<br><1% |
| 103 | | 27 uM<br>30 min<br><1% | 25 uM<br>60 min<br><1% |
| 104 | | 25 uM<br>30 min<br><1% | 25 uM<br>60 min<br><1% |
| 105 | | 27 uM<br>30 min<br><1% | 25 uM<br>60 min<br><1% |

TABLE 2-continued

Compounds and Biological Activity.

| # | Structure | SUMO E1 | Atg7 |
|---|---|---|---|
| 106 | 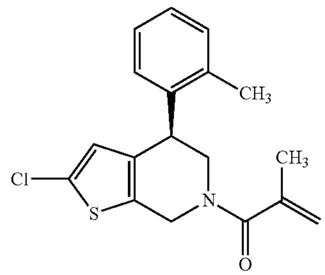 | 27 uM 30 min <1% | 25 uM 60 min <1% |
| 107 | 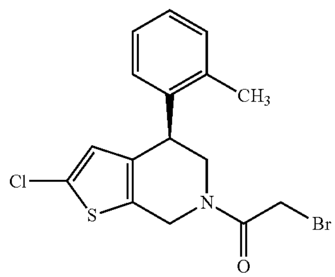 | 9 uM 30 min 100% | 25 uM 60 min 100% |
| 108 | 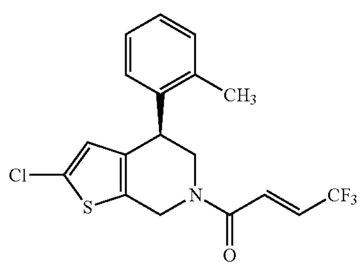 | 1 uM 30 min 100% | 25 uM 60 min <1% |
| 109 | 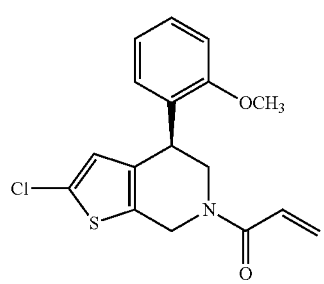 | 27 uM 30 min 30% | 25 uM 60 min 80% |
| 110 | 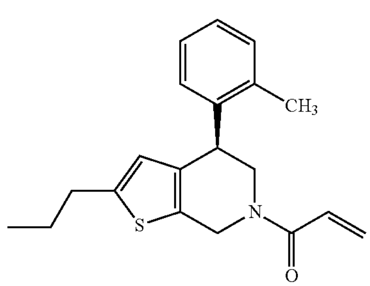 | 27 uM 30 min 30% | 25 uM 60 min 80% |

TABLE 2-continued

Compounds and Biological Activity.

| # | Structure | SUMO E1 | Atg7 |
|---|---|---|---|
| 111 | | 27 uM 30 min 80% | 25 uM 60 min <1% |
| 112 | | 27 uM 30 min 95% | 25 uM 60 min <1% |
| | | | |
| 113 | | 1 uM 30 min 95% | 25 uM 60 min <1% |
| 114 | | 1 uM 30 min 100% | 25 uM 60 min <1% |

TABLE 2-continued

Compounds and Biological Activity.

| # | Structure | SUMO E1 | Atg7 |
|---|-----------|---------|------|
| 115 | 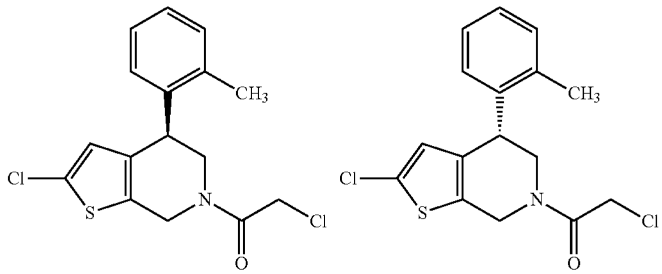 | 27 uM 30 min 80% | 25 uM 60 min 100% |
| 116 | 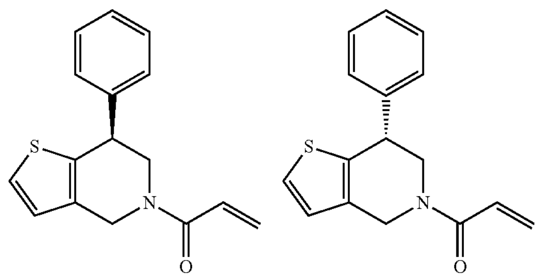 | 27 uM 30 min <1% | 25 uM 60 min <1% |
| 117 | 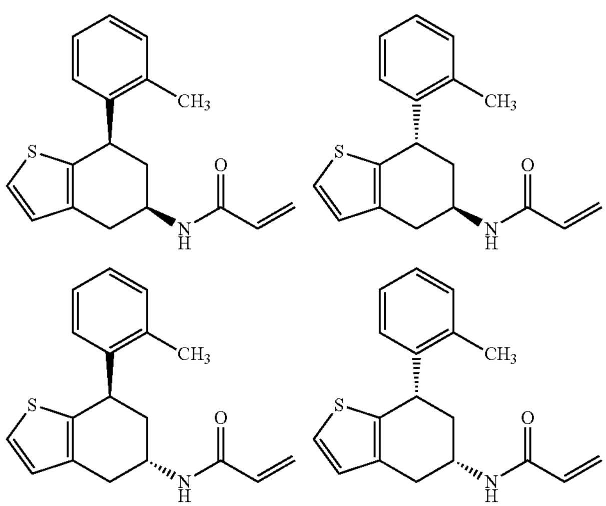 | 27 uM 30 min <1% | 25 uM 60 min <1% |
| 118 | 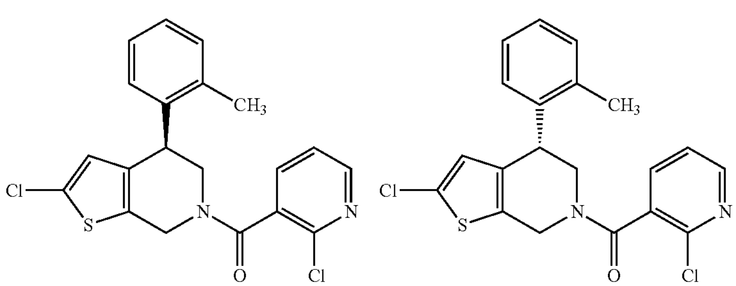 | 27 uM 30 min <1% | 25 uM 60 min <1% |

TABLE 2-continued

Compounds and Biological Activity.

| # | Structure | SUMO E1 | Atg7 |
|---|---|---|---|
| 119 | | 27 uM 30 min <1% | 25 uM 60 min <1% |
| 120 | | 1 uM 30 min 100% | 25 uM 60 min <1% |
| 121 | | 27 uM 30 min <1% | 25 uM 60 min <1% |
| 122 | | 1 uM 30 min 100% | 25 uM 60 min <1% |
| 123 | | 9 uM 30 min 40% | 25 uM 60 min <1% |
| 124 | | 1 uM 30 min 100% | No entry |

TABLE 2-continued

Compounds and Biological Activity.

| # | Structure | SUMO E1 | Atg7 |
|---|---|---|---|
| 125 | | 27 uM 30 min 100% | No entry |
| 126 | | 27 uM 20 min 40% | No entry |
| 127 | | 27 uM 20 min 95% | 25 uM 60 min <1% |
| 128 | | 1 uM 20 min 95% | 25 uM 60 min <1% |
| 129 | | 1 uM 20 min 95% | 25 uM 60 min <1% |

TABLE 2-continued

Compounds and Biological Activity.

| # | Structure | SUMO E1 | Atg7 |
|---|-----------|---------|------|
| 130 | 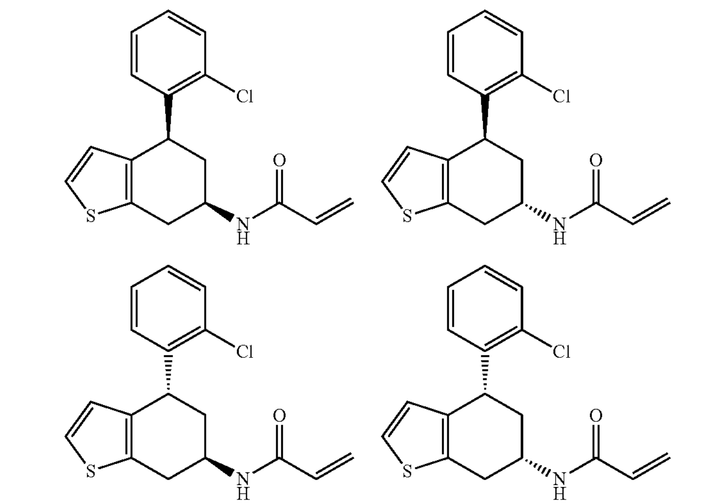 | 3 uM 30 min <1% | 25 uM 60 min <1% |
| 131 | 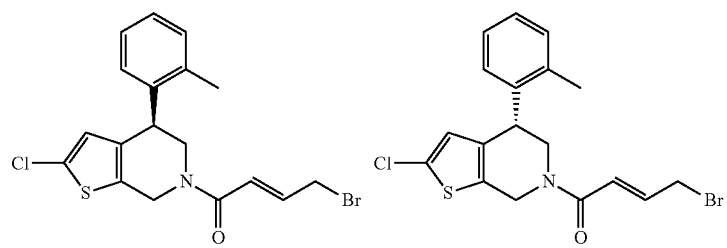 [SMILES: Cc1ccccc1[C@H]1CN(C(=O)/C=C/CBr)Cc2sc(Cl)cc21 ; Cc1ccccc1[C@@H]1CN(C(=O)/C=C/CBr)Cc2sc(Cl)cc21] | 9 uM 15 min <1% | No entry |
| 132 | 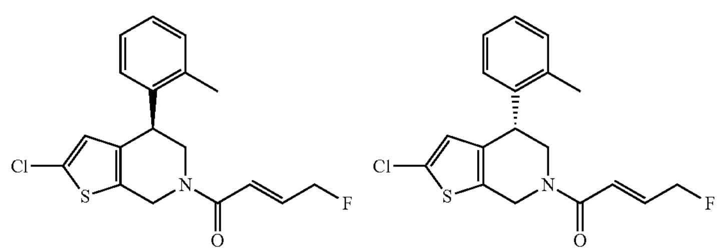 [SMILES: Cc1ccccc1[C@H]1CN(C(=O)/C=C/CF)Cc2sc(Cl)cc21 ; Cc1ccccc1[C@@H]1CN(C(=O)/C=C/CF)Cc2sc(Cl)cc21] | 9 uM 30 min 10% | 25 uM 60 min <1% |
| 133 | 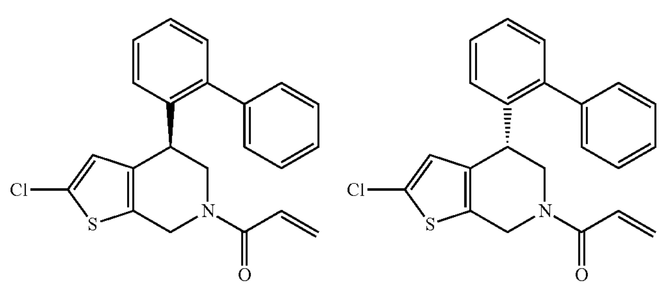 [SMILES: C=CC(=O)N1Cc2sc(Cl)cc2[C@@H](c2ccccc2-c2ccccc2)C1 ; C=CC(=O)N1Cc2sc(Cl)cc2[C@H](c2ccccc2-c2ccccc2)C1] | 1 uM 30 min 95% | 25 uM 60 min <1% |

TABLE 2-continued

Compounds and Biological Activity.

| # | Structure | SUMO E1 | Atg7 |
|---|---|---|---|
| 134 | 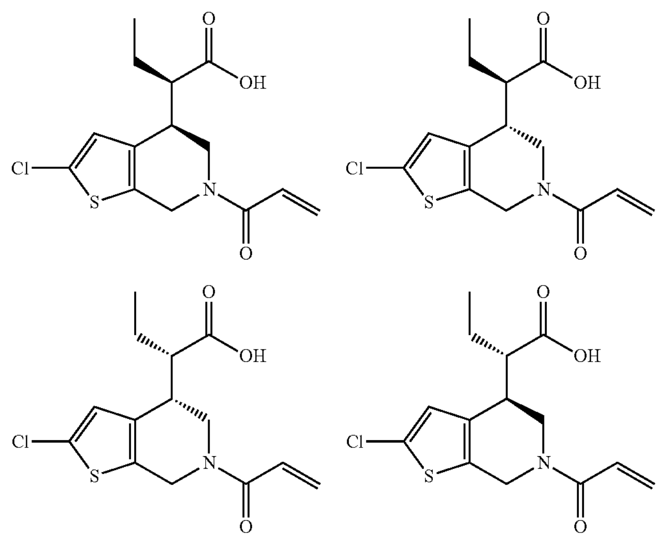 | 27 uM<br>15 min<br><1% | 25 uM<br>60 min<br><1% |
| 135 | 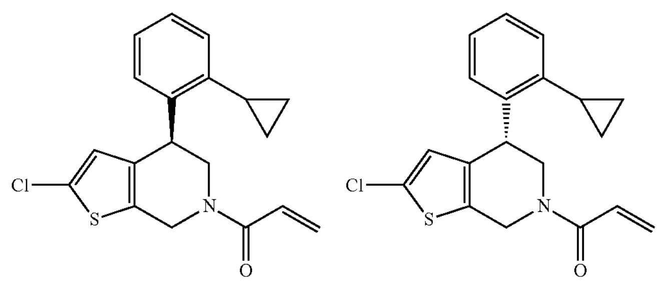 | 27 uM<br>30 min<br>95% | 25 uM<br>60 min<br><1% |
| 136 | 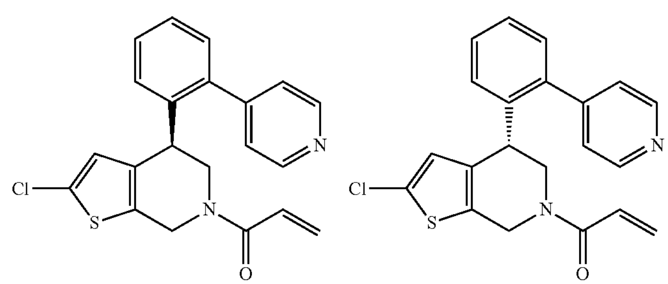 [SMILES: C=CC(=O)N1Cc2sc(Cl)cc2[C@@H](c2ccccc2-c2ccncc2)C1 ; C=CC(=O)N1Cc2sc(Cl)cc2[C@H](c2ccccc2-c2ccncc2)C1] | 3 uM<br>30 min<br>100% | 25 uM<br>60 min<br><1% |
| 137 | 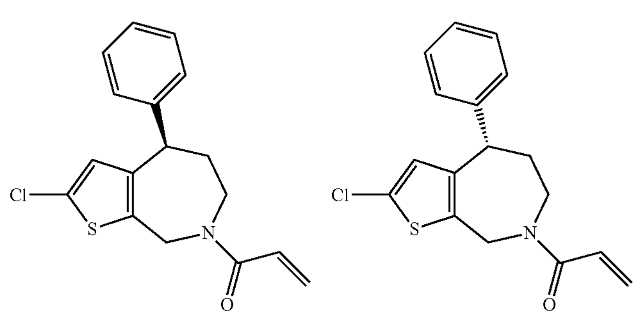 [SMILES: C=CC(=O)N1CC[C@H](c2ccccc2)c2cc(Cl)sc2C1 ; C=CC(=O)N1CC[C@@H](c2ccccc2)c2cc(Cl)sc2C1] | 27 uM<br>30 min<br><1% | 25 uM<br>60 min<br><1% |

TABLE 2-continued

Compounds and Biological Activity.

| # | Structure | SUMO E1 | Atg7 |
|---|---|---|---|
| 138 | | 9 uM<br>15 min<br>50% | 25 uM<br>60 min<br><1% |
| 139 | | 27 uM<br>30 min<br><1% | 25 uM<br>60 min<br><1% |
| 140 | | 27 uM<br>30 min<br><1% | 25 uM<br>60 min<br><1% |
| 141 | | 1 uM<br>30 min<br>50% | 25 uM<br>60 min<br><1% |
| 142 | | 9 uM<br>30 min<br>80% | 25 uM<br>60 min<br><1% |

TABLE 2-continued

Compounds and Biological Activity.

| # | Structure | SUMO E1 | Atg7 |
|---|---|---|---|
| 143 | 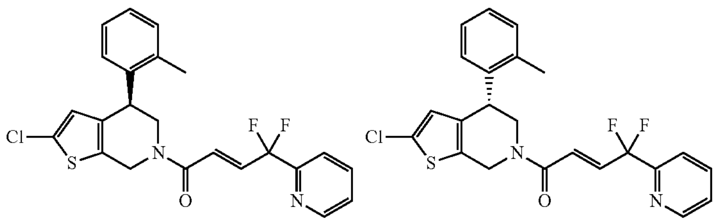 | 27 uM 30 min <1% | 25 uM 60 min <1% |
| 144 | 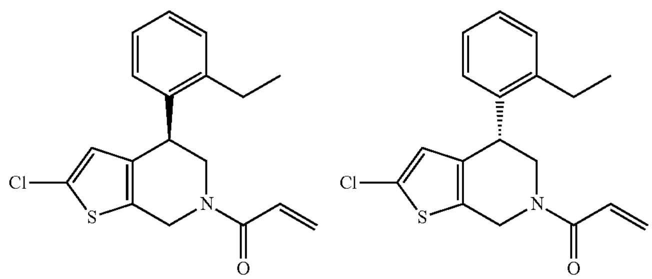 | 27 uM 30 min 95% | No entry |
| 145 | 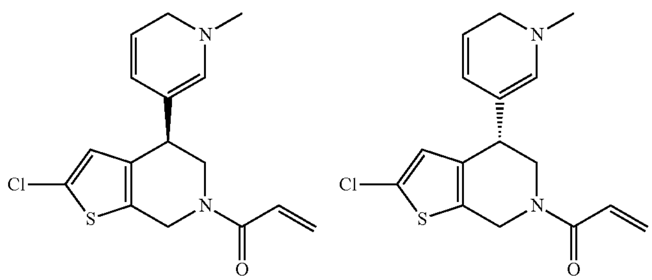 | 9 uM 30 min <1% | 25 uM 60 min <1% |
| 146 | 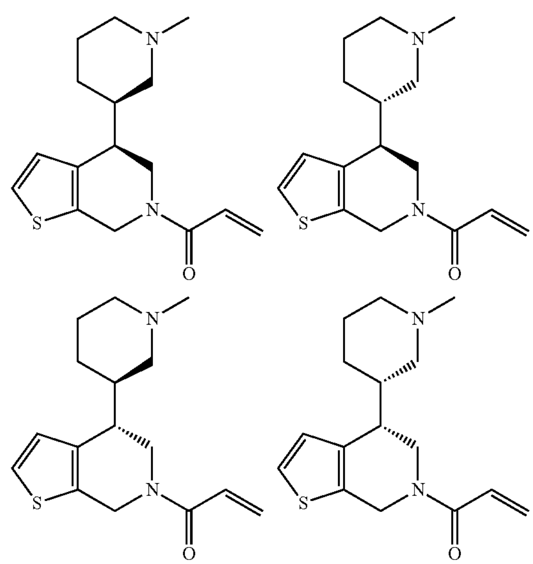 | 9 uM 30 min <1% | 25 uM 60 min <1% |

TABLE 2-continued

Compounds and Biological Activity.

| # | Structure | SUMO E1 | Atg7 |
|---|-----------|---------|------|
| 147 | 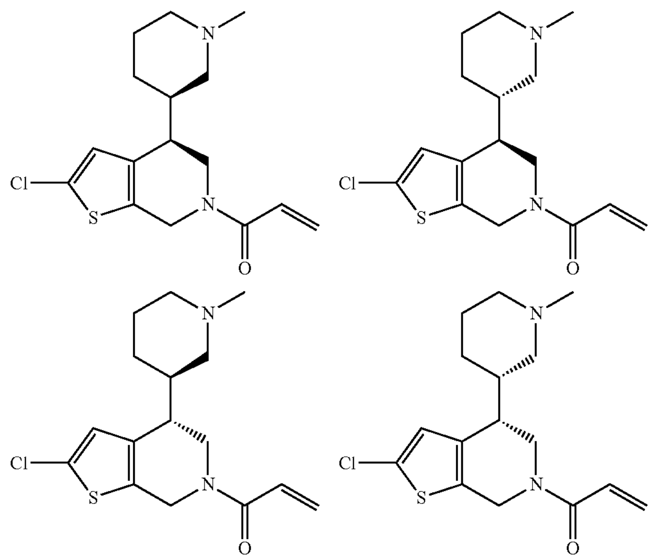 | 9 uM<br>30 min<br><1% | 25 uM<br>60 min<br><1% |
| 148 | 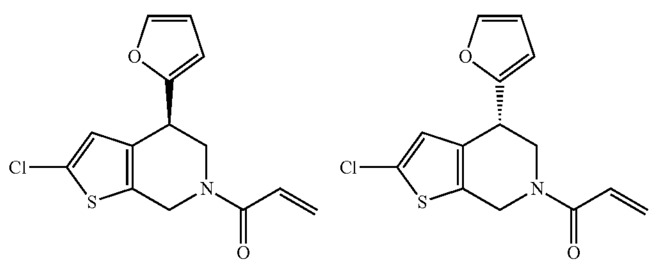 | 9 uM<br>30 min<br><1% | 25 uM<br>60 min<br><1% |
| 149 | 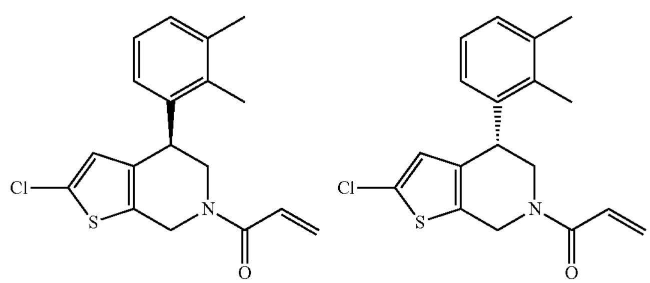 | 1 uM<br>30 min<br>90% | No entry |
| 150 | 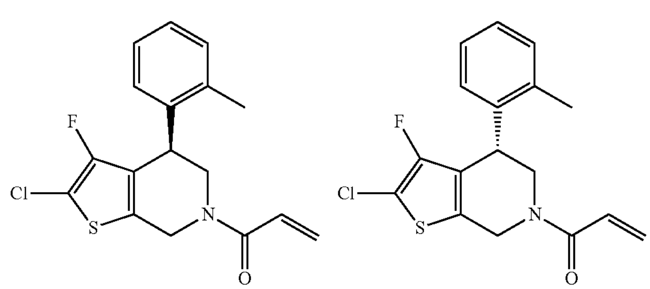 | 22 uM<br>30 min<br>50% | 25 uM<br>60 min<br><1% |

TABLE 2-continued

Compounds and Biological Activity.

| # | Structure | SUMO E1 | Atg7 |
|---|---|---|---|
| 151 | | 6 uM<br>15 min<br><1% | 25 uM<br>60 min<br><1% |
| 152 | | 6 uM<br>15 min<br><1% | 25 uM<br>60 min<br><1% |
| 153 | | 6 uM<br>15min<br><1% | 25 uM<br>60 min<br><1% |
| 154 | | 18 uM<br>15 min<br><1% | 25 uM<br>60 min<br><1% |
| 155 | | 15 uM<br>15 min<br><1% | 25 uM<br>60 min<br><1% |

TABLE 2-continued

Compounds and Biological Activity.

| # | Structure | SUMO E1 | Atg7 |
|---|---|---|---|
| 156 | | 9 uM<br>15 min<br><1% | No entry |
| 157 | | 16 uM<br>45 min<br><1% | No entry |
| 158 | | 16 uM<br>45 min<br><1% | No entry |

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound of formula I or an isomer or a pharmaceutically acceptable salt thereof:

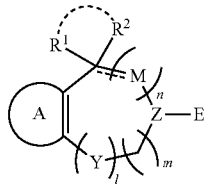

(I)

wherein
==== is selected from a single bond or double bond;
l is 1, m is 0, and n is 0 or 1;

M is selected from $CR^3R^4$, $-NR^5$, C=O, O, S=O, O=S=O, and S;
Y is selected from $CR^6R^7$, $-NR^8$, C=O, O, S=O, O=S=O, and S;
Z is N;
ring A is 5-membered heteroaryl;
wherein ring A is optionally substituted with one or more substituent groups;
E is selected from

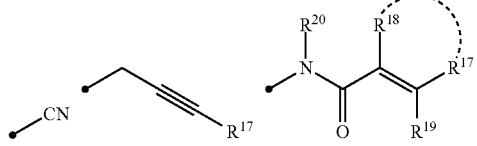

-continued
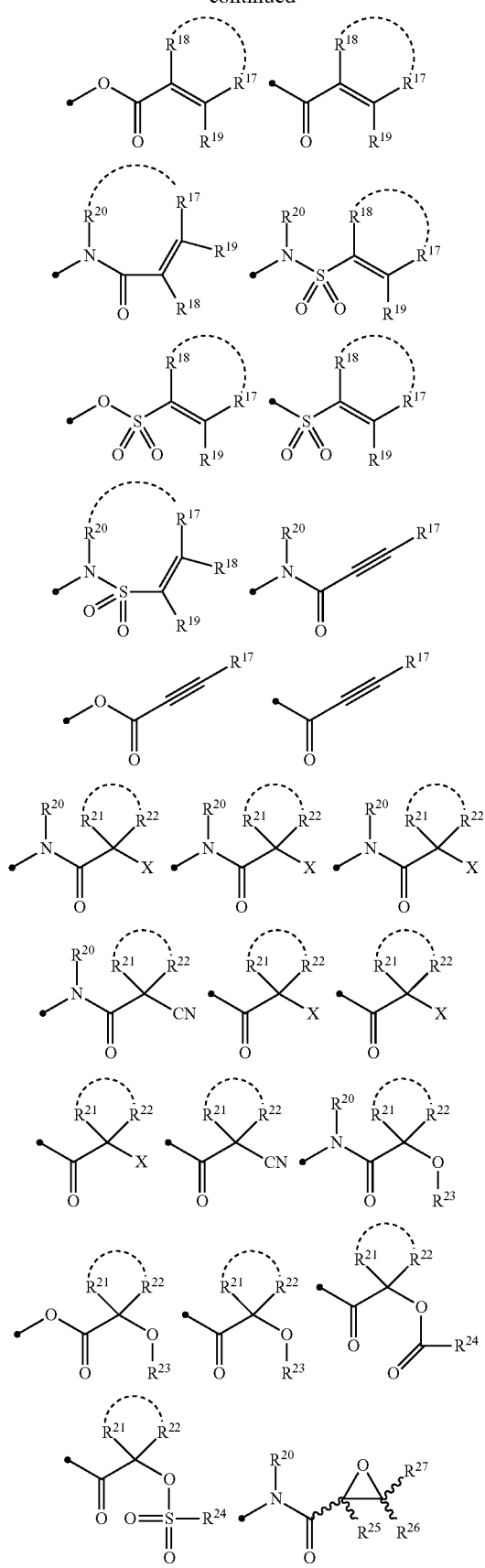
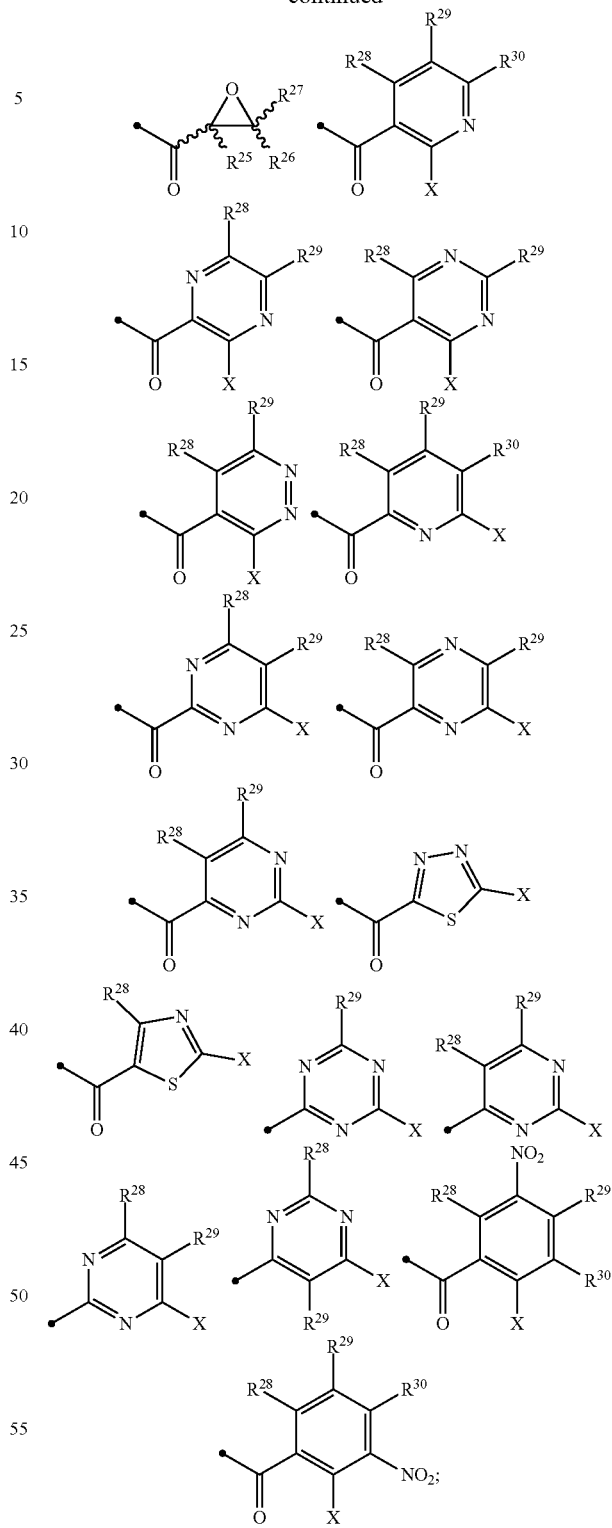
R[1] is selected from hydrogen, halogen, substituted or unsubstituted alkyl, cyano, —CX[1]$_3$, —CHX[1]$_2$, —CH$_2$X[1], —OCX[1]$_3$, —OCH$_2$X[1], —OCHX[1]$_2$, —SO$_{n1}$R[1A], —SO$_{v1}$NR[1A]R[1B], —NHC(O)NR[1A]R[1B], —N(O)$_{m1}$, —NR[1A]R[1B], —NHNR[1A]R[1B], —C(O)R[1A], —(O)OR[1A], —C(O)NR[1A]R[1B], —C(O)NHNR[1A]R[1B], —OR[1A], —NR[1A]SO$_2$R[1B], —NR[1A]C(O)R[1B], —NR[1A]C $-(O)OR^{1B}$, $-NR^{1A}OR^{1B}$, azido, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^2$ is selected from substituted or unsubstituted aryl, and substituted or unsubstituted heteroaryl; or $R^1$ and $R^2$ substituents join to form a substituted or unsubstituted cycloalkyl or heterocycloalkyl;

$R^3$ is selected from hydrogen, halogen, $-CX^3_3$, $-CHX^3_2$, $-CH_2X^3$, $-OCX^3_3$, $-OCH_2X^3$, $-OCHX^3_2$, $-CN$, $-SO_{n3}R^{3A}$, $-SO_{v3}NR^{3A}R^{3B}$, $-NHC(O)NR^{3A}R^{3B}$, $-N(O)_{m3}$, $-NR^{3A}R^{3B}$, $-NHNR^{3A}R^{3B}$, $-C(O)R^{3A}$, $-C(O)-OR^{3A}$, $-C(O)NR^{3A}R^{3B}$, $-OR^{3A}$, $-NR^{3A}SO_2R^{3B}$, $-NR^{3A}C(O)R^{3B}$, $-NR^{3A}C(O)OR^{3B}$, $-NR^{3A}OR^{3B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^4$ is selected from hydrogen, halogen, $-CX^4_3$, $-CHX^4_2$, $-CH_2X^4$, $-OCX^4_3$, $-OCH_2X^4$, $-OCHX^4_2$, $-CN$, $-SO_{n4}R^{4A}$, $-SO_{v4}NR^{4A}R^{4B}$, $-NHC(O)NR^{4A}R^{4B}$, $-N(O)_{m4}$, $-NR^{4A}R^{4B}$, $-NHNR^{4A}R^{4B}$, $-C(O)R^{4A}$, $-C(O)-OR^{4A}$, $-C(O)NR^{4A}R^{4B}$, $-C(O)NHNR^{4A}R^{4B}$, $-OR^{4A}$, $-NR^{4A}SO_2R^{4B}$, $-NR^{4A}C(O)R^{4B}$, $-NR^{4A}C(O)OR^{4B}$, $-NR^{4A}OR^{4B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; or $R^3$ and $R^4$ substituents join to form a substituted or unsubstituted cycloalkyl or heterocycloalkyl;

$R^5$ is selected from hydrogen, halogen, $-CX^5_3$, $-CHX^5_2$, $-CH_2X^5$, $-OCX^5_3$, $-OCH_2X^5$, $-OCHX^5_2$, $-CN$, $-SO_{n5}R^{5A}$, $-SO_{v5}NR^{5A}R^{5B}$, $-NHC(O)NR^{5A}R^{5B}$, $-N(O)_{m5}$, $-NR^{5A}R^{5B}$, $-NHNR^{5A}R^{5B}$, $-C(O)R^{5A}$, $-C(O)-OR^{5A}$, $-C(O)NR^{5A}R^{5B}$, $-C(O)NHNR^{5A}R^{5B}$, $-OR^{5A}$, $-NR^{5A}SO_2R^{5B}$, $-NR^{5A}C(O)R^{5B}$, $-NR^{5A}C(O)OR^{5B}$, $-NR^{5A}OR^{5B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^6$ is selected from hydrogen, halogen, $-CX^6_3$, $-CHX^6_2$, $-CH_2X^6$, $-OCX^6_3$, $-OCH_2X^6$, $-OCHX^6_2$, $-CN$, $-SO_{n6}R^{6A}$, $-SO_6NR^{6A}R^{6B}$, $-NHC(O)NR^{6A}R^{6B}$, $-N(O)_{m6}$, $-NR^{6A}R^{6B}$, $-NHNR^{6A}R^{6B}$, $-C(O)R^{6A}$, $-C(O)OR^{6A}$, $-C(O)NR^{6A}R^{6B}$, $-C(O)NHNR^{6A}R^{6B}$, $-OR^{6A}$, $-NR^{6A}SO_2R^{6B}$, $-NR^{6A}C(O)R^{6B}$, $-NR^{6A}C(O)OR^{6B}$, $-NR^{6A}OR^{6B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^7$ is selected from hydrogen, halogen, $-CX^7_3$, $-CHX^7_2$, $-CH_2X^7$, $-OCX^7_3$, $-OCH_2X^7$, $-OCHX^7_2$, $-CN$, $-SO_{n7}R^{7A}$, $-SO_7NR^{7A}R^{7B}$, $-NHC(O)NR^{7A}R^{7B}$, $-N(O)_{m7}$, $-NR^{7A}R^{7B}$, $-NHNR^{7A}R^{7B}$, $-C(O)R^{7A}$, $-C(O)OR^{7A}$, $-C(O)NR^{7A}R^{7B}$, $-C(O)NHNR^{7A}R^{7B}$, $-OR^{7A}$, $-NR^{7A}SO_2R^{7B}$, $-NR^{7A}C(O)R^{7B}$, $-NR^{7A}C(O)OR^{7B}$, $-NR^{7A}OR^{7B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^8$ is selected from hydrogen, halogen, $-CX^8_3$, $-CHX^8_2$, $-CH_2X^8$, $-OCX^8_3$, $-OCH_2X^8$, $-OCHX^8_2$, $-CN$, $-SO_{18}R^{8A}$, $-SO_8NR^{8A}R^{8B}$, $-NHC(O)NR^{8A}R^{8B}$, $-N(O)_{m8}$, $-NR^{8A}R^{8B}$, $-NHNR^{8A}R^{8B}$, $-C(O)R^{8A}$, $-C(O)-OR^{8A}$, $-C(O)NR^{8A}R^{8B}$, $-C(O)NHNR^{8A}R^{8B}$, $-OR^{8A}$, $-NR^{8A}SO_2R^{8B}$, $-NR^{8A}C(O)R^{8B}$, $-NR^{8A}C(O)OR^{8B}$, $-NR^{8A}OR^{8B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{17}$ is selected from hydrogen, halogen, $-CX^{17}_3$, $-CHX^{17}_2$, $-CH_2X^{17}$, $-OCX^{17}_3$, $-OCH_2X^{17}$, $-OCHX^{17}_2$, $-CN$, $-SO_{n11}R^{17A}$, $-SO_{v17}NR^{17A}R^{17B}$, $-NHC(O)NR^{17A}R^{17B}$, $-N(O)_{m17}$, $-NR^{17A}R^{17B}$, $-NHNR^{17A}R^{17B}$, $-C(O)R^{17A}$, $-C(O)-OR^{17A}$, $-C(O)NR^{17A}R^{17B}$, $-C(O)NHNR^{17A}R^{17B}$, $-OR^{17A}$, $-NR^{17A}SO_2R^{17B}$, $-NR^{17A}C(O)R^{17B}$, $-NR^{17A}C(O)OR^{17B}$, $-NR^{17A}OR^{17B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{18}$ is selected from hydrogen, halogen, $-CX^{18}_3$, $-CHX^{18}_2$, $-CH_2X^{18}$, $-OCX^{18}_3$, $-OCH_2X^{18}$, $-OCHX^{18}_2$, $-CN$, $-SO_{n18}R^{18A}$, $-SO_{v18}NR^{18A}R^{18B}$, $-NHC(O)NR^{18A}R^{18B}$, $-N(O)_{m18}$, $-NR^{18A}R^{18B}$, $-NHNR^{18A}R^{18B}$, $-C(O)R^{18A}$, $-C(O)-OR^{18A}$, $-C(O)NR^{18A}R^{18B}$, $-C(O)NHNR^{18A}R^{18B}$, $-OR^{18A}$, $-NR^{18A}SO_2R^{18B}$, $-NR^{18A}C(O)R^{18B}$, $-NR^{18A}C(O)OR^{18B}$, $-NR^{18A}OR^{18B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; or $R^{17}$ and $R^{18}$ substituents join to form a substituted or unsubstituted cycloalkyl or heterocycloalkyl;

$R^{19}$ is selected from hydrogen, halogen, $-CX^{19}_3$, $-CHX^{19}_2$, $-CH_2X^{19}$, $-OCX^{19}_3$, $-OCH_2X^{19}$, $-OCHX^{19}_2$, $-CN$, $-SO_{n19}R^{19A}$, $-SO_{v19}NR^{19A}R^{19B}$, $-NHC(O)NR^{19A}R^{19B}$, $-N(O)_{m19}$, $-NR^{19A}R^{19B}$, $-NHNR^{19A}R^{19B}$, $-C(O)R^{19A}$, $-C(O)-OR^{19A}$, $-C(O)NR^{19A}R^{19B}$, $-C(O)NHNR^{19A}R^{19B}$, $-OR^{19A}$, $-NR^{19A}SO_2R^{19B}$, $-NR^{19A}C(O)R^{19B}$, $-NR^{19A}C(O)OR^{19B}$, $-NR^{19A}OR^{19B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{20}$ is selected from hydrogen, halogen, substituted or unsubstituted alkyl, $-CX^{20}_3$, $-CHX^{20}_2$, $-CH_2X^{20}$, $-OCX^{20}_3$, $-OCH_2X^{20}$, $-OCHX^{20}_2$, $-CN$, $-SO_{n20}R^{20A}$, $-SO_{v20}NR^{20A}R^{20B}$, $-NHC(O)NR^{20A}R^{20B}$, $-N(O)_{m20}$, $-NR^{20A}R^{20B}$, $-NHNR^{20A}R^{20B}$, $-C(O)R^{20A}$, $-C(O)-OR^{20A}$, $-C(O)NR^{20A}R^{20B}$, $-C(O)NHNR^{20A}R^{20B}$, $-OR^{20A}$, $-NR^{20A}SO_2R^{20B}$, $-NR^{20A}C(O)R^{20B}$, $-NR^{20A}C(O)OR^{20B}$, $-NR^{20A}OR^{20B}$, $-N_3$, substituted or unsubstituted heteroalkyl, substituted or unsubstituted cycloalkyl, substituted or unsubstituted heterocycloalkyl, substituted or unsubstituted aryl, and substituted or unsubstituted heteroaryl; or $R^{17}$ and $R^{20}$ substituents join to form a substituted or unsubstituted cycloalkyl or heterocycloalkyl;

$R^{21}$ is selected from hydrogen, halogen, $-CX^{21}_3$, $-CHX^{21}_2$, $-CH_2X^{21}$, $-OCX^{21}_3$, $-OCH_2X^{21}$, $-OCHX^{21}_2$, $-CN$, $-SO_{n21}R^{21A}$, $-SO_{v21}NR^{21A}R^{21B}$, $-NHC(O)NR^{21A}R^{2B}$, $-N(O)_{m21}$, $-NR^{21A}R^{2B}$, $-NHNR^{21A}R^{2B}$, $-C(O)R^{21A}$, $-C(O)-OR^{21A}$, $-C(O)NR^{21A}R^{2B}$, $-C(O)NHNR^{21A}R^{21B}$, $-OR^{21A}$, $-NR^{21A}SO_2R^{21B}$, $-NR^{21A}C(O)R^{21B}$, $-NR^{21A}C(O)OR^{21B}$, $-NR^{21A}OR^{21B}$, $-N_3$, substituted or unsubstituted alkyl, substituted or unsubstituted heteroalkyl, substituted or unsubstituted and substituted or unsubstituted heteroaryl;

$R^{22}$ is selected from hydrogen, halogen, $-CX^{22}_3$, $-CHX^{22}_2$, $-CH_2X^{22}$, $-OCX^{22}_3$, $-OCH_2X^{22}$, $-OCHX^{22}_2$, $-CN$, $-SO_{n22}R^{22A}$, $-SO_{v22}NR^{22A}R^{22B}$, $-NHC(O)NR^{22A}R^{22B}$, $-N(O)_{m22}$, $-NR^{22A}R^{22B}$, $-NHNR^{22A}R^{22B}$, $-C(O)R^{22A}$, $-C(O)-OR^{22A}$, $-C(O)NR^{22A}R^{22B}$, $-C(O)NHNR^{22A}R^{22B}$, $-OR^{22A}$, $-NR^{22A}SO_2R^{22B}$, $-NR^{22A}C(O)R^{22B}$, $-NR^{22A}C(O)OR^{22B}$, $-NR^{22A}OR^{22B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; or $R^{21}$ and $R^{22}$ substituents join to form a substituted or unsubstituted cycloalkyl or heterocycloalkyl;

$R^{23}$ is selected from hydrogen, halogen, $-CX^{23}_3$, $-CHX^{23}_2$, $-CH_2X^{23}$, $-OCX^{23}_3$, $-OCH_2X^{23}$, $-OCHX^{23}_2$, $-CN$, $-SO_{n23}R^{23A}$, $-SO_{v23}NR^{23A}R^{23B}$, $-NHC(O)NR^{23A}R^{23B}$, $-N(O)_{m23}$, $-NR^{23A}R^{23B}$, $-NHNR^{23A}R^{23B}$, $-C(O)R^{23A}$, $-C(O)-OR^{23A}$, $-C(O)NR^{23A}R^{23B}$, $-C(O)NHNR^{23A}R^{23B}$, $-OR^{23A}$, $-NR^{23A}SO_2R^{23B}$, $-NR^{23A}C(O)R^{23B}$, $-NR^{23A}C(O)OR^{23B}$, $-NR^{23A}OR^{23B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{24}$ is selected from hydrogen, halogen, $-CX^{24}_3$, $-CHX^{24}_2$, $-CH_2X^{24}$, $-OCX^{24}_3$, $-OCH_2X^{24}$, $-OCHX^{24}_2$, $-CN$, $-SO_{n24}R^{24A}$, $-SO_{v24}NR^{24A}R^{24B}$, $-NHC(O)NR^{24A}R^{24B}$, $-N(O)_{m24}$, $-NR^{24A}R^{24B}$, $-NHNR^{24A}R^{24B}$, $-C(O)R^{24A}$, $-C(O)-OR^{24A}$, $-C(O)NR^{24A}R^{24B}$, $-C(O)NHNR^{24A}R^{24B}$, $-OR^{24A}$, $-NR^{24A}SO_2R^{24B}$, $-NR^{24A}C(O)R^{24B}$, $-NR^{24A}C(O)OR^{24B}$, $-NR^{24A}OR^{24B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{25}$ is selected from hydrogen, halogen, $-CX^{25}_3$, $-CHX^{25}_2$, $-CH_2X^{25}$, $-OCX^{25}_3$, $-OCH_2X^{25}$, $-OCHX^{25}_2$, $-CN$, $-SO_{n25}R^{25A}$, $-SO_{v25}NR^{25A}R^{25B}$, $-NHC(O)NR^{25A}R^{25B}$, $-NHNR^{25A}R^{25B}$, $-C(O)R^{25A}$, $-N(O)_{m25}$, $-NR^{25A}R^{25B}$, $-C(O)-OR^{25A}$, $-C(O)NR^{25A}R^{25B}$, $-C(O)NHNR^{25A}R^{25B}$, $-OR^{25A}$, $-NR^{25A}SO_2R^{25B}$, $-NR^{25A}C(O)R^{25B}$, $-NR^{25A}C(O)OR^{25B}$, $-NR^{25A}OR^{25B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{26}$ is selected from hydrogen, halogen, substituted or unsubstituted alkyl, $-CX^{26}_3$, $-CHX^{26}_2$, $-CH_2X^{26}$, $-OCX^{26}_3$, $-OCH_2X^{26}$, $-OCHX^{26}_2$, $-CN$, $-SO_{n26}R^{26A}$, $-SO_{v26}NR^{26A}R^{26B}$, $-NHC(O)NR^{26A}R^{26B}$, $-N(O)_{m26}$, $-NR^{26A}R^{26B}$, $-NHNR^{26A}R^{26B}$, $-C(O)R^{26A}$, $-C(O)-OR^{26A}$, $-C(O)NR^{26A}R^{26B}$, $-C(O)NHNR^{26A}R^{26B}$, $-OR^{26A}$, $-NR^{26A}SO_2R^{26B}$, $-NR^{26A}C(O)R^{26B}$, $-NR^{26A}C(O)OR^{26B}$, $-NR^{26A}OR^{26B}$, $-N_3$, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{27}$ is selected from hydrogen, halogen, substituted or unsubstituted alkyl, $-CX^{27}_3$, $-CHX^{27}_2$, $-CH_2X^{27}$, $-OCX^{27}_3$, $-OCH_2X^{27}$, $-OCHX^{27}_2$, $-CN$, $-SO_{n27}R^{27A}$, $-SO_{v27}NR^{27A}R^{27B}$, $-NHC(O)NR^{27A}R^{27B}$, $-N(O)_{m27}$, $-NR^{27A}R^{27B}$, $-NHNR^{27A}R^{27B}$, $-C(O)R^{27A}$, $-C(O)-OR^{27}$-A, $-C(O)NR^{27A}R^{27B}$, $-C(O)NHNR^{27A}R^{27B}$, $-OR^{27A}$, $-NR^{27A}SO_2R^{27B}$, $-NR^{27A}C(O)R^{27B}$, $-NR^{27A}C(O)OR^{27B}$, $-NR^{27A}OR^{27B}$, $-N_3$, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{28}$ is selected from hydrogen, halogen, substituted or unsubstituted alkyl, $-CX^{28}_3$, $-CHX^{28}_2$, $-CH_2X^{28}$, $-OCX^{28}_3$, $-OCH_2X^{28}$, $-OCHX^{28}_2$, $-CN$, $-SO_{n28}R^{28A}$, $-SO_{v28}NR^{28A}R^{28B}$, $-NHC(O)NR^{28A}R^{28B}$, $-N(O)_{m28}$, $-NR^{28A}R^{28B}$, $-NHNR^{28A}R^{28B}$, $-C(O)R^{28A}$, $-C(O)-OR^{28}$-A, $-C(O)NR^{28A}R^{28B}$, $-C(O)NHNR^{28A}R^{28B}$, $-OR^{28A}$, $-NR^{28A}SO_2R^{28B}$, $-NR^{28A}C(O)R^{28B}$, $-NR^{28A}C(O)OR^{28B}$, $-NR^{28A}OR^{28B}$, $-N_3$ substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{29}$ is selected from hydrogen, halogen, $-CX^{29}_3$, $-CHX^{29}_2$, $-CH_2X^{29}$, $-OCX^{29}_3$, $-OCH_2X^{29}$, $-OCHX^{29}_2$, $-CN$, $-SO_{n29}R^{29A}$, $-SO_{v29}NR^{29A}R^{29B}$, $-NHC(O)NR^{29A}R^{29B}$, $-N(O)_{m29}$, $-NR^{29A}R^{29B}$, $-NHNR^{29A}R^{29B}$, $-C(O)R^{29A}$, $-C(O)-OR^{29A}$, $-C(O)NR^{29A}R^{29B}$, $-C(O)NHNR^{29A}R^{29B}$, $-OR^{29A}$, $-NR^{29A}SO_2R^{29B}$, $-NR^{29A}C(O)R^{29B}$, $-NR^{29A}C(O)OR^{29B}$, $-NR^{29A}OR^{29B}$, $-N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{30}$ is selected from hydrogen, halogen, substituted or unsubstituted alkyl, $-CX^{30}_3$, $-CHX^{30}_2$, $-CH_2X^{30}$, $-OCX^{30}_3$, $-OCH_2X^{30}$, $-OCHX^{30}_2$, $-CN$, $-SO_{n30}R^{30A}$, $-SO_{v30}NR^{30A}R^{30B}$, $-NHC(O)NR^{30A}R^{30B}$, $-N(O)_{m30}$, $-NR^{30A}R^{30B}$, $-NHNR^{30A}R^{30B}$, $-C(O)R^{30A}$, $-C(O)OR^{30A}$, $-C(O)NR^{30A}R^{30B}$, $-C(O)NHNR^{30A}R^{30B}$, $-OR^{30A}$, $-NR^{30A}SO_2R^{30B}$, $-NR^{30A}C(O)R^{30B}$, $-NR^{30A}C(O)OR^{30B}$, $-NR^{30A}OR^{30B}$, $-N_3$, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

Each $R^{1A}$, $R^{1B}$, $R^{3A}$, $R^{3B}$, $R^{4A}$, $R^{4B}$, $R^{5A}$, $R^{5B}$, $R^{6A}$, $R^{6B}$, $R^{7A}$, $R^{7B}$, $R^{8A}$, $R^{8B}$, $R^{17A}$, $R^{17B}$, $R^{18A}$, $R^{18B}$, $R^{19A}$, $R^{19B}$, $R^{20A}$, $R^{20B}$, $R^{21A}$, $R^{21B}$, $R^{22A}$, $R^{22B}$, $R^{23A}$, $R^{23B}$, $R^{24A}$, $R^{24B}$, $R^{25A}$, $R^{25B}$, $R^{26A}$, $R^{26B}$, $R^{27A}$, $R^{27B}$, $R^{28A}$, $R^{28B}$, $R^{29A}$, $R^{29B}$, $R^{30A}$, and $R^{30B}$ is independently selected from hydrogen, —$CX_3$, —$CHX_2$, —$CH_2X$, —C(O)OH, —C(O)$NH_2$, —CN, —OH, —$NH_2$, —COOH, —CONH$_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)OH, —NHOH, —$OCX_3$, —$OCHX_2$, —$OCH_2X$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{1A}$ and $R^{1B}$ substituents bonded to the same nitrogen atom may optionally be joined to form a substituted or unsubstituted heterocycloalkyl or substituted or unsubstituted heteroaryl;

$R^{4A}$ and $R^{4B}$ substituents bonded to the same nitrogen atom may optionally be joined to form a substituted or unsubstituted heterocycloalkyl or substituted or unsubstituted heteroaryl;

$R^{5A}$ and $R^{5B}$ substituents bonded to the same nitrogen atom may optionally be joined to form a substituted or unsubstituted heterocycloalkyl or substituted or unsubstituted heteroaryl;

$R^{6A}$ and $R^{6B}$ substituents bonded to the same nitrogen atom may optionally be joined to form a substituted or unsubstituted heterocycloalkyl or substituted or unsubstituted heteroaryl;

$R^{7A}$ and $R^{7B}$ substituents bonded to the same nitrogen atom may optionally be joined to form a substituted or unsubstituted heterocycloalkyl or substituted or unsubstituted heteroaryl;

$R^{8A}$ and $R^{8B}$ substituents bonded to the same nitrogen atom may optionally be joined to form a substituted or unsubstituted heterocycloalkyl or substituted or unsubstituted heteroaryl;

$R^{17A}$ and $R^{17B}$ substituents bonded to the same nitrogen atom may optionally be joined to form a substituted or unsubstituted heterocycloalkyl or substituted or unsubstituted heteroaryl;

$R^{18A}$ and $R^{18B}$ substituents bonded to the same nitrogen atom may optionally be joined to form a substituted or unsubstituted heterocycloalkyl or substituted or unsubstituted heteroaryl;

$R^{19A}$ and $R^{19B}$ substituents bonded to the same nitrogen atom may optionally be joined to form a substituted or unsubstituted heterocycloalkyl or substituted or unsubstituted heteroaryl;

$R^{20A}$ and $R^{20B}$, substituents bonded to the same nitrogen atom may optionally be joined to form a substituted or unsubstituted heterocycloalkyl or substituted or unsubstituted heteroaryl;

$R^{21A}$ and $R^{21B}$ substituents bonded to the same nitrogen atom may optionally be joined to form a substituted or unsubstituted heterocycloalkyl or substituted or unsubstituted heteroaryl;

$R^{22A}$ and $R^{22B}$ substituents bonded to the same nitrogen atom may optionally be joined to form a substituted or unsubstituted heterocycloalkyl or substituted or unsubstituted heteroaryl;

$R^{23A}$ and $R^{23B}$ substituents bonded to the same nitrogen atom may optionally be joined to form a substituted or unsubstituted heterocycloalkyl or substituted or unsubstituted heteroaryl;

$R^{24A}$ and $R^{24B}$ substituents bonded to the same nitrogen atom may optionally be joined to form a substituted or unsubstituted heterocycloalkyl or substituted or unsubstituted heteroaryl;

$R^{25A}$ and $R^{25B}$ substituents bonded to the same nitrogen atom may optionally be joined to form a substituted or unsubstituted heterocycloalkyl or substituted or unsubstituted heteroaryl;

$R^{26A}$ and $R^{26B}$ substituents bonded to the same nitrogen atom may optionally be joined to form a substituted or unsubstituted heterocycloalkyl or substituted or unsubstituted heteroaryl;

$R^{27A}$ and $R^{27B}$ substituents bonded to the same nitrogen atom may optionally be joined to form a substituted or unsubstituted heterocycloalkyl or substituted or unsubstituted heteroaryl;

$R^{28A}$ and $R^{28B}$ substituents bonded to the same nitrogen atom may optionally be joined to form a substituted or unsubstituted heterocycloalkyl or substituted or unsubstituted heteroaryl;

$R^{29A}$ and $R^{29B}$ substituents bonded to the same nitrogen atom may optionally be joined to form a substituted or unsubstituted heterocycloalkyl or substituted or unsubstituted heteroaryl;

$R^{30A}$ and $R^{30B}$ substituents bonded to the same nitrogen atom may optionally be joined to form a substituted or unsubstituted heterocycloalkyl or substituted or unsubstituted heteroaryl;

Each m1, m3, m4, m5, m6, m7, m8, m17, m18, m19, m20, m21, m22, m23, m24, m25, m26, m27, m28, m29, and m30 are independently 1 or 2;

Each v1, v3, v4, v5, v6, v7, v8, v17, v18, v19, v20, v21, v22, v23, v24, v25, v26, v27, v28, v29 and v30 are independently 1 or 2;

Each n1, n3, n4, n5, n6, n7, n8, n17, n18, n19, n20, n21, n22, n23, n24, n25, n26, n27, n28, n29 and n30 are independently an integer from 0 to 2; and Each X, $X^1$, $X^3$, $X^4$, $X^5$, $X^6$, $X^7$, $X^8$, $X^{17}$, $X^{18}$, $X^{19}$, $X^{20}$, $X^{21}$, $X^{22}$, $X^{23}$, $X^{24}$, $X^{25}$, $X^{26}$, $X^{27}$, $X^{28}$, $X^{29}$ and $X^{30}$ are independently —Cl, —Br, —I or —F;

provided the compound is not 1-{4-[4-amino-3-(3-fluoro-5-hydroxyphenyl)-1H-pyrazolo[3,4-d]pyrimidin-1-yl]-1,2,3,4-tetrahydroisoquinolin-2-yl}prop-2-en-1-one; further provided the compound is not ethyl 2-{4-chloro-2-[2-(prop-2-enoyl)-1,2,3,4-tetrahydroisoquinolin-1-yl]phenoxy}acetate; further provided the compound is not 1-(1-cyclohexyl-1,2,3,4-tetrahydroisoquinolin-2-yl)prop-2-en-1-one; further provided the compound is not 1-(6,7-dimethoxy-1,2,3,4-tetrahydroisoquinolin-2-yl)prop-2-en-1-one; further provided the compound is not 1-(1,2,3,4-tetrahydroisoquinolin-2-yl)prop-2-en-1-one; further provided the compound is not substituted 2'-(prop-2-enoyl)-3',4'-dihydro-2'H-spiro[cyclohexane-1,1'-isoquinoline]-4-carboxylic acid; further provided the compound is not 1-(7-chloro-1,2,3,4-tetrahydroisoquinolin-2-yl)prop-2-en-1-one.

2. The compound of claim 1 wherein ring A is selected from thienyl, furanyl, pyrrolyl, thiazolyl, oxazolyl, imidazolyl, pyrazolyl, isoxazolyl, triazolyl and isothiazolyl, wherein ring A is optionally substituted with one or more substituent groups.

3. The compound of claim 1 wherein ring A is selected from

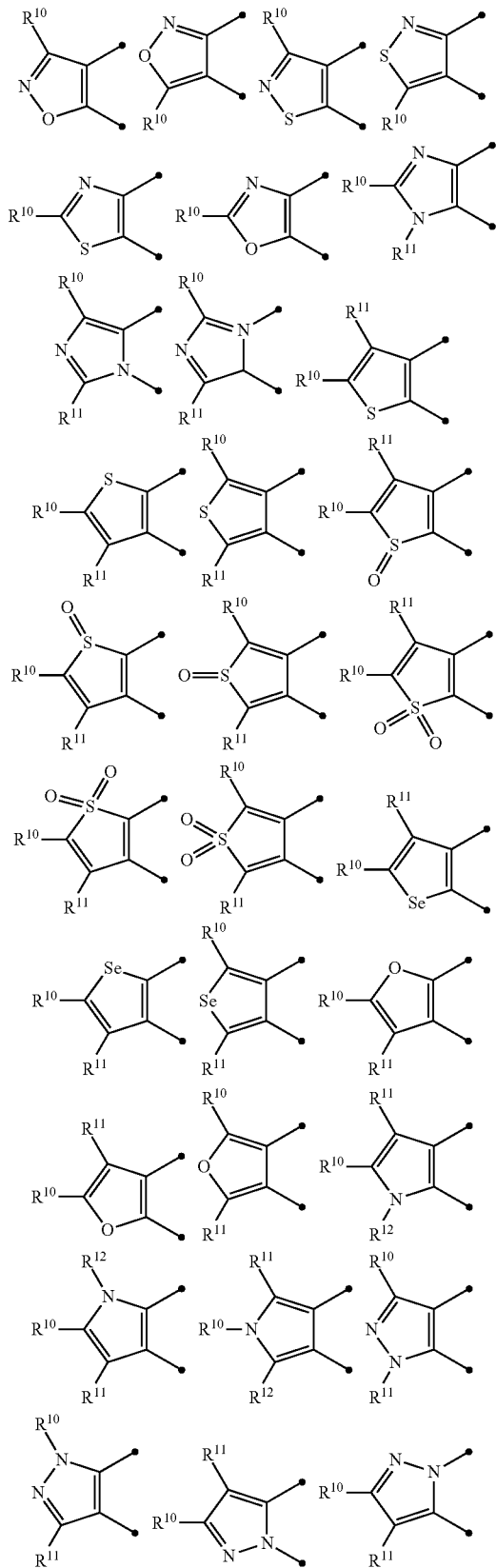

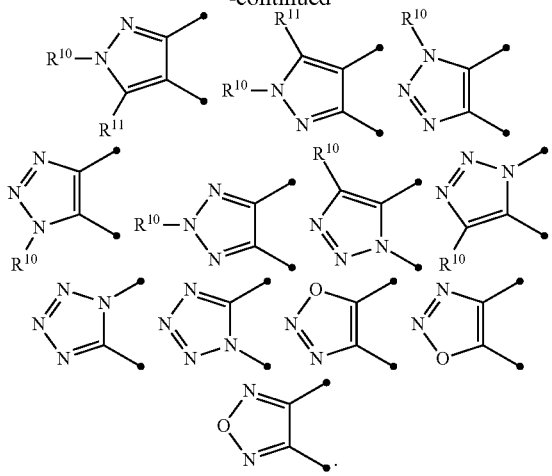

R[10] is selected from hydrogen, halogen, —CX[10]$_3$, —CHX[10]$_2$, —CH$_2$X[10], —OCX[10]$_3$, —OCH$_2$X[10], —OCHX[10]$_2$, —CN, —SO$_{n10}$R[10A], —SO$_{v10}$NR[10A]R[10B], —NHC(O)NR[10A]R[10B], —N(O)$_{m10}$, —NR[10A]R[10B], —NHNR[10A]R[10B], —C(O)R[10A]C(O)OR[10A], —C(O)NR[10A]R[10B], —C(O)NHNR[10A]R[10B], —OR[10A]—NR[10A]SO$_2$R[10B], —NR[10A]C(O)R[10B], —NR[10A]C(O)OR[10B], —NR[10A]OR[10B], —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R[11] is selected from hydrogen, halogen, —CX[11]$_3$, —CHX[11]$_2$, —CH$_2$X[11], —OCX[11]$_3$, —OCH$_2$X[11], —OCHX[11]$_2$, —CN, —SO$_{n11}$R[11A], —SO$_{v11}$NR[11A]R[11B], —NHC(O)NR[11A]R[11B], —N(O)$_{m11}$, —NR[11A]R[11B], —NHNR[11A]R[11B], —C(O)R[11A], —C(O)—OR[11A], —C(O)NR[11A]R[11B], —C(O)NHNR[11A]R[11B], —OR[11A], —NR[11A]SO$_2$R[11B], —NR[11A]C(O)R[11B], —NR[11A]C(O)OR[11B], —NR[11A]OR[11B]—N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R[12] is selected from hydrogen, halogen, —CX[12]$_3$, —CHX[12]$_2$, —CH$_2$X[12], —OCX[12]$_3$, —OCH$_2$X[12], —OCHX[12]$_2$, —CN, —SO$_{n12}$R[12A], —SO$_{v12}$NR[12A]R[12B], —NHC(O)NR[12A]R[12B], —N(O)$_{m12}$, —NR[12A]R[12B], —NHNR[12A]R[12B], —C(O)R[12A], —C(O)R[12A], —C(O)NR[12A]R[12B], —C(O)NHNR[12A]R[12B], —OR[12A], —NR[12A]SO$_2$R[12B], —NR[12A]C(O)R[12B], —NR[12A]C(O)OR[12B], —NR[12A]OR[12B], —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

Each R[10A], R[10B], R[11A], R[11B], R[12A], and R[12B] is independently selected from hydrogen, —CX$_3$, —CHX$_2$, —CH$_2$X, —C(O)OH, —C(O)NH$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$_3$, —OCHX$_2$, —OCH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{10A}$ and $R^{10B}$ substituents bonded to the same nitrogen atom may optionally be joined to form a substituted or unsubstituted heterocycloalkyl or substituted or unsubstituted heteroaryl;

$R^{11A}$ and $R^{11B}$ substituents bonded to the same nitrogen atom may optionally be joined to form a substituted or unsubstituted heterocycloalkyl or substituted or unsubstituted heteroaryl;

$R^{12A}$ and $R^{12B}$ substituents bonded to the same nitrogen atom may optionally be joined to form a substituted or unsubstituted heterocycloalkyl or substituted or unsubstituted heteroaryl;

Each m10, m11, and m12 are independently 1 or 2;

Each v10, v11, and v12 are independently 1 or 2;

Each n1, n2, n3, n4, n5, n6, n7, n8, n9, n10, n11, n12, n13, n14, n15, n16, n17, n18, n19, n20, n21, n22, n23, n24, n25, n26, n27, n28, n29 and n30 are independently an integer from 0 to 2; and Each $X^{10}$, $X^{11}$, and $X^{12}$ are independently —Cl, —Br, —I or —F.

4. The compound of claim 1 wherein ring A is thienyl, wherein ring A is optionally substituted with one or more substituent groups.

5. The compound of claim 1 wherein $R^2$ is selected from substituted or unsubstituted phenyl, substituted or unsubstituted cycloalkyl and substituted or unsubstituted 5- or 6-membered heteroaryl.

6. The compound of claim 1 wherein $R^2$ is selected from substituted or unsubstituted phenyl, substituted or unsubstituted cyclopentyl, substituted or unsubstituted cyclohexyl and substituted or unsubstituted pyridyl.

7. The compound of claim 1 wherein E is selected from —C(═O)CH═CH$_2$, —C(═O)-ethynyl, —C(═O)CH═CHCF$_3$, —C(═O)CH═CHCHF$_2$, —C(═O)CH═CHCH$_2$F, 4-(dimethylamino)but-2-en-1-one and —C(═O)CH$_2$Br.

8. A compound of claim 1, comprising a compound of Formula VIII:

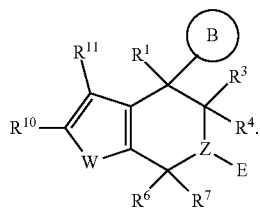

(VIII)

wherein

Z is N;

W is selected from NR$^{12}$, O, and S;

ring B is selected from 5- or 6-membered heteroaryl, 9- or 10-membered fused heteroaryl, 6-membered aryl, and naphthyl;

wherein ring B is optionally substituted with one or more substituent groups;

E is selected from

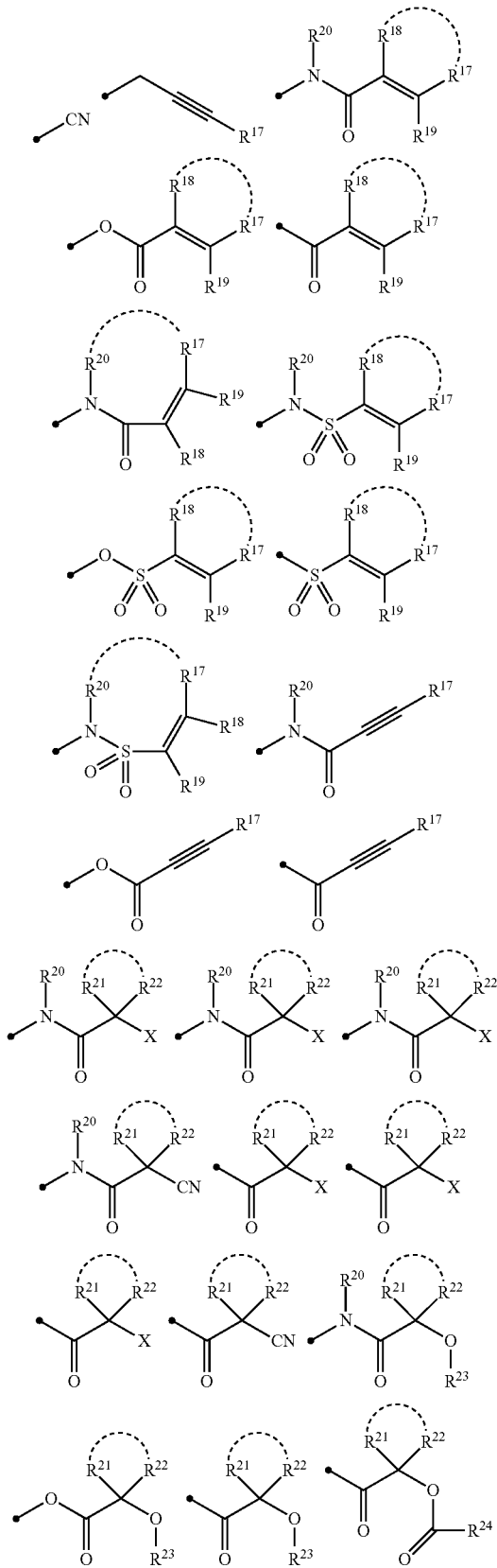

-continued

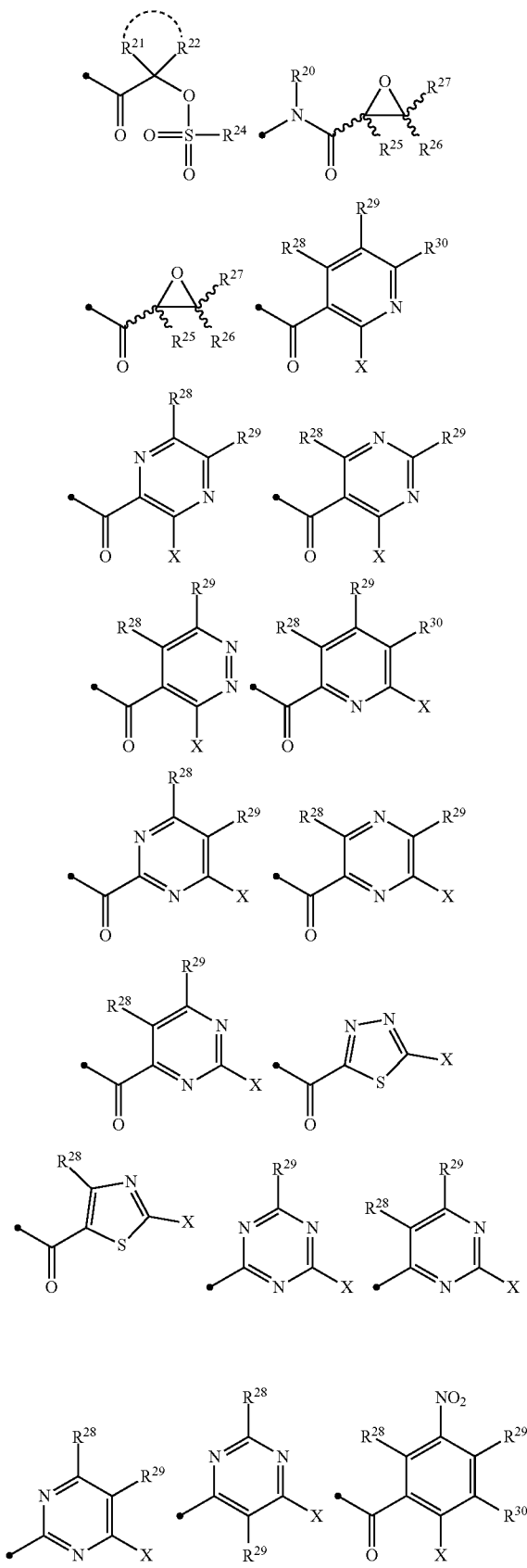

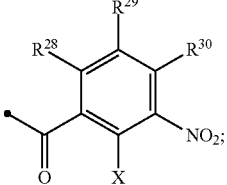

wherein $R^1$ is hydrogen,
$R^3$ is selected from hydrogen, halogen, $—CX^3_3$, $—CHX^3_2$, $—CH_2X^3$, $—OCX^3_3$, $—OCH_2X^3$, $—OCHX^3_2$, $—CN$, $—SO_{n3}R^{3A}$, $—SO_{v3}NR^{3A}R^{3B}$, $—NHC(O)NR^{3A}R^{3B}$, $—N(O)_{m3}$, $—NR^{3A}R^{3B}$, $—NHNR^{3A}R^{3B}$, $—C(O)R^{3A}$, $—C(O)—OR^{3A}$, $—C(O)NR^{3A}R^{3B}$, $—OR^{3A}$, $—NR^{3A}SO_2R^{3B}$, $—NR^{3A}C(O)R^{3B}$, $—NR^{3A}C(O)OR^{3B}$, $—NR^{3A}OR^{3B}$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;
$R^4$ is selected from hydrogen, halogen, $—CX^4_3$, $—CHX^4_2$, $—CH_2X^4$, $—OCX^4_3$, $—OCH_2X^4$, $—OCHX^4_2$, $—CN$, $—SO_{14}R^{4A}$, $—SO_{v4}NR^{4A}R^{4B}$, $—NHC(O)NR^{4A}R^{4B}$, $—N(O)_{m4}$, $—NR^{4A}R^{4B}$, $—NHNR^{4A}R^{4B}$, $—C(O)R^{4A}$, $—C(O)—OR^{4A}$, $—C(O)NR^{4A}R^{4B}$, $—C(O)NHNR^{4A}R^{4B}$, $—OR^{4A}$, $—NR^{4A}SO_2R^{4B}$, $—NR^{4A}C(O)R^{4B}$, $—NR^{4A}C(O)OR^{4B}$, $—NR^{4A}OR^{4B}$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; or
$R^3$ and $R^4$ substituents join to form a substituted or unsubstituted cycloalkyl or heterocycloalkyl;
$R^6$ is selected from hydrogen, halogen, $—CX^6_3$, $—CHX^6_2$, $—CH_2X^6$, $—OCX^6_3$, $—OCH_2X^6$, $—OCHX^6_2$, $—CN$, $—SO_{16}R^{6A}$, $—SO_6NR^{6A}R^{6B}$, $—NHC(O)NR^{6A}R^{6B}$, $—N(O)_{m6}$, $—NR^{6A}R^{6B}$, $—NHNR^{6A}R^{6B}$, $—C(O)R^{6A}$, $—C(O)—OR^{6A}$, $—C(O)NR^{6A}R^{6B}$, $—C(O)NHNR^{6A}R^{6B}$, $—OR^{6A}$, $—NR^{6A}SO_2R^{6B}$, $—NR^{6A}C(O)R^{6B}$, $—NR^{6A}C(O)OR^{6B}$, $—NR^{6A}OR^{6B}$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;
$R^7$ is selected from hydrogen, halogen, $—CX^7_3$, $—CHX^7_2$, $—CH_2X^7$, $—OCX^7_3$, $—OCH_2X^7$, $—OCHX^7_2$, $—CN$, $—SO_{17}R^{7A}$, $—SO_7NR^{7A}R^{7B}$, $—NHC(O)NR^{7A}R^{7B}$, $—N(O)_{m7}$, $—NR^{7A}R^{7B}$, $—NHNR^{7A}R^{7B}$, $—C(O)R^{7A}$, $—C(O)—OR^{7A}$, $—C(O)NR^{7A}R^{7B}$, $—C(O)NHNR^{7A}R^{7B}$, $—OR^{7A}$, $—NR^{7A}SO_2R^{7B}$, $—NR^{7A}C(O)R^{7B}$, $—NR^{7A}C(O)OR^{7B}$, $—NR^{7A}OR^{7B}$, $—N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;
$R^{10}$ is selected from hydrogen, halogen, $—CX^{10}_3$, $—CHX^{10}_2$, $—CH_2X^{10}$, $—OCX^{10}_3$, $—OCH_2X^{10}$, $—OCHX^{10}_2$, $—CN$, $—SO_{n10}R^{10A}$, $—SO_{v10}NR^{10A}R^{10B}$, $—NHC(O)NR^{10A}R^{10B}$, $—N(O)_{m10}$, $—NR^{10A}R^{10B}$, $—NHNR^{10A}R^{10B}$, $—C(O)R^{10A}$, $—C(O)OR^{10A}$, $—C(O)NR^{10A}R^{10B}$, $—C(O)$ NHNR$^{10A}$R$^{10B}$, —OR$^{10A}$, —NR$^{10A}$SO$_2$R$^{10B}$, —NR$^{10A}$C(O)R$^{10B}$, —NR$^{10A}$C(O)OR$^{10B}$, —NR$^{10A}$OR$^{10B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{11}$ is selected from hydrogen, halogen, —CX$^{11}_3$, —CHX$^{11}_2$, —CH$_2$X$^{11}$, —OCX$^{11}_3$, —OCH$_2$X$^{11}$, —OCHX$^{11}_2$, —CN, —SO$_{n11}$R$^{11A}$, —SO$_{v11}$NR$^{11A}$R$^{11B}$, —NHC(O)NR$^{11A}$R$^{11B}$, —N(O)$_{m11}$, —NR$^{11A}$R$^{11B}$, —NHNR$^{11A}$R$^{11B}$, —C(O)R$^{11A}$, —C(O)—OR$^{11A}$, —C(O)NR$^{11A}$R$^{11B}$, —C(O)NHNR$^{11A}$R$^{11B}$, —OR$^{11A}$, —NR$^{11A}$SO$_2$R$^{11B}$, —NR$^{11A}$C(O)R$^{11B}$, —NR$^{11A}$C(O)OR$^{11B}$, —NR$^{11A}$OR$^{11B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{12}$ is selected from hydrogen, halogen, —CX$^{12}_3$, —CHX$^{12}_2$, —CH$_2$X$^{12}$, —OCX$^{12}_3$, —OCH$_2$X$^{12}$, —OCHX$^{12}_2$, —CN, —SO$_{n12}$R$^{12A}$, —SO$_{v12}$NR$^{12A}$R$^{12B}$, —NHC(O)NR$^{12A}$R$^{12B}$, —N(O)$_{m12}$, —NR$^{12A}$R$^{12B}$, —NHNR$^{12A}$R$^{12B}$, —C(O)R$^{12A}$, —C(O)R$^{12A}$, —C(O)NR$^{12A}$R$^{12B}$, —C(O)NHNR$^{12A}$R$^{12B}$, —OR$^{12A}$, —NR$^{12A}$SO$_2$R$^{12B}$, —NR$^{12A}$C(O)R$^{12B}$, —NR$^{12A}$C(O)OR$^{12B}$, —NR$^{12A}$OR$^{12B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{17}$ is selected from hydrogen, halogen, —CX$^{17}_3$, —CHX$^{17}_2$, —CH$_2$X$^{17}$, —OCX$^{17}_3$, —OCH$_2$X$^{17}$, —OCHX$^{17}_2$, —CN, —SO$_{n17}$R$^{17A}$, —SO$_{v17}$NR$^{17A}$R$^{17B}$, —NHC(O)NR$^{17A}$R$^{17B}$, —N(O)$_{m17}$, —NR$^{17A}$R$^{17B}$, —NHNR$^{17A}$R$^{17B}$, —C(O)R$^{17A}$, —(O)—OR$^{17A}$, —C(O)NR$^{17A}$R$^{17B}$, —C(O)NHNR$^{17A}$R$^{17B}$, —OR$^{17A}$, —NR$^{17A}$SO$_2$R$^{17B}$, —NR$^{17A}$C(O)R$^{17B}$, —NR$^{17A}$C(O)OR$^{17B}$, —NR$^{17A}$OR$^{17B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{18}$ is selected from hydrogen, halogen, —CX$^{18}_3$, —CHX$^{18}_2$, —CH$_2$X$^{18}$, —OCX$^{18}_3$, —OCH$_2$X$^{18}$, —OCHX$^{18}_2$, —CN, —SO$_{n18}$R$^{18A}$, —SO$_{v18}$NR$^{18A}$R$^{18B}$, —NHC(O)NR$^{18A}$R$^{18B}$, —N(O)$_{m18}$, —NR$^{18A}$R$^{18B}$, —NHNR$^{18A}$R$^{18B}$, —C(O)R$^{18A}$, —C(O)OR$^{18A}$, —C(O)NR$^{18A}$R$^{18B}$, —C(O)NHNR$^{18A}$R$^{18B}$, —OR$^{18A}$, —NR$^{18A}$SO$_2$R$^{18B}$, —NR$^{18A}$C(O)R$^{18B}$, —NR$^{18A}$C(O)OR$^{18B}$, —NR$^{18A}$OR$^{18B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; or R$^{17}$ and R$^{18}$ substituents join to form a substituted or unsubstituted cycloalkyl or heterocycloalkyl;

R$^{19}$ is selected from hydrogen, halogen, —CX$^{19}_3$, —CHX$^{19}_2$, —CH$_2$X$^{19}$, —OCX$^{19}_3$, —OCH$_2$X$^{19}$, —OCHX$^{19}_2$, —CN, —SO$_{n19}$R$^{19A}$, —SO$_{v19}$NR$^{19A}$R$^{19B}$, —NHC(O)NR$^{19A}$R$^{19B}$, —N(O)$_{m19}$, —NR$^{19A}$R$^{19B}$, —NHNR$^{19A}$R$^{19B}$, —C(O)R$^{19A}$, —(O)—OR$^{19A}$, —C(O)NR$^{19A}$R$^{19B}$, —C(O)NHNR$^{19A}$R$^{19B}$, —OR$^{19A}$, —NR$^{19A}$SO$_2$R$^{19B}$, —NR$^{19A}$C(O)R$^{19B}$, —NR$^{19A}$C(O)OR$^{19B}$, —NR$^{19A}$OR$^{19B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{20}$ is selected from hydrogen, halogen, —CX$^{20}_3$, —CHX$^{20}_2$, —CH$_2$X$^{20}$, —OCX$^{20}_3$, —OCH$_2$X$^{20}$, —OCHX$^{20}_2$, —CN, —SO$_{n20}$R$^{20A}$, —SO$_{v20}$NR$^{20A}$R$^{20B}$, —NHC(O)NR$^{20A}$R$^{20B}$, —N(O)$_{m20}$, —NR$^{20A}$R$^{20B}$, —NHNR$^{20A}$R$^{20B}$, —C(O)R$^{20A}$, —C(O)OR$^{20A}$, —C(O)NR$^{20A}$R$^{20B}$, —C(O)NHNR$^{20A}$R$^{20B}$, —OR$^{20A}$, —NR$^{20A}$SO$_2$R$^{20B}$, —NR$^{20A}$C(O)R$^{20B}$, —NR$^{20A}$C(O)OR$^{20B}$, —NR$^{20A}$OR$^{20B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; or R$^{17}$ and R$^{20}$ substituents join to form a substituted or unsubstituted cycloalkyl or heterocycloalkyl;

R$^{21}$ is selected from hydrogen, halogen, —CX$^{21}_3$, —CHX$^{21}_2$, —CH$_2$X$^{21}$, —OCX$^{21}_3$, —OCH$_2$X$^{21}$, —OCHX$^{21}_2$, —CN, —SO$_{n21}$R$^{21A}$, —SO$_{v21}$NR$^{21A}$R$^{21B}$, —NHC(O)NR$^{21A}$R$^{21B}$, —N(O)$_{m21}$, —NR$^{21A}$R$^{21B}$, —NHNR$^{21A}$R$^{21B}$, —C(O)R$^{21A}$, —(O)—OR$^{21A}$, —C(O)NR$^{21A}$R$^{21B}$, —C(O)NHNR$^{21A}$R$^{21B}$, —OR$^{21A}$, —NR$^{21A}$SO$_2$R$^{21B}$, —NR$^{21A}$C(O)R$^{21B}$, —NR$^{21A}$C(O)OR$^{21B}$, —NR$^{21A}$OR$^{21B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl; or R$^{20}$ and R$^{21}$ substituents join to form a substituted or unsubstituted cycloalkyl or heterocycloalkyl;

R$^{22}$ is selected from hydrogen, halogen, —CX$^{22}_3$, —CHX$^{22}_2$, —CH$_2$X$^{22}$, —OCX$^{22}_3$, —OCH$_2$X$^{22}$, —OCHX$^{22}_2$, —CN, —SO$_{n22}$R$^{22A}$, —SO$_{v22}$NR$^{22A}$R$^{22B}$, —NHC(O)NR$^{22A}$R$^{22B}$, —N(O)$_{m22}$, —NR$^{22A}$R$^{22B}$, —NHNR$^{22A}$R$^{22B}$, —C(O)R$^{22A}$, —C(O)R$^{22A}$, —C(O)NR$^{22A}$R$^{22B}$, —C(O)NHNR$^{22A}$R$^{22B}$, —OR$^{22A}$, —NR$^{22A}$SO$_2$R$^{22B}$, —NR$^{22A}$C(O)R$^{22B}$, —NR$^{22A}$C(O)OR$^{22B}$, —NR$^{22A}$OR$^{22B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{23}$ is selected from hydrogen, halogen, —CX$^{23}_3$, —CHX$^{23}_2$, —CH$_2$X$^{23}$, —OCX$^{23}_3$, —OCH$_2$X$^{23}$, —OCHX$^{23}_2$, —CN, —SO$_{n23}$R$^{23A}$, —SO$_{v23}$NR$^{23A}$R$^{23B}$, —NHC(O)NR$^{23A}$R$^{23B}$, —N(O)$_{m23}$, —NR$^{23A}$R$^{23B}$, —NHNR$^{23A}$R$^{23B}$, —C(O)R$^{23A}$, —C(O)R$^{23A}$, —C(O)NR$^{23A}$R$^{23B}$, —C(O)NHNR$^{23A}$R$^{23B}$, —OR$^{23A}$, —NR$^{23A}$SO$_2$R$^{23B}$, —NR$^{23A}$C(O)R$^{23B}$, —NR$^{23A}$C(O)OR$^{23B}$, —NR$^{23A}$OR$^{23B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{24}$ is selected from hydrogen, halogen, —CX$^{24}_3$, —CHX$^{24}_2$, —CH$_2$X$^{24}$, —OCX$^{24}_3$, —OCH$_2$X$^{24}$, —OCHX$^{24}_2$, —CN, —SO$_{n24}$R$^{24A}$, —SO$_{v24}$NR$^{24A}$R$^{24B}$, —NHC(O)NR$^{24A}$R$^{24B}$, —N(O)$_{m24}$, —NR$^{24A}$R$^{24B}$, —NHNR$^{24A}$R$^{24B}$, —C(O)R$^{24A}$, —C(O)—OR$^{24A}$, —C(O)NR$^{24A}$R$^{24B}$, —C(O)NHNR$^{24A}$R$^{24B}$, —OR$^{24A}$, —NR$^{24A}$SO$_2$R$^{24B}$, —NR$^{24A}$C(O)R$^{24B}$, —NR$^{24A}$C(O)OR$^{24B}$, —NR$^{24A}$OR$^{24B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{25}$ is selected from hydrogen, halogen, —CX$^{25}_3$, —CHX$^{25}_2$, —CH$_2$X$^{25}$, —OCX$^{25}_3$, —OCH$_2$X$^{25}$, —OCHX$^{25}_2$, —CN, —SO$_{n25}$R$^{25A}$, —SO$_{v25}$NR$^{25A}$R$^{25B}$, —NHC(O)NR$^{25A}$R$^{25B}$, —N(O)$_{m25}$, —NR$^{25A}$R$^{25B}$, —NHNR$^{25A}$R$^{25B}$, —C(O)R$^{25A}$, —C(O)R$^{25A}$, —C(O)NR$^{25A}$R$^{25B}$, —C(O)NHNR$^{25A}$R$^{25B}$, —OR$^{25A}$, —NR$^{25A}$SO$_2$R$^{25B}$, —NR$^{25A}$C(O)R$^{25B}$, —NR$^{25A}$C(O)OR$^{25B}$, —NR$^{25A}$OR$^{25B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{26}$ is selected from hydrogen, halogen, —CX$^{26}_3$, —CHX$^{26}_2$, —CH$_2$X$^{26}$, —OCX$^{26}_3$, —OCH$_2$X$^{26}$, —OCHX$^{26}_2$, —CN, —SO$_{n26}$R$^{26A}$, —SO$_{v26}$NR$^{26A}$R$^{26B}$, —NHC(O)NR$^{26A}$R$^{26B}$, —N(O)$_{m26}$, —NR$^{26A}$R$^{26B}$, —NHNR$^{26A}$R$^{26B}$, —C(O)R$^{26A}$, —(O)—OR$^{26A}$, —C(O)NR$^{26A}$R$^{26B}$, —C(O)NHNR$^{26A}$R$^{26B}$, —OR$^{26A}$, —NR$^{26A}$SO$_2$R$^{26B}$, —NR$^{26A}$C(O)R$^{26B}$, —NR$^{26A}$C(O)OR$^{26B}$, —NR$^{26A}$OR$^{26B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{27}$ is selected from hydrogen, halogen, —CX$^{27}_3$, —CHX$^{27}_2$, —CH$_2$X$^{27}$, —OCX$^{27}_3$, —OCH$_2$X$^{27}$, —OCHX$^{27}_2$, —CN, —SO$_{n27}$R$^{27A}$, —SO$_{v27}$NR$^{27A}$R$^{27B}$, —NHC(O)NR$^{27A}$R$^{27B}$, —N(O)$_{m27}$, —NR$^{27A}$R$^{27B}$, —NHNR$^{27A}$R$^{27B}$, —C(O)R$^{27A}$, —C(O)R$^{27A}$, —C(O)NR$^{27A}$R$^{27B}$, —C(O)NHNR$^{27A}$R$^{27B}$, —OR$^{27A}$, —NR$^{27A}$SO$_2$R$^{27B}$, —NR$^{27A}$C(O)R$^{27B}$, —NR$^{27A}$C(O)OR$^{27B}$, —NR$^{27A}$OR$^{27B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{28}$ is selected from hydrogen, halogen, —CX$^{28}_3$, —CHX$^{28}_2$, —CH$_2$X$^{28}$, —OCX$^{28}_3$, —OCH$_2$X$^{28}$, —OCHX$^{28}_2$, —CN, —SO$_{n28}$R$^{28A}$, —SO$_{v28}$NR$^{28A}$R$^{28B}$, —NHC(O)NR$^{28A}$R$^{28B}$, —N(O)$_{m28}$, —NR$^{28A}$R$^{28B}$, —NHNR$^{28A}$R$^{28B}$, —C(O)R$^{28A}$, —C(O)—OR$^{28A}$, —C(O)NR$^{28A}$R$^{28B}$, —C(O)NHNR$^{28A}$R$^{28B}$, —OR$^{28A}$, —NR$^{28A}$SO$_2$R$^{28B}$, —NR$^{28A}$C(O)R$^{28B}$, —NR$^{28A}$C(O)OR$^{28B}$, —NR$^{28A}$OR$^{28B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted and unsubstituted heteroaryl;

R$^{29}$ is selected from hydrogen, halogen, —CX$^{29}_3$, —CHX$^{29}_2$, —CH$_2$X$^{29}$, —OCX$^{29}_3$, —OCH$_2$X$^{29}$, —OCHX$^{29}_2$, —CN, —SO$_{n29}$R$^{29A}$, —SO$_{v29}$NR$^{29A}$R$^{29B}$, —NHC(O)NR$^{29A}$R$^{29B}$, —N(O)$_{m29}$, —NR$^{29A}$R$^{29B}$, —NHNR$^{29A}$R$^{29B}$, —C(O)R$^{29A}$, —(O)—OR$^{29A}$, —C(O)NR$^{29A}$R$^{29B}$, —C(O)NHNR$^{29A}$R$^{29B}$, —OR$^{29A}$, —NR$^{29A}$SO$_2$R$^{29B}$, —NR$^{29A}$C(O)R$^{29B}$, —NR$^{29A}$C(O)OR$^{29B}$, —NR$^{29A}$OR$^{29B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{30}$ is selected from hydrogen, halogen, —CX$^{30}_3$, —CHX$^{30}_2$, —CH$_2$X$^{30}$, —OCX$^{30}_3$, —OCH$_2$X$^{30}$, —OCHX$^{30}_2$, —CN, —SO$_{n30}$R$^{30A}$, —SO$_{v30}$NR$^{30A}$R$^{30B}$, —NHC(O)NR$^{30A}$R$^{30B}$, —N(O)$_{m30}$, —NR$^{30A}$R$^{30B}$, —NHNR$^{30A}$R$^{30B}$, —C(O)R$^{30A}$, —C(O)OR$^{30A}$, —C(O)NR$^{30A}$R$^{30B}$, —C(O)NHNR$^{30A}$R$^{30B}$, —OR$^{30A}$, —NR$^{30A}$SO$_2$R$^{30B}$, —NR$^{30A}$C(O)R$^{30B}$, —NR$^{30A}$C(O)OR$^{30B}$, —NR$^{30A}$OR$^{30B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

Each R$^{3A}$, R$^{3B}$, R$^{4A}$, R$^{4B}$, R$^{6A}$, R$^{6B}$, R$^{7A}$, R$^{7B}$, R$^{10A}$, R$^{10B}$, R$^{11A}$, R$^{11B}$, R$^{12A}$, R$^{12B}$, R$^{17A}$, R$^{17B}$, R$^{18A}$, R$^{18B}$, R$^{19A}$, R$^{19B}$, R$^{20A}$, R$^{20B}$, R$^{21A}$, R$^{21B}$, R$^{22A}$, R$^{22B}$, R$^{23A}$, R$^{23B}$, R$^{24A}$, R$^{24B}$, R$^{25A}$, R$^{25B}$, R$^{26A}$, R$^{26B}$, R$^{27A}$, R$^{27B}$, R$^{28A}$, R$^{28B}$, R$^{29A}$, R$^{29B}$, R$^{30A}$, and R$^{30B}$ is independently selected from hydrogen, —CX$_3$, —CHX$_2$, —CH$_2$X, —C(O)OH, —C(O)NH$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$_3$, —OCHX$_2$, —OCH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^{4A}$ and R$^{4B}$ substituents bonded to the same nitrogen atom may optionally be joined to form a substituted or unsubstituted heterocycloalkyl or substituted or unsubstituted heteroaryl; R$^{6A}$ and R$^{6B}$ substituents bonded to the same nitrogen atom may optionally be joined to form a substituted or unsubstituted heterocycloalkyl or substituted or unsubstituted heteroaryl; R$^{7A}$ and R$^{7B}$ substituents bonded to the same nitrogen atom may optionally be joined to form a substituted or unsubstituted heterocycloalkyl or substituted or unsubstituted heteroaryl; R$^{17A}$ and R$^{17B}$ substituents bonded to the same nitrogen atom may optionally be joined to form a substituted or unsubstituted heterocycloalkyl or substituted or unsubstituted heteroaryl; R$^{18A}$ and R$^{18B}$ substituents bonded to the same nitrogen atom may optionally be joined to form a substituted or unsubstituted heterocycloalkyl or substituted or unsubstituted heteroaryl; R$^{19A}$ and R$^{19B}$ substituents bonded to the same nitrogen atom may optionally be joined to form a substituted or unsubstituted heterocycloalkyl or substituted or unsubstituted heteroaryl; R$^{20A}$ and R$^{20B}$ substituents bonded to the same nitrogen atom may optionally be joined to form a substituted or unsubstituted heterocycloalkyl or substituted or unsubstituted heteroaryl; R$^{21A}$ and R$^{21B}$ substituents bonded to the same nitrogen atom may optionally be joined to form a substituted or unsubstituted heterocycloalkyl or substituted or unsubstituted heteroaryl; R$^{22A}$ and R$^{22B}$ substituents bonded to the same nitrogen atom may optionally be joined to form a substituted or unsubstituted heterocycloalkyl or substituted or unsubstituted heteroaryl; $R^{23A}$ and $R^{23B}$ substituents bonded to the same nitrogen atom may optionally be joined to form a substituted or unsubstituted heterocycloalkyl or substituted or unsubstituted heteroaryl; $R^{24A}$ and $R^{24B}$ substituents bonded to the same nitrogen atom may optionally be joined to form a substituted or unsubstituted heterocycloalkyl or substituted or unsubstituted heteroaryl; $R^{25A}$ and $R^{25B}$ substituents bonded to the same nitrogen atom may optionally be joined to form a substituted or unsubstituted heterocycloalkyl or substituted or unsubstituted heteroaryl; $R^{26A}$ and $R^{26B}$ substituents bonded to the same nitrogen atom may optionally be joined to form a substituted or unsubstituted heterocycloalkyl or substituted or unsubstituted heteroaryl; $R^{27A}$ and $R^{27B}$ substituents bonded to the same nitrogen atom may optionally be joined to form a substituted or unsubstituted heterocycloalkyl or substituted or unsubstituted heteroaryl; $R^{28A}$ and $R^{28B}$ substituents bonded to the same nitrogen atom may optionally be joined to form a substituted or unsubstituted heterocycloalkyl or substituted or unsubstituted heteroaryl; $R^{29A}$ and $R^{29B}$ substituents bonded to the same nitrogen atom may optionally be joined to form a substituted or unsubstituted heterocycloalkyl or substituted or unsubstituted heteroaryl; $R^{30A}$ and $R^{30B}$ substituents bonded to the same nitrogen atom may optionally be joined to form a substituted or unsubstituted heterocycloalkyl or substituted or unsubstituted heteroaryl;

Each m4, m4, m6, m7, m10, m11, m12, m17, m18, m19, m20, m21, m22, m23, m24, m25, m26, m27, m28, m29, and m30 is independently 1 or 2;

Each v3, v4, v6, v7, v10, v11, v12, v17, v18, v19, v20, v21, v22, v23, v24, v25, v26, v27, v28, v29, and v30 is independently 1 or 2;

Each n3, n4, n6, n7, n10, n11, n12, n17, n18, n19, n20, n21, n22, n23, n24, n25, n26, n27, n28, n29, and n30 is independently an integer from 0 to 2; and Each $X^3$, $X^4$, $X^6$, $X^7$, $X^{10}$, $X^{11}$, $X^{12}$, $X^{17}$, $X^{18}$, $X^{19}$, $X^{20}$, $X^{21}$, $X^{22}$, $X^{23}$, $X^{24}$, $X^{25}$, $X^{26}$, $X^{27}$, $X^{28}$, $X^{29}$, and $X^{30}$ is independently —Cl, —Br, —I or —F.

9. Compound of claim 8 wherein ring B is selected from thienyl, furanyl, pyrrolyl, thiazolyl, oxazolyl, imidazolyl, pyrazolyl, isoxazolyl, triazolyl and isothiazolyl, wherein Ring B is optionally substituted with one or more substituents.

10. Compound of claim 8 wherein ring B is selected from phenyl, pyridyl, pyrazinyl, pyrimidinyl, pyridazinyl, and triazinyl, wherein ring B is optionally substituted with one or more substituent groups.

11. Compound of claim 8 wherein ring B is selected from

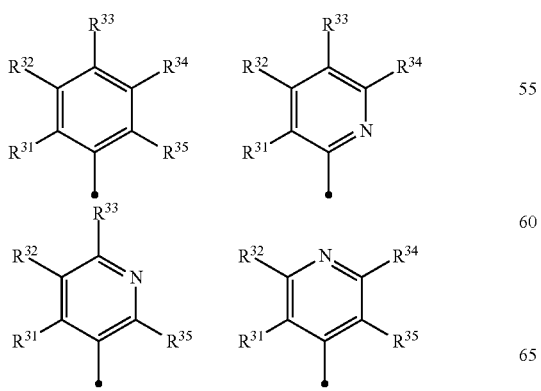

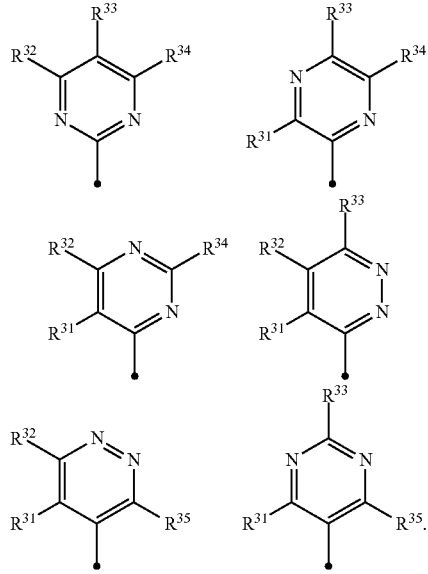

$R^{31}$ is selected from hydrogen, halogen, —$CX^{31}_3$, —$CHX^{31}_2$, —$CH_2X^{31}$, —$OCX^{31}_3$, —$OCH_2X^{31}$, —$OCHX^{31}_2$, —CN, —$SO_{n31}R^{31A}$, —$SO_{v31}NR^{31A}R^{31B}$, —NHC(O)$NR^{31A}R^{31B}$, —$N(O)_{m31}$, —$NR^{31A}R^{31B}$, —$NHNR^{31A}R^{31B}$, —C(O)$R^{31A}$, —C(O)$OR^{31A}$, —C(O)$NR^{31A}R^{31B}$, —C(O)$NHNR^{31A}R^{31B}$, —$OR^{31A}$, —$NR^{31A}SO_2R^{31B}$, —$NR^{31A}C(O)R^{31B}$, —$NR^{31A}C(O)OR^{31B}$, —$NR^{31A}OR^{31B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{32}$ is selected from hydrogen, halogen, —$CX^{32}_3$, —$CHX^{32}_2$, —$CH_2X^{32}$, —$OCX^{32}_3$, —$OCH_2X^{32}$, —$OCHX^{32}_2$, —CN, —$SO_{n32}R^{32A}$, —$SO_{v32}NR^{32A}R^{32B}$, —NHC(O)$NR^{32A}R^{32B}$, —$N(O)_{m32}$, —$NR^{32A}R^{32B}$, —$NHNR^{32A}R^{32B}$, —C(O)$R^{32A}$, —C(O)$OR^{32A}$, —C(O)$NR^{32A}R^{32B}$, —C(O)$NHNR^{32A}R^{32B}$, —$OR^{32A}$, —$NR^{32A}SO_2R^{32B}$, —$NR^{32A}C(O)R^{32B}$, —$NR^{32A}C(O)OR^{32B}$, —$NR^{32A}OR^{32B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted and unsubstituted heteroaryl;

$R^{33}$ is selected from hydrogen, halogen, —$CX^{33}_3$, —$CHX^{33}_2$, —$CH_2X^{33}$, —$OCX^{33}_3$, —$OCH_2X^{33}$, —$OCHX^{33}_2$, —CN, —$SO_{n33}R^{33A}$, —$SO_{v33}NR^{33A}R^{33B}$, —NHC(O)$NR^{33A}R^{33B}$, —$N(O)_{m33}$, —$NR^{33A}R^{33B}$, —$NHNR^{33A}R^{33B}$, —C(O)$R^{33A}$, —C(O)$OR^{33A}$, —C(O)$NR^{33A}R^{33B}$, —C(O)$NHNR^{33A}R^{33B}$, —$OR^{33A}$, —$NR^{33A}SO_2R^{33B}$, —$NR^{33A}C(O)R^{33B}$, —$NR^{33A}C(O)OR^{33B}$, —$NR^{33A}OR^{33B}$, —$N_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

$R^{34}$ is selected from hydrogen, halogen, —$CX^{34}_3$, —$CHX^{34}_2$, —$CH_2X^{34}$, —$OCX^{34}_3$, —$OCH_2X^{34}$, —$OCHX^{34}_2$, —CN, —$SO_{n34}R^{34A}$, —SO$_{v34}$NR$^{34A}$R$^{34B}$, —NHC(O)NR$^{34A}$R$^{34B}$, —N(O)$_{m34}$, —NR$^{34A}$R$^{34B}$, —NHNR$^{34A}$R$^{34B}$, —C(O)R$^{34A}$, —C(O)—OR$^{34A}$, —C(O)NR$^{34A}$R$^{34B}$, —C(O)NHNR$^{34A}$R$^{34B}$, —OR$^{34A}$, —NR$^{34A}$SO$_2$R$^{34B}$, —NR$^{34A}$C(O)R$^{34B}$, —NR$^{34A}$C(O)OR$^{34B}$, —NR$^{34A}$OR$^{34B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

R$^{35}$ is selected from hydrogen, halogen, —CX$^{35}$$_3$, —CHX$^{35}$$_2$, —CH$_2$X$^{35}$, —OCX$^{35}$$_3$, —OCH$_2$X$^{35}$, —OCHX$^{35}$$_2$, —CN, —SO$_{n35}$R$^{35A}$, —SO$_{v35}$NR$^{35A}$R$^{35B}$, —NHC(O)NR$^{35A}$R$^{35B}$, —N(O)$_{m35}$, —NR$^{35A}$R$^{35B}$, —NHNR$^{35A}$R$^{35B}$, —C(O)R$^{35A}$, —C(O)OR$^{35A}$, —C(O)NR$^{35A}$R$^{35B}$, —C(O)NHNR$^{35A}$R$^{35B}$, —OR$^{35A}$, —NR$^{35A}$SO$_2$R$^{35B}$, —NR$^{35A}$C(O)R$^{35B}$, —NR$^{35A}$C(O)OR$^{35B}$, —NR$^{35A}$OR$^{35B}$, —N$_3$, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl;

Each R$^{31A}$, R$^{31B}$, R$^{32A}$, R$^{32B}$, R$^{33A}$, R$^{33B}$, R$^{34A}$, R$^{34B}$, R$^{35A}$, and R$^{35B}$ is independently selected from hydrogen, —CX$_3$, —CHX$_2$, —CH$_2$X, —C(O)OH, —C(O)NH$_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)OH, —NHOH, —OCX$_3$, —OCHX$_2$, —OCH$_2$X, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

Each m31, m32, m33, m34, and m35 is independently 1 or 2;

Each v31, v32, v33, v34, and v35 is independently 1 or 2;

Each n31, n32, n33, n34, and n35 is independently an integer from 0 to 2; and

Each X31, X32, X33, X34, and X35 is independently C, Br, I or —F.

12. Compound of claim 8 wherein ring B is selected from benzothienyl, benzothiazolyl, indolyl, benzimidazolyl, benzoxazolyl, benzofuryl, indazolyl and isolindolyl, wherein ring B is optionally substituted with one or more substituent groups.

13. Compound of claim 8 wherein ring B is selected from quinolyl, isoquinolyl, naphthpyridinyl, quinoxalinyl and quinazolinyl, wherein ring B is optionally substituted with one or more substituent groups.

14. Compound of claim 8 wherein E is selected from —C(=O)CH=CH$_2$, —C(=O)-ethynyl, —C(=O)CH=CHCF$_3$, —C(=O)CH=CHCHF$_2$, —C(=O)CH=CHCH$_2$F, 4-(dimethylamino)but-2-en-1-one and —C(=O)CH$_2$Br.

15. Compound of claim 8 wherein W is S.

16. Compound of claim 8 wherein R$^{10}$ is selected from hydrogen, fluoro, chloro, substituted or unsubstituted C$_{1-6}$ alkyl, substituted or unsubstituted C$_{1-6}$ heteroalkyl, substituted or unsubstituted C$_{3-6}$ cycloalkyl, substituted or unsubstituted 3-6 membered heterocycloalkyl, substituted or unsubstituted 6-10 membered aryl, and substituted or unsubstituted 5-10 membered heteroaryl; and R$^{11}$ is selected from hydrogen, fluoro, chloro, substituted or unsubstituted C$_{1-6}$ alkyl, substituted or unsubstituted C$_{1-6}$ heteroalkyl, substituted or unsubstituted C$_{3-6}$ cycloalkyl, substituted or unsubstituted 3-6 membered heterocycloalkyl, substituted or unsubstituted 6-10 membered aryl, and substituted or unsubstituted 5-10 membered heteroaryl.

17. A pharmaceutical composition, comprising the compound of claim 1 or the pharmaceutically acceptable salt thereof and at least one pharmaceutically acceptable excipient.

18. A method of inhibiting E1 in a subject in need thereof, said method comprising administering to said subject a therapeutically effective amount of a compound of claim 1.

19. The method of claim 18 wherein said compound is administered at a rate approximately equal to the half life of an E1 enzyme.

20. The method of claim 18, wherein said compound is covalently attached to an E1 cysteine amino acid corresponding to Cys30 of Uba2 subunit 2.

21. The method of claim 18, wherein E comprises an electrophilic moiety.

22. The method of claim 18, wherein E contains a moiety that is at least sufficiently electron withdrawing to allow said compound to covalently bind to an E1 cysteine amino acid corresponding to Cys30 of Uba2 subunit 2, wherein said E1 acysteine amino acid is bound to carbon attached to R$^{17}$ and R$^{19}$.

23. The method of claim 18, wherein said compound covalently binds to an E1 cysteine amino acid corresponding to Cys30 of Uba2 subunit 2; and forms a complex of formula:

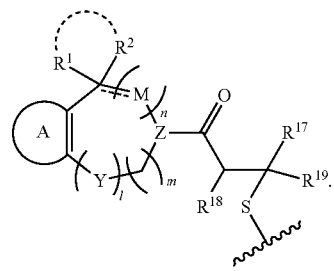

24. A method of treating cancer in a subject in need thereof, said method comprising administering to said subject a therapeutically effective amount of a compound of claim 1.

25. A method of inhibiting cell proliferation in a subject in need thereof, said method comprising administering to said subject a therapeutically effective amount of a compound of claim 1.

26. The method of claim 25 wherein the cancer is selected from multiple myeloma, head and neck cancer, stomach cancer, renal cancer, prostate cancer, melanoma or endometrial cancer.

27. The method of claim 25 wherein the cancer is Non-Hodgkins Lymphoma (NHL).

28. A method of identifying novel druggable sites in a therapeutic target protein, said method comprising contacting the therapeutic target protein with a compound of claim 1.

29. The compound of claim 1 wherein M is CR$^3$R$^4$.

30. The compound of claim 1 wherein Y is CR$^6$R$^7$.

31. The compound of claim 1 wherein E is
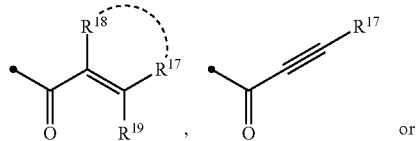, 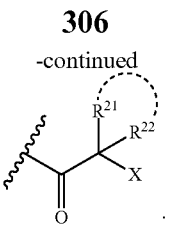 or
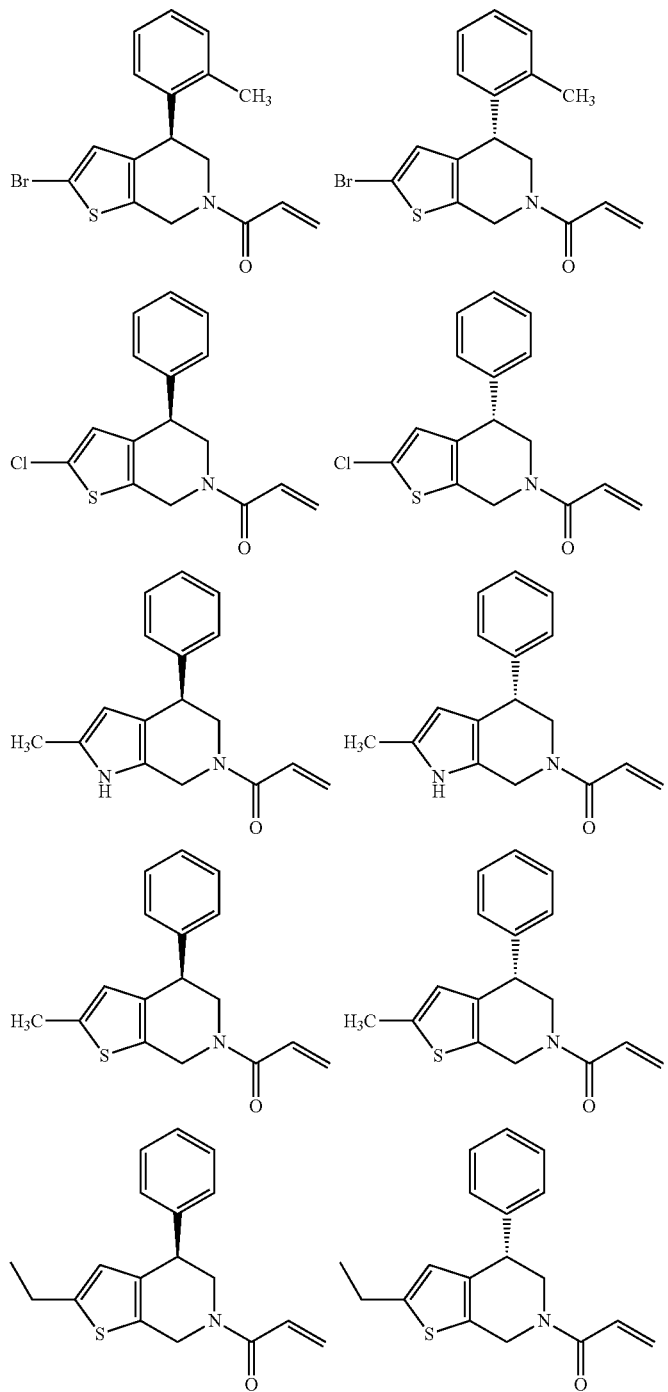
32. The compound of claim 1 selected from

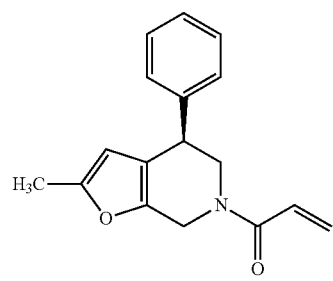 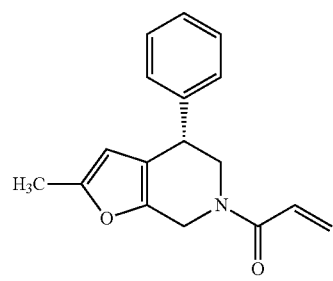
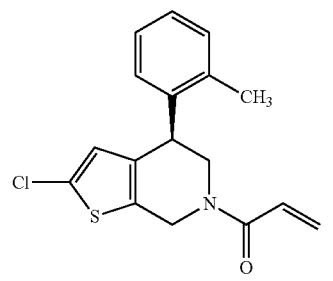 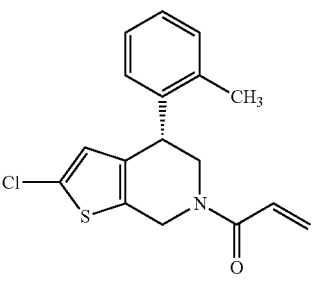
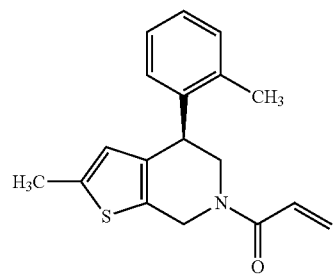 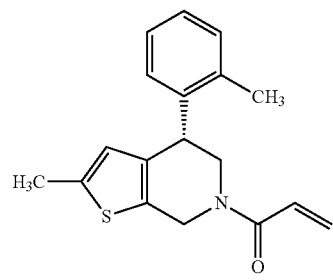
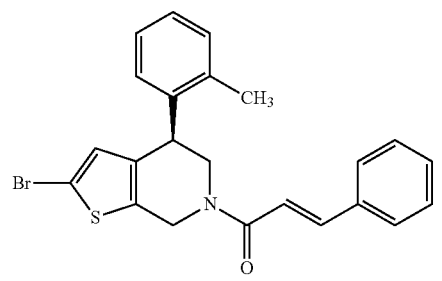 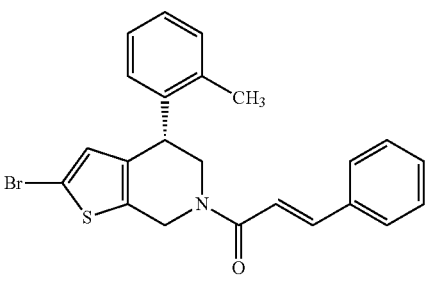
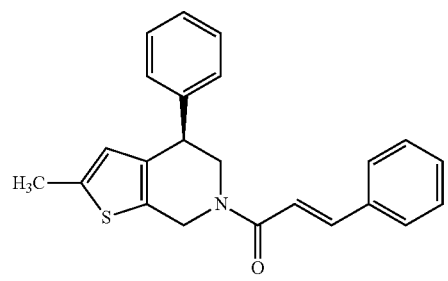 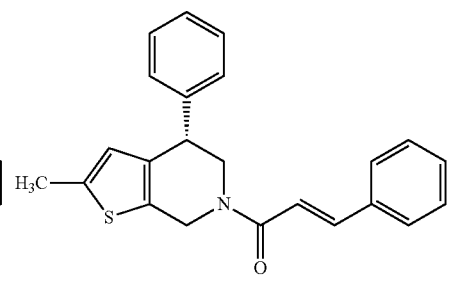
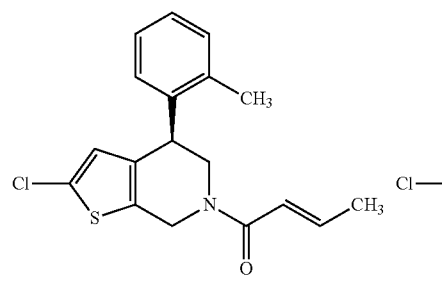 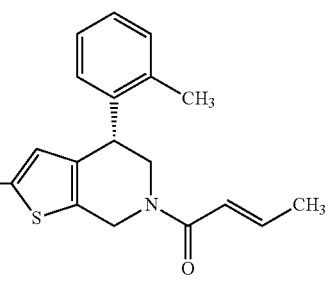

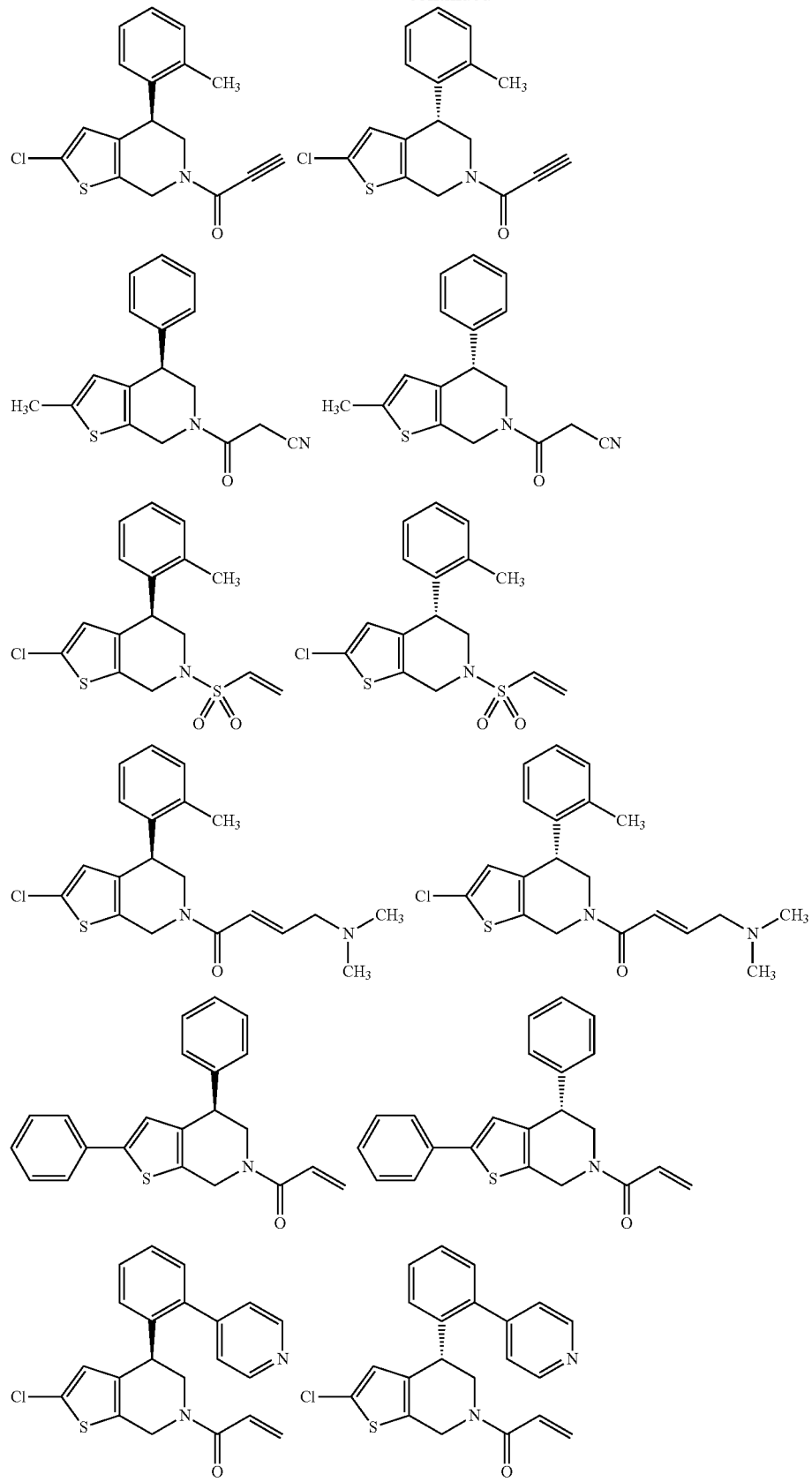

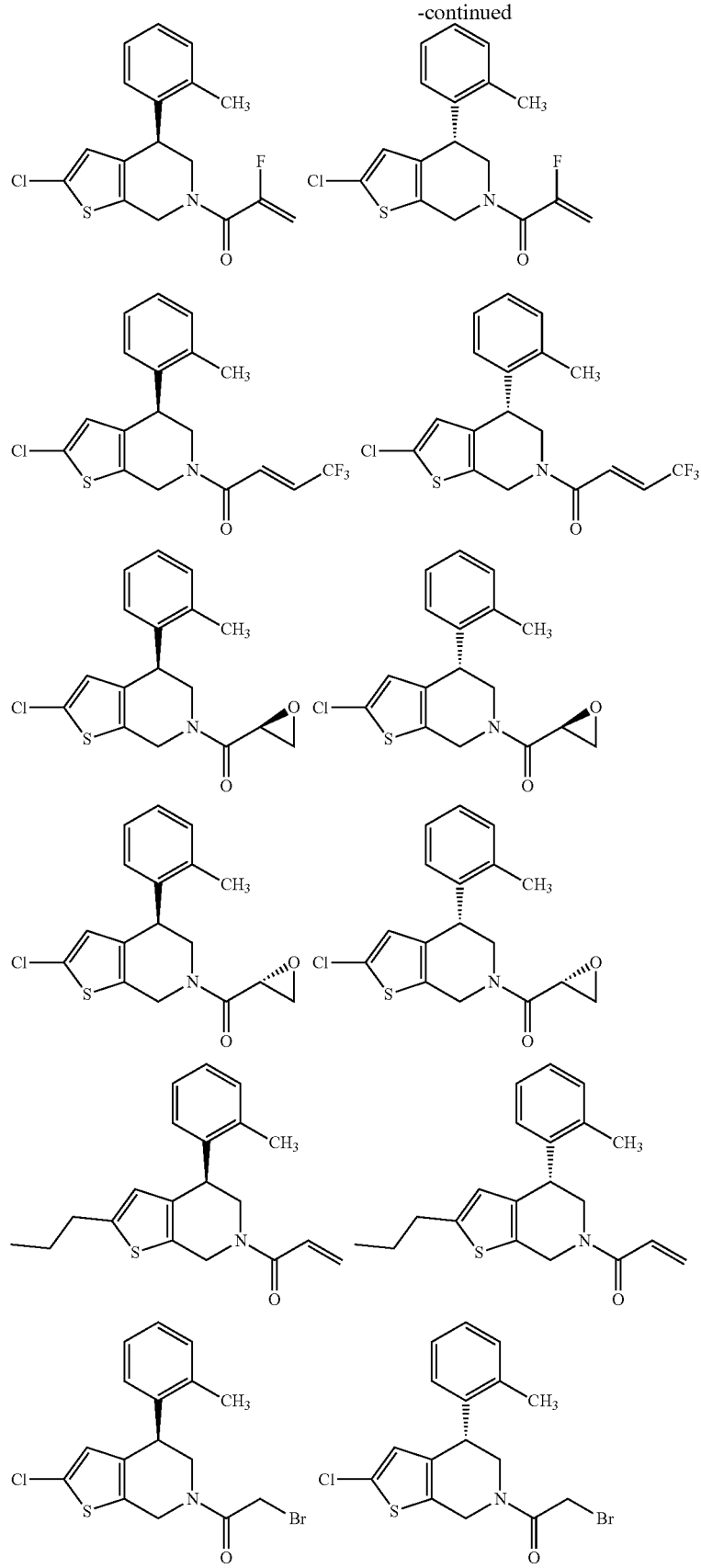

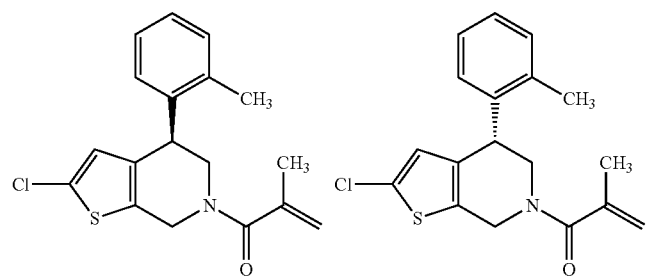
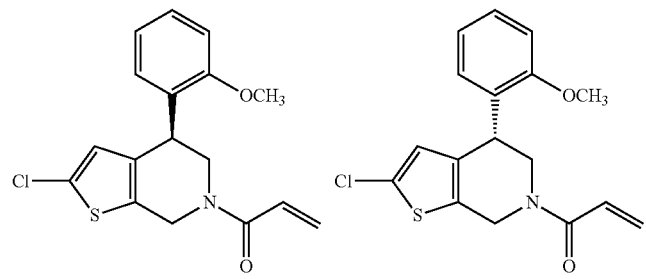
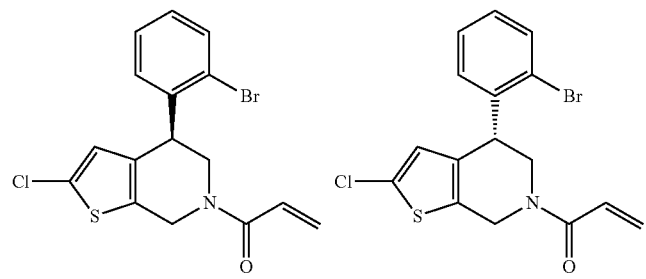
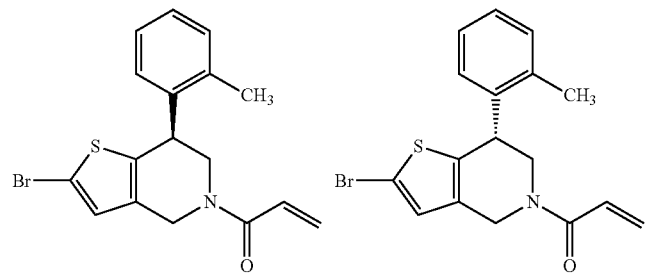
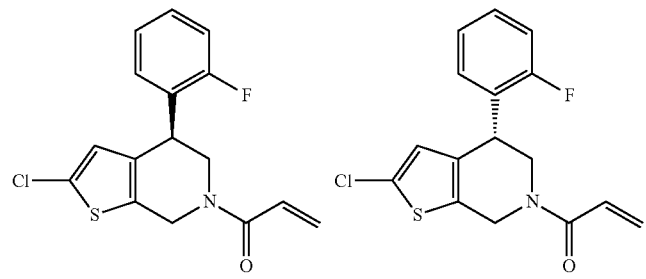

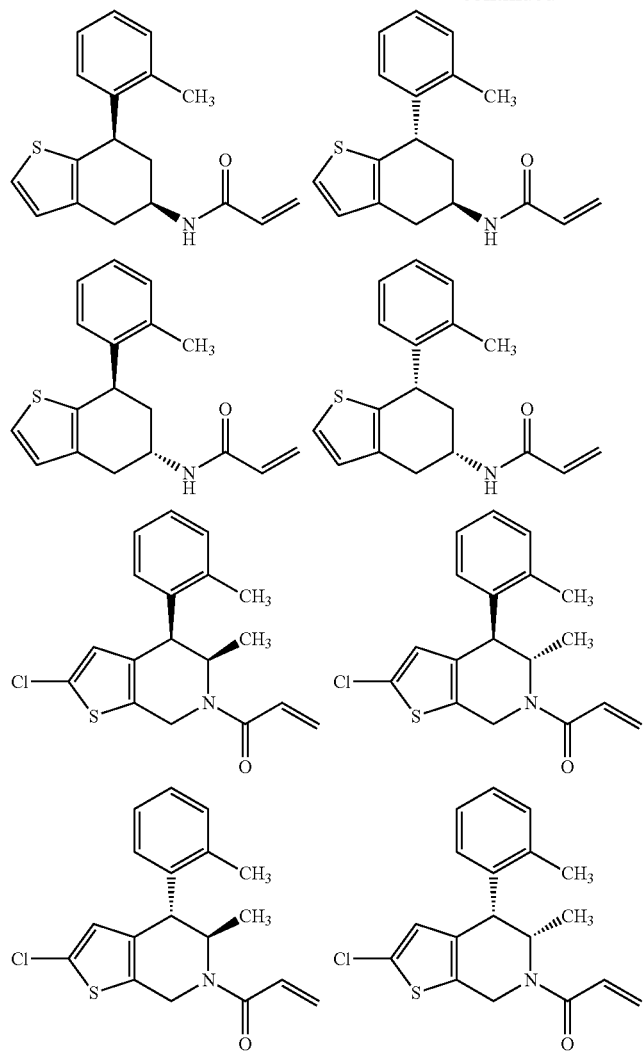
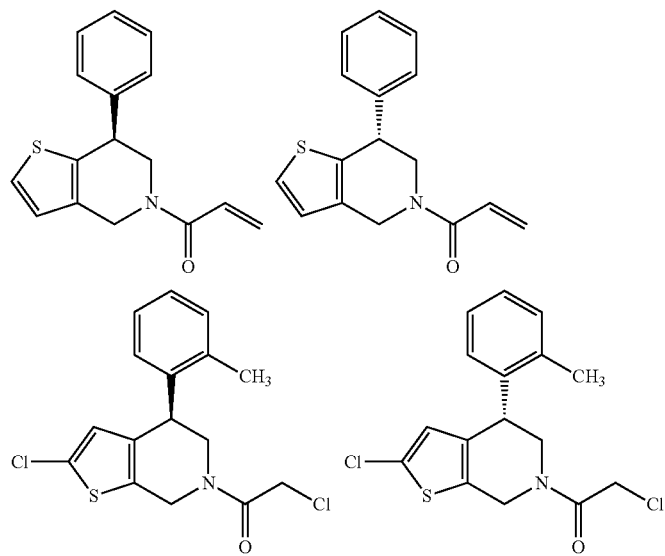

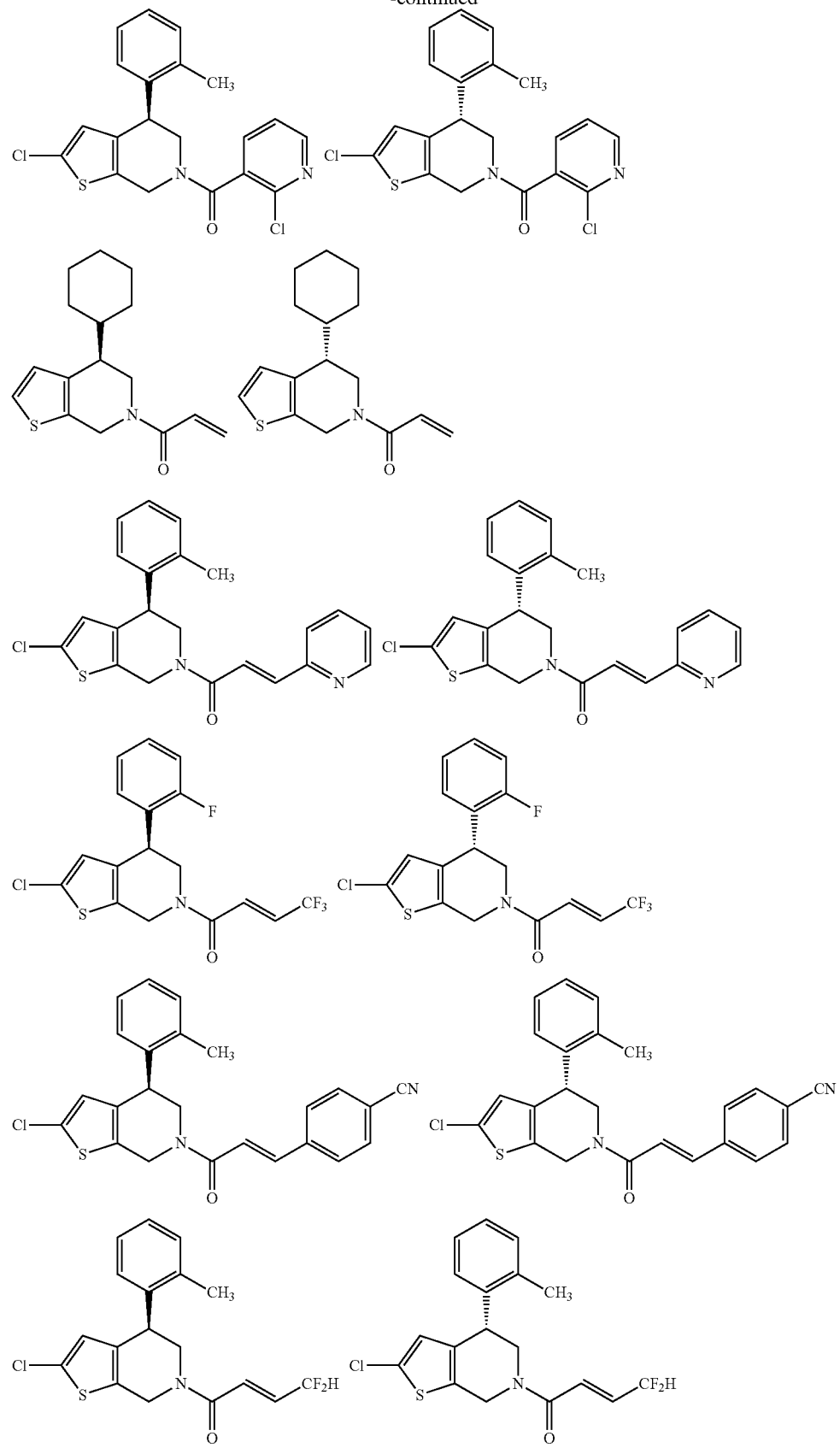

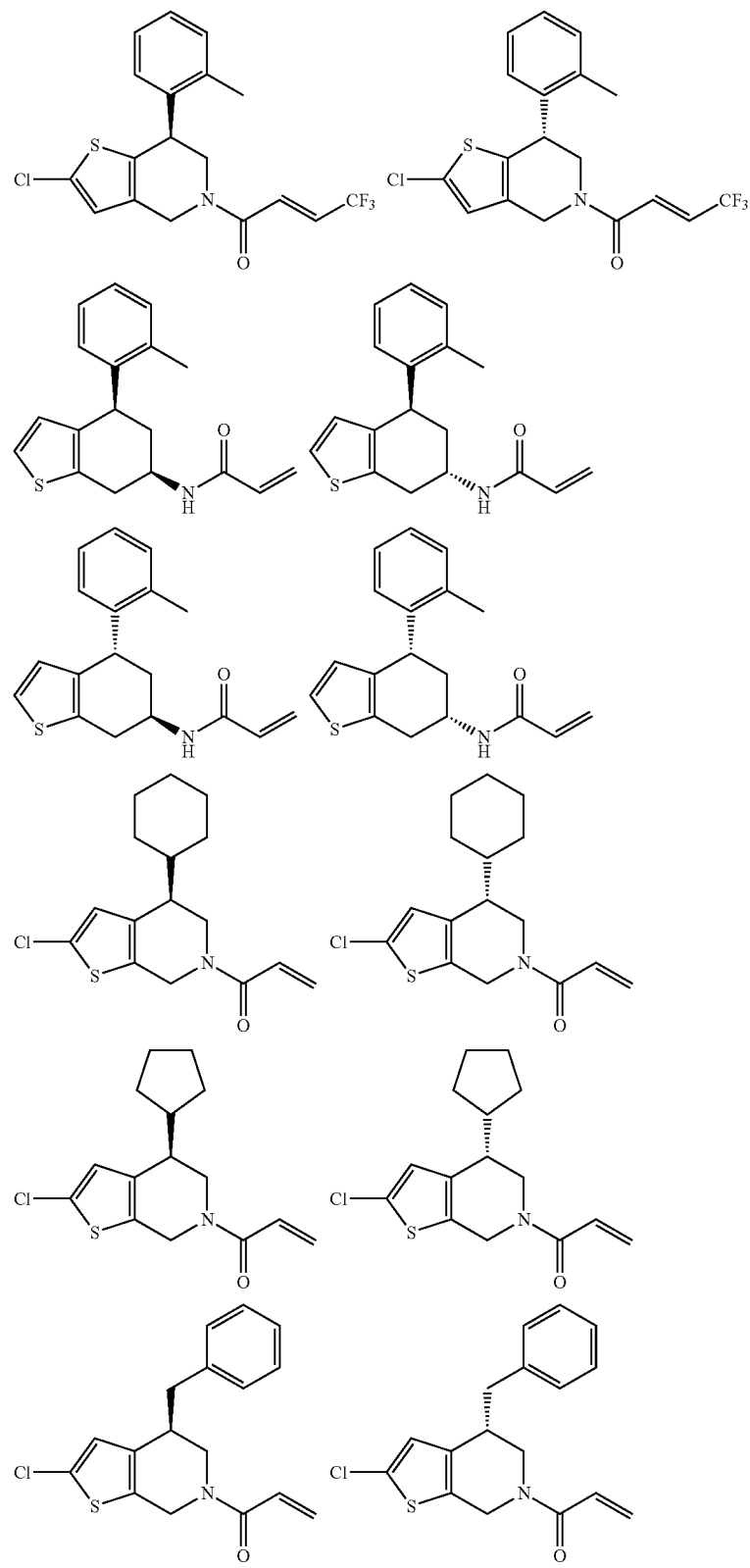

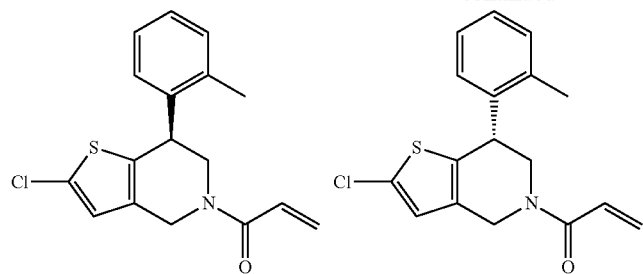
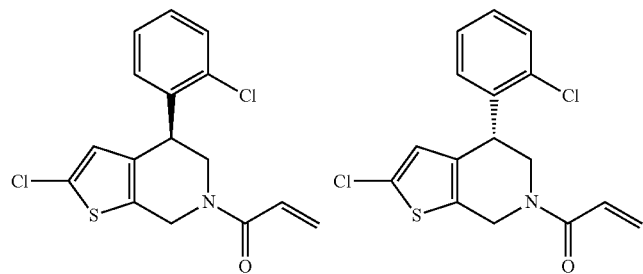
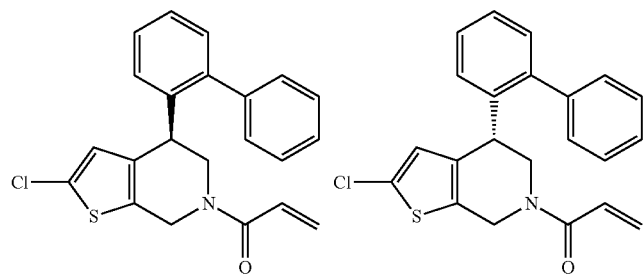
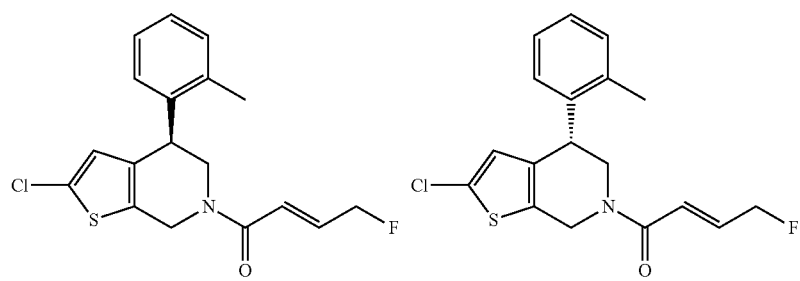
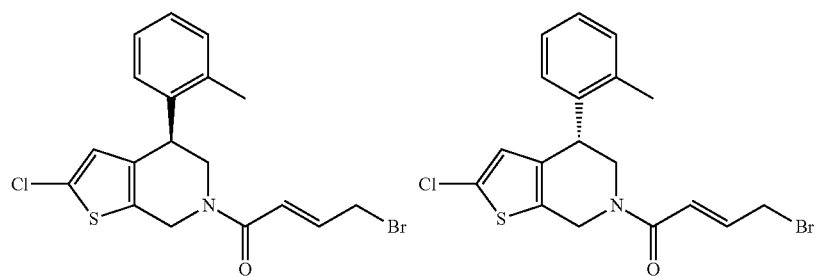

-continued
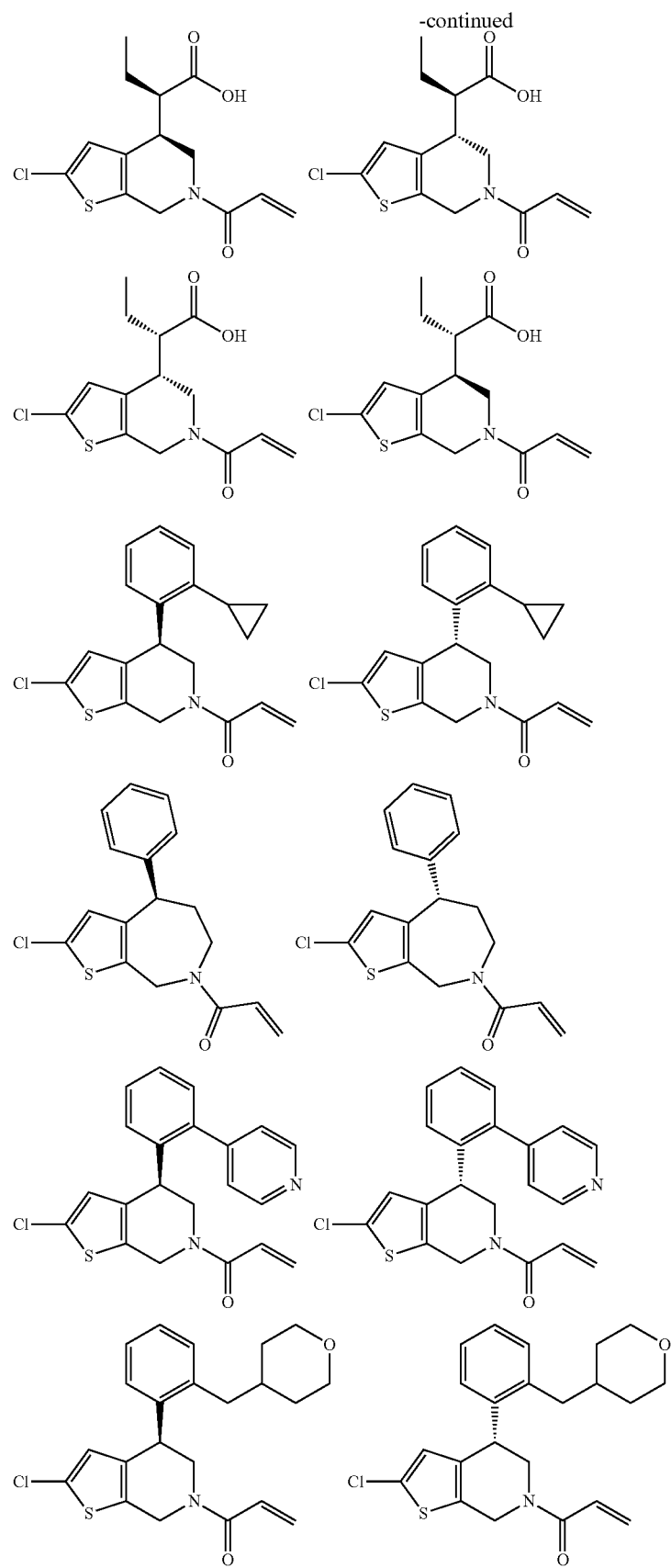

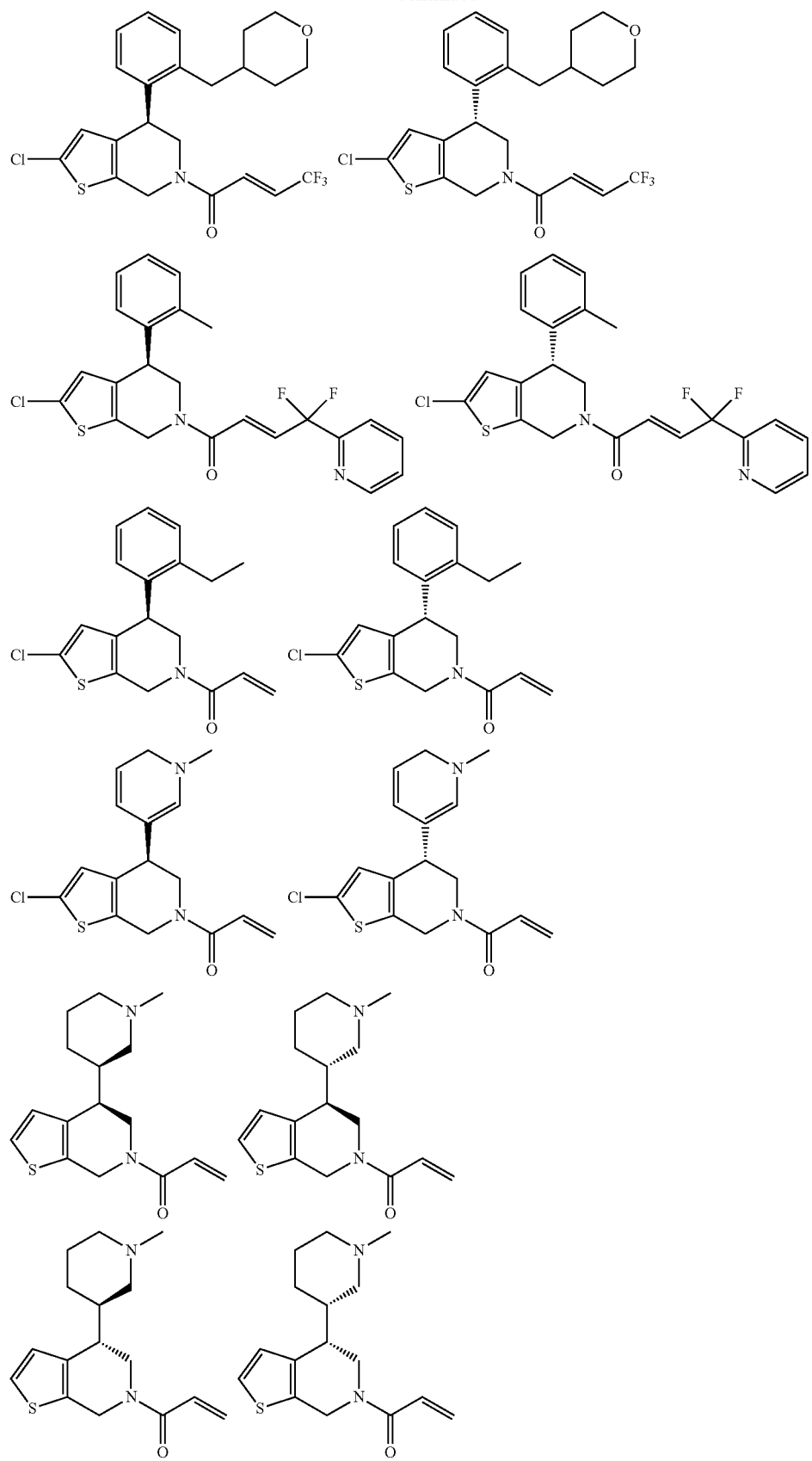

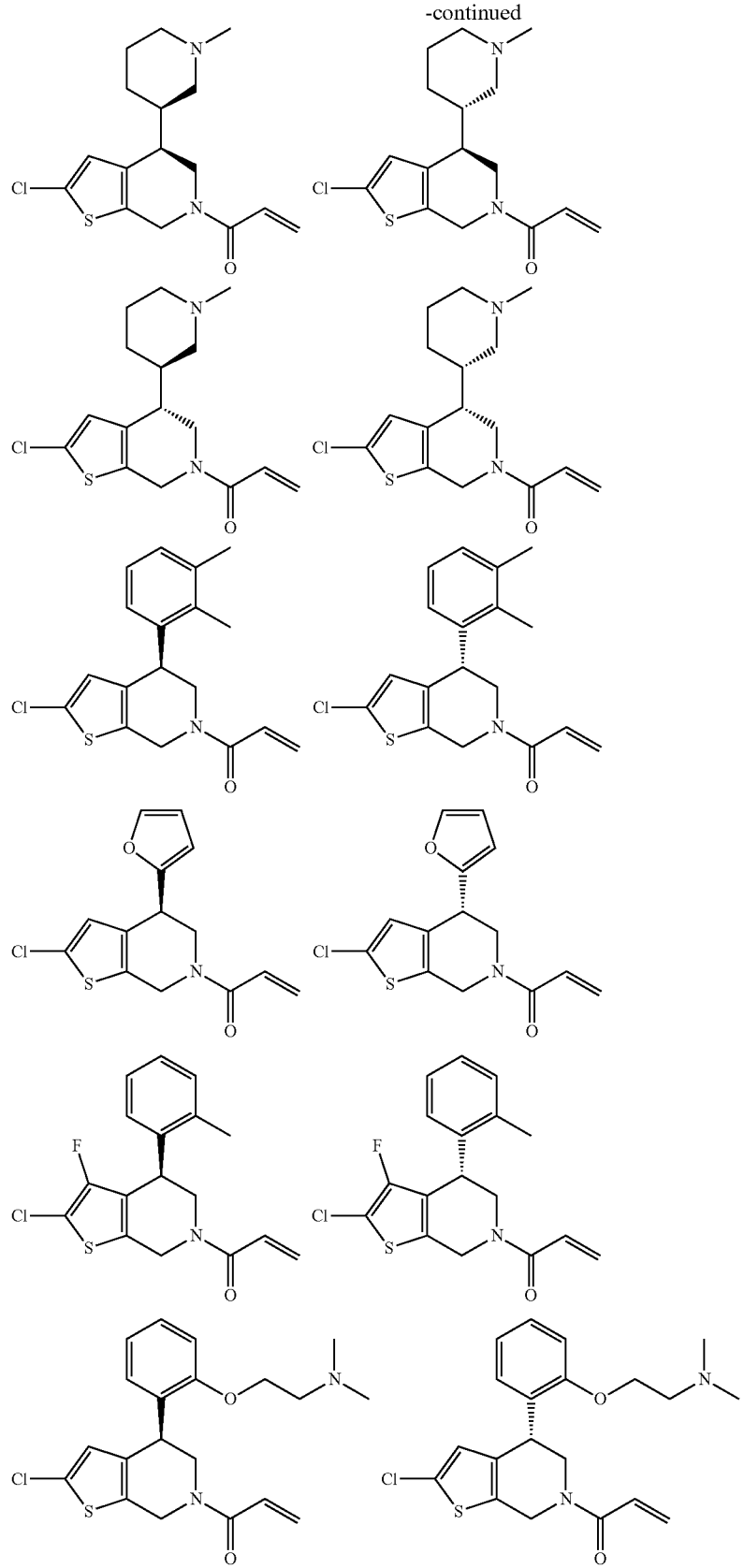
-continued

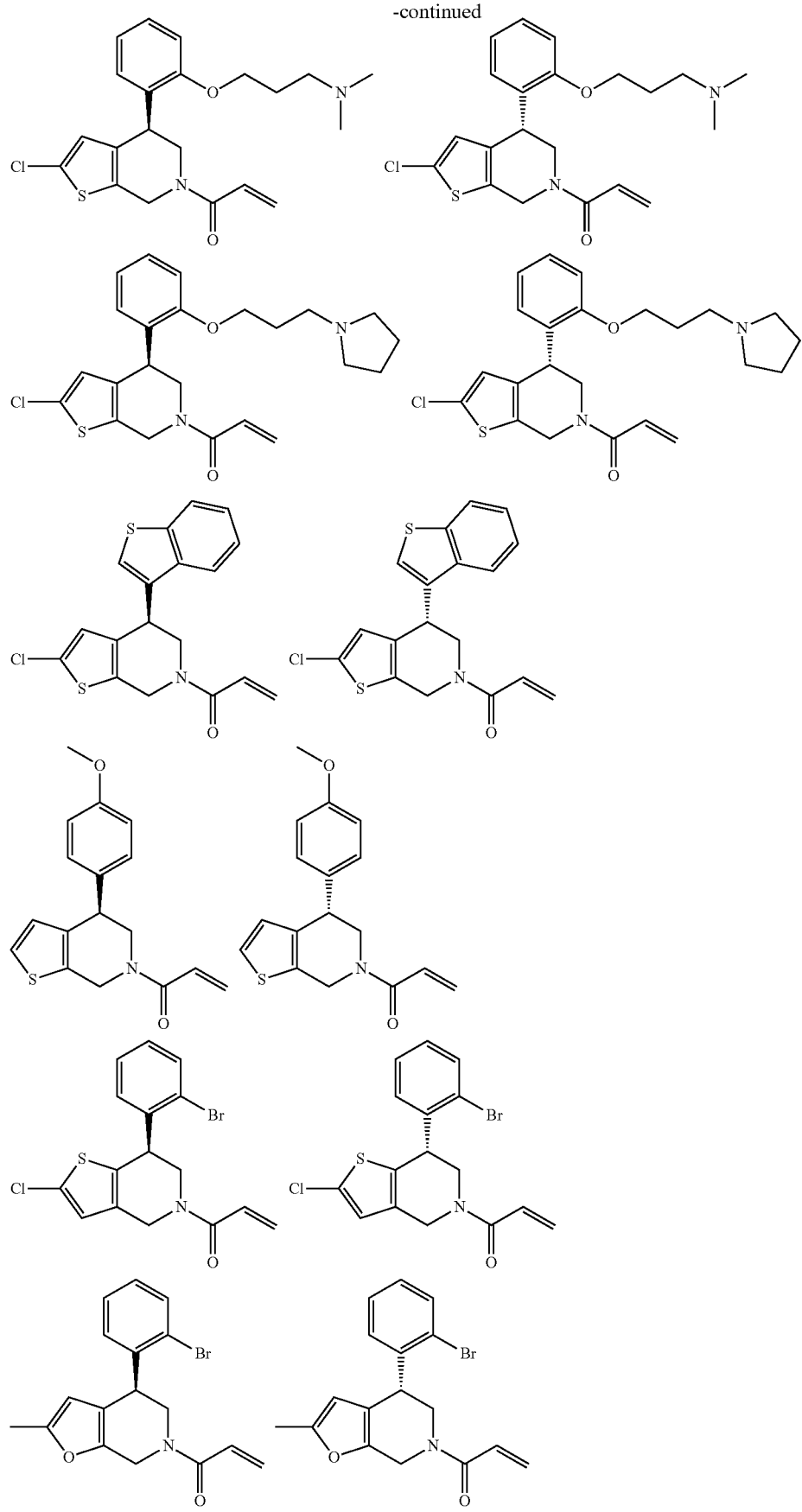

331

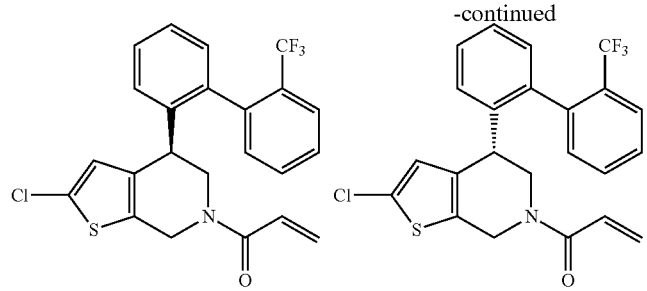

1-(2-chloro-4-(o-tolyl)-4,7-dihydrothienol[2,3-c]pyridin-6(5H-yl)prop-2-en-1-one;
(E)-1-(2-chloro-4-(o-tolyl)-4,7-dihydrothieno[2,3-c]pyridin-6(5H-yl)-4,4,4-trifluorobut-2-en-1-one;
2-chloro-1-(2-chloro-4-(o-tolyl)-4,7-dihydrothieno[2,3-c]pyridin-6(5H)-yl)ethan-1-one;
(E)-1-(2-chloro-4-(o-tolyl)-4,7-dihydrothieno[2,3-c]pyridin-6(5H)-yl)-4,4-difluorobut-2-en-1-one;
(E)-1-(2-chloro-4-(o-tolyl)-4,7-dihydrothieno[2,3-c]pyridin-6(5H)-yl)-4-fluorobut-2-en-1-one;

332

1-(4-([1,1'-biphenyl]-2-yl)-2-chloro-4,7-dihydrothieno[2,3-c]pyridin-6(5H)-yl)prop-2-en-1-one;
(E)-4-bromo-1-(2-chloro-4-(o-tolyl)-4,7-dihydrothieno[2,3-c]pyridin-6(5H)-yl)but-2-en-1-one;
(E)-1-(2-chloro-4-(o-tolyl)-4,7-dihydrothieno[2,3-c]pyridin-6(5H)-yl)-4-(dimethylamino)but-2-en-1-one;
1-(2-chloro-4-cyclohexyl-4,7-dihydrothieno[2,3-c]pyridin-6(5H)-yl)prop-2-en-1-one; and
1-(2-chloro-5-methyl-4-phenyl-4,7-dihydrothieno[2,3-c]pyridin-6(5H)-yl)prop-2-en-1-one.

* * * * *